United States Patent
Wigginton et al.

(10) Patent No.: US 11,078,279 B2
(45) Date of Patent: Aug. 3, 2021

(54) COMBINATION THERAPY FOR THE TREATMENT OF CANCER

(71) Applicant: MacroGenics, Inc., Rockville, MD (US)

(72) Inventors: Jon Marc Wigginton, Rockville, MD (US); Naimish Bharat Pandya, Clarksville, MD (US); Robert Joseph Lechleider, Bethesda, MD (US); Scott Koenig, Rockville, MD (US); Ezio Bonvini, Potomac, MD (US)

(73) Assignee: MacroGenics, Inc., Rockville, MD (US)

( * ) Notice: Subject to any disclaimer, the term of this patent is extended or adjusted under 35 U.S.C. 154(b) by 373 days.

(21) Appl. No.: 15/580,969

(22) PCT Filed: Jun. 9, 2016

(86) PCT No.: PCT/US2016/036608
§ 371 (c)(1),
(2) Date: Dec. 8, 2017

(87) PCT Pub. No.: WO2016/201051
PCT Pub. Date: Dec. 15, 2016

(65) Prior Publication Data
US 2018/0298100 A1 Oct. 18, 2018

Related U.S. Application Data

(60) Provisional application No. 62/242,640, filed on Oct. 16, 2015, provisional application No. 62/211,109, filed on Aug. 28, 2015, provisional application No. 62/175,039, filed on Jun. 12, 2015.

(51) Int. Cl.
C07K 16/28 (2006.01)
C07K 16/32 (2006.01)
A61P 35/00 (2006.01)
A61K 39/00 (2006.01)

(52) U.S. Cl.
CPC ......... *C07K 16/2818* (2013.01); *A61P 35/00* (2018.01); *C07K 16/2803* (2013.01); *C07K 16/2863* (2013.01); *C07K 16/32* (2013.01); *A61K 2039/505* (2013.01); *C07K 2317/24* (2013.01); *C07K 2317/41* (2013.01); *C07K 2317/524* (2013.01); *C07K 2317/526* (2013.01); *C07K 2317/567* (2013.01); *C07K 2317/71* (2013.01); *C07K 2317/72* (2013.01); *C07K 2317/73* (2013.01); *C07K 2317/732* (2013.01); *C07K 2317/74* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,449,736 A | 5/1984 | Blackwell |
| 4,816,567 A | 3/1989 | Cabilly et al. |
| 5,624,821 A | 4/1997 | Winter et al. |
| 5,633,425 A | 5/1997 | Lonberg et al. |
| 5,677,171 A | 10/1997 | Hudziak et al. |
| 5,739,277 A | 4/1998 | Presta et al. |
| 5,807,715 A | 9/1998 | Morrison et al. |
| 5,866,692 A | 2/1999 | Shitara et al. |
| 5,885,573 A | 3/1999 | Bluestone et al. |
| 5,952,136 A | 9/1999 | Herentals et al. |
| 6,054,297 A | 4/2000 | Carter et al. |
| 6,194,551 B1 | 2/2001 | Presta et al. |
| 6,218,149 B1 | 4/2001 | Morrison et al. |
| 6,472,511 B1 | 10/2002 | Leung et al. |
| 6,541,214 B1 | 4/2003 | Clinton |
| 6,803,192 B1 | 10/2004 | Chen |
| 6,808,710 B1 | 10/2004 | Wood et al. |
| 6,946,292 B2 | 9/2005 | Kanda et al. |
| 7,101,550 B2 | 9/2006 | Wood et al. |
| 7,112,439 B2 | 9/2006 | Johnson et al. |
| 7,276,586 B2 | 10/2007 | Goddard et al. |
| 7,317,091 B2 | 1/2008 | Lazar et al. |
| 7,355,008 B2 | 4/2008 | Stavenhagen et al. |
| 7,425,619 B2 | 9/2008 | Koenig et al. |
| 7,425,620 B2 | 9/2008 | Koenig et al. |
| 7,488,802 B2 | 2/2009 | Collins et al. |

(Continued)

FOREIGN PATENT DOCUMENTS

| | | |
|---|---|---|
| EP | 0 359 096 | 11/1997 |
| EP | 2 158 221 | 3/2010 |

(Continued)

OTHER PUBLICATIONS

Tame (J. Comput. Aided Mol. Des. Mar. 1999; 13 (2): 99-108).*
Dixon (Proteins. 1997; Suppl 1: 198-204).*
Lensink et al. (Proteins. 2007; 69: 704-718).*
Lloyd et al (Protein Engineering, Design & Selection, 22:159-168, 2009).*
Philips, G.K. et al. (2014) "Therapeutic Uses Of Anti-PD1 and Anti-PD-L1 Antibodies," Intl. Immunol. 27(1):39-46.
Savas, P. et al. (2014) "Investigation of the Positive Relationship Between Tumour-Infiltrating Lymphocyte and Trastuzumab Therapy," Immunother. 6(7):803-880.

(Continued)

*Primary Examiner* — Brad Duffy
(74) *Attorney, Agent, or Firm* — Jeffrey I. Auerbach; AuerbachSchrot LLC

(57) ABSTRACT

This invention relates to a pharmaceutical composition that comprises a first molecule that specifically binds HER2/neu and a second molecule that specifically binds a cell-surface receptor (or its ligand) that is involved in regulating an immune checkpoint (or the ligand thereof). The invention particularly relates to the embodiment wherein the second molecule binds to PD-1. The invention also relates to the use of such pharmaceutical compositions to treat cancer and other diseases.

20 Claims, 15 Drawing Sheets

Specification includes a Sequence Listing.

(56) References Cited

U.S. PATENT DOCUMENTS

| | | |
|---|---|---|
| 7,521,051 B2 | 4/2009 | Collins et al. |
| 7,563,869 B2 | 7/2009 | Honjo et al. |
| 7,595,048 B2 | 9/2009 | Honjo et al. |
| 7,618,628 B2 | 11/2009 | Johnson et al. |
| 7,632,497 B2 | 12/2009 | Stavenhagen |
| 7,635,757 B2 | 12/2009 | Freeman et al. |
| 7,638,492 B2 | 12/2009 | Wood et al. |
| 7,722,868 B2 | 5/2010 | Freeman et al. |
| 7,794,710 B2 | 9/2010 | Chen et al. |
| 7,838,635 B2 | 11/2010 | Johnson et al. |
| 7,906,327 B2 | 3/2011 | Johnson et al. |
| 7,943,743 B2 | 5/2011 | Korman et al. |
| 7,960,512 B2 | 6/2011 | Stavenhagen et al. |
| 8,008,449 B2 | 8/2011 | Korman et al. |
| 8,062,852 B2 | 11/2011 | Mozaffarian et al. |
| 8,087,074 B2 | 12/2011 | Popp et al. |
| 8,088,737 B2 | 1/2012 | Friedman et al. |
| 8,088,905 B2 | 1/2012 | Collins et al. |
| 8,217,147 B2 | 7/2012 | Stavenhagen et al. |
| 8,354,509 B2 | 1/2013 | Carven et al. |
| 8,552,154 B2 | 10/2013 | Freeman et al. |
| 8,609,089 B2 | 12/2013 | Langermann et al. |
| 8,652,466 B2 | 2/2014 | Stavenhagen et al. |
| 8,663,634 B2 | 3/2014 | Koenig et al. |
| 8,709,416 B2 | 4/2014 | Langermann et al. |
| 8,779,105 B2 | 7/2014 | Korman et al. |
| 8,785,599 B2 | 7/2014 | Johnson |
| 8,802,093 B2 * | 8/2014 | Johnson .................. A61P 43/00 424/133.1 |
| 8,900,587 B2 | 12/2014 | Carven et al. |
| 9,062,112 B2 | 6/2015 | Chen et al. |
| 9,084,776 B2 | 7/2015 | Korman et al. |
| 9,205,148 B2 | 12/2015 | Langermann et al. |
| 9,243,069 B2 * | 1/2016 | Johnson .................. A61P 43/00 |
| 9,284,375 B2 | 3/2016 | Johnson et al. |
| 9,296,816 B2 | 3/2016 | Johnson et al. |
| 9,469,692 B2 * | 10/2016 | Johnson .................. A61K 45/06 |
| 9,676,853 B2 | 6/2017 | Zhou et al. |
| 9,889,197 B2 | 2/2018 | Johnson et al. |
| 10,131,713 B2 * | 11/2018 | Johnson ........... A61K 39/39558 |
| 2002/0028486 A1 | 3/2002 | Morrison et al. |
| 2004/0197347 A1 | 10/2004 | Sykes et al. |
| 2004/0241745 A1 | 12/2004 | Honjo et al. |
| 2005/0059051 A1 | 3/2005 | Chen |
| 2006/0177439 A1 | 8/2006 | Koenig et al. |
| 2007/0166281 A1 | 7/2007 | Kosak |
| 2008/0102069 A1 | 5/2008 | Friess et al. |
| 2008/0112961 A1 | 5/2008 | Stavenhagen et al. |
| 2008/0311117 A1 | 12/2008 | Collins et al. |
| 2009/0060910 A1 | 3/2009 | Johnson et al. |
| 2010/0040614 A1 | 2/2010 | Ahmed et al. |
| 2011/0097323 A1 | 4/2011 | Johnson et al. |
| 2013/0017199 A1 | 1/2013 | Langermann |
| 2013/0230514 A1 | 9/2013 | Langermann et al. |
| 2015/0203579 A1 | 7/2015 | Papadopoulos et al. |

FOREIGN PATENT DOCUMENTS

| | | |
|---|---|---|
| EP | 2 376 109 | 10/2011 |
| EP | 2 714 079 | 9/2016 |
| EP | 2 601 216 | 1/2018 |
| WO | WO 1999/058572 | 11/1999 |
| WO | WO 2001/014557 | 3/2001 |
| WO | WO 2001/039722 | 6/2001 |
| WO | WO 2002/086083 | 10/2002 |
| WO | WO 2003/099196 | 12/2003 |
| WO | WO 2004/056875 | 7/2004 |
| WO | WO 2004/063351 | 7/2004 |
| WO | WO 2006/088494 | 8/2006 |
| WO | WO 2006/113665 | 10/2006 |
| WO | WO 2006/121168 | 11/2006 |
| WO | WO 2007/005874 | 1/2007 |
| WO | WO 2007/021841 | 2/2007 |
| WO | WO 2007/024249 | 3/2007 |
| WO | WO 2008/083174 | 7/2008 |
| WO | WO 2008/140603 | 11/2008 |
| WO | WO 2008/145142 | 12/2008 |
| WO | WO 2008/156712 | 12/2008 |
| WO | WO 2008/157379 | 12/2008 |
| WO | WO 2009/014708 | 1/2009 |
| WO | WO 2009/073533 | 6/2009 |
| WO | WO 2010/080538 | 7/2010 |
| WO | WO 2011/159877 | 12/2011 |
| WO | WO 2012/018687 | 2/2012 |
| WO | WO 2012/135408 | 10/2012 |
| WO | WO 2012/145493 | 10/2012 |
| WO | WO 2012/145549 | 10/2012 |
| WO | WO 2012/162068 | 11/2012 |
| WO | WO 2013/014668 | 1/2013 |
| WO | WO 2003/035835 | 5/2013 |
| WO | WO 2014/055648 | 4/2014 |
| WO | WO 2014/179664 | 11/2014 |
| WO | WO 2014/194302 | 12/2014 |
| WO | WO 2015/036394 | 3/2015 |
| WO | WO 2015/095418 | 6/2015 |
| WO | WO 2015/112800 | 7/2015 |
| WO | WO 2017/019846 | 2/2017 |

OTHER PUBLICATIONS

Stagg, J. et al. (2011) "Anti-Erbb2 Mab Therapy Requires Type I and Type II Interferons and Synergizes With Anti-PD1 or Anti-CD137 Mab Therapy," Proc. Natl. Acad. Sci. (U.S.A.) 108(17):7142-7147.

International Search Report PCT/US2016/036608 (WO 2016/201051) (dated 2016) (3 pages).

Written Opinion of the International Searching Authority PCT/US2016/036608 (WO 2016/201051) (dated 2016) (5 pages).

Extended European Search Report, EP 16808255.0 (dated 2018) pp. 1-14.

Garon, E.B. et al. (2015) "Pembrolizumab for the Treatment of Non-Small-Cell Lung Cancer," New Engl. J. Med. 372(21):2018-2028.

Karrels, J. et al. (2015) "MacroGenics Presents Updated Data from Phase 1 Study of Margetuximab at ASCO Annual Meeting 2015," Retrieved from the Internet: URL:http://ir.macrogenics.com/static-files/dc17198f-ce6e-4de0-a58ae55f439487642; pages.

Xu, M. et al. (2012) "The Tumor Immunosuppressive Microenvironment Impairs The Therapy of Anti-Her2/neu Antibody," Protein Cell 3(6):441-449.

Agarwal, A. et al. (2008) "The Role of Positive Costimulatory Molecules in Transplantation and Tolerance," Curr. Opin. Organ Transplant. 13:366-372.

Agata, T. et al. (1996) "Expression of The PD-1 Antigen on The Surface of Stimulated Mouse T and B Lymphocytes," Int. Immunol. 8(5):765-772.

Al Hussaini, M. et al. (2015) "Targeting CD123 in AML Using A T-Cell Directed Dual-Affinity Re-Targeting (DART®) Platform," Blood 127(1):122-131.

Aldington, S. et al. (2007) "Scale-Up Of Monoclonal Antibody Purification Processes," J. Chromatogr. B Analyt. Technol. Biomed. Life Sci. 848(1):64-78.

Alegre, M.L. et al. (1994) "A Non-Activating "Humanized" Anti-CD3 Monoclonal Antibody Retains Immunosuppressive Properties In Vivo," Transplantation 57:1537-1543.

Altschul, S.F. (1991) "Amino Acid Substitution Matrices From an Information Theoretic Perspective," J. Mol. Biol. 219, 555-565.

Altschul, S.F. et al., (1990) "Basic Local Alignment Search Tool," J. Mol. Biol. 215:403-10.

Armour, K.L. et al. (1999) "Recombinant human IgG Molecules Lacking Fcgamma Receptor I Binding and Monocyte Triggering Activities," Eur. J. Immunol. 29:2613-24.

Arteaga, C.L. et al. (1994) "p185c-erbB-2 Signal Enhances Cisplatin Induced Cytotoxicity in Human Breast Carcinoma Cells: Association Between An Oncogenic Receptor Tyrosine Kinase and Drug-Induced DNA Repair," Cancer 54:3758-3765.

(56) References Cited

OTHER PUBLICATIONS

Arteaga, C.L. et al. (2001) "The Epidermal Growth Factor Receptor: From Mutant Oncogene in Nonhuman Cancers to Therapeutic Target in Human Neoplasia," J Clinical Oncology 19(18s):32s-40s (Abstract Only).
Atwell et al. (1997) "Stable Heterodimers From Remodeling the Domain Interface Of A Homodimer Using a Phage Display Library," J. Mol. Biol. 270: 26-35.
Bacus, S.S. et al. (1992) "A Ligand for the erbB-2 Oncogene Product (gp30) Induces Differentiation of Human Breast Cancer Cells," Cell Growth & Diff. 3:401-411.
Bacus, S.S. et al. (1993) "Neu Differentiation Factor (Heregulin) Induces Expression of Intercellular Adhesion Molecule 1: Implications for Mammary Tumors," Cancer Res. 53:5251-5261.
Bacus, S.S. et al. (2002) "AKT2 Is Frequently Upregulated in HER-2/neu-Positive Breast Cancers and May Contribute to Tumor Aggressiveness by Enhancing Cell Survival," Oncogene 21:3532-3540.
Baggiolini, M. et al. (1988) "Cellular Models for the Detection and Evaluation of Drugs That Modulate Human Phagocyte Activity," Experientia 44(10):841-848.
Bargmann, C.I. et al. (1986) "Multiple Independent Activations of the Neu Oncogene by a Point Mutation Altering The Transmembrane Domain of p185," Cell 45:649-657.
Baselga, J. et al. (2001) "Mechanism Of Action of anti-HER2 Monoclonal Antibodies," Ann. Oncol. 12 (suppl. 1) S35-S41.
Baselga, J. et al. (2001) "Mechanism Of Action of Trastuzumab and Scientific Update," Seminars in Oncology 28(5) (suppl. 16):4-11.
Benz, C.C. et al. (1993) "Estrogen-Dependent, Tamoxifen-Resistant Tumorigenic Growth Of MCF-7 Cells Transfected With HER2/neu," Breast Cancer Res. Treat. 24:85-95.
Berger, R. et al. (2008) "Phase I Safety and Pharmacokinetic Study of CT-011, A Humanized Antibody Interacting With PD-1, in Patients With Advanced Hematologic Malignancies," Clin. Cancer Res. 14(10):3044-3051.
Birch, J.R. et al. (2006) "Antibody Production," Adv. Drug Deliv. Rev. 58(5-6):671-685.
Blank, C. et al. (2006) "Contribution of the PD-L1/PD-1 Pathway to T-Cell Exhaustion: An Update On Implications for Chronic Infections and Tumor Evasion Cancer," Immunol. Immunother. 56(5):739-745.
Blobel, C.P. (2005) "ADAMs: Key Components in EGFR Signalling and Development," Nat. Rev. Mol. Cell. Biol. 6:32-43.
Brown, E.J. (1994) "In Vitro Assays of Phagocytic Function of Human Peripheral Blood Leukocytes: Receptor Modulation and Signal Transduction," Methods Cell Biol. 45:147-164.
Brown, J.A. 0. (2003) "Blockade of Programmed Death-1 Ligands on Dendritic Cells Enhances T-Cell Activation and Cytokine Production," J. Immunol. 170:1257-1266.
Brüggemann, M. et al. (1987) "Comparison of the Effector Functions of Human Immunoglobulins Using A Matched Set of Chimeric Antibodies," J. Exp. Med 166:1351-1361.
Burris, H.A. . . (2013) "Phase I Study of margetuximab (MGAH22), An FC-Modified Chimeric Monoclonal Antibody (MAb), in Patients (pts) With Advanced Solid Tumors Expressing the HER2 Oncoprotein," J. Clin. Oncol. Suppl: abstr. 3004.
Burstein, H.J. (2005) "The Distinctive Nature of HER2-Positive Breast Cancers," N. Engl. J. Med. 353 (16): 1652-1654.
Capece, D. et al. (2012) "Targeting Costimulatory Molecules to Improve Antitumor Immunity," J. Biomed. Biotech. 2012:926321.
Caron, P.C. et al. (1992) "Engineered Humanized Dimeric Forms of IgG Are More Effective Antibodies," J. Exp. Med. 176:1191-1195.
Carpenter, G. et al. (1979) "Epidermal Growth Factor," Annu Rev Biochem. 48:193-216.
Carraway, K.L. et al. (1994) "The erbB3 Gene Product Is a Receptor for Heregulin," J. Biol. Chem. 269:14303-14306.
Carter, L. et al. (2002) "PD-1:PD-L Inhibitory Pathway Affects Both CD4(+) and CD8(+) T-cells and Is Overcome by IL-2," Eur. J. Immunol. 32(3):634-643.
Carter, P. et al. (1992) "Humanization Of An anti-p185HER2 Antibody for Human Cancer Therapy," Proc. Natl. Acad. Sci. (U.S.A.) 89:4285-4289.
Cartron, G. et al. (2002) "Therapeutic Activity of Humanized Anti-CD20 Monoclonal Antibody and Polymorphism in IgG Fc Receptor FcgammaRIIIa Gene," Blood 99:754-758.
Chan, C.E. et al. (2009) "The Use Of Antibodies in the Treatment of Infectious Diseases," Singapore Med. J. 50(7):663-666.
Chang, C. and Werb, Z. (2001) "The Many Faces Of Metalloproteases: Cell Growth, Invasion, Angiogenesis and Metastasis," Trends in Cell Biology 11:S37-S43.
Chappel, M.S. et al. (1991) "Identification of the Fc Gamma Receptor Class I Binding Site in Human IgG Through the Use of Recombinant IgG1/IgG2 Hybrid and Point-Mutated Antibodies," Proc. Natl. Acad. Sci. (U.S.A.) 88:9036-9040.
Chappel, M.S. et al. (1993) "Identification Of A Secondary Fc Gamma RI Binding Site Within a Genetically Engineered Human IgG Antibody," J. Biol. Chem. 33:25124-25131.
Chen, Y. et al. (2005) "Expression of B7-H1 in Inflammatory Renal Tubular Epithelial Cells," Nephron. Exp. Nephrol. 102:e81-e92.
Chichili, G.R. et al. (2015) "A CD3xCD123 Bispecific DART for Redirecting Host T Cells to Myelogenous Leukemia: Preclinical Activity and Safety in Nonhuman Primates," Sci. Transl. Med. 7(289):289ra82.
Citri, A. et al. (2003) "The Deaf And The Dumb: The Biology of ErbB-2 and ErbB-3," Exp. Cell Res. 284:54-65.
Co, M. S. et al. (1991) "Humanized Antibodies for Antiviral Therapy," Proc. Natl. Acad. Sci. (U.S.A.) 88:2869-2873.
Co, M.S. et al. (1992) "Chimeric and Humanized Antibodies With Specificity for the CD33 Antigen," J. Immunol. 148:1149-1154.
Cobleigh, M.A. et al. (1999) "Multinational Study of the Efficacy and Safety of Humanized anti-HER2 Monoclonal Antibody in Women Who Have HER2-Overexpressing Metastatic Breast Cancer That Has Progressed After Chemotherapy for Metastatic Disease," J. Clin. Oncol. 17:2639-2648.
Collins, M. et al. (2005) "The B7 Family of Immune-Regulatory Ligands," Genome Biol. 6:223.1-223.7.
Coussens, L. et al. (1985) "Tyrosine Kinase Receptor With Extensive Homology to EGF Receptor Shares Chromosomal Location With neu Oncogene," Science 230:1132-1139.
Cunningham and Wells (1989) "High-resolution epitope mapping of hGH-receptor interactions by alanine-scanning mutagenesis" Science 244:1081-1085 (Abstract Only).
Dawson, P.E. et al.(2000) "Synthesis of Native Proteins by Chemical Ligation," Annu. Rev Biochem. 69:923-960.
De Haij, S. et al. (2005) "Renal Tubular Epithelial Cells Modulate T-Cell Responses Via iCOS-L and B7-H1" Kidney Int. 68:2091-2102.
Dong, C. et al. (2003) "Immune Regulation by Novel Costimulatory Molecules," Immunolog. Res. 28(1):39-48.
Dong, H. (2003) "B7-H1 Pathway and Its Role in the Evasion of Tumor Immunity," J. Mol. Med. 81:281-287.
Dougall, W.C. et al. (1994) "The neu-Oncogene: Signal Transduction Pathways, Transformation Mechanisms and Evolving Therapies," Oncogene 9:2109-2123 (Abstract Only).
Duncan, A.R. et al. (1988) "Localization of The Binding Site for the Human High-Affinity Fc Receptor on IgG," Nature 332:563-564.
Eddy, S.R. (2004) "Where Did the BLOSUM62 Alignment Score Matrix Come From?, " Nature Biotech. 22(8):1035-1036.
Eigenbrot, C. et al. (1993) "X-ray Structures of the Antigen-Binding Domains From Three Variants of Humanized anti-p185HER2 Antibody 4D5 and Comparison With Molecular Modeling," J. Mol. Biol. 229:969-995.
Even, M.S. et al. (2006) "Serum-Free Hybridoma Culture: Ethical, Scientific and Safety Considerations," Trends Biotechnol. 24(3):105-108.
Flajnik, M.F. et al. (2012) "Evolution of the B7 Family: Co-Evolution of B7H6 And Nkp30, Identification Of A New B7 Family Member, B7H7, and of B7's Historical Relationship With the MHC," Immunogenetics 64(8):571-590.
Flesch, B.K. and Neppert, J. (1999) "Functions of The Fc Receptors for Immunoglobulin G," J. Clin. Lab. Anal. 14:141-156.

(56) References Cited

OTHER PUBLICATIONS

Flies, D.B. et al. (2007) "The New B7s: Playing a Pivotal Role in Tumor Immunity," J. Immunother. 30(3):251-260.
Formisano, L. et al. (2014) "Epidermal Growth Factor-Receptor Activation Modulates Src-Dependent Resistance to Lapatinib in Breast Cancer Models," Breast Cancer Research 16:R45.
Franklin, M.C. et al. (2004) "Insights Into ErbB Signaling From The Structure of The ErbB2-Pertuzumab Complex," Cancer Cell. 5(4):317-328.
Freeman, G.J. et al. (2000) "Engagement of the PD-1 Immunoinhibitory Receptor by a Novel B7 Family Member Leads to Negative Regulation of Lymphocyte Activation," J. Exp. Med. 192:1-9.
Fujimoto-Ouchi, K. et al. (2002) "Antitumor Activity of Combinations of anti-HER-2 Antibody Trastuzumab and Oral Fluoropyrimidines Capecitabine/5'-Dfurd in Human Breast Cancer Models," Cancer Chemother. Pharmacol. 49:211-216.
Fukazawa, T. et al. (1996) "Tyrosine Phosphorylation of Cbl Upon Epidermal Growth Factor (EGF) Stimulation and Its Association With EGF Receptor and Downstream Signaling Proteins," J. Biol. Chem. 271:14554-14559.
Gandhi, M.D. et al. (2014) "Targeted Treatment of Head and Neck Squamous-Cell Carcinoma: Potential of Lapatinib," Onco. Targets Ther. 7:245-251.
Gilcrease M.Z. et al. (2009) "Even Low-Level HER2 Expression May Be Associated With Worse Outcome in Node-Positive Breast Cancer," Am J Surg Pathol. 2009 33(5):759-767.
Glaser, S.M. et al. (1992) "Antibody Engineering by Codon-Based Mutagenesis in a Filamentous Phage Vector System," J. Immunology 149:3903.
Gorman, S. D. et al. (1991) "Reshaping A Therapeutic CD4 Antibody," Proc. Natl. Acad. Sci. (U.S.A.) 88:4181-4185.
Graumann, K. et al. (2006) "Manufacturing of Recombinant Therapeutic Proteins in Microbial Systems," Biotechnol. J. 1(2):164-186.
Greenwald, R.J. et al. (2005) "The B7 Family Revisited," Ann. Rev. Immunol. 23:515-548.
Gross, J., et al. (1992) "Identification and Distribution of the Costimulatory Receptor CD28 in the Mouse," J. Immunol. 149:380-388.
Hackel, P.O. et al. (1999) "Epidermal Growth Factor Receptors: Critical Mediators of Multiple Receptor Pathways," Curr. Opin. Cell Biol. 11:184-189.
Hancock, M.C. et al. (1991) "A Monoclonal Antibody Against the c-erbB-2 Protein Enhances the Cytotoxicity of Cis-Diamminedichloroplatinum Against Human Breast and Ovarian Tumor Cell Lines," Cancer Res. 51:4575-4580.
Henikoff, J.G. (1992) "Amino acid substitution matrices from protein blocks," Proc. Natl. Acad. Sci. (USA) 89:10915-10919.
Holliger, P. et al. (1993) "'Diabodies': Small Bivalent and Bispecific Antibody Fragments," Proc. Natl. Acad. Sci. (U.S.A.) 90:6444-6448.
Hoogenboom, H.R. et al. (1991) "By-Passing Immunisation. Human Antibodies From Synthetic Repertoires of Germline VH Gene Segments Rearranged In Vitro," J. Mol. Biol. 227:381.
Huang, S.M. et al. (2000) "Modulation of Radiation Response After Epidermal Growth Factor Receptor Blockade in Squamous Cell Carcinomas: Inhibition of Damage Repair, Cell Cycle Kinetics, and Tumor Angiogenesis," Clinical Cancer Res. 7:2166-2174.
Hutchins et al. (1995) "Improved Biodistribution, Tumor Targeting, and Reduced Immunogenicity in Mice With a Gamma 4 Variant of Campath-1H," Proc. Natl. Acad. Sci. (U.S.A.) 92:11980-84.
Hynes, N.E. et al. (1994) "The Biology of erbB-2/neu/HER-2 and Its Role in Cancer," Biochim. et Biophys. Acta 1198:165-184.
Idusogie, E.E. et al. (2000) "Mapping of the C1q Binding Site on Rituxan, A Chimeric Antibody With a Human IgG Fc," J. Immunol. 164:4178-184.
Idusogie, E.E. et al. (2001) "Engineered Antibodies With Increased Activity to Recruit Complement," J. Immunol. 166:2571-2575.
Ishida, Y. et al. (1992) "Induced Expression of PD-1, A Novel Member of the Immunoglobulin Gene Superfamily, Upon Programmed Cell Death," EMBO J. 11:3887-3895.
Jefferis, R. et al. (1995) "Recognition Sites on Human IgG for Fc Gamma Receptors: The Role of Glycosylation," Immunol. Lett. 44:111-117.
Jefferis, R. et al. (1996) "Modulation of Fc(Gamma)R and Human Complement Activation by IgG3-Core Oligosaccharide Interactions," Immunol. Lett. 54:101-04.
Jefferis, R. et al. (2002) "Interaction Sites on Human IgG-Fc for FcgammaR: Current Models," Immunol. Lett. 82:57-65.
Jennings, V.M. (1995) "Review of Selected Adjuvants Used in Antibody Production," ILAR J. 37(3):119-125.
Jespers, L.S. et al. (1994) "Guiding the Selection of Human Antibodies From Phage Display Repertoires to a Single Epitope Of An Antigen," Biotechnology 12:899-903.
Johnson, S. et al. (2010) "Effector Cell Recruitment With Novel Fv-Based Dual-Affinity Re-Targeting Protein Leads to Potent Tumor Cytolysis and in vivo B-Cell Depletion," J. Mol. Biol. 399(3):436-449.
Karlin, S. et al. (1990) "Methods for Assessing the Statistical Significance of Molecular Sequence Features by Using General Scoring Schemes," Proc. Natl. Acad. Sci. (USA) 87:2264-2268.
Kettleborough, C. A. et al. (1991) "Humanization Of A Mouse Monoclonal Antibody by CDR-Grafting: The Importance of Framework Residues on Loop Conformation," Protein Engineering 4:773-3783.
King, C.R. et al. (1985) "Amplification Of A Novel v-erbB-Related Gene in a Human Mammary Carcinoma," Science 229:974 (Abstract Only).
Klapper, L.N. et al. (1997) "A Subclass of Tumor-Inhibitory Monoclonal Antibodies to ErbB-2/HER2 Blocks Crosstalk With Growth Factor Receptors," Oncogene 14:2099-2109.
Klapper, L.N. et al. (2000) "Tumor-Inhibitory Antibodies to HER-2/ErbB-2 May Act by Recruiting c-Cbl and Enhancing Ubiquitination of HER-2," Cancer Res. 60:3384-3388.
Kochendoerfer, G.G. et al. (1999) "Chemical Protein Synthesis," Curr. Opin. Chem. Biol. 3(6):665-671.
Kohler, G. et al. (1975) "Continuous Cultures of Fused Cells Secreting Antibody of Predefined Specificity," Nature 256:495-497.
Korman, A.J. et al. (2007) "Checkpoint Blockade in Cancer Immunotherapy," Adv. Immunol. 90:297-339.
Kraus, M.H. et al. (1989) "Isolation and Characterization of ERBB3, A Third Member of the ERBB/Epidermal Growth Factor Receptor Family: Evidence for Overexpression in a Subset of Human Mammary Tumors," Proc. Natl. Acad. Sci. (U.S.A.) 86:9193-9197.
Kurokawa, H. et al. (2001) "Inhibition of erbB Receptor (HER) Tyrosine Kinases As a Strategy to Abrogate Antiesfrogen Resistance in Human Breast Cancer," Clin. Cancer Res. 7:4436s-42s, 4411s-4412s.
Laffly, E. et al. (2005) "Monoclonal and Recombinant Antibodies, 30 Years After . . . ," Hum. Antibodies. 14(1-2):33-55.
Lange, C.A. et al. (1998) "Convergence of Progesterone and Epidermal Growth Factor Signaling in Breast Cancer. Potentiation Of Mitogen-Activated Protein Kinase Pathways," J. Biol. Chem. 273:31308-31316.
Lanitis, E. (2012) "Primary Human Ovarian Epithelial Cancer Cells Broadly Express HER2 At Immunologically-Detectable Levels," PloS One 7(11):e49829.
Latchman, Y. et al. (2001) "PD-L2 Is a Second Ligand for PD-1 and Inhibits T-Cell Activation," Nat. Immunol 2:261-268.
Latchman, Y.E. et al. (2004) "PD-L1-Deficient Mice Show That PD-L1 on T-Cells, Antigen-Presenting Cells, and Host Tissues Negatively Regulates T-Cells." Proc. Natl. Acad. Sci. (U.S.A.) 101(29):10691-10696.
Lee, H. et al. (1998) "Isolation and Characterization of Four Alternate c-erbB3 Transcripts Expressed in Ovarian Carcinoma-Derived Cell Lines and Normal Human Tissues," Oncogene 16:3243-3252.
Lee, K.F. et al. (1995) "Requirement for Neuregulin Receptor erbB2 in Neural and Cardiac Development," Nature 378:394-398.
Lefranc, G. et al., (1979) "Gm, Am and Km Immunoglobulin Allotypes of Two Populations in Tunisia," Hum. Genet. 50:199-211.
Lehmann, A.K. et al. (2000) "Phagocytosis: Measurement by Flow Cytometry," J. Immunol. Methods 243(1-2):229-242.

(56) References Cited

OTHER PUBLICATIONS

Leitzel, K. et al. (1992) "Elevated Soluble c-erbB-2 Antigen Levels in the Serum and Effusions Of A Proportion of Breast Cancer Patients," J. Clin. Oncol. 10:1436-1443.
Lepenies, B. et al. (2008) "The Role of Negative Costimulators During Parasitic Infections," Endocrine, Metabolic & Immune Disorders—Drug Targets 8:279-288.
Liao, J. et al. (2010) "Lapatinib: New Opportunities for Management of Breast Cancer," Breast Cancer (Dove Med Press) 2:79-91.
Lindley, P.S. et al. (2009) "The Clinical Utility of Inhibiting CD28-Mediated Costimulation," Immunol. Rev. 229:307-321.
Linsley, P. et al. (1996) "Intracellular Trafficking of CTLA4 and Focal Localization Towards Sites of TCR Engagement," Immunity 4:535-543.
LoBuglio, A.F. et al. (1989) "Mouse/Human Chimeric Monoclonal Antibody in Man: Kinetics and Immune Response," Proc. Natl. Acad. Sci. (U.S.A.) 86:4220-4224.
Loke, P. et al. (2004) "Emerging Mechanisms of Immune Regulation: The Extended B7 Family and Regulatory T-Cells." Arthritis Res. Ther. 6:208-214.
Lonberg, N. et al. (1995) "Human Antibodies From Transgenic Mice," Int. Rev. Immunol 13:65-93.
Lu et al., (2008) "The Effect Of A Point Mutation on the Stability of Igg4 As Monitored by Analytical Ultracentrifugation," J. Pharmaceutical Sciences 97:960-969.
Lund et al. (1991) "Human Fc Gamma RI and Fc Gamma RII Interact With Distinct But Overlapping Sites on Human IgG," J. Immunol. 147:2657-2662.
Lund et al. (1992) "Multiple Binding Sites on the CH2 Domain of IgG for Mouse Fc Gamma R11," Mol. Immunol. 29:53-59.
Lund, J. et al. (1995) "Oligosaccharide-Protein Interactions in IgG Can Modulate Recognition by Fc Gamma Receptors," FASEB J. 9:115-119.
Lund, J. et al. (1996) "Multiple Interactions of IgG With Its Core Oligosaccharide Can Modulate Recognition by Complement and Human Fc Gamma Receptor I and Influence The Synthesis of Its Oligosaccharide Chains," J. Immunol. 157:4963-4969.
Maeda, H. et al. (1991) "Construction of Reshaped Human Antibodies With HIV-Neutralizing Activity," Human Antibodies Hybridoma 2:124-134.
Marks, J.D. et al. (1991) "By-Passing Immunization. Human Antibodies From V-Gene Libraries Displayed on Phage," J. Mol. Biol. 222:581.
Martin-Orozco, N. et al. (2007) "Inhibitory Costimulation and Anti-Tumor Immunity," Semin. Cancer Biol. 17(4):288-298.
Marvin, J.S. et al. (2005) "Recombinant Approaches to IgG-Like Bispecific Antibodies," Acta Pharmacol. Sin. 26:649-658.
Mazanet, M.M. et al. (2002) "B7-H1 Is Expressed by Human Endothelial Cells and Suppresses T-Cell Cytokine Synthesis," J. Immunol. 169:3581-3588.
McCann, A. et al. (1990) "c-erbB-2 Oncoprotein Expression in Primary Human Tumors," Cancer 65:88-92.
Melero, I. et al.(2013) "Agonist Antibodies to TNFR Molecules That Costimulate T and NK Cells," Clin. Cancer Res. 19(5):1044-1053.
Mellinghoff, I.K. et al. (2004) "HER2/neu Kinase-Dependent Modulation Of Androgen Receptor Function Through Effects on DNA Binding and Stability," Cancer Cell 6:517-527.
Mitri, Z. et al. (2012). "The HER2 Receptor in Breast Cancer: Pathophysiology, Clinical Use, and New Advances in Therapy," Chemother Res Pract 2012:Article ID: 742193 (7 Pages).
Molina, M.A. et al. (2001) "Trastuzumab (Herceptin), A Humanized anti-Her2 Receptor Monoclonal Antibody, Inhibits Basal and Activated Her2 Ectodomain Cleavage in Breast Cancer Cells," Cancer Res. 61:4744-4749.
Moore, P.A. et al. (2011) "Application of Dual Affinity Retargeting Molecules to Achieve Optimal Redirected T-Cell Killing of B-Cell Lymphoma," Blood 117(17):4542-4551.
Moss, M.L. et al. (2002) "Shedding Of Membrane Proteins by ADAM Family Proteases," Essays in Biochemistry 38:141-153.
Munn, D.H. et al. (1990) "Phagocytosis of Tumor Cells by Human Monocytes Cultured in Recombinant Macrophage Colony-Stimulating Factor," J. Exp. Med. 172:231-237.
Needleman, S.B. & Wunsch, C.D. (1970) "A General Method Applicable to the Search for Similarities In The Amino Acid Sequence of Two Proteins," J. Mol. Biol. 48:443.
Nishimura, H. et al. (2000) "Facilitation of Beta Selection and Modification of Positive Selection in the Thymus of PD-1-Deficient Mice," J. Exp. Med. 191:891-898.
Nordstrom, J.L. et al. (2011) "Anti-tumor Activity and Toxicokinetics Analysis Of MGAH22, An anti-HER2 Monoclonal Antibody With Enhanced Fcγ Receptor Binding Properties," Breast Cancer Research 13(6):R123.
Olafsen, T. et al. (2004) "Covalent Disulfide-Linked Anti-CEA Diabody Allows Site-Specific Conjugation and Radiolabeling for Tumor Targeting Applications," Prot. Engr. Des. Sel. 17:21-27.
Olayioye, M.A. et al. (1998) "ErbB-1 and ErbB-2 Acquire Distinct Signaling Properties Dependent Upon Their Dimerization Partner," Mol. Cell. Biol. 18:5042-5051.
Opdam, F.L. et al. (2012) "Lapatinib for Advanced or Metastatic Breast Cancer," Oncologist 17(4):536-542.
Pearson, W.R. & Lipman, D.J. (1988) "Improved Tools for Biological Sequence Comparison," Proc. Natl. Acad. Sci. (U.S.A.) 85:2444.
Peeters, K. et al. (2001) "Production Of Antibodies and Antibody Fragments in Plants," Vaccine 19:2756.
Pegram, M.D. et al. (1998) "Phase II Study of Receptor-Enhanced Chemosensitivity Using Recombinant Humanized anti-p185HER2/neu Monoclonal Antibody Plus Cisplatin in Patients With HER2/neu-Overexpressing Metastatic Breast Cancer Refractory to Chemotherapy Treatment," J. Clin. Oncology 16(8):2659-2671.
Perussia, B. et al. (2000) "Assays for antibody-dependent cell-mediated cytotoxicity (ADCC) and Reverse ADCC (Redirected Cytotoxicity) in Human Natural Killer Cells," Methods Mol. Biol. 121:179-192.
Petch, L.A. et al. (1990) "A Truncated, Secreted Form of the Epidermal Growth Factor Receptor Is Encoded by an Alternatively Spliced Transcript in Normal Rat Tissue," Mol. Cell. Biol. 10:2973-2982.
Peters, P et al., (2012) "Engineering an Improved IgG4 Molecule with Reduced Disulfide Bond Heterogeneity and Increased Fab Domain Thermal Stability," J. Biol. Chem. 287:24525-24533.
Petroff, M.G. et al. (2002) "B7 Family Molecules: Novel Immunomodulators At the Maternal-Fetal Interface," Placenta 23:S95-S101.
Pietras, R.J. et al. (1994) "Antibody to HER-2/neu receptor Blocks DNA Repair After Cisplatin in Human Breast and Ovarian Cancer Cells," Oncogene 9:1829-1838 (Abstract Only).
Plowman, G.D. et al. (1993) "Heregulin Induces Tyrosine Phosphorylation of HER4/p180erbB4," Nature 366: 473-475.
Plowman, G.D. et al. (1993) "Ligand-Specific Activation of HER4/p180erbB4, A Fourth Member of The Epidermal Growth Factor Receptor Family," Proc. Natl. Acad. Sci. (U.S.A.) 90:1746-1750.
Pollock et al. (1999) "Transgenic Milk As a Method for the Production of Recombinant Antibodies," J. Immunol Methods 231:147-157.
Presta, L.G. et al. (2002) "Engineering Therapeutic Antibodies for Improved Function," Biochem. Soc. Trans. 30:487-490.
Reddy, M.P. et al. (2000) "Elimination of Fc Receptor-Dependent Effector Functions Of A Modified IgG4 Monoclonal Antibody to Human CD4," J. Immunol. 164:1925-1933.
Ridgway et al. (1996) "'Knobs-Into-Holes' Engineering Of Antibody CH3 Domains for Heavy Chain Heterodimerization," Protein Engr. 9:617-621.
Riechmann, L. et al. (1988) "Reshaping Human Antibodies for Therapy," Nature 332:323-327.
Rudikoff, S. etc. (1982) "Single Amino Acid Substitution Altering Antigen-Binding Specificity," Proc. Natl. Acad. Sci. (USA) 79(6):1979-1983.
S.S. Farid (2006) "Process economics of industrial monoclonal antibody manufacture" J. Chromatogr. B Analyt. Technol. Biomed. Life Sci. 848(1):8-18 (Abstract Only).

(56) References Cited

OTHER PUBLICATIONS

Sachs et al. (1987) "Cell Differentiation and Bypassing of Genetic Defects in the Suppression of Malignancy," Cancer Res. 47:1981-1986.
Sato, K. et al. (1993) "Reshaping a Human Antibody to Inhibit the Interleukin 6-Dependent Tumor Cell Growth," Cancer Res 53:851-856.
Schier, R et al. (1996) "Isolation of Picomolar Affinity anti-c-erbB-2 Single-Chain Fv by Molecular Evolution of the Complementarity Determining Regions in the Center of the Antibody Binding Site," J. Mol. Bio. 263:551-567.
Scott, G.K. et al. (1993) "A Truncated Intracellular HER2/neu Receptor Produced by Alternative RNA Processing Affects Growth of Human Carcinoma Cells," Mol. Cell. Biol. 13:2247-2257.
Seals, D.F. et al. (2003) "The ADAMs Family Of Metalloproteases: Multidomain Proteins With Multiple Functions," Genes and Development 17:7-30.
Semba, K. et al. (1985) "A v-erbB-Related Protooncogene, c-erbB-2, Is Distinct From the c-erbB-1/Epidermal Growth Factor-Receptor Gene and Is Amplified in a Human Salivary Gland Adenocarcinoma," Proc. Natl. Acad. Sci. (U.S.A.) 82:6497-6501.
Shak, S. (1999) "Overview of the Trastuzumab (Herceptin) anti-HER2 Monoclonal Antibody Clinical Program in HER2-Overexpressing Metastatic Breast Cancer," Semin. Oncol. Suppl 12:71-77 (Abstract Only).
Sharpe, A.H. et al. (2002) "The B7-CD28 Superfamily," Nature Rev. Immunol. 2:116-126.
Shields, R.L. et al. (2001) "High Resolution Mapping of the Binding Site on Human IgG1 for Fc Gamma RI, Fc Gamma RII, Fc Gamma RIII, and FcRn and Design of IgG1 Variants With Improved Binding to the Fc gamma R," J. Biol. Chem. 276:6591-6604.
Shopes, B. (1992) "A Genetically Engineered Human IgG Mutant With Enhanced Cytolytic Activity," J. Immunol. 148(9):2918-2922.
Singh et al. (2014) "HER2-Positive Advanced Breast Cancer: Optimizing Patient Outcomes and Opportunities for Drug Development," British Journal of Cancer 111:1888-1898.
Slamon, D.J. et al. (1987) "Human Breast Cancer: Correlation of Relapse and Survival With Amplification of the HER-2/neu Oncogene," Science 235:177-182 (Abstract Only).
Slamon, D.J. et al. (1989) "Studies of the HER-2/neu Proto-Oncogene in Human Breast and Ovarian Cancer," Science 244:707-712 (Abstract Only).
Sliwkowski, M.X. et al. (1999) "Nonclinical Studies Addressing the Mechanism Of Action of Trastuzumab (Herceptin)," Sem. in Oncol. 26:60-70 (Abstract Only).
Sloan, D.D. et al. (2015) "Targeting HIV Reservoir in Infected CD4 T Cells by Dual-Affinity Re-targeting Molecules (DARTs) that Bind HIV Envelope and Recruit Cytotoxic T Cells," PLoS Pathog. 11(11):e1005233. doi: 10.1371/journal.ppat.1005233.
Smith, T.F. & Waterman, M.S. (1981) "Comparison of Biosequences," Adv. Appl. Math. 2:482.
Sondermann, P. et al. (2000) "The 3.2-A Crystal Structure of the Human IgG1 Fc Fragment-Fc GammaRIII Complex," Nature 406:267-273.
Stancovski, I. et al. (1991) "Mechanistic Aspects of the Opposing Effects Of Monoclonal Antibodies to the ERBB2 Receptor on Tumor Growth," Proc. Natl. Acad. Sci. (U.S.A.) 88:8691-8695.
Stevenson, G.T. et al. (1989) "A Chimeric Antibody With Dual Fc Regions (bisFabFc) Prepared by Manipulations At the IgG Hinge," Anti-Cancer Drug Design 3:219-230 (Abstract Only).
Subudhi, S.K. et al. (2005) "The Balance of Immune Responses: Costimulation Verse Coinhibition," J. Molec. Med. 83:193-202.
Tan, M. et al. (2007). "Molecular Mechanisms of erbB2-Mediated Breast Cancer Chemoresistance," Adv. Exp. Med. Biol. 608: 119-129.
Tempest, P.R. et al. (1991) "Reshaping a Human Monoclonal Antibody to Inhibit Human Respiratory Syncytial Virus Infection in vivo," Bio/Technology 9:266-271.
Tzahar, E. et al. (1994) "ErbB-3 and ErbB-4 Function As the Respective Low and High Affinity Receptors Of All neu Differentiation Factor/Heregulin Isoforms," Biol. Chem. 269: 25226-25233.
Tzahar, E. et al. (1996) "A Hierarchical Network of Interreceptor Interactions Determines Signal Transduction by neu Differentiation Factor/Neuregulin and Epidermal Growth Factor," Mol. Cell. Biol. 16:5276-5287.
Verhoeyen, M. et al. (1988) "Reshaping Human Antibodies: Grafting an Antilysozyme Activity," Science 239:1534-1536.
Veri, M.C. et al. (2010) "Therapeutic Control of B Cell Activation Via Recruitment of Fcgamma Receptor IIb (CD32B) Inhibitory Function With a Novel Bispecific Antibody Scaffold," Arthritis Rheum. 62(7):1933-1943.
Viglietta, V. et al. (2007) "Modulating Co-Stimulation," Neurotherapeutics 4:666-675.
Vogel, C.L et al. (2002) "Efficacy and Safety of Trastuzumab As A Single Agent in First-Line Treatment of HER2-Overexpressing Metastatic Breast Cancer," J. Clin. Oncol. 20(3):719-726.
Vogel, C.L. et al. (2001) "First-Line Herceptin Monotherapy in Metastatic Breast Cancer," Oncology 61(suppl 2):37-42.
Wang, L. et al. (2011) "VISTA, A Novel Mouse Ig Superfamily Ligand That Negatively Regulates T-Cell Responses," J. Exp. Med. 10.1084/jem.20100619:1-16.
Wang, S. et al. (2004) "Co-Signaling Molecules of the B7-CD28 Family in Positive and Negative Regulation of T Lymphocyte Responses," Microbes Infect. 6:759-766.
Wang, W. et al. (2008) "PD-L1/PD-1 Signal Deficiency Promotes Allogeneic Immune Responses and Accelerates Heart Allograft Rejection," Transplantation 86(6):836-44.
Weng, W.K. et al. (2003) "Two Immunoglobulin G Fragment C Receptor Polymorphisms Independently Predict Response to Rituximab in Patients With Follicular Lymphoma," J Clin Oncol. 21(21):3940-3947.
Wilken, J. et al. (1998) "Chemical Protein Synthesis," Curr. Opin. Biotechnol. 9(4):412-426.
Wolff, E.A. et al. (1993) "Monoclonal Antibody Homodimers: Enhanced Antitumor Activity in Nude Mice," Cancer Research 53:2560-2565.
Wright, C. et. al. (1989) "Expression of c-erbB-2 Oncoprotein: A Prognostic Indicator in Human Breast Cancer," Cancer Res. 49:2087-2090.
Wu G.Y. and Wu C.H. (1987) "Receptor-Mediated in Vitro Gene Transformation By A Soluble DNA Carrier System," J. Biol. Chem. 262:4429-4432.
Wu, H. et al. (1998) "Stepwise in vitro Affinity Maturation of Vitaxin, an AlphaV Beta3-mAb," Proc. Natl. Acad. Sci. (U.S.A.) 95:6037-6042.
Xie et al. (2005) "A New Format of Bispecific Antibody: Highly Efficient Heterodimerization, Expression and Tumor Cell Lysis," J. Immunol. Methods 296:95-101.
Xu, D. et al. (2000) "In Vitro Characterization of Five Humanized OKT3 Effector Function Variant Antibodies," Cell. Immunol. 200:16-26.
Yamamoto, T. et al. (1986) "Similarity of Protein Encoded by the Human c-erb-B-2 Gene to Epidermal Growth Factor Receptor," Nature 319:230-234.
Yamazaki, T. et al. (2002) "Expression of Programmed Death 1 Ligands by Murine T-Cells and APC," J. Immunol. 169:5538-5545.
Ye, D. et al. (1999) "Augmentation Of A Humanized anti-HER2 mAb 4D5 Induced Growth Inhibition By A Human-Mouse Chimeric anti-EGF Receptor mAb C225," Oncogene 18:731-738.
Yelton, D.E. et al. (1995) "Affinity Maturation of the BR96 Anti-Carcinoma Antibody by Codon-Based Mutagenesis," J. Immunology 155:1994-2004.
Yonemura, Y. et al. (1991) "Evaluation of Immunoreactivity for erbB-2 Protein As a Marker of Poor Short Term Prognosis in Gastric Cancer" Cancer Research 51:1034.
NCT02129556. Anti-PD-1 Monoclonal Antibody in Advanced, Trastuzumab-resistant, HER2 positive Breast Cancer. Mar. 13, 2015 Sections on Study Description and Study design, clinicaltrials.gov/ct2/history/NCT02129556; pp. 1-17.

(56) References Cited

OTHER PUBLICATIONS

MacroGenics Presents Updated Data from Phase 1 Study of Margetuximab at ASCO Annual Meeting 2015. May 30, 2015; pp. 1-2.
Boyerinas, B. et al. (2015) "Antibody-Dependent Cellular Cytotoxicity Activity Of A Novel Anti-PD-L1 Antibody Avelumab (MSB0010718C) on Human Tumor Cells," Cancer Immunol. Res. 3(10):1148-1157.

* cited by examiner

```
                       10         20         30
Murine     DIVMTQSHKF MSTSVGDRVS ITCKASQDVN
Chimeric   DIVMTQSHKF MSTSVGDRVS ITCKASQDVN
Humanized  DIQMTQSPSS LSASVGDRVT ITCRASQDVN 40         50         60
Murine     TAVAWYQQKP GHSPKLLIYS ASFRYTGVPD
Chimeric   TAVAWYQQKP GHSPKLLIYS ASFRYTGVPD
Humanized  TAVAWYQQKP GKAPKLLIYS ASFLESGVPS 70         80         90
Murine     RFTGNRSGTD FTFTISSVQA EDLAVYYCQQ
Chimeric   RFTGSRSGTD FTFTISSVQA EDLAVYYCQQ
Humanized  RFSGSRSGTD FTLTISSLQP EDFATYYCQQ 100        109
Murine     HYTTPPTFGG GTKLEIKRA    SEQ ID NO:3
Chimeric   HYTTPPTFGG GTKVEIKRT    SEQ ID NO:4
Humanized  HYTTPPTFGQ GTKVEIKRT    SEQ ID NO:5
```

Figure 1

```
MT1  QVQLQQSGPELVKPGASLKLSCTASGFNIKDTYIHWVKQRPEQGLEWIGRIYPTNGYTRY  60
MT2  QVQLQQSGPELVKPGASLKLSCTASGFNIKDTYIHWVKQRPEQGLEWIGRIYPTNGYTRY  60
MT3  QVQLQQSGPELVKPGASLKLSCTASGFNIKDTYIHWVKQRPEQGLEWIGRIYPTNGYTRY  60
WT   QVQLQQSGPELVKPGASLKLSCTASGFNIKDTYIHWVKQRPEQGLEWIGRIYPTNGYTRY  60

MT1  DPKFQDKATITADTSSNTAYLQVSRLTSEDTAVYYCSRWGGDGFYAMDYWGQGASVTVSS 120
MT2  DPKFQDKATITADTSSNTAYLQVSRLTSEDTAVYYCSRWGGDGFYAMDYWGQGASVTVSS 120
MT3  DPKFQDKATITADTSSNTAYLQVSRLTSEDTAVYYCSRWGGDGFYAMDYWGQGASVTVSS 120
WT   DPKFQDKATITADTSSNTAYLQVSRLTSEDTAVYYCSRWGGDGFYAMDYWGQGASVTVSS 120

MT1  ASTKGPSVFPLAPSSKSTSGGTAALGCLVKDYFPEPVTVSWNSGALTSGVHTFPAVLQSS 180
MT2  ASTKGPSVFPLAPSSKSTSGGTAALGCLVKDYFPEPVTVSWNSGALTSGVHTFPAVLQSS 180
MT3  ASTKGPSVFPLAPSSKSTSGGTAALGCLVKDYFPEPVTVSWNSGALTSGVHTFPAVLQSS 180
WT   ASTKGPSVFPLAPSSKSTSGGTAALGCLVKDYFPEPVTVSWNSGALTSGVHTFPAVLQSS 180

MT1  GLYSLSSVVTVPSSSLGTQTYICNVNHKPSNTKVDKRVEPKSCDKTHTCPPCPAPELLGG 240
MT2  GLYSLSSVVTVPSSSLGTQTYICNVNHKPSNTKVDKRVEPKSCDKTHTCPPCPAPELVGG 240
MT3  GLYSLSSVVTVPSSSLGTQTYICNVNHKPSNTKVDKRVEPKSCDKTHTCPPCPAPELLGG 240
WT   GLYSLSSVVTVPSSSLGTQTYICNVNHKPSNTKVDKRVEPKSCDKTHTCPPCPAPELLGG 240

MT1  PSVFLLPPKPKDTLMISRTPEVTCVVVDVSHEDPEVKFNWYVDGVEVHNAKTKPPEEQYN 300
MT2  PSVFLLPPKPKDTLMISRTPEVTCVVVDVSHEDPEVKFNWYVDGVEVHNAKTKPPEEQYN 300
MT3  PSVFLLPPKPKDTLMISRTPEVTCVVVDVSHEDPEVKFNWYVDGVEVHNAKTKPPEEQYN 300
WT   PSVFLFPPKPKDTLMISRTPEVTCVVVDVSHEDPEVKFNWYVDGVEVHNAKTKPREEQYN 300

MT1  STLRVVSILTVLHQDWLNGKEYKCKVSNKALPAPIEKTISKAKGQPREPQVYTLPPSRDE 360
MT2  STLRVVSVLTVLHQDWLNGKEYKCKVSNKALPAPIEKTISKAKGQPREPQVYTLPPSRDE 360
MT3  STLRVVSVLTVLHQDWLNGKEYKCKVSNKALPAPIEKTISKAKGQPREPQVYTLPPSRDE 360
WT   STYRVVSVLTVLHQDWLNGKEYKCKVSNKALPAPIEKTISKAKGQPREPQVYTLPPSRDE 360

MT1  LTKNQVSLTCLVKGFYPSDIAVEWESNGQPENNYKTTPLVLDSDGSFFLYSKLTVDKSRW 420
MT2  LTKNQVSLTCLVKGFYPSDIAVEWESNGQPENNYKTTPLVLDSDGSFFLYSKLTVDKSRW 420
MT3  LTKNQVSLTCLVKGFYPSDIAVEWESNGQPENNYKTTPPVLDSDGSFFLYSKLTVDKSRW 420
WT   LTKNQVSLTCLVKGFYPSDIAVEWESNGQPENNYKTTPPVLDSDGSFFLYSKLTVDKSRW 420

MT1  QQGNVFSCSVMHEALHNHYTQKSLSLSPGK  450    SEQ ID NO:9
MT2  QQGNVFSCSVMHEALHNHYTQKSLSLSPGK  450    SEQ ID NO:11
MT3  QQGNVFSCSVMHEALHNHYTQKSLSLSPGK  450    SEQ ID NO:13
WT   QQGNVFSCSVMHEALHNHYTQKSLSLSPGK  450    SEQ ID NO:7
```

Figure 2

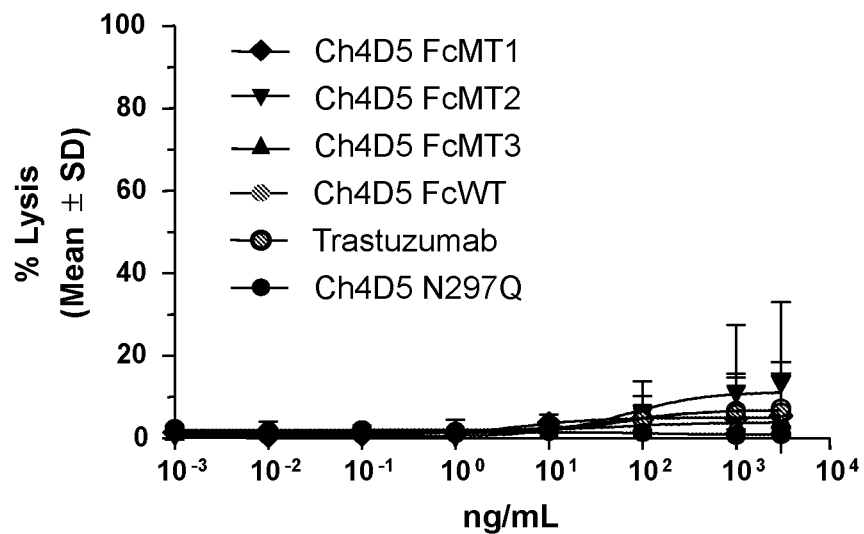
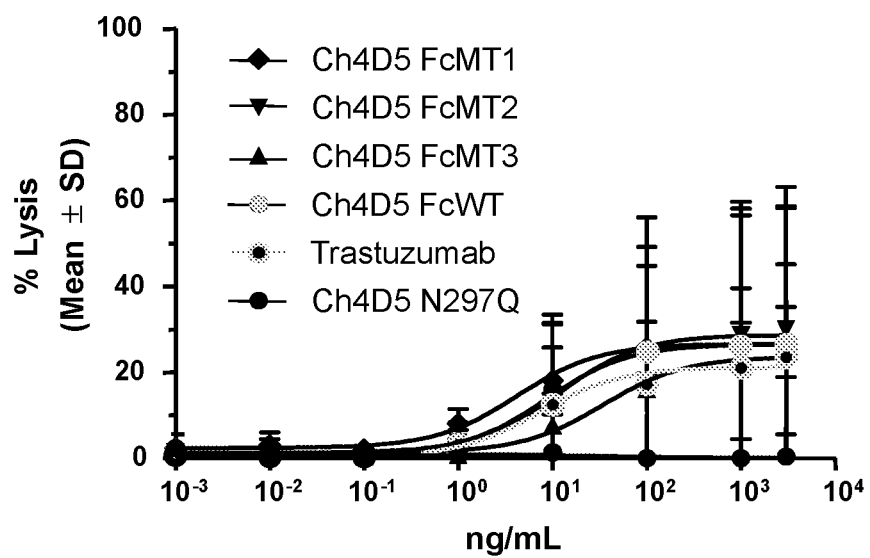
Figure 10

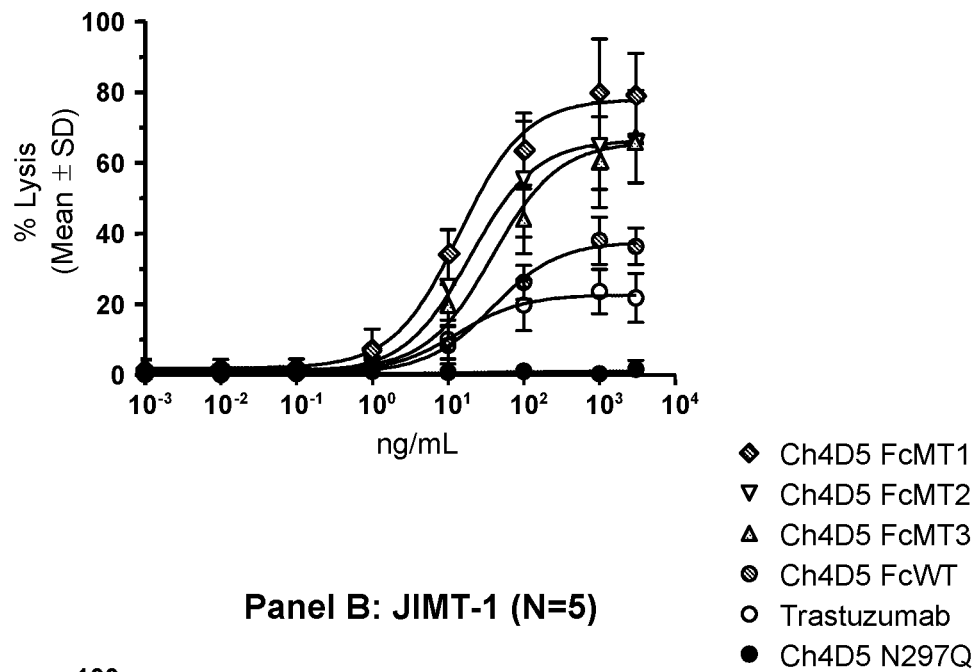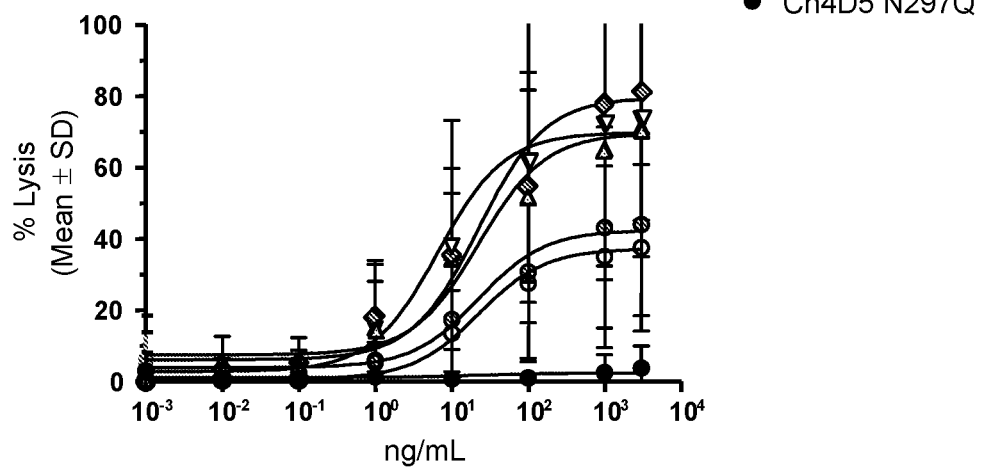
FIG. 12

SEQUENCE LISTING

<160> NUMBER OF SEQ ID NOS: 88

<210> SEQ ID NO 1
<211> LENGTH: 645
<212> TYPE: DNA
<213> ORGANISM: Artificial Sequence
<220> FEATURE:
<223> OTHER INFORMATION: Polynucleotide Encoding light chain of
      preferred Variant Chimeric 4D5 Antibodies

<400> SEQUENCE: 1

```
gacatcgtga tgacccagtc ccacaagttc atgtccacct ctgtgggcga tagggtcagc        60
atcacctgca aggccagcca ggatgtgaat actgctgtag cctggtatca gcagaaacca       120
ggacattctc ccaaactgct gatttactcc gcatccttcc ggtacactgg agtccctgat       180
cgcttcactg gcagcagatc tgggacagat ttcactttca ccatcagcag tgtgcaggct       240
gaagacctgg cagtttatta ctgtcagcaa cattatacta cactcccac cttcggaggg        300 ggtaccaagg tggagatcaa acgtacggtg gctgcaccat ctgtcttcat cttcccgcca       360
tctgatgagc agttgaaatc tggaactgcc tctgttgtgt gcctgctgaa taacttctat       420
cccagagagg ccaaagtaca gtggaaggtg gataacgccc tccaatcggg taactcccag       480
gagagtgtca cagagcagga cagcaaggac agcacctaca gcctcagcag cacccttgacg      540
```

```
ctgagcaaag cagactacga gaaacacaaa gtctacgcct gcgaagtcac ccatcagggc    600
ctgagctcgc ccgtcacaaa gagcttcaac aggggagagt gttag                   645
```

<210> SEQ ID NO 2
<211> LENGTH: 214
<212> TYPE: PRT
<213> ORGANISM: Artificial Sequence
<220> FEATURE:
<223> OTHER INFORMATION: light chain of preferred Variant Chimeric 4D5
      Antibodies

<400> SEQUENCE: 2

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly His Ser Pro Lys Leu Leu Ile
        35                  40                  45

Tyr Ser Ala Ser Phe Arg Tyr Thr Gly Val Pro Asp Arg Phe Thr Gly
    50                  55                  60

Ser Arg Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Thr Thr Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 3
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: Light Chain Variable Domain of Murine 4D5
      Antibody

<400> SEQUENCE: 3

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly His Ser Pro Lys Leu Leu Ile
        35                  40                  45
```

-continued

Tyr Ser Ala Ser Phe Arg Tyr Thr Gly Val Pro Asp Arg Phe Thr Gly
    50                  55                  60

Asn Arg Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Thr Thr Pro Pro
                85                  90                  95

Thr Phe Gly Gly Gly Thr Lys Leu Glu Ile Lys
            100                 105

<210> SEQ ID NO 4
<211> LENGTH: 107
<212> TYPE: PRT
<213> ORGANISM: Artificial Sequence
<220> FEATURE:
<223> OTHER INFORMATION: Chimeric 4D5 VL region

<400> SEQUENCE: 4

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
                20                  25                  30

Val Ala Trp Tyr Gln Gln Lys Pro Gly His Ser Pro Lys Leu Leu Ile
            35                  40                  45

Tyr Ser Ala Ser Phe Arg Tyr Thr Gly Val Pro Asp Arg Phe Thr Gly
    50                  55                  60

Ser Arg Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Thr Thr Pro Pro
                85                  90                  95

Thr Phe Gly Gly Gly Thr Lys Val Glu Ile Lys
            100                 105

<210> SEQ ID NO 5
<211> LENGTH: 107
<212> TYPE: PRT
<213> ORGANISM: Artificial Sequence
<220> FEATURE:
<223> OTHER INFORMATION: Light Chain Variable Domain of Humanized 4D5
    Antibody

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Glu Ser Gly Val Pro Ser Arg Phe Ser Gly
    50                  55                  60

Ser Arg Ser Gly Thr Asp Phe Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 6
<211> LENGTH: 1353
<212> TYPE: DNA

<213> ORGANISM: Artificial Sequence
<220> FEATURE:
<223> OTHER INFORMATION: Polynucleotide Encoding Chimeric 4D5 heavy chain having a wild-type Fc Region

<400> SEQUENCE: 6

```
caggttcagc tgcagcagtc tggccctgag ctggtgaagc caggggcctc actcaagttg      60
tcctgtacag cttctggctt caacatcaaa gacacctata tccactgggt gaaacagagg     120
cctgaacagg gcctggaatg gattggaagg atttatccta ccaatggcta ctactagatat    180
gacccaaagt tccaggacaa ggccactatc acagcagaca catcctccaa cacagcctac     240
ctgcaagtca gccgcctgac atctgaggac actgccgtct attactgctc ccggtgggga     300
ggggacggct tctatgctat ggactactgg ggtcaggag cctccgtgac cgtgagctcc      360
gcctccacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagag agttgagccc     660
aaatcttgtg acaaaactca cacatgccca ccgtgcccag cacctgaact cctggggga     720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag   960
gagtacaagt gcaaggtctc caacaaagcc ctcccagccc ccatcgagaa aaccatctcc   1020
aaagccaaag ggcagccccg agaaccacag gtgtacaccc tgcccccatc ccgggatgag   1080
ctgaccaaga accaggtcag cctgacctgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctac agcaagctca ccgtggacaa gagcaggtgg   1260
cagcagggga acgtcttctc atgctccgtg atgcatgagg ctctgcacaa ccactacacg   1320
cagaagagcc tctccctgtc tccgggtaaa tga                                 1353
```

<210> SEQ ID NO 7
<211> LENGTH: 450
<212> TYPE: PRT
<213> ORGANISM: Artificial Sequence
<220> FEATURE:
<223> OTHER INFORMATION: Chimeric 4D5 heavy chain having a wild-type Fc Region

<400> SEQUENCE: 7

```
Gln Val Gln Leu Gln Gln Ser Gly Pro Glu Leu Val Lys Pro Gly Ala
1               5                   10                  15

Ser Leu Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Tyr Pro Thr Asn Gly Tyr Thr Arg Tyr Asp Pro Lys Phe
    50                  55                  60

Gln Asp Lys Ala Thr Ile Thr Ala Asp Thr Ser Ser Asn Thr Ala Tyr
65                  70                  75                  80
```

```
Leu Gln Val Ser Arg Leu Thr Ser Glu Asp Thr Ala Val Tyr Tyr Cys
             85                  90                  95

Ser Arg Trp Gly Gly Asp Gly Phe Tyr Ala Met Asp Tyr Trp Gly Gln
            100                 105                 110

Gly Ala Ser Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 8
<211> LENGTH: 1353
<212> TYPE: DNA
<213> ORGANISM: Artificial Sequence
<220> FEATURE:
<223> OTHER INFORMATION: Polynucleotide Encoding heavy chain of a
```

Variant Chimeric 4D5 Antibody having the FcMT1 variant Fc Region

<400> SEQUENCE: 8

```
caggttcagc tgcagcagtc tggccctgag ctggtgaagc caggggcctc actcaagttg      60
tcctgtacag cttctggctt caacatcaaa gacacctata tccactgggt gaaacagagg     120
cctgaacagg gcctggaatg gattggaagg atttatccta ccaatggcta ctagatat      180
gacccaaagt tccaggacaa ggccactatc acagcagaca catcctccaa cacagcctac     240
ctgcaagtca gccgcctgac atctgaggac actgccgtct attactgctc ccggtgggga     300
ggggacggct tctatgctat ggactactgg ggtcagggag cctccgtgac cgtgagctcc     360
gcctccacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagag agttgagccc     660
aaatcttgtg acaaaactca cacatgccca ccgtgcccag cacctgaact cctggggggga     720
ccgtcagtct tcctcttacc cccaaaaccc aaggacaccc tcatgatctc ccggacccct     780
gaggtcacat gcgtggtggt ggacgtgagc cacgaagacc ctgaggtcaa gttcaactgg     840
tacgtggacg gcgtggaggt gcataatgcc aagacaaagc cgcggagga gcagtacaac     900
agcacgctcc gtgtggtcag catcctcacc gtcctgcacc aggactggct gaatggcaag     960
gagtacaagt gcaaggtctc caacaaagcc ctcccagccc ccatcgagaa aaccatctcc    1020
aaagccaaag gcagccccg agaaccacag gtgtacaccc tgcccccatc ccgggatgag    1080
ctgaccaaga accaggtcag cctgacctgc ctggtcaaag gcttctatcc cagcgacatc    1140
gccgtggagt gggagagcaa tgggcagccg gagaacaact acaagaccac gcctctcgtg    1200
ctggactccg acggctcctt cttcctctac agcaagctca ccgtggacaa gagcaggtgg    1260
cagcagggga acgtcttctc atgctccgtg atgcatgagg ctctgcacaa ccactacacg    1320
cagaagagcc tctccctgtc tccgggtaaa tga                                 1353
```

<210> SEQ ID NO 9
<211> LENGTH: 450
<212> TYPE: PRT
<213> ORGANISM: Artificial Sequence
<220> FEATURE:
<223> OTHER INFORMATION: heavy chain of a Variant Chimeric 4D5 Antibody having the FcMT1 variant Fc Region

<400> SEQUENCE: 9

```
Gln Val Gln Leu Gln Gln Ser Gly Pro Glu Leu Val Lys Pro Gly Ala
1               5                   10                  15

Ser Leu Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Tyr Pro Thr Asn Gly Tyr Thr Arg Tyr Asp Pro Lys Phe
    50                  55                  60

Gln Asp Lys Ala Thr Ile Thr Ala Asp Thr Ser Ser Asn Thr Ala Tyr
65                  70                  75                  80

Leu Gln Val Ser Arg Leu Thr Ser Glu Asp Thr Ala Val Tyr Tyr Cys
                85                  90                  95
```

-continued

```
Ser Arg Trp Gly Gly Asp Gly Phe Tyr Ala Met Asp Tyr Trp Gly Gln
            100                 105                 110

Gly Ala Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Leu Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Pro Glu Glu Gln Tyr Asn Ser Thr Leu Arg
    290                 295                 300

Val Val Ser Ile Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Leu Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 10
<211> LENGTH: 1353
<212> TYPE: DNA
<213> ORGANISM: Artificial Sequence
<220> FEATURE:
<223> OTHER INFORMATION: Polynucleotide Encoding heavy chain of a
      Variant Chimeric 4D5 Antibody having the FcMT2 variant Fc Region

<400> SEQUENCE: 10
```

-continued

```
caggttcagc tgcagcagtc tggccctgag ctggtgaagc caggggcctc actcaagttg      60
tcctgtacag cttctggctt caacatcaaa gacacctata tccactgggt gaaacagagg     120
cctgaacagg gcctggaatg gattggaagg atttatccta ccaatggcta tactagatat     180
gacccaaagt tccaggacaa ggccactatc acagcagaca catcctccaa cacagcctac     240
ctgcaagtca gccgcctgac atctgaggac actgccgtct attactgctc ccggtgggga     300
ggggacggct tctatgctat ggactactgg ggtcagggag cctccgtgac cgtgagctcc     360
gcctccacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagag agttgagccc     660
aaatcttgtg acaaaactca cacatgccca ccgtgcccag cacctgaact cgtgggggga     720
ccgtcagtct tcctcttacc cccaaaaccc aaggacaccc tcatgatctc ccggacccct     780
gaggtcacat gcgtggtggt ggacgtgagc cacgaagacc ctgaggtcaa gttcaactgg     840
tacgtggacg gcgtggaggt gcataatgcc aagacaaagc cgcggagga gcagtacaac     900 agcacgctcc gtgtggtcag cgtcctcacc gtcctgcacc aggactggct gaatggcaag     960
gagtacaagt gcaaggtctc caacaaagcc ctcccagccc catcgagaa aaccatctcc    1020 aaagccaaag gcagccccg agaaccacag gtgtacaccc tgcccccatc ccgggatgag    1080
ctgaccaaga accaggtcag cctgacctgc ctggtcaaag gcttctatcc cagcgacatc    1140
gccgtggagt gggagagcaa tgggcagccg gagaacaact acaagaccac gcctctcgtg    1200
ctggactccg acggctcctt cttcctctac agcaagctca ccgtggacaa gagcaggtgg    1260
cagcagggga acgtcttctc atgctccgtg atgcatgagg ctctgcacaa ccactacacg    1320
cagaagagcc tctccctgtc tccgggtaaa tga                                 1353
```

<210> SEQ ID NO 11
<211> LENGTH: 450
<212> TYPE: PRT
<213> ORGANISM: Artificial Sequence
<220> FEATURE:
<223> OTHER INFORMATION: heavy chain of a Variant Chimeric 4D5 Antibody having the FcMT2 variant Fc Region

<400> SEQUENCE: 11

```
Gln Val Gln Leu Gln Gln Ser Gly Pro Glu Leu Val Lys Pro Gly Ala
1               5                   10                  15

Ser Leu Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Tyr Pro Thr Asn Gly Tyr Thr Arg Tyr Asp Pro Lys Phe
    50                  55                  60

Gln Asp Lys Ala Thr Ile Thr Ala Asp Thr Ser Ser Asn Thr Ala Tyr
65                  70                  75                  80

Leu Gln Val Ser Arg Leu Thr Ser Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110
```

```
Gly Ala Ser Val Thr Val Ser Ala Ser Thr Lys Gly Pro Ser Val
            115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Arg Val Glu Pro Lys Ser Cys Asp
    210                 215                 220
Lys Thr His Thr Cys Pro Pro Cys Pro Ala Pro Glu Leu Val Gly Gly
225                 230                 235                 240
Pro Ser Val Phe Leu Leu Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Leu Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Leu Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 12
<211> LENGTH: 1353
<212> TYPE: DNA
<213> ORGANISM: Artificial Sequence
<220> FEATURE:
<223> OTHER INFORMATION: Polynucleotide Encoding Variant Chimeric 4D5
      Antibody having the FcMT3 variant Fc Region

<400> SEQUENCE: 12
caggttcagc tgcagcagtc tggccctgag ctggtgaagc caggggcctc actcaagttg      60
```

```
tcctgtacag cttctggctt caacatcaaa gacacctata tccactgggt gaaacagagg      120
cctgaacagg gcctggaatg gattggaagg atttatccta ccaatggcta tactagatat      180
gacccaaagt tccaggacaa ggccactatc acagcagaca catcctccaa cacagcctac      240
ctgcaagtca gccgcctgac atctgaggac actgccgtct attactgctc ccggtgggga      300
ggggacggct tctatgctat ggactactgg ggtcagggag cctccgtgac cgtgagctcc      360
gcctccacca agggcccatc ggtcttcccc ctggcaccct cctccaagag cacctctggg      420
ggcacagcgg ccctgggctg cctggtcaag gactacttcc ccgaaccggt gacggtgtcg      480
tggaactcag gcgccctgac cagcggcgtg cacaccttcc cggctgtcct acagtcctca      540
ggactctact ccctcagcag cgtggtgacc gtgccctcca gcagcttggg cacccagacc      600
tacatctgca acgtgaatca caagcccagc aacaccaagg tggacaagag agttgagccc      660
aaatcttgtg acaaaactca cacatgccca ccgtgcccag cacctgaact cctggggga      720 ccgtcagtct tcctcttacc cccaaaaccc aaggacaccc tcatgatctc ccggacccct      780
gaggtcacat gcgtggtggt ggacgtgagc cacgaagacc ctgaggtcaa gttcaactgg      840
tacgtggacg gcgtggaggt gcataatgcc aagacaaagc cgcggagga gcagtacaac      900 agcacgctcc gtgtggtcag cgtcctcacc gtcctgcacc aggactggct gaatggcaag      960
gagtacaagt gcaaggtctc caacaaagcc ctcccagccc ccatcgagaa aaccatctcc     1020
aaagccaaag gcagccccg agaaccacag gtgtacaccc tgcccccatc ccgggatgag     1080
ctgaccaaga accaggtcag cctgacctgc ctggtcaaag gcttctatcc cagcgacatc     1140
gccgtggagt gggagagcaa tgggcagccg gagaacaact acaagaccac gcctcccgtg     1200
ctggactccg acggctcctt cttcctctac agcaagctca ccgtggacaa gagcaggtgg     1260
cagcagggga acgtcttctc atgctccgtg atgcatgagg ctctgcacaa ccactacacg     1320
cagaagagcc tctccctgtc tccgggtaaa tga                                  1353
```

<210> SEQ ID NO 13
<211> LENGTH: 450
<212> TYPE: PRT
<213> ORGANISM: Artificial Sequence
<220> FEATURE:
<223> OTHER INFORMATION: Variant Chimeric 4D5 Antibody having the FcMT3
      variant Fc Region
<220> FEATURE:
<221> NAME/KEY: MISC_FEATURE
<222> LOCATION: (1)..(450)
<223> OTHER INFORMATION: Variant Chimeric 4D5 Antibody having the FcMT3
      variant Fc Region

<400> SEQUENCE: 13

```
Gln Val Gln Leu Gln Gln Ser Gly Pro Glu Leu Val Lys Pro Gly Ala
1               5                   10                  15

Ser Leu Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Tyr Pro Thr Asn Gly Tyr Thr Arg Tyr Asp Pro Lys Phe
    50                  55                  60

Gln Asp Lys Ala Thr Ile Thr Ala Asp Thr Ser Ser Asn Thr Ala Tyr
65                  70                  75                  80

Leu Gln Val Ser Arg Leu Thr Ser Glu Asp Thr Ala Val Tyr Tyr Cys
                85                  90                  95

Ser Arg Trp Gly Gly Asp Gly Phe Tyr Ala Met Asp Tyr Trp Gly Gln
```

```
            100                 105                 110
Gly Ala Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Leu Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Leu Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 14
<211> LENGTH: 288
<212> TYPE: PRT
<213> ORGANISM: Homo sapiens
<220> FEATURE:
<221> NAME/KEY: MISC_FEATURE
<222> LOCATION: (1)..(288)
<223> OTHER INFORMATION: Human PD-1

<400> SEQUENCE: 14
```

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
                195                 200                 205

Leu Lys Glu Asp Pro Ser Ala Val Pro Val Phe Ser Val Asp Tyr Gly
        210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
                275                 280                 285

<210> SEQ ID NO 15
<211> LENGTH: 113
<212> TYPE: PRT
<213> ORGANISM: Mus musculus
<220> FEATURE:
<221> NAME/KEY: MISC_FEATURE
<222> LOCATION: (1)..(113)
<223> OTHER INFORMATION: heavy chain variable domain of PD-1 mAb 1

<400> SEQUENCE: 15

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
                20                  25                  30

Gly Met His Trp Val Arg Gln Ala Pro Gly Lys Gly Leu Glu Trp Val
            35                  40                  45

Ala Val Ile Trp Tyr Asp Gly Ser Lys Arg Tyr Tyr Ala Asp Ser Val
50                  55                  60
```

```
Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Tyr Cys
                 85                  90                  95

Ala Thr Asn Asp Asp Tyr Trp Gly Gln Gly Thr Leu Val Thr Val Ser
            100                 105                 110

Ser

<210> SEQ ID NO 16
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: CDRH1 of PD-1 mAb 1

<400> SEQUENCE: 16

Asn Ser Gly Met His
1               5

<210> SEQ ID NO 17
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: CDRH2 of PD-1 mAb 1

<400> SEQUENCE: 17

Val Ile Trp Tyr Asp Gly Ser Lys Arg Tyr Tyr Ala Asp Ser Val Lys
1               5                   10                  15

Gly

<210> SEQ ID NO 18
<211> LENGTH: 4
<212> TYPE: PRT
<213> ORGANISM: Mus musculus
<220> FEATURE:
<221> NAME/KEY: MISC_FEATURE
<222> LOCATION: (1)..(4)
<223> OTHER INFORMATION: CDRH3 of PD-1 mAb 1

<400> SEQUENCE: 18

Asn Asp Asp Tyr
1

<210> SEQ ID NO 19
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: light chain variable domain of PD-1 mAb 1

<400> SEQUENCE: 19

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45
```

```
Tyr Asp Ala Ser Asn Arg Ala Thr Gly Ile Pro Ala Arg Phe Ser Gly
            50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Ser Asn Trp Pro Arg
                 85                  90                  95

Thr Phe Gly Gln Gly Thr Lys Val Glu Ile Lys
            100                 105

<210> SEQ ID NO 20
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: CDRL1 of PD-1 mAb 1

<400> SEQUENCE: 20

Arg Ala Ser Gln Ser Val Ser Ser Tyr Leu Ala
 1               5                  10

<210> SEQ ID NO 21
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: CDRL2 of PD-1 mAb 1

<400> SEQUENCE: 21

Asp Ala Ser Asn Arg Ala Thr
 1               5

<210> SEQ ID NO 22
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: CDRL3 of PD-1 mAb 1

<400> SEQUENCE: 22

Gln Gln Ser Ser Asn Trp Pro Arg Thr
 1               5

<210> SEQ ID NO 23
<211> LENGTH: 120
<212> TYPE: PRT
<213> ORGANISM: Mus musculus
<220> FEATURE:
<221> NAME/KEY: MISC_FEATURE
<222> LOCATION: (1)..(120)
<223> OTHER INFORMATION: heavy chain variable domain of PD-1 mAb 2

<400> SEQUENCE: 23

Gln Val Gln Leu Val Gln Ser Gly Val Glu Val Lys Lys Pro Gly Ala
 1               5                  10                  15

Ser Val Lys Val Ser Cys Lys Ala Ser Gly Tyr Thr Phe Thr Asn Tyr
                 20                  25                  30

Tyr Met Tyr Trp Val Arg Gln Ala Pro Gly Gln Gly Leu Glu Trp Met
             35                  40                  45

Gly Gly Ile Asn Pro Ser Asn Gly Gly Thr Asn Phe Asn Glu Lys Phe
```

```
             50                  55                  60
Lys Asn Arg Val Thr Leu Thr Thr Asp Ser Ser Thr Thr Thr Ala Tyr
 65                  70                  75                  80

Met Glu Leu Lys Ser Leu Gln Phe Asp Thr Ala Val Tyr Tyr Cys
                 85                  90                  95

Ala Arg Arg Asp Tyr Arg Phe Asp Met Gly Phe Asp Tyr Trp Gly Gln
            100                 105                 110

Gly Thr Thr Val Thr Val Ser Ser
        115                 120
```

<210> SEQ ID NO 24
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: heavy chain variable domain of PD-1 mAb 2 CDR1

<400> SEQUENCE: 24

```
Asn Tyr Tyr Met Tyr
1               5
```

<210> SEQ ID NO 25
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: heavy chain variable domain of PD-1 mAb 2 CDR2

<400> SEQUENCE: 25

```
Gly Ile Asn Pro Ser Asn Gly Gly Thr Asn Phe Asn Glu Lys Phe Lys
1               5                   10                  15

Asn
```

<210> SEQ ID NO 26
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: heavy chain variable domain of PD-1 mAb 2 CDR3

<400> SEQUENCE: 26

```
Arg Asp Tyr Arg Phe Asp Met Gly Phe Asp Tyr
1               5                   10
```

<210> SEQ ID NO 27
<211> LENGTH: 111
<212> TYPE: PRT
<213> ORGANISM: Mus musculus
<220> FEATURE:
<221> NAME/KEY: MISC_FEATURE
<222> LOCATION: (1)..(111)
<223> OTHER INFORMATION: light chain variable domain of PD-1 mAb 2

<400> SEQUENCE: 27

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30
```

```
Gly Tyr Ser Tyr Leu His Trp Tyr Gln Gln Lys Pro Gly Gln Ala Pro
             35                  40                  45

Arg Leu Leu Ile Tyr Leu Ala Ser Tyr Leu Glu Ser Gly Val Pro Ala
 50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln His Ser Arg
                 85                  90                  95

Asp Leu Pro Leu Thr Phe Gly Gly Gly Thr Lys Val Glu Ile Lys
             100                 105                 110
```

```
<210> SEQ ID NO 28
<211> LENGTH: 15
<212> TYPE: PRT
<213> ORGANISM: Mus musculus
<220> FEATURE:
<221> NAME/KEY: MISC_FEATURE
<222> LOCATION: (1)..(15)
<223> OTHER INFORMATION: light chain variable domain of PD-1 mAb 2 CDR1

<400> SEQUENCE: 28

Arg Ala Ser Lys Gly Val Ser Thr Ser Gly Tyr Ser Tyr Leu His
 1               5                  10                  15
```

```
<210> SEQ ID NO 29
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: light chain variable domain of PD-1 mAb 2 CDR2

<400> SEQUENCE: 29

Leu Ala Ser Tyr Leu Glu Ser
 1               5
```

```
<210> SEQ ID NO 30
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: light chain variable domain of PD-1 mAb 2 CDR3

<400> SEQUENCE: 30

Gln His Ser Arg Asp Leu Pro Leu Thr
 1               5
```

```
<210> SEQ ID NO 31
<211> LENGTH: 121
<212> TYPE: PRT
<213> ORGANISM: Mus musculus
<220> FEATURE:
<221> NAME/KEY: MISC_FEATURE
<222> LOCATION: (1)..(121)
<223> OTHER INFORMATION: heavy chain variable domain of PD-1 mAb 3

<400> SEQUENCE: 31

Gln Val Gln Leu Gln Gln Ser Gly Ala Glu Leu Ala Lys Pro Gly Ala
 1               5                  10                  15

Ser Val Gln Met Ser Cys Lys Ala Ser Gly Tyr Ser Phe Thr Ser Ser
                 20                  25                  30

Trp Ile His Trp Val Lys Gln Arg Pro Gly Gln Gly Leu Glu Trp Ile
```

```
                35                  40                  45
Gly Tyr Ile Tyr Pro Ser Thr Gly Phe Thr Glu Tyr Asn Gln Lys Phe
    50                  55                  60

Lys Asp Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Trp Arg Asp Ser Ser Gly Tyr His Ala Met Asp Tyr Trp Gly
            100                 105                 110

Gln Gly Thr Ser Val Thr Val Ser Ser
            115                 120

<210> SEQ ID NO 32
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: heavy chain variable domain of PD-1 mAb 3 CDR1

<400> SEQUENCE: 32

Ser Ser Trp Ile His
1               5

<210> SEQ ID NO 33
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: heavy chain variable domain of PD-1 mAb 3 CDR2

<400> SEQUENCE: 33

Tyr Ile Tyr Pro Ser Thr Gly Phe Thr Glu Tyr Asn Gln Lys Phe Lys
1               5                   10                  15

Asp

<210> SEQ ID NO 34
<211> LENGTH: 13
<212> TYPE: PRT
<213> ORGANISM: Mus musculus
<220> FEATURE:
<221> NAME/KEY: MISC_FEATURE
<222> LOCATION: (1)..(13)
<223> OTHER INFORMATION: heavy chain variable domain of PD-1 mAb 3 CDR3

<400> SEQUENCE: 34

Arg Trp Arg Asp Ser Ser Gly Tyr His Ala Met Asp Tyr
1               5                   10

<210> SEQ ID NO 35
<211> LENGTH: 111
<212> TYPE: PRT
<213> ORGANISM: Mus musculus
<220> FEATURE:
<221> NAME/KEY: MISC_FEATURE
<222> LOCATION: (1)..(111)
<223> OTHER INFORMATION: light chain variable domain of PD-1 mAb 3

<400> SEQUENCE: 35

Asp Ile Val Leu Thr Gln Ser Pro Ala Ser Leu Thr Val Ser Leu Gly
1               5                   10                  15
```

Gln Arg Ala Thr Ile Ser Cys Arg Ala Ser Gln Ser Val Ser Thr Ser
                20                  25                  30

Gly Tyr Ser Tyr Met His Trp Tyr Gln Gln Lys Pro Gly Gln Pro Pro
            35                  40                  45

Lys Leu Leu Ile Lys Phe Gly Ser Asn Leu Glu Ser Gly Ile Pro Ala
50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys
            100                 105                 110

<210> SEQ ID NO 36
<211> LENGTH: 15
<212> TYPE: PRT
<213> ORGANISM: Mus musculus
<220> FEATURE:
<221> NAME/KEY: MISC_FEATURE
<222> LOCATION: (1)..(15)
<223> OTHER INFORMATION: light chain variable domain of PD-1 mAb 3 CDR1

<400> SEQUENCE: 36

Arg Ala Ser Gln Ser Val Ser Thr Ser Gly Tyr Ser Tyr Met His
1               5                   10                  15

<210> SEQ ID NO 37
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: light chain variable domain of PD-1 mAb 3 CDR2

<400> SEQUENCE: 37

Phe Gly Ser Asn Leu Glu Ser
1               5

<210> SEQ ID NO 38
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: light chain variable domain of PD-1 mAb 3 CDR3

<400> SEQUENCE: 38

Gln His Ser Trp Glu Ile Pro Tyr Thr
1               5

<210> SEQ ID NO 39
<211> LENGTH: 117
<212> TYPE: PRT
<213> ORGANISM: Mus musculus
<220> FEATURE:
<221> NAME/KEY: MISC_FEATURE
<222> LOCATION: (1)..(117)
<223> OTHER INFORMATION: heavy chain variable domain of PD-1 mAb 4

<400> SEQUENCE: 39

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr

```
                20                  25                  30
Gly Met Asn Trp Val Arg Gln Ala Pro Gly Gln Gly Leu Gln Trp Met
                35                  40                  45

Gly Trp Ile Asn Thr Asp Ser Gly Glu Ser Thr Tyr Ala Glu Glu Phe
    50                  55                  60

Lys Gly Arg Phe Val Phe Ser Leu Asp Thr Ser Val Asn Thr Ala Tyr
65                  70                  75                  80

Leu Gln Ile Thr Ser Leu Thr Ala Glu Asp Thr Gly Met Tyr Phe Cys
                85                  90                  95

Val Arg Val Gly Tyr Asp Ala Leu Asp Tyr Trp Gly Gln Gly Thr Leu
                100                 105                 110

Val Thr Val Ser Ser
        115

<210> SEQ ID NO 40
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: heavy chain variable domain of PD-1 mAb 4 CDR1

<400> SEQUENCE: 40

Asn Tyr Gly Met Asn
1               5

<210> SEQ ID NO 41
<211> LENGTH: 16
<212> TYPE: PRT
<213> ORGANISM: Mus musculus
<220> FEATURE:
<221> NAME/KEY: MISC_FEATURE
<222> LOCATION: (1)..(16)
<223> OTHER INFORMATION: heavy chain variable domain of PD-1 mAb 4 CDR2

<400> SEQUENCE: 41

Trp Ile Asn Thr Asp Ser Gly Glu Ser Thr Tyr Ala Glu Glu Phe Lys
1               5                   10                  15

<210> SEQ ID NO 42
<211> LENGTH: 8
<212> TYPE: PRT
<213> ORGANISM: Mus musculus
<220> FEATURE:
<221> NAME/KEY: MISC_FEATURE
<222> LOCATION: (1)..(8)
<223> OTHER INFORMATION: heavy chain variable domain of PD-1 mAb 4 CDR3

<400> SEQUENCE: 42

Val Gly Tyr Asp Ala Leu Asp Tyr
1               5

<210> SEQ ID NO 43
<211> LENGTH: 106
<212> TYPE: PRT
<213> ORGANISM: Mus musculus
<220> FEATURE:
<221> NAME/KEY: MISC_FEATURE
<222> LOCATION: (1)..(106)
<223> OTHER INFORMATION: light chain variable domain of PD-1 mAb 4

<400> SEQUENCE: 43

Glu Ile Val Leu Thr Gln Ser Pro Ser Ser Leu Ser Ala Ser Val Gly
1               5                   10                  15
```

```
Asp Arg Val Thr Ile Thr Cys Ser Ala Arg Ser Ser Val Ser Tyr Met
            20                  25                  30

His Trp Phe Gln Gln Lys Pro Gly Lys Ala Pro Lys Leu Trp Ile Tyr
                35                  40                  45

Arg Thr Ser Asn Leu Ala Ser Gly Val Pro Ser Arg Phe Ser Gly Ser
    50                  55                  60

Gly Ser Gly Thr Ser Tyr Cys Leu Thr Ile Asn Ser Leu Gln Pro Glu
65                  70                  75                  80

Asp Phe Ala Thr Tyr Tyr Cys Gln Gln Arg Ser Ser Phe Pro Leu Thr
                85                  90                  95

Phe Gly Gly Gly Thr Lys Leu Glu Ile Lys
            100                 105

<210> SEQ ID NO 44
<211> LENGTH: 10
<212> TYPE: PRT
<213> ORGANISM: Mus musculus
<220> FEATURE:
<221> NAME/KEY: MISC_FEATURE
<222> LOCATION: (1)..(10)
<223> OTHER INFORMATION: light chain variable domain of PD-1 mAb 4 CDR1

<400> SEQUENCE: 44

Ser Ala Arg Ser Ser Val Ser Tyr Met His
1               5                   10

<210> SEQ ID NO 45
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: light chain variable domain of PD-1 mAb 4 CDR2

<400> SEQUENCE: 45

Arg Thr Ser Asn Leu Ala Ser
1               5

<210> SEQ ID NO 46
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: light chain variable domain of PD-1 mAb 4 CDR3

<400> SEQUENCE: 46

Gln Gln Arg Ser Ser Phe Pro Leu Thr
1               5

<210> SEQ ID NO 47
<211> LENGTH: 120
<212> TYPE: PRT
<213> ORGANISM: Mus musculus
<220> FEATURE:
<221> NAME/KEY: MISC_FEATURE
<222> LOCATION: (1)..(120)
<223> OTHER INFORMATION: Heavy Chain Variable Domain of Murine 4D5
      Antibody

<400> SEQUENCE: 47

Gln Val Gln Leu Gln Gln Ser Gly Pro Glu Leu Val Lys Pro Gly Ala
1               5                   10                  15
```

```
Ser Leu Lys Leu Ser Cys Thr Ala Ser Gly Phe Asn Ile Lys Asp Thr
         20                  25                  30

Tyr Ile His Trp Val Lys Gln Arg Pro Glu Gln Gly Leu Glu Trp Ile
         35                  40                  45

Gly Arg Ile Tyr Pro Thr Asn Gly Tyr Thr Arg Tyr Asp Pro Lys Phe
 50                  55                  60

Gln Asp Lys Ala Thr Ile Thr Ala Asp Thr Ser Ser Asn Thr Ala Tyr
 65                  70                  75                  80

Leu Gln Val Ser Arg Leu Thr Ser Glu Asp Thr Ala Val Tyr Tyr Cys
                 85                  90                  95

Ser Arg Trp Gly Gly Asp Gly Phe Tyr Ala Met Asp Tyr Trp Gly Gln
                100                 105                 110

Gly Ala Ser Val Thr Val Ser Ser
        115                 120

<210> SEQ ID NO 48
<211> LENGTH: 120
<212> TYPE: PRT
<213> ORGANISM: Artificial Sequence
<220> FEATURE:
<223> OTHER INFORMATION: Heavy Chain Variable Domain of Humanized 4D5
      Antibody

<400> SEQUENCE: 48

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Asn Ile Lys Asp Thr
         20                  25                  30

Tyr Ile His Trp Val Arg Gln Ala Pro Gly Lys Gly Leu Glu Trp Val
         35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Val Trp Gly Gln
                100                 105                 110

Gly Thr Leu Val Thr Val Ser Ser
        115                 120

<210> SEQ ID NO 49
<211> LENGTH: 217
<212> TYPE: PRT
<213> ORGANISM: Homo sapiens
<220> FEATURE:
<221> NAME/KEY: MISC_FEATURE
<222> LOCATION: (1)..(217)
<223> OTHER INFORMATION: IgG1 Fc Region
<220> FEATURE:
<221> NAME/KEY: MISC_FEATURE
<222> LOCATION: (217)..(217)
<223> OTHER INFORMATION: Xaa is Lys or is absent

<400> SEQUENCE: 49

Ala Pro Glu Leu Leu Gly Gly Pro Ser Val Phe Leu Phe Pro Pro Lys
1               5                  10                  15

Pro Lys Asp Thr Leu Met Ile Ser Arg Thr Pro Glu Val Thr Cys Val
         20                  25                  30
```

```
Val Val Asp Val Ser His Glu Asp Pro Glu Val Lys Phe Asn Trp Tyr
        35                  40                  45
Val Asp Gly Val Glu Val His Asn Ala Lys Thr Lys Pro Arg Glu Glu
 50                  55                  60
Gln Tyr Asn Ser Thr Tyr Arg Val Val Ser Val Leu Thr Val Leu His
 65                  70                  75                  80
Gln Asp Trp Leu Asn Gly Lys Glu Tyr Lys Cys Lys Val Ser Asn Lys
                85                  90                  95
Ala Leu Pro Ala Pro Ile Glu Lys Thr Ile Ser Lys Ala Lys Gly Gln
               100                 105                 110
Pro Arg Glu Pro Gln Val Tyr Thr Leu Pro Pro Ser Arg Glu Glu Met
               115                 120                 125
Thr Lys Asn Gln Val Ser Leu Thr Cys Leu Val Lys Gly Phe Tyr Pro
130                 135                 140
Ser Asp Ile Ala Val Glu Trp Glu Ser Asn Gly Gln Pro Glu Asn Asn
145                 150                 155                 160
Tyr Lys Thr Thr Pro Pro Val Leu Asp Ser Asp Gly Ser Phe Phe Leu
               165                 170                 175
Tyr Ser Lys Leu Thr Val Asp Lys Ser Arg Trp Gln Gln Gly Asn Val
               180                 185                 190
Phe Ser Cys Ser Val Met His Glu Ala Leu His Asn His Tyr Thr Gln
               195                 200                 205
Lys Ser Leu Ser Leu Ser Pro Gly Xaa
               210                 215

<210> SEQ ID NO 50
<211> LENGTH: 216
<212> TYPE: PRT
<213> ORGANISM: Homo sapiens
<220> FEATURE:
<221> NAME/KEY: MISC_FEATURE
<222> LOCATION: (1)..(216)
<223> OTHER INFORMATION: CH2-CH3 domain of an exemplary human IgG2
<220> FEATURE:
<221> NAME/KEY: MISC_FEATURE
<222> LOCATION: (216)..(216)
<223> OTHER INFORMATION: Xaa is Lys or is absent

<400> SEQUENCE: 50

Ala Pro Pro Val Ala Gly Pro Ser Val Phe Leu Phe Pro Pro Lys Pro
 1               5                  10                  15
Lys Asp Thr Leu Met Ile Ser Arg Thr Pro Glu Val Thr Cys Val Val
                20                  25                  30
Val Asp Val Ser His Glu Asp Pro Glu Val Gln Phe Asn Trp Tyr Val
        35                  40                  45
Asp Gly Val Glu Val His Asn Ala Lys Thr Lys Pro Arg Glu Glu Gln
 50                  55                  60
Phe Asn Ser Thr Phe Arg Val Val Ser Val Leu Thr Val Val His Gln
 65                  70                  75                  80
Asp Trp Leu Asn Gly Lys Glu Tyr Lys Cys Lys Val Ser Asn Lys Gly
                85                  90                  95
Leu Pro Ala Pro Ile Glu Lys Thr Ile Ser Lys Thr Lys Gly Gln Pro
               100                 105                 110
Arg Glu Pro Gln Val Tyr Thr Leu Pro Pro Ser Arg Glu Glu Met Thr
               115                 120                 125
Lys Asn Gln Val Ser Leu Thr Cys Leu Val Lys Gly Phe Tyr Pro Ser
130                 135                 140
```

```
Asp Ile Ser Val Glu Trp Glu Ser Asn Gly Gln Pro Glu Asn Asn Tyr
145                 150                 155                 160

Lys Thr Thr Pro Pro Met Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Xaa
    210                 215

<210> SEQ ID NO 51
<211> LENGTH: 217
<212> TYPE: PRT
<213> ORGANISM: Homo sapiens
<220> FEATURE:
<221> NAME/KEY: MISC_FEATURE
<222> LOCATION: (1)..(217)
<223> OTHER INFORMATION: CH2-CH3 Domain of an exemplary human IgG3
<220> FEATURE:
<221> NAME/KEY: MISC_FEATURE
<222> LOCATION: (217)..(217)
<223> OTHER INFORMATION: Xaa is Lys or is absent

<400> SEQUENCE: 51

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
    50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Ser Gly Gln Pro Glu Asn Asn
145                 150                 155                 160

Tyr Asn Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Ile
            180                 185                 190

Phe Ser Cys Ser Val Met His Glu Ala Leu His Asn Arg Phe Thr Gln
        195                 200                 205

Lys Ser Leu Ser Leu Ser Pro Gly Xaa
    210                 215

<210> SEQ ID NO 52
<211> LENGTH: 217
<212> TYPE: PRT
<213> ORGANISM: Homo sapiens
<220> FEATURE:
```

```
<221> NAME/KEY: MISC_FEATURE
<222> LOCATION: (1)..(217)
<223> OTHER INFORMATION: CH2-CH3 domain of an exemplary human IgG4
<220> FEATURE:
<221> NAME/KEY: MISC_FEATURE
<222> LOCATION: (217)..(217)
<223> OTHER INFORMATION: Xaa is Lys or is absent

<400> SEQUENCE: 52

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Xaa
    210                 215

<210> SEQ ID NO 53
<211> LENGTH: 116
<212> TYPE: PRT
<213> ORGANISM: Mus musculus
<220> FEATURE:
<221> NAME/KEY: MISC_FEATURE
<222> LOCATION: (1)..(116)
<223> OTHER INFORMATION: heavy chain variable domain of PD-1 mAb 5

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Val Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Gly Ser Met Ser Ile Tyr Ala Asp Thr Val
    50                  55                  60

Lys Gly Arg Phe Thr Ile Ser Arg Asp Asn Ala Lys Asn Thr Leu Tyr
65                  70                  75                  80
```

```
Leu Gln Met Asn Ser Leu Arg Thr Glu Asp Thr Ala Leu Tyr Tyr Cys
                85                  90                  95

Ala Ser Leu Ser Asp Tyr Phe Asp Tyr Trp Gly Gln Gly Thr Thr Val
            100                 105                 110

Thr Val Ser Ser
        115

<210> SEQ ID NO 54
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: heavy chain variable domain of PD-1 mAb 5 CDR1

<400> SEQUENCE: 54

Ser Phe Gly Met His
1               5

<210> SEQ ID NO 55
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: heavy chain variable domain of PD-1 mAb 5 CDR2

<400> SEQUENCE: 55

Tyr Ile Ser Ser Gly Ser Met Ser Ile Ser Tyr Ala Asp Thr Val Lys
1               5                   10                  15

Gly

<210> SEQ ID NO 56
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: heavy chain variable domain of PD-1 mAb 5 CDR3

<400> SEQUENCE: 56

Leu Ser Asp Tyr Phe Asp Tyr
1               5

<210> SEQ ID NO 57
<211> LENGTH: 112
<212> TYPE: PRT
<213> ORGANISM: Mus musculus
<220> FEATURE:
<221> NAME/KEY: MISC_FEATURE
<222> LOCATION: (1)..(112)
<223> OTHER INFORMATION: light chain variable domain of PD-1 mAb 5

<400> SEQUENCE: 57

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Thr Gly Asn Thr Tyr Leu His Trp Tyr Leu Gln Lys Pro Gly Gln Ser
        35                  40                  45

Pro Gln Leu Leu Ile Tyr Arg Val Ser Asn Arg Phe Ser Gly Val Pro
    50                  55                  60
```

```
Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Thr
                85                  90                  95

Thr His Val Pro Trp Thr Phe Gly Gln Gly Thr Lys Leu Glu Ile Lys
            100                 105                 110

<210> SEQ ID NO 58
<211> LENGTH: 16
<212> TYPE: PRT
<213> ORGANISM: Mus musculus
<220> FEATURE:
<221> NAME/KEY: MISC_FEATURE
<222> LOCATION: (1)..(16)
<223> OTHER INFORMATION: light chain variable domain of PD-1 mAb 5 CDR1

<400> SEQUENCE: 58

Arg Ser Ser Gln Ser Leu Val His Ser Thr Gly Asn Thr Tyr Leu His
1               5                   10                  15

<210> SEQ ID NO 59
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: light chain variable domain of PD-1 mAb 5 CDR2

<400> SEQUENCE: 59

Arg Val Ser Asn Arg Phe Ser
1               5

<210> SEQ ID NO 60
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: light chain variable domain of PD-1 mAb 5 CDR3

<400> SEQUENCE: 60

Ser Gln Thr Thr His Val Pro Trp Thr
1               5

<210> SEQ ID NO 61
<211> LENGTH: 119
<212> TYPE: PRT
<213> ORGANISM: Mus musculus
<220> FEATURE:
<221> NAME/KEY: MISC_FEATURE
<222> LOCATION: (1)..(119)
<223> OTHER INFORMATION: heavy chain variable domain of PD-1 mAb 6
<220> FEATURE:
<221> NAME/KEY: MISC_FEATURE
<222> LOCATION: (48)..(48)
<223> OTHER INFORMATION: Xaa is Ile or Ala

<400> SEQUENCE: 61

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
                20                  25                  30

Trp Met Asn Trp Val Arg Gln Ala Pro Gly Gln Gly Leu Glu Trp Xaa
            35                  40                  45
```

```
Gly Val Ile His Pro Ser Asp Ser Glu Thr Trp Leu Asp Gln Lys Phe
        50                  55                  60

Lys Asp Arg Val Thr Ile Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu His Tyr Gly Thr Ser Pro Phe Ala Tyr Trp Gly Gln Gly
            100                 105                 110

Thr Leu Val Thr Val Ser Ser
        115
```

```
<210> SEQ ID NO 62
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: heavy chain variable domain of PD-1 mAb 6 CDR1

<400> SEQUENCE: 62

Ser Tyr Trp Met Asn
 1               5
```

```
<210> SEQ ID NO 63
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: heavy chain variable domain of PD-1 mAb 6 CDR2

<400> SEQUENCE: 63

Val Ile His Pro Ser Asp Ser Glu Thr Trp Leu Asp Gln Lys Phe Lys
 1               5                  10                  15

Asp
```

```
<210> SEQ ID NO 64
<211> LENGTH: 10
<212> TYPE: PRT
<213> ORGANISM: Mus musculus
<220> FEATURE:
<221> NAME/KEY: MISC_FEATURE
<222> LOCATION: (1)..(10)
<223> OTHER INFORMATION: heavy chain variable domain of PD-1 mAb 6 CDR3

<400> SEQUENCE: 64

Glu His Tyr Gly Thr Ser Pro Phe Ala Tyr
 1               5                  10
```

```
<210> SEQ ID NO 65
<211> LENGTH: 111
<212> TYPE: PRT
<213> ORGANISM: Mus musculus
<220> FEATURE:
<221> NAME/KEY: MISC_FEATURE
<222> LOCATION: (1)..(111)
<223> OTHER INFORMATION: light chain variable domain of PD-1 mAb 6
<220> FEATURE:
<221> NAME/KEY: MISC_FEATURE
<222> LOCATION: (26)..(26)
<223> OTHER INFORMATION: Xaa is Asn or Ser
<220> FEATURE:
<221> NAME/KEY: MISC_FEATURE
<222> LOCATION: (58)..(58)
```

<223> OTHER INFORMATION: Xaa is Gln or Arg

<400> SEQUENCE: 65

Glu Ile Val Leu Thr Gln Ser Pro Ala Thr Leu Ser Leu Ser Pro Gly
1               5                   10                  15

Glu Arg Ala Thr Leu Ser Cys Arg Ala Xaa Glu Ser Val Asp Asn Tyr
            20                  25                  30

Gly Met Ser Phe Met Asn Trp Phe Gln Gln Lys Pro Gly Gln Pro Pro
        35                  40                  45

Lys Leu Leu Ile His Ala Ala Ser Asn Xaa Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Lys
                85                  90                  95

Glu Val Pro Tyr Thr Phe Gly Gly Gly Thr Lys Val Glu Ile Lys
            100                 105                 110

<210> SEQ ID NO 66
<211> LENGTH: 15
<212> TYPE: PRT
<213> ORGANISM: Mus musculus
<220> FEATURE:
<221> NAME/KEY: MISC_FEATURE
<222> LOCATION: (1)..(15)
<223> OTHER INFORMATION: light chain variable domain of PD-1 mAb 6 CDR1
<220> FEATURE:
<221> NAME/KEY: MISC_FEATURE
<222> LOCATION: (3)..(3)
<223> OTHER INFORMATION: Xaa is Asn or Ser

<400> SEQUENCE: 66

Arg Ala Xaa Glu Ser Val Asp Asn Tyr Gly Met Ser Phe Met Asn
1               5                   10                  15

<210> SEQ ID NO 67
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: light chain variable domain of PD-1 mAb 6 CDR2
<220> FEATURE:
<221> NAME/KEY: MISC_FEATURE
<222> LOCATION: (5)..(5)
<223> OTHER INFORMATION: Xaa is Gln or Arg

<400> SEQUENCE: 67

Ala Ala Ser Asn Xaa Gly Ser
1               5

<210> SEQ ID NO 68
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: light chain variable domain of PD-1 mAb 6 CDR3

<400> SEQUENCE: 68

Gln Gln Ser Lys Glu Val Pro Tyr Thr
1               5

<210> SEQ ID NO 69
<211> LENGTH: 119
<212> TYPE: PRT
<213> ORGANISM: Mus musculus
<220> FEATURE:
<221> NAME/KEY: MISC_FEATURE
<222> LOCATION: (1)..(119)
<223> OTHER INFORMATION: heavy chain variable domain of PD-1 mAb 7
<220> FEATURE:
<221> NAME/KEY: MISC_FEATURE
<222> LOCATION: (12)..(12)
<223> OTHER INFORMATION: Xaa is Val or Ala
<220> FEATURE:
<221> NAME/KEY: MISC_FEATURE
<222> LOCATION: (35)..(35)
<223> OTHER INFORMATION: Xaa is Ser or Gly
<220> FEATURE:
<221> NAME/KEY: MISC_FEATURE
<222> LOCATION: (48)..(48)
<223> OTHER INFORMATION: Xaa is is Val or Thr
<220> FEATURE:
<221> NAME/KEY: MISC_FEATURE
<222> LOCATION: (86)..(86)
<223> OTHER INFORMATION: Xaa is is Leu or Ala

<400> SEQUENCE: 69

Glu Val Gln Leu Val Glu Ser Gly Gly Gly Leu Xaa Arg Pro Gly Gly
1               5                   10                  15

Ser Leu Lys Leu Ser Cys Ala Ala Ser Gly Phe Thr Phe Ser Ser Tyr
            20                  25                  30

Leu Val Xaa Trp Val Arg Gln Ala Pro Gly Lys Gly Leu Glu Trp Xaa
        35                  40                  45

Ala Thr Ile Ser Gly Gly Gly Asn Thr Tyr Tyr Ser Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Xaa Arg Ala Glu Asp Thr Ala Thr Tyr Tyr Cys
                85                  90                  95

Ala Arg Tyr Gly Phe Asp Gly Ala Trp Phe Ala Tyr Trp Gly Gln Gly
            100                 105                 110

Thr Leu Val Thr Val Ser Ser
        115

<210> SEQ ID NO 70
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: heavy chain variable domain of PD-1 mAb 7 CDR1
<220> FEATURE:
<221> NAME/KEY: MISC_FEATURE
<222> LOCATION: (5)..(5)
<223> OTHER INFORMATION: Xaa is Gln or Arg

<400> SEQUENCE: 70

Ser Tyr Leu Val Xaa
1               5

<210> SEQ ID NO 71
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: heavy chain variable domain of PD-1 mAb 7 CDR2

<400> SEQUENCE: 71

Thr Ile Ser Gly Gly Gly Asn Thr Tyr Tyr Ser Asp Ser Val Lys
1               5                   10                  15

Gly

<210> SEQ ID NO 72
<211> LENGTH: 10
<212> TYPE: PRT
<213> ORGANISM: Mus musculus
<220> FEATURE:
<221> NAME/KEY: MISC_FEATURE
<222> LOCATION: (1)..(10)
<223> OTHER INFORMATION: heavy chain variable domain of PD-1 mAb 7 CDR3

<400> SEQUENCE: 72

Tyr Gly Phe Asp Gly Ala Trp Phe Ala Tyr
1               5                   10

<210> SEQ ID NO 73
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: light chain variable domain of PD-1 mAb 7
<220> FEATURE:
<221> NAME/KEY: MISC_FEATURE
<222> LOCATION: (31)..(31)
<223> OTHER INFORMATION: Xaa is Asn or Ser
<220> FEATURE:
<221> NAME/KEY: MISC_FEATURE
<222> LOCATION: (50)..(50)
<223> OTHER INFORMATION: Xaa is Asn or Asp

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Xaa Tyr
                20                  25                  30

Leu Ala Trp Tyr Gln Gln Lys Pro Gly Lys Ala Pro Lys Leu Leu Ile
            35                  40                  45

Tyr Xaa Ala Lys Thr Leu Ala Ala Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Ala Val Pro Trp
                85                  90                  95

Thr Phe Gly Gln Gly Thr Lys Leu Glu Ile Lys
            100                 105

<210> SEQ ID NO 74
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: PD-1 mAb 7  CDRL1
<220> FEATURE:
<221> NAME/KEY: MISC_FEATURE
<222> LOCATION: (8)..(8)
<223> OTHER INFORMATION: Xaa is Asn or Ser

<400> SEQUENCE: 74

Arg Ala Ser Glu Asn Ile Tyr Xaa Tyr Leu Ala
1               5                   10

<210> SEQ ID NO 75
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: PD-1 mAb 7  CDRL2
<220> FEATURE:
<221> NAME/KEY: MISC_FEATURE
<222> LOCATION: (1)..(1)
<223> OTHER INFORMATION: Xaa is Asn or Asp

<400> SEQUENCE: 75

Xaa Ala Lys Thr Leu Ala Ala
1               5

<210> SEQ ID NO 76
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: PD-1 mAb 7  CDRL3

<400> SEQUENCE: 76

Gln His His Tyr Ala Val Pro Trp Thr
1               5

<210> SEQ ID NO 77
<211> LENGTH: 117
<212> TYPE: PRT
<213> ORGANISM: Mus musculus
<220> FEATURE:
<221> NAME/KEY: MISC_FEATURE
<222> LOCATION: (1)..(117)
<223> OTHER INFORMATION: heavy chain variable domain of PD-1 mAb 8

<400> SEQUENCE: 77

Glu Val Gln Leu Val Glu Ser Gly Gly Gly Leu Val Arg Pro Gly Gly
1               5                   10                  15

Ser Leu Arg Leu Ser Cys Ala Ala Ser Gly Phe Thr Phe Ser Ser Tyr
            20                  25                  30

Leu Ile Ser Trp Val Arg Gln Ala Pro Gly Lys Gly Leu Glu Trp Val
        35                  40                  45

Ala Ala Ile Ser Gly Gly Gly Ala Asp Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Thr Tyr Tyr Cys
                85                  90                  95

Ala Arg Arg Gly Thr Tyr Ala Met Asp Tyr Trp Gly Gln Gly Thr Leu
            100                 105                 110

Val Thr Val Ser Ser
        115

<210> SEQ ID NO 78
<211> LENGTH: 5
<212> TYPE: PRT
<213> ORGANISM: Mus musculus

```
<220> FEATURE:
<221> NAME/KEY: MISC_FEATURE
<222> LOCATION: (1)..(5)
<223> OTHER INFORMATION: PD-1 mAb 8  CDRH1

<400> SEQUENCE: 78

Ser Tyr Leu Ile Ser
1               5

<210> SEQ ID NO 79
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: PD-1 mAb 8  CDRH2

<400> SEQUENCE: 79

Ala Ile Ser Gly Gly Gly Ala Asp Thr Tyr Tyr Ala Asp Ser Val Lys
1               5                   10                  15

Gly

<210> SEQ ID NO 80
<211> LENGTH: 8
<212> TYPE: PRT
<213> ORGANISM: Mus musculus
<220> FEATURE:
<221> NAME/KEY: MISC_FEATURE
<222> LOCATION: (1)..(8)
<223> OTHER INFORMATION: PD-1 mAb 8  CDRH3

<400> SEQUENCE: 80

Arg Gly Thr Tyr Ala Met Asp Tyr
1               5

<210> SEQ ID NO 81
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: light chain variable domain of PD-1 mAb 8

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Asn Tyr
                20                  25                  30

Leu Ala Trp Tyr Gln Gln Lys Pro Gly Lys Ala Pro Lys Leu Leu Ile
            35                  40                  45

Tyr Asp Ala Lys Thr Leu Ala Ala Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Ala Val Pro Trp
                85                  90                  95

Thr Phe Gly Gln Gly Thr Lys Leu Glu Ile Lys
            100                 105

<210> SEQ ID NO 82
<211> LENGTH: 11
<212> TYPE: PRT
```

```
<213> ORGANISM: Mus musculus
<220> FEATURE:
<221> NAME/KEY: MISC_FEATURE
<222> LOCATION: (1)..(11)
<223> OTHER INFORMATION: PD-1 mAb 8  CDRL1

<400> SEQUENCE: 82

Arg Ala Ser Glu Asn Ile Tyr Asn Tyr Leu Ala
1               5                   10

<210> SEQ ID NO 83
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: PD-1 mAb 8  CDRL2

<400> SEQUENCE: 83

Asp Ala Lys Thr Leu Ala Ala
1               5

<210> SEQ ID NO 84
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: PD-1 mAb 8  CDRL3

<400> SEQUENCE: 84

Gln His His Tyr Ala Val Pro Trp Thr
1               5

<210> SEQ ID NO 85
<211> LENGTH: 107
<212> TYPE: PRT
<213> ORGANISM: Artificial Sequence
<220> FEATURE:
<223> OTHER INFORMATION: kappa CL Domain

<400> SEQUENCE: 85

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 86
<211> LENGTH: 110
<212> TYPE: PRT
<213> ORGANISM: Homo sapiens
<220> FEATURE:
<221> NAME/KEY: MISC_FEATURE
```

```
<222> LOCATION: (1)..(110)
<223> OTHER INFORMATION: IgG4 CH1 Domain and Stabilized Hinge

<400> SEQUENCE: 86

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro
            100                 105                 110

<210> SEQ ID NO 87
<211> LENGTH: 218
<212> TYPE: PRT
<213> ORGANISM: Mus musculus
<220> FEATURE:
<221> NAME/KEY: 1MISC_FEATURE
<222> LOCATION: (1)..(218)
<223> OTHER INFORMATION: complete light chain of PD-1 mAb 6-ISQ

<400> SEQUENCE: 87

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
                20                  25                  30

Gly Met Ser Phe Met Asn Trp Phe Gln Gln Lys Pro Gly Gln Pro Pro
            35                  40                  45

Lys Leu Leu Ile His Ala Ala Ser Asn Gln Gly Ser Gly Val Pro Ser
        50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Phe Cys Gln Gln Ser Lys
                85                  90                  95

Glu Val Pro Tyr Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

```
<210> SEQ ID NO 88
<211> LENGTH: 445
<212> TYPE: PRT
<213> ORGANISM: Mus musculus
<220> FEATURE:
<221> NAME/KEY: MISC_FEATURE
<222> LOCATION: (1)..(445)
<223> OTHER INFORMATION: complete heavy chain of PD-1 mAb 6-ISQ

<400> SEQUENCE: 88

Gln Val Gln Leu Val Gln Ser Gly Ala Glu Lys Lys Pro Gly Ala
1               5                   10                  15

Ser Val Lys Val Ser Cys Lys Ala Ser Gly Tyr Ser Phe Thr Ser Tyr
            20                  25                  30

Trp Met Asn Trp Val Arg Gln Ala Pro Gly Gln Gly Leu Glu Trp Ile
        35                  40                  45

Gly Val Ile His Pro Ser Asp Ser Glu Thr Trp Leu Asp Gln Lys Phe
    50                  55                  60

Lys Asp Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu His Tyr Gly Thr Ser Pro Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350
```

-continued

```
Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly
        435                 440                 445
```

COMBINATION THERAPY FOR THE TREATMENT OF CANCER

CROSS-REFERENCE TO RELATED APPLICATIONS

This Application is a § 371 National Stage Application of PCT/US2016/036608 (filed on Jun. 9, 2016; now expired), which application claims priority to U.S. Provisional Patent Appln. Ser. Nos. 62/175,039 (filed on Jun. 12, 2015;), 62/211,109 (filed on Aug. 28, 2015;), and 62/242,640 (filed on Oct. 16, 2015;), which applications are hereby incorporated by reference herein in their entireties.

REFERENCE TO SEQUENCE LISTING

This application includes one or more Sequence Listings pursuant to 37 C.F.R. 1.821 et seq., which are disclosed in computer-readable media (file name: 1301-0120PCT_ST25.txt, created on May 23, 2016, and having a size of 82,289 bytes), which file is herein incorporated by reference in its entirety.

BACKGROUND OF THE INVENTION

Field of the Invention

This invention relates to a pharmaceutical composition that comprises a first molecule that specifically binds to HER2/neu and a second molecule that specifically binds to a cell-surface receptor that is involved in regulating an immune checkpoint (or the ligand thereof). The invention particularly relates to the embodiment wherein the second molecule binds to PD-1. The invention also relates to the use of such pharmaceutical compositions to treat cancer and other diseases.

Description of the Related Art

I. HER2/neu and HER2/neu Receptors

Cellular growth and differentiation processes involve growth factors that exert their actions through specific receptors such as the tyrosine kinases. The binding of ligand to a tyrosine kinase receptor triggers a cascade of events that eventually leads to cellular proliferation and differentiation (Carpenter, G. et al. (1979) "*Epidermal Growth Factor*," Annu Rev Biochem. 48:193-216; Sachs et al. (1987) "*Cell Differentiation And Bypassing Of Genetic Defects In The Suppression Of Malignancy*," Cancer Res. 47:1981-1986). Tyrosine kinase receptors can be classified into several groups on the basis of sequence similarity and distinct features. One such family is the ErbB or epidermal growth factor receptor family, which includes multiple receptors known as HER-1 (also known as erbB-1 or EGFR) HER2/neu (also known as HER-2, erbB-2, c-neu, or p185), HER-3 (also known as erbB-3), and HER4 (also known as erbB-4) (see, e.g., Carpenter, G. et al. (1979) "*Epidermal Growth Factor*," Annu. Rev. Biochem. 48:193-216; Semba, K. et al. (1985) "*A v-erbB-Related Protooncogene, c-erbB-2, Is Distinct From The c-erbB-I/Epidermal Growth Factor-Receptor Gene And Is Amplified In A Human Salivary Gland Adenocarcinoma*," Proc. Natl. Acad. Sci. (U.S.A.) 82:6497-6501; Coussens, L. et al. (1985) "*Tyrosine Kinase Receptor With Extensive Homology To EGF Receptor Shares Chromosomal Location With neu Oncogene*," Science 230:1132-1139; Bargmann, C. I. et al. (1986) "*Multiple Independent Activations Of The Neu Oncogene By A Point Mutation Altering The Transmembrane Domain Of p185*," Cell 45:649-657; Kraus, M. H. et al. (1989) "*Isolation And Characterization Of ERBB3, A Third Member Of The ERBB/Epidermal Growth Factor Receptor Family: Evidence For Overexpression In A Subset Of Human Mammary Tumors*," Proc. Natl. Acad. Sci. (U.S.A.) 86:9193-9197; Carraway, K. L. et al. (1994) "*The erbB3 Gene Product Is A Receptor For Heregulin*," J. Biol. Chem. 269:14303-14306; Plowman, G. D. et al (1993) "*Heregulin Induces Tyrosine Phosphorylation Of HER4/p180erbB4*," Nature 366:473-475; and Tzahar, E. et al (1994) "*ErbB-3 and ErbB-4 Function As The Respective Low And High Affinity Receptors Of All neu Differentiation Factor/Heregulin Isoforms*," Biol. Chem. 269:25226-25233).

The ErbB receptors play important roles in propagating signals regulating cell proliferation, differentiation, motility, and apoptosis, both in normal developmental processes and in human tumorigenesis (Slamon, D. J. et al. (1989) "*Studies Of The HER-2/neu Proto-Oncogene In Human Breast And Ovarian Cancer*," Science 244:707-712). For example, the activation of erbB receptors is coupled to and stimulates downstream MAPK-Erk1/2 and phosphoinositide-3-kinase ($PI_3K$)/AKT growth and survival pathways. The deregulation of these pathways in cancer has been linked to disease progression and refractoriness to therapy (Fukazawa, T. et al. (1996) "*Tyrosine Phosphorylation Of Cbl Upon Epidermal Growth Factor (EGF) Stimulation And Its Association With EGF Receptor And Downstream Signaling Proteins*," J. Biol. Chem. 271:14554-14559; Tzahar, E. et al. (1996) "*A Hierarchical Network Of Interceptor Interactions Determines Signal Transduction By neu Differentiation Factor/Neuregulin And Epidermal Growth Factor*," Mol. Cell. Biol. 16:5276-5287; Lange, C. A. et al. (1998) "*Convergence Of Progesterone And Epidermal Growth Factor Signaling In Breast Cancer. Potentiation Of Mitogen-Activated Protein Kinase Pathways*," J. Biol. Chem. 273:31308-31316; Olayioye, M. A. et al. (1998) "*ErbB-1 And ErbB-2 Acquire Distinct Signaling Properties Dependent Upon Their Dimerization Partner*," Mol. Cell. Biol. 18:5042-5051; Hackel, P. O. et al. (1999) "*Epidermal Growth Factor Receptors: Critical Mediators Of Multiple Receptor Pathways*," Curr. Opin. Cell Biol. 11:184-189). Activation of $PI_3K$/AKT promotes cell survival and enhanced tumor aggressiveness, and AKT2 was reported to be activated and overexpressed in HER2/neu-overexpressing breast cancers (Shak, S. (1999) "*Overview Of The Trastuzumab (Herceptin) anti-HER2 Monoclonal Antibody Clinical Program In HER2-Overexpressing Metastatic Breast Cancer*," Semin. Oncol. Suppl 12:71-77; Huang, S. M. et al. (2000) "*Modulation Of Radiation Response After Epidermal Growth Factor Receptor Blockade In Squamous Cell Carcinomas: Inhibition Of Damage Repair, Cell Cycle Kinetics, And Tumor Angiogenesis*," Clinical Cancer Res. 7:2166-2174; Bacus, S. S. et al. (2002) "*AKT2 Is Frequently Upregulated In HER-2/neu-Positive Breast Cancers And May Contribute To Tumor Aggressiveness By Enhancing Cell Survival*," Oncogene 21:3532-3540).

Signaling by the ErbB family of receptors is initiated by ligand binding which triggers homo- or hetero-receptor dimerization, reciprocal tyrosine phosphorylation of the cytoplasmic tails, and activation of intracellular signal transduction pathways (Citri, A. et al. (2003) "*The Deaf And The Dumb: The Biology Of ErbB-2 And ErbB-3*," Exp. Cell Res. 284:54-65). The availability of ligands that bind to and activate the ErbB receptors is mediated by various metalloproteases, such as the ADAM (a disintegrin and metalloprotease) family of zinc-dependent metalloproteases, which catalyze cell-surface ectodomain shedding of specific proteins (see Chang, C. and Werb, Z. (2001) "*The Many Faces Of Metalloproteases: Cell Growth, Invasion, Angiogenesis And Metastasis,*" Trends in Cell Biology 11:S37-S43; Moss, M. L. et al. (2002) "*Shedding Of Membrane Proteins By ADAM Family Proteases,*" Essays in Biochemistry 38:141-153; Seals, D. F. et al. (2003) "*The ADAMs Family Of Metalloproteases: Multidomain Proteins With Multiple Functions,*" Genes and Development 17:7-30). Specifically, the ADAM family has been shown to cleave ligands responsible for activating the ErbB receptors, such as APP and Notch (Blobel, C. P. (2005) "*ADAMs: Key Components In EGFR Signalling And Development,*" Nat. Rev. Mol. Cell. Biol. 6:32-43).

HER2/neu is an important member of the ErbB family. It is a 185 kDa receptor protein that was originally identified as the product of the ERBB2 transforming gene from neuroblastomas of chemically treated rats. HER2/neu has been extensively investigated because of its role in several human carcinomas and in mammalian development (Hynes, N. E. et al. (1994) "*The Biology Of erbB-2/neu/HER-2 And Its Role In Cancer,*" Biochim. et Biophys. Acta 1198:165-184; Dougall, W. C. et al. (1994) "*The neu-Oncogene: Signal Transduction Pathways, Transformation Mechanisms And Evolving Therapies,*" Oncogene 9:2109-2123; Lee, K. F. et al. (1995) "*Requirement For Neuregulin Receptor erbB2 In Neural And Cardiac Development.*" Nature 378: 394-398). The human HER2/neu gene and HER2/neu protein are described in Semba, K. et al. (1985) "*A v-erbB-Related Protooncogene, c-erbB-2, Is Distinct From The c-erbB-1/Epidermal Growth Factor-Receptor Gene And Is Amplified In A Human Salivary Gland Adenocarcinoma,*" Proc. Natl. Acad. Sci. (U.S.A.) 82: 6497-6501 and Yamamoto, T. et al. (1986) "*Similarity Of Protein Encoded By The Human c-erb-B-2 Gene To Epidermal Growth Factor Receptor,*" Nature 319:230-234, and the sequence is available in GenBank, as accession number X03363. HER2/neu comprises four domains: an extracellular domain to which ligand binds; a lipophilic transmembrane domain; a conserved intracellular tyrosine kinase domain; and a carboxyl-terminal signaling domain harboring several tyrosine residues that can be phosphorylated (Plowman, G. D. et al (1993) "*Ligand-Specific Activation Of HER4/p180erbB4, A Fourth Member Of The Epidermal Growth Factor Receptor Family,*" Proc. Natl. Acad. Sci. (U.S.A.) 90:1746-1750). The sequence of the HER2/neu extracellular domain (ECD) was described by Franklin, M. C. et al. (2004) "*Insights Into ErbB Signaling From The Structure Of The ErbB2-Pertuzumab Complex,*" Cancer Cell. 5(4):317-328, and is available in Protein DataBank Record 1S78 (2004).

HER2/neu functions as a growth factor receptor and is often expressed by cancer cells of breast cancer, ovarian cancer or lung cancer. HER2/neu is overexpressed in 25-30% of human breast and ovarian cancers, and its overexpression is associated with aggressive clinical progression and poor prognosis in affected patients (Slamon, D. J. et al. (1987) "*Human Breast Cancer: Correlation Of Relapse And Survival With Amplification Of The HER-2/neu Oncogene,*" Science 235:177-182; Slamon, D. J. et al. (1989) "*Studies Of The HER-2/neu Proto-Oncogene In Human Breast And Ovarian Cancer,*" Science 244:707-712). Overexpression of HER2/neu has also been observed in cancer cells of other carcinomas including carcinomas of the stomach, endometrium, salivary gland, lung, kidney, colon, thyroid, pancreas and bladder (See, e.g., King, C. R. et al. (1985) "*Amplification Of A Novel v-erbB-Related Gene In A Human Mammary Carcinoma,*" Science 229:974; McCann, A. et al. (1990) "*c-erbB-2 Oncoprotein Expression In Primary Human Tumors,*" Cancer 65:88-92; Yonemura, Y. et al. (1991) "*Evaluation Of Immunoreactivity For erbB-2 Protein As A Marker Of Poor Short Term Prognosis In Gastric Cancer*" Cancer Research 51:1034).

Activation of HER2/neu has been correlated with reduced clinical responsiveness to hormone therapy in breast cancer patients (Wright, C. et. al. (1989) "*Expression Of c-erbB-2 Oncoprotein: A Prognostic Indicator In Human Breast Cancer,*" Cancer Res. 49:2087-2090; Kurokawa, H. et al. (2001) "*Inhibition Of erbB Receptor (HER) Tyrosine Kinases As A Strategy To Abrogate Antiestrogen Resistance In Human Breast Cancer,*" Clin. Cancer Res. 7:4436s-42s, 4411s-4412s). Indeed, HER2/neu expression is sufficient to convey anti-estrogen resistance (Benz, C. C. et al. (1993) "*Estrogen-Dependent, Tamoxifen-Resistant Tumorigenic Growth Of MCF-7 Cells Transfected With HER2/neu,*" Breast Cancer Res. Treat. 24:85-95). HER2/neu, as well as HER-3, appears to be involved in the onset of hormone resistance in prostate cancer patients. Approximately one-third of prostate cancer patients receive hormone therapy treatment aimed at disrupting the action of testicular and adrenal androgens. As with breast cancer, resistance is inevitable. Recent data suggests that signals emanating from HER2/neu and HER-3 induce a "hormone-refractory" state (Mellinghoff, I. K. et al. (2004) "*HER2neu Kinase-Dependent Modulation Of Androgen Receptor Function Through Effects On DNA Binding And Stability,*" Cancer Cell 6:517-527).

Several truncated and spliced versions of HER2/neu are known. For example, a truncated ECD located in the perinuclear cytoplasm of some gastric carcinoma cells is produced by an alternative transcript generated by use of a polyadenylation signal within an intron (Yamamoto, T. et al. (1986) "*Similarity Of Protein Encoded By The Human c-erb-B-2 Gene To Epidermal Growth Factor Receptor,*" Nature 319:230-234; and Scott, G. K. et al (1993) "*A Truncated Intracellular HER2/neu Receptor Produced By Alternative RNA Processing Affects Growth Of Human Carcinoma Cells,*" Mol. Cell. Biol. 13:2247-2257). The ECD of HER2/neu can also be proteolytically shed from breast cancer cells in culture, and is found in the serum of some cancer patients and may be a serum marker of metastatic breast cancer and overall poor prognosis (Petch, L. A. et al. (1990) "*A Truncated Secreted Form Of The Epidermal Growth Factor Receptor Is Encoded By An Alternatively Spliced Transcript In Normal Rat Tissue,*" Mol. Cell. Biol. 10:2973-2982; Leitzel, K. et al. (1992) "*Elevated Soluble c-erbB-2 Antigen Levels In The Serum And Effusions Of A Proportion Of Breast Cancer Patients,*" J. Clin. Oncol. 10:1436-1443; Scott, G. K. et al. (1993) "*A Truncated Intracellular HER2/neu Receptor Produced By Alternative RNA Processing Affects Growth Of Human Carcinoma Cells,*" Mol. Cell. Biol. 13:2247-2257; and Lee, H. et al. (1998) "*Isolation And Characterization Of Four Alternate c-erbB3 Transcripts Expressed In Ovarian Carcinoma-Derived Cell Lines And Normal Human Tissues,*" Oncogene 16:3243-3252). In some HER2/neu-overexpressing cancer cells, the well-known metalloprotease activator, 4-aminophenylmercuric acetate (APMA), activates metalloproteases such as ADAM10 and ADAM15 to cleave the HER2/neu receptor into two parts: a truncated membrane-associated receptor known as p95, and a soluble ECD known as p105 or ECD105 (see, e.g., Molina, M. A. et al. (2001) "*Trastuzumab (Herceptin), A Humanized anti-Her2 Receptor Monoclonal Antibody, Inhibits Basal And Activated Her2 Ectodomain Cleavage In Breast Cancer Cells,*" Cancer Res.

61:4744-4749; U.S. Patent Publication No. 2004/0247602). Loss of the ECD renders the p95 receptor a constitutively active tyrosine kinase that can deliver growth and survival signals to cancer cells (see, e.g., U.S. Pat. No. 6,541,214).

Studies have shown that in HER2/neu-overexpressing breast cancer cells, treatment with antibodies specific to HER2/neu in combination with chemotherapeutic agents (e.g., cisplatin, doxorubicin, taxol) elicits a higher cytotoxic response than treatment with chemotherapy alone (Hancock, M. C. et al. (1991) "A Monoclonal Antibody Against The c-erbB-2 Protein Enhances The Cytotoxicity Of Cis-Diaminedichloroplatinum Against Human Breast And Ovarian Tumor Cell Lines," Cancer Res. 51:4575-4580; Arteaga, C. L. et al. (1994) "p185c-erbB-2 Signal Enhances Cisplatin-Induced Cytotoxicity In Human Breast Carcinoma Cells: Association Between An Oncogenic Receptor Tyrosine Kinase And Drug-Induced DNA Repair," Cancer 54:3758-3765; Pietras, R. J. et al. (1994) "Antibody to HER-2/neu receptor Blocks DNA Repair After Cisplatin In Hunan Breast And Ovarian Cancer Cells," Oncogene 9:1829-1838). Possible mechanisms by which HER2/neu antibodies might enhance a response to chemotherapeutic agents are through the modulation of HER2/neu protein expression or by interfering with DNA repair (Stancovski, I. et al. (1991) "Mechanistic Aspects Of The Opposing Effects Of Monoclonal Antibodies To The ERBB2Receptor On Tumor Growth," Proc. Natl. Acad. Sci. (U.S.A.) 88:8691-8695; Bacus, S. S. et al. (1992) "A Ligand For The erbB-2 Oncogene Product (gp30) Induces Differentiation Of Human Breast Cancer Cells," Cell Growth & Diff. 3:401-411; Bacus, S. S. et al. (1993) "Neu Differentiation Factor (Heregulin) Induces Expression Of Intercellular Adhesion Molecule 1: Implications For Mammary Tumors," Cancer Res. 53:5251-5261; Klapper, L. N. et al. (1997) "A Subclass Of Tumor-Inhibitory Monoclonal Antibodies To ErbB-2/HER2 Blocks Crosstalk With Growth Factor Receptors," Oncogene 14:2099-2109; Klapper, L. N. et al. (2000) "Tumor-Inhibitory Antibodies To HER-2/ErbB-2 May Act By Recruiting c-Cbl And Enhancing Ubiquitination Of HER-2," Cancer Res. 60:3384-3388; Arteaga, C. L. et al. (2001) "The Epidermal Growth Factor Receptor: From Mutant Oncogene In Nonhuman Cancers To Therapeutic Target In Human Neoplasia," J Clinical Oncology 19(18s):32s-40s).

A number of monoclonal antibodies and small molecule tyrosine kinase inhibitors targeting HER-1 or HER2/neu have been developed. For example, a murine monoclonal antibody known as Murine Antibody "4D5" recognizes an extracellular epitope (amino acids 529 to 627) in the cysteine-rich II domain of HER2/neu that resides very close to the transmembrane region. Treatment of breast cancer cells with murine 4D5 and humanized 4D5 partially blocks NDF/heregulin activation of HER2/neu-HER-3 complexes, as measured by receptor phosphorylation assays (Carter, P. et al. (1992) "Humanization Of An anti-p185HER2 Antibody For Human Cancer Therapy," Proc. Natl. Acad. Sci. (U.S.A.) 89:4285-4289; Sliwkowski, M. X. et al. (1999) "Nonclinical Studies Addressing The Mechanism Of Action Of Trastuzumab (Herceptin)," Sem. in Oncol. 26:60-70; Ye, D. et al. (1999) "Augmentation Of A Humanized anti-HER2 mAb 4D5 Induced Growth Inhibition By A Human-Mouse Chimeric anti-EGF Receptor mAb C225," Oncogene 18:731-738; Vogel, C. L. et al. (2001) "First-Line Herceptin Monotherapy In Metastatic Breast Cancer," Oncology 61(suppl 2):37-42; Vogel, C. L et al. (2002) "Efficacy And Safety Of Trastuzumab As A Single Agent In First-Line Treatment Of HER2-Overexpressing Metastatic Breast Cancer," J. Clin. Oncol. 20(3):719-726; Fujimoto-Ouchi, K. et al. (2002) "Antitumor Activity Of Combinations Of anti-HER-2 Antibody Trastuzumab And Oral Fluoropyrimidines Capecitabine/5'-Dfurd In Human Breast Cancer Models," Cancer Chemother. Pharmacol. 49:211-216). Administration of murine 4D5 to humans, however, was a clinical failure because patients quickly developed human anti-murine antibody (HAMA) responses, so humanized forms of murine 4D5 were developed. The sequence and crystal structure of humanized 4D5 antibody have been described in U.S. Pat. No. 6,054,297, Carter, P. et al. (1992) "Humanization Of An anti-p185HER2 Antibody For Human Cancer Therapy," Proc. Nat. Acad. Sci. (U.S.A.) 89:4285-4289; and Eigenbrot, C. et al. (1993) "X-ray Structures Of The Antigen-Binding Domains From Three Variants Of Humanized anti-p185HER2 Antibody 4D5 And Comparison With Molecular Modeling," J. Mol. Biol. 229:969-995.

A humanized form of Murine 4D5 Antibody known as "trastuzumab" (sold as Herceptin® by Genentech, Inc.) was developed and has been approved for treating cancers that involve the overexpression or gene amplification of HER2/neu, including breast cancer (Cobleigh, M. A. et al. (1999) "Multinational Study Of The Efficacy And Safety Of Humanized anti-HER2 Monoclonal Antibody In Women Who Have HER2-Overexpressing Metastatic Breast Cancer That Has Progressed After Chemotherapy For Metastatic Disease," J. Clin. Oncol. 17:2639-2648). Trastuzumab inhibits the APMA-mediated cleavage of HER2/neu into the ECD and p95 portions in vitro, and is believed to work in vitro through different mechanisms, including the possible inhibition of HER2/neu shedding (Pegram, M. D. et al. (1998) "Phase II Study Of Receptor-Enhanced Chemosensitivity Using Recombinant Humanized anti-p185HER2/neu Monoclonal Antibody Plus Cisplatin In Patients With HER2/neu-Overexpressing Metastatic Breast Cancer Refractory To Chemotherapy Treatment," J. Clin. Oncology 16(8):2659-2671; Baselga, J. et al. (2001) "Mechanism Of Action Of Trastuzumab And Scientific Update," Seminars in Oncology 28(5suppl. 16):4-11; Baselga, J. et al. (2001) "Mechanism Of Action Of anti-HER2 Monoclonal Antibodies," Ann. Oncol. 12 (suppl. 1):S35-S41). Trastuzumab therapy has various drawbacks, however, such as cardiotoxicity and development of human anti-humanized antibody (HAHA) responses in some patients.

New and improved forms of anti-HER2/neu antibodies for use in cancer therapies, for example engineered chimeric 4D5 antibodies having increasing affinity or specificity, reduced potential for HAMA or HAHA responses, enhanced effector functions, and the like are provided herein and have been described in PCT Publication WO 2009/123894. Such engineered 4D5 antibodies have been shown to exhibit enhanced ADCC activity against HER2/neu positive tumors, including low HER2/neu expressors, independently of the FcγR variant for the effector cells in pre-clinical studies (Nordstrom, J. L. et al. (2011) "Anti-tumor Activity And Toxicokinetics Analysis Of MGAH22, An anti-HER2 Monoclonal Antibody With Enhanced Fcγ Receptor Binding Properties," Breast Cancer Research 13(6):R123). In addition, phase I studies indicate that such antibodies are well tolerated with promising activity in patients with breast cancer and gastroesophageal cancer who have failed prior HER-2/neu therapies and in patients with HER2/neu-expressing tumors for which trastuzumab is considered ineffective (Burris, H. A. (2013) "Phase I Study Of margetuximab (MGAH22), An FC-Modified Chimeric Monoclonal Antibody (MAb), in Patients (pts)With Advanced Solid Tumors Expressing The HER2 Oncoprotein," J. Clin. Oncol. Suppl: abstr. 3004). Thus, such improved anti-HER2/neu antibodies open up new treatment options for patients whose tumors express low levels of HER2/neu or who have failed on other HER2/neu therapies.

II. Cell-Mediated Immune Responses

The immune system of humans and other mammals is responsible for providing protection against infection and disease. Such protection is provided both by a humoral immune response and by a cell-mediated immune response. The humoral response results in the production of antibodies and other biomolecules that are capable of recognizing and neutralizing foreign targets (antigens). In contrast, the cell-mediated immune response involves the activation of macrophages, natural killer cells (NK), and antigen-specific cytotoxic T-lymphocytes by T-cells, and the release of various cytokines in response to the recognition of an antigen (Dong, C. et al. (2003) "*Immune Regulation by Novel Costimulatory Molecules,*" Immunolog. Res. 28(1): 39-48).

The ability of T-cells to optimally mediate an immune response against an antigen requires two distinct signaling interactions (Viglietta, V. et al. (2007) "*Modulating Co-Stimulation,*" Neurotherapeutics 4:666-675; Korman, A. J. et al. (2007) "*Checipoint Blockade in Cancer Immunotherapy,*" Adv. Immunol. 90:297-339). First, antigen that has been arrayed on the surface of Antigen-Presenting Cells (APC) must be presented to an antigen-specific naïve CD4+ T-cell. Such presentation delivers a signal via the T-Cell Receptor (TCR) that directs the T-cell to initiate an immune response that will be specific to the presented antigen. Second, a series of costimulatory and inhibitory signals, mediated through interactions between the APC and distinct T-cell surface molecules, triggers first the activation and proliferation of the T-cells and ultimately their inhibition. Thus, the first signal confers specificity to the immune response whereas the second signal serves to determine the nature, magnitude and duration of the response.

The immune system is tightly controlled by costimulatory and co-inhibitory ligands and receptors. These molecules provide the second signal for T-cell activation and provide a balanced network of positive and negative signals to maximize immune responses against infection while limiting immunity to self (Wang, L. et al. (2011) "*VISTA, A Novel Mouse Ig Superfamily Ligand That Negatively Regulates T-Cell Responses,*" J. Exp. Med. 10.1084/jem.20100619:1-16; Lepenies, B. et al. (2008) "*The Role Of Negative Costimulators During Parasitic Infections,*" Endocrine, Metabolic & Immune Disorders—Drug Targets 8:279-288). The inhibitory pathways crucial for maintaining self-tolerance and modulating the duration and amplitude of immune responses are collectively referred to as immune checkpoints. Of particular importance is binding between the B7.1 (CD80) and B7.2 (CD86) ligands of the Antigen-Presenting Cell and the CD28 and CTLA-4 receptors of the CD4 T-lymphocyte (Sharpe, A. H. et al. (2002) "*The B7-CD28 Superfamily,*" Nature Rev. Immunol. 2:116-126; Dong, C. et al. (2003) "*Immune Regulation by Novel Costimulatory Molecules,*" Immunolog. Res. 28(1):39-48; Lindley, P. S. et al. (2009) "*The Clinical Utility Of Inhibiting CD28-Mediated Costimulation,*" Immunol. Rev. 229:307-321). Binding of B7.1 or of B7.2 to CD28 stimulates T-cell activation; binding of B7.1 or B7.2 to CTLA-4 inhibits such activation (Dong, C. et al. (2003) "*Immune Regulation by Novel Costimulatory Molecules,*" Immunolog. Res. 28(1):39-48; Lindley, P. S. et al. (2009) "*The Clinical Utility Of Inhibiting CD28-Mediated Costimulation,*" Immunol. Rev. 229:307-321; Greenwald, R. J. et al. (2005) "*The B7 Family Revisited,*" Ann. Rev. Immunol. 23:515-548). CD28 is constitutively expressed on the surface of T-cells (Gross, J., et al. (1992) "*Identification and Distribution Of The Costimulatory Receptor CD28 In The Mouse,*" J. Immunol. 149:380-388), whereas CTLA-4 expression is rapidly upregulated following T-cell activation (Linsley, P. et al. (1996) "*Intracellular Trafficking Of CTLA4 and Focal Localization Towards Sites Of TCR Engagement,*" Immunity 4:535-543). Since CTLA-4 is the higher affinity receptor (Sharpe, A. H. et al. (2002) "*The B7-CD28 Superfamily,*" Nature Rev. Immunol. 2:116-126), binding first initiates T-cell proliferation (via CD28) and then inhibits it (via nascent expression of CTLA-4), thereby dampening the effect when proliferation is no longer needed.

Further investigations into the ligands of the CD28 receptor have led to the identification and characterization of a set of related B7 molecules (the "B7 Superfamily") (Sharpe, A. H. et al. (2002) "*The B7-CD28 Superfamily,*" Nature Rev. Immunol. 2:116-126; Greenwald, R. J. et al. (2005) "*The B7 Family Revisited,*" Ann. Rev. Immunol. 23:515-548; Collins, M. et al. (2005) "*The B7 Family Of Immune-Regulatory Ligands,*" Genome Biol. 6:223.1-223.7; Loke, P. et al. (2004) "*Emerging Mechanisms Of Immune Regulation: The Extended B7 Family And Regulatory T-Cells.*" Arthritis Res. Ther. 6:208-214; Korman, A. J. et al. (2007) "*Checkpoint Blockade in Cancer Immunotherapy,*" Adv. Immunol. 90:297-339; Flies, D. B. et al. (2007) "*The New B7s: Playing a Pivotal Role in Tumor Immunity,*" J. Immunother. 30(3): 251-260; Agarwal, A. et al. (2008) "*The Role Of Positive Costimulatory Molecules In Transplantation And Tolerance,*" Curr. Opin. Organ Transplant. 13:366-372; Wang, S. et al. (2004) "*Co-Signaling Molecules Of The B7-CD28 Family In Positive And Negative Regulation Of T Lymphocyte Responses,*" Microbes Infect. 6:759-766). There are currently several known members of the family: B7.1 (CD80), B7.2 (CD86), the inducible co-stimulator ligand (ICOS-L), the programmed death-1 ligand (PD-L1; B7-H1), the programmed death-2 ligand (PD-L2; B7-DC), B7-H3, B7-H4 and B7-H6 (Collins, M. et al. (2005) "*The B7 Family Of Immune-Regulatory Ligands,*" Genome Biol. 6:223.1-223.7; Flajnik, M. F. et al. (2012) "*Evolution Of The B7 Family: Co-Evolution Of B7H6 And Nkp30, Identification Of A New B7 Family Member, B7H7, And Of B7's Historical Relationship With The MIC,*" Immunogenetics 64(8):571-90).

III. PD-1

Programmed Death-1 ("PD-1") is an approximately 31 kD type I membrane protein member of the extended CD28/CTLA-4 family of T-cell regulators that broadly negatively regulates immune responses (Ishida, Y. et al. (1992) "*Induced Expression Of PD-1, A Novel Member Of The Immunoglobulin Gene Superfamily, Upon Programmed Cell Death,*" EMBO J. 11:3887-3895; United States Patent Application Publication No. 2007/0202100; 2008/0311117; 2009/00110667; U.S. Pat. Nos. 6,808,710; 7,101,550; 7,488, 802; 7,635,757; 7,722,868; PCT Publication No. WO 01/14557).

PD-1 is expressed on activated T-cells, B-cells, and monocytes (Agata, Y. et al. (1996) "*Expression Of The PD-1 Antigen On The Surface Of Stimulated Mouse T And B Lymphocytes,*" Int. Immunol. 8(5):765-772; Yamazaki, T. et al. (2002) "*Expression Of Programmed Death 1 Ligands By Murine T-Cells And APC,*" J. Immunol. 169:5538-5545) and at low levels in natural killer (NK) T-cells (Nishimura, H. et al. (2000) "*Facilitation Of Beta Selection And Modification Of Positive Selection In The Thymus Of PD-1-Deficient Mice,*" J. Exp. Med. 191:891-898; Martin-Orozco, N. et al. (2007) "*Inhibitory Costimulation And Anti-Tumor Immunity,*" Semin. Cancer Biol. 17(4):288-298).

The extracellular region of PD-1 consists of a single immunoglobulin (Ig)V domain with 23% identity to the equivalent domain in CTLA-4 (Martin-Orozco, N. et al. (2007) "*Inhibitory Costimulation And Anti-Tumor Immunity,*" Semin. Cancer Biol. 17(4):288-298). The extracellular IgV domain is followed by a transmembrane region and an intracellular tail. The intracellular tail contains two phosphorylation sites located in an immunoreceptor tyrosine-based inhibitory motif and an immunoreceptor tyrosine-based switch motif, which suggests that PD-1 negatively regulates TCR signals (Ishida, Y. et al. (1992) "*Induced Expression Of PD-1, A Novel Member Of The Immunoglobulin Gene Superfamily, Upon Programmed Cell Death,*" EMBO J. 11:3887-3895; Blank, C. et al. (2006) "*Contribution Of The PD-L1/PD-1 Pathway To T-Cell Exhaustion: An Update On Implications For Chronic Infections And Tumor Evasion Cancer,*" Immunol. Immunother. 56(5):739-745).

PD-1 mediates its inhibition of the immune system by binding to B7-H1 and B7-DC (Flies, D. B. et al. (2007) "*The New B7s: Playing a Pivotal Role in Tumor Immunity,*" J. Immunother. 30(3):251-260; U.S. Pat. Nos. 6,803,192; 7,794,710; United States Patent Application Publication Nos. 2005/0059051; 2009/0055944; 2009/0274666; 2009/0313687; PCT Publication Nos. WO 01/39722; WO 02/086083).

B7-H1 and B7-DC are broadly expressed on the surfaces of human and murine tissues, such as heart, placenta, muscle, fetal liver, spleen, lymph nodes, and thymus as well as murine liver, lung, kidney, islets cells of the pancreas and small intestine (Martin-Orozco, N. et al. (2007) "*Inhibitory Costimulation And Anti-Tumor Immunity,*" Semin. Cancer Biol. 17(4):288-298). In humans, B7-H1 protein expression has been found in human endothelial cells (Chen, Y. et al. (2005) "*Expression of B7-H1 in Inflammatory Renal Tubular Epithelial Cells,*" Nephron. Exp. Nephrol. 102:e81-e92; de Haij, S. et al. (2005) "*Renal Tubular Epithelial Cells Modulate T-Cell Responses Via ICOS-L And B7-H1*" Kidney Int. 68:2091-2102; Mazanet, M. M. et al. (2002) "*B7-H1 Is Expressed By Human Endothelial Cells And Suppresses T-Cell Cytokine Synthesis,*" J. Immunol. 169:3581-3588), myocardium (Brown, J. A. et al. (2003) "*Blockade Of Programmed Death-1 Ligands On Dendritic Cells Enhances T-Cell Activation And Cytokine Production,*" J. Immunol. 170:1257-1266), syncyciotrophoblasts (Petroff; M. G. et al. (2002) "*B7 Family Molecules: Novel Immunomodulators At The Maternal-Fetal Interface,*" Placenta 23:S95-S101). The molecules are also expressed by resident macrophages of some tissues, by macrophages that have been activated with interferon (IFN)-γ or tumor necrosis factor (TNF)-α (Latchman, Y. et al. (2001) "*PD-L2 Is A Second Ligand For PD-1 And Inhibits T-Cell Activation,*" Nat. Immunol 2:261-268), and in tumors (Dong, H. (2003) "*B7-H1 Pathway And Its Role In The Evasion Of Tumor Immunity,*" J. Mol. Med. 81:281-287).

The interaction between B7-H1 and PD-1 has been found to provide a crucial negative costimulatory signal to T- and B-cells (Martin-Orozco, N. et al. (2007) "*Inhibitory Costimulation And Anti-Tumor Immunity,*" Semin. Cancer Biol. 17(4):288-298) and functions as a cell death inducer (Ishida, Y. et al. (1992) "*Induced Expression Of PD-1, A Novel Member Of The Immunoglobulin Gene Superfamily, Upon Programmed Cell Death,*" EMBO J. 11:3887-3895; Subudhi, S. K. et al. (2005) "*The Balance Of Immune Responses: Costimulation Verse Coinhibition,*" J. Molec. Med. 83:193-202). More specifically, interaction between low concentrations of the PD-1 receptor and the B7-H1 ligand has been found to result in the transmission of an inhibitory signal that strongly inhibits the proliferation of antigen-specific $CD8^+$ T-cells; at higher concentrations, the interactions with PD-1 do not inhibit T-cell proliferation but markedly reduce the production of multiple cytokines (Sharpe, A. H. et al. (2002) "*The B7-CD28 Superfamily,*" Nature Rev. Immunol. 2:116-126). T-cell proliferation and cytokine production by both resting and previously activated CD4 and CD8 T-cells, and even naive T-cells from umbilical-cord blood, have been found to be inhibited by soluble B7-H1-Fc fusion proteins (Freeman, G. J. et al. (2000) "*Engagement Of The PD-1 Immunoinhibitory Receptor By A Novel B7 Family Member Leads To Negative Regulation Of Lymphocyte Activation,*" J. Exp. Med. 192:1-9; Latchman, Y. et al. (2001) "*PD-L2 Is A Second Ligand For PD-1 And Inhibits T-Cell Activation,*" Nature Immunol. 2:261-268; Carter, L. et al. (2002) "*PD-1:PD-L Inhibitory Pathway Affects Both CD4(+) and CD8(+) T-cells And Is Overcome By IL-2,*" Eur. J. Immunol. 32(3):634-643; Sharpe, A. H. et al. (2002) "*The B7-CD28 Superfamily,*" Nature Rev. Immunol. 2:116-126).

The role of B7-H1 and PD-1 in inhibiting T-cell activation and proliferation has suggested that these biomolecules might serve as therapeutic targets for treatments of inflammation and cancer. Thus, the use of anti-PD-1 antibodies to treat infections and tumors and up-modulate an adaptive immune response has been proposed (see, United States Patent Application Publication Nos. 2010/0040614; 2010/0028330; 2004/0241745; 2008/0311117; 2009/0217401; U.S. Pat. Nos. 7,521,051; 7,563,869; 7,595,048; PCT Publications Nos. WO 2004/056875; WO 2008/083174). Antibodies capable of specifically binding to PD-1 have been reported by Agata, T. et al. (1996) "*Expression Of The PD-1 Antigen On The Surface Of Stimulated Mouse T And B Lymphocytes,*" Int. Immunol. 8(5):765-772; and Berger, R et al. (2008) "*Phase I Safety And Pharmacokinetic Study Of CT-011, A Humanized Antibody Interacting With PD-1, In Patients With Advanced Hematologic Malignancies,*" Clin. Cancer Res. 14(10):3044-3051 (see, also, U.S. Pat. Nos. 8,008,449 and 8,552,154; US Patent Publication Nos. 2007/0166281; 2012/0114648; 2012/0114649; 2013/0017199; 2013/0230514 and 2014/0044738; and PCT Patent Publication Nos. WO 2003/099196; WO 2004/004771; WO 2004/056875; WO 2004/072286; WO 2006/121168; WO 2007/005874; WO 2008/083174; WO 2009/014708; WO 2009/073533; WO 2012/135408, WO 2012/145549; and WO 2013/014668).

IV. HER2/neu-Expressing Cancers

Amplification or overexpression of HER2/neu occurs in approximately 25-30/of breast cancers (Mitri, Z. et al. (2012). "*The HER2 Receptor in Breast Cancer: Pathophysiology, Clinical Use, and New Advances in Therapy,*" Chemother Res Pract 2012:742193; Burstein, H. J. (2005) "*The Distinctive Nature of HER2-Positive Breast Cancers,*" N. Engl. J. Med. 353 (16): 1652-4). Overexpression is also known to occur in ovarian, stomach, and aggressive forms of uterine cancer (see for example, Yonemura, Y. et al. (1991) "*Evaluation Of Immunoreactivity For erbB-2 Protein As A Marker Of Poor Short Term Prognosis In Gastric Cancer*" Cancer Research 51:1034; Lanitis, E. (2012) "*Primary Human Ovarian Epithelial Cancer Cells Broadly Express*

HER2 At Immunologically-Detectable Levels," PloS One 7(11):e49829; and Tan, M. et al. (2007). "*Molecular Mechanisms Of erbB2-Mediated Breast Cancer Chemoresistance*," Adv. Exp. Med. Biol. 608: 119-29). As stated above, the overexpression of HER2/neu is strongly associated with increased disease recurrence and a poor prognosis. However, HER2/neu is also an important target for anti-HER2/neu drugs, including monoclonal antibodies that target the extracellular domain of the receptor, such as trastuzumab and margetuximab, and small molecule adenosine triphosphate (ATP) competitors able to block tyrosine kinase (TK) activity within the intracellular domain of HER2 target specific agents, such as lapatinib (Gandhi, M. D. et al. (2014) "*Targeted Treatment Of Head And Neck Squamous-Cell Carcinoma: Potential Of Lapatinib*," Onco. Targets Ther. 7:245-251; Opdam, F. L. et al. (2012) "*Lapatinib For Advanced Or Metastatic Breast Cancer*," Oncologist 17(4): 536-542; Liao, J. et al. (2010) "*Lapatinib: New Opportunities For Management Of Breast Cancer*," Breast Cancer (Dove Med Press) 2:79-91).

Although effective targeting of cancers overexpressing HER2/neu has improved progression-free survival (PFS) and overall survival (OS) rates, HER2/neu-expressing metastatic breast cancer remains an incurable disease. Indeed, many breast cancer patients relapse after treatment with HER2/neu targeted agents such as trastuzumab and lapatinib, indicating the presence of de novo or acquired resistance (Tan, M. et al. (2007). "*Molecular Mechanisms Of erbB2-Mediated Breast Cancer Chemoresistance*," Adv. Exp. Med. Biol. 608: 119-29; Singh et al. (2014) "*HER2-Positive Advanced Breast Cancer: Optimizing Patient Outcomes And Opportunities For Drug Development*," British Journal of Cancer 111:1888-1898; Formisano, L. et al. (2014) "*Epidermal Growth Factor-Receptor Activation Modulates Src-Dependent Resistance To Lapatinib In Breast Cancer Models*," Breast Cancer Research 16:R45). Furthermore, low HER2/neu expression can also be associated with a poor prognosis (Gilcrease M. Z. et al. (2009) "*Even Low-Level HER2 Expression May Be Associated With Worse Outcome In Node-Positive Breast Cancer*," Am J Surg Pathol. 2009 33(5):759-67). However, no HER2/neu targeted treatment therapies have been approved for patients with cancers expressing low levels of HER2/neu. These findings highlight the importance of developing improved therapies for cancers expressing HER2/neu.

Thus, despite prior advances, a need remains for improved compositions, and methods for treating cancers expressing HER2/neu, and particularly metastatic breast cancer and cancers expressing low levels of HER2/neu. The present invention is directed to such compositions and to methods for their use in the treatment of HER2/neu-positive breast cancer and other cancers expressing HER2/neu.

SUMMARY OF THE INVENTION

This invention relates to a pharmaceutical composition that comprises a first molecule that specifically binds to HER2/neu and a second molecule that specifically binds to a cell-surface receptor that is involved in regulating an immune checkpoint (or the ligand thereof). The invention particularly relates to the embodiment wherein the second molecule binds to PD-1. The invention also relates to the use of such pharmaceutical compositions to treat cancer and other diseases.

In detail, the invention provides a method of treating a cancer comprising administering to a subject in need thereof, an antibody that specifically binds HER2/neu and a molecule that specifically binds a cell-surface receptor, or a ligand thereof, that regulates an immune checkpoint.

The invention particularly concerns embodiments of such methods wherein the antibody that specifically binds HER2/neu is a "Variant Chimeric 4D5 Antibody" comprising a light chain variable domain having the amino acid sequence of SEQ ID NO:4 and a heavy chain having an amino acid sequence selected from the group consisting of SEQ ID NO:9, SEQ ID NO:11, and SEQ ID NO:13.

The invention particularly concerns the embodiment of such methods wherein the molecule that specifically binds a cell-surface receptor, or a ligand thereof, that regulates an immune checkpoint is an anti-PD-1 antibody, or an antigen-binding fragment thereof.

The invention further concerns embodiments of such methods wherein the anti-PD-1 antibody, or antigen-binding fragment thereof:
  (a) competes for PD-1 binding with nivolumab, pembrolizumab, pidilizumab, antibody EH12.2H7, antibody hPD-1 mAb 2, antibody hPD-1 mAb 7, antibody hPD-1 mAb 9, antibody hPD-1 mAb 15, or with another anti-PD-1 antibody selected from Table 1; or WO 2016/201051 PCT/US2016/03660
  (b) has the three heavy chain CDRs and the three light chain CDRs of nivolumab, pembrolizumab, pidilizumab, antibody EH12.2H7, antibody hPD-1 mAb 2, antibody hPD-1 mAb 7, antibody hPD-1 mAb 9, antibody hPD-1 mAb 15, or of another anti-PD-1 antibody selected from Table 1; or
  (c) has the heavy chain variable domain and the light chain variable domain of nivolumab, pembrolizumab, pidilizumab, antibody EH12.2H7, antibody hPD-1 mAb 2, antibody hPD-1 mAb 7, antibody hPD-1 mAb 9, antibody hPD-1 mAb 15, or of another anti-PD-1 antibody selected from Table 1.

The invention further concerns embodiments of such methods wherein the anti-PD-1 antibody, or antigen-binding fragment thereof comprises an Fc Region. The invention further concerns the embodiments of such methods wherein the Fc Region comprises one or more amino acid modifications that reduce the affinity of the variant Fc Region for FcγRIIIa (CD16A) and/or reduces ADCC activity. The invention further concerns the embodiments of such methods, wherein the modifications comprise the substitution of L234A; L235A; or L234A and L235A.

The invention further concerns embodiments of such methods wherein the anti-PD-1 antibody is nivolumab, pembrolizumab, pidilizumab, antibody EH12.2H7, antibody hPD-1 mAb 2, antibody hPD-1 mAb 7, antibody hPD-1 mAb 9, antibody hPD-1 mAb 15, or another anti-PD-1 antibody selected from Table 1. The invention further concerns embodiments of such methods wherein the antigen-binding fragment of the anti-PD-1 antibody is an antigen-binding fragment of nivolumab, pembrolizumab, pidilizumab, antibody EH12.2H7, antibody hPD-1 mAb 2, antibody hPD-1 mAb 7, antibody hPD-1 mAb 9, antibody hPD-1 mAb 15, or of another anti-PD-1 antibody selected from Table 1.

The invention additionally concerns embodiments of such methods wherein the antibody that specifically binds HER2/neu (particularly a Variant Chimeric 4D5 Antibody) is administered at a dosage of approximately 6-18 mg/kg body weight every three weeks and the molecule that specifically binds a cell-surface receptor, or ligand thereof, that regulates an immune checkpoint (particularly an anti-PD-1 antibody) is administered at a fixed dosage of approximately 200 mg every three weeks. The invention also concerns embodiments of such methods wherein the antibody that specifically binds HER2/neu (particularly a Variant Chimeric 4D5 Antibody) is administered at a dosage of approximately 6-18 mg/kg body weight every three weeks and the molecule that specifically binds a cell-surface receptor, or ligand thereof, that regulates an immune checkpoint (particularly an anti-PD-1 antibody) is administered at a dosage of approximately 1-10 mg/kg body weight every three weeks. The invention further concerns embodiments of such methods wherein the antibody that specifically binds HER2/neu (particularly a Variant Chimeric 4D5 Antibody) is administered at a dosage of approximately 6 mg/kg body weight, approximately 10 mg/kg body weight, approximately 15 mg/kg body weight, or approximately 18 mg/kg body weight every three weeks. The invention further concerns embodiments of such methods wherein the molecule that specifically binds a cell-surface receptor, or ligand thereof, that regulates an immune checkpoint (particularly an anti-PD-1 antibody) is administered at a dosage of approximately 1 mg/kg body weight, approximately 2 mg/kg body weight, approximately 3 mg/kg body weight, or approximately 10 mg/kg body weight.

The invention additionally concerns embodiments of such methods wherein the antibody that specifically binds HER2/neu (particularly a Variant Chimeric 4D5 Antibody) and the molecule that specifically binds a cell-surface receptor, or ligand thereof, that regulates an immune checkpoint (particularly an anti-PD-1 antibody) are administered concurrently to the subject in a single pharmaceutical composition.

The invention additionally concerns embodiments of such methods wherein the antibody that specifically binds HER2/neu (particularly a Variant Chimeric 4D5 Antibody) and the molecule that specifically binds a cell-surface receptor, or ligand thereof, that regulates an immune checkpoint (particularly an anti-PD-1 antibody) are administered concurrently in separate compositions such that both compositions are administered within a 24-hour period.

The invention additionally concerns embodiments of such methods wherein the antibody that specifically binds HER2/neu (particularly a Variant Chimeric 4D5 Antibody) and the molecule that specifically binds a cell-surface receptor, or ligand thereof, that regulates an immune checkpoint (particularly an anti-PD-1 antibody) are administered sequentially to the subject in separate pharmaceutical compositions, particularly wherein second administered composition is administered at least 24 hours, or more, after the administration of the first administered composition.

The invention particularly concerns embodiments of such methods wherein the cancer is a HER2/neu-expressing cancer. Invention further concerns embodiments of such methods wherein the cancer is breast cancer, gastric cancer, prostate cancer, uterine cancer, ovarian cancer, colon cancer, endometrial cancer, adrenal carcinoma, non-small cell lung cancer, head and neck cancer, laryngeal cancer, liver cancer, renal cancer, glioblastoma, or pancreatic cancer.

The invention additionally concerns embodiments of such methods further comprising the step of administering a third therapeutic agent, particularly wherein the third therapeutic agent is an anti-angiogenic agent, an anti-neoplastic agent, a chemotherapeutic agent, or a cytotoxic agent.

The invention further concerns embodiments of such methods wherein the third therapeutic agent is administered concurrently with, or separately from, the antibody that specifically binds HER2/neu (particularly a Variant Chimeric 4D5 Antibody) and/or the molecule that specifically binds a cell-surface receptor, or ligand thereof, that regulates an immune checkpoint (particularly an anti-PD-1 antibody).

The invention further concerns embodiments of such methods wherein the antibody that specifically binds HER2/neu is margetuximab and the molecule that specifically binds a cell-surface receptor, or ligand thereof, that regulates an immune checkpoint is the anti-PD-1 antibody pembrolizumab.

The invention further concerns embodiments of such methods wherein the antibody that specifically binds HER2/neu is margetuximab and the molecule that specifically binds a cell-surface receptor, or ligand thereof, that regulates an immune checkpoint is the anti-PD-1 antibody nivolumab.

The invention further concerns embodiments of such methods wherein the antibody that specifically binds HER2/neu is margetuximab and the molecule that specifically binds a cell-surface receptor, or ligand thereof, that regulates an immune checkpoint is the anti-PD-1 antibody pidilizumab.

The invention further concerns embodiments of such methods wherein the antibody that specifically binds HER2/neu is margetuximab and the molecule that specifically binds a cell-surface receptor, or ligand thereof, that regulates an immune checkpoint is the anti-PD-1 antibody EH12.2H7.

The invention further concerns embodiments of such methods wherein the antibody that specifically binds HER2/neu is margetuximab and the molecule that specifically binds a cell-surface receptor, or ligand thereof, that regulates an immune checkpoint is the anti-PD-1 antibody hPD-1 mAb 2.

The invention further concerns embodiments of such methods wherein the antibody that specifically binds HER2/neu is margetuximab and the molecule that specifically binds a cell-surface receptor, or ligand thereof, that regulates an immune checkpoint is the anti-PD-1 antibody hPD-1 mAb 7.

The invention further concerns embodiments of such methods wherein the antibody that specifically binds HER2/neu is margetuximab and the molecule that specifically binds a cell-surface receptor, or ligand thereof, that regulates an immune checkpoint is the anti-PD-1 antibody hPD-1 mAb 9.

The invention further concerns embodiments of such methods wherein the antibody that specifically binds HER2/neu is margetuximab and the molecule that specifically binds a cell-surface receptor, or ligand thereof, that regulates an immune checkpoint is the anti-PD-1 antibody hPD-1 mAb 15.

The invention further concerns embodiments of such methods wherein the antibody that specifically binds HER2/neu is margetuximab and the molecule that specifically binds a cell-surface receptor, or ligand thereof, that regulates an immune checkpoint is an anti-PD-1 antibody selected from Table 1.

Additional advantages and features of the present invention will be apparent from the following detailed description, drawings and examples, which illustrate preferred embodiments of the invention.

BRIEF DESCRIPTION OF THE DRAWINGS

FIG. 1 depicts a sequence alignment comparing the sequences of the light chain variable domain of the "Chimeric 4D5 Antibody" (SEQ ID NO:4) with the light chain variable domain of "Murine 4D5 Antibody" (SEQ ID NO:3) and the light chain variable domain of "Humanized 4D5 Antibody" (SEQ ID NO:5).

FIG. 2 depicts a comparison between the sequences of the heavy chain of a "*Chimeric 4D5 Antibody*," having a wild-type ("WT") Fc Region (SEQ ID NO:7), the heavy chain of "Variant Chimeric 4D5 Antibody MT1," which has a first variant Fc Region ("MT1") (SEQ ID NO:9), the heavy chain of "Variant Chimeric 4D5 Antibody MT2," which has a second variant Fc Region ("MT2") (SEQ ID NO:11), and the heavy chain of "Variant Chimeric 4D5 Antibody MT3," which has a third variant Fc Region ("MT3") (SEQ ID NO:13). Residues of the CDRs are indicated with black bars shown underneath such residues.

FIG. 10 (Panels A-B) depicts the results of ADCC assays performed to test the ability of Chimeric 4D5 Antibody variants of the present invention to mediate ADCC in cancer cell lines (MDA-MB-435 in Panel A; MDA-MB-231 in Panel B) having very low or no HER2/neu expression levels (DAKO score of 0).

FIG. 12 (Panels A-B) depicts the results of ADCC assays performed to test the ability of Variant Chimeric 4D5 Antibodies of the present invention to mediate ADCC in cancer cell lines (ZR75-1 in Panel A; JIMT-1 in Panel B) having moderate HER2/neu expression levels (DAKO score of 2+).

DETAILED DESCRIPTION OF THE INVENTION

Figure 3:
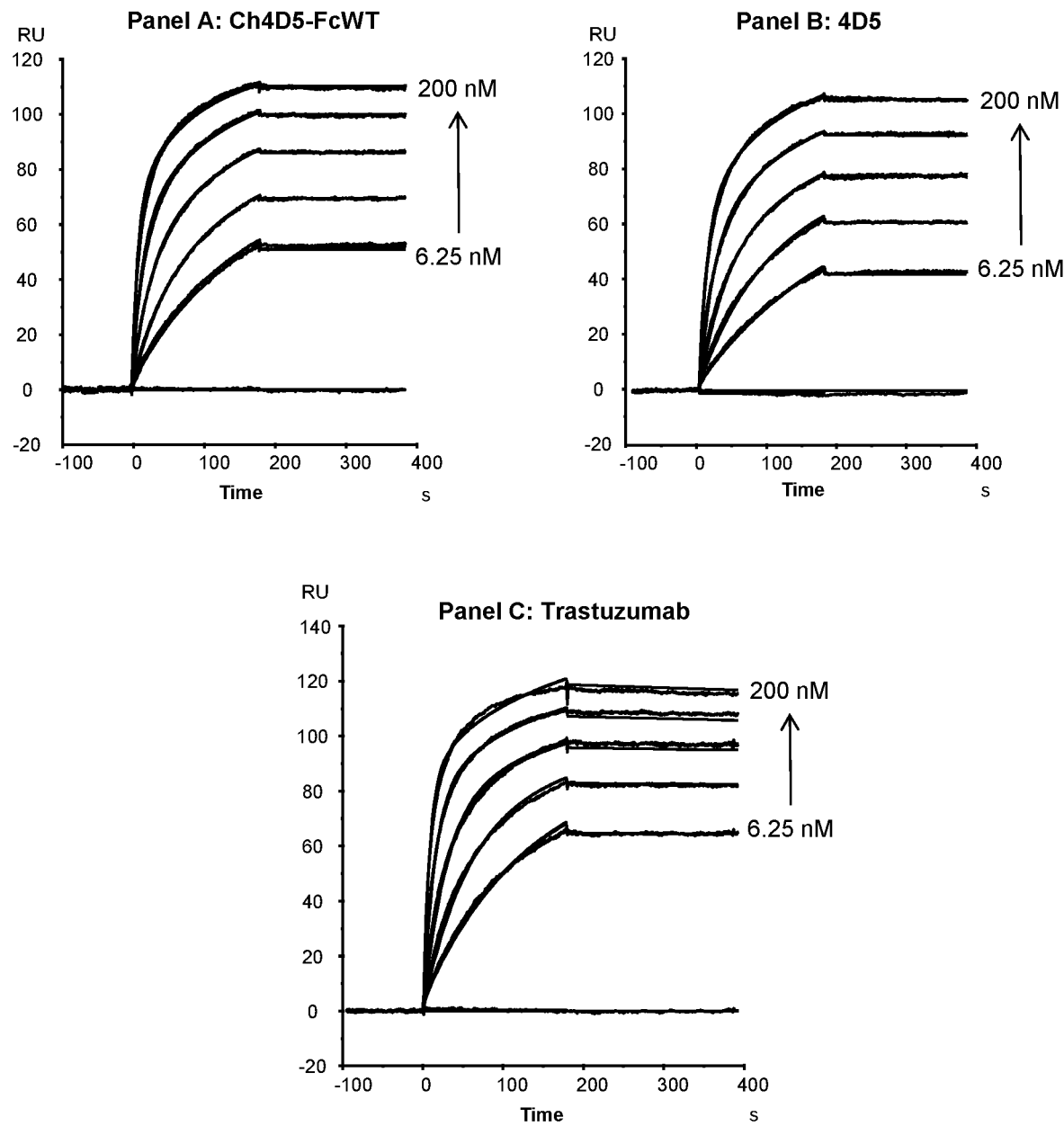
FIG. 3 (Panels A-C) depicts a BIACore® analysis of the Chimeric 4D5 Antibody having a wild-type Fc ("ch4D5-wild-type Fc") (Panel A), 4D5 (Panel B) and trastuzumab (Panel C) binding.

This invention relates to a pharmaceutical composition that comprises a first molecule that specifically binds to HER2/neu and a second molecule that specifically binds to a cell-surface receptor that is involved in regulating an immune checkpoint (or the ligand thereof). The invention particularly relates to the embodiment wherein the second molecule binds to PD-1. The invention also relates to the use of such pharmaceutical compositions to treat cancer and other diseases.

In particular, the present invention provides a pharmaceutical composition that comprises:
(I) a first antibody that specifically binds to HER2/neu so as to be useful as a selective cytotoxic agent for HER2/neu-overexpressing cells (for example, a Variant Chimeric 4D5 Antibody to HER2/neu having reduced glycosylation and altered effector functions as compared to known 4D5 antibodies); and
(II) a second antibody that specifically binds to PD-1 so as to be useful to antagonize or block PD-1/PD-L1 engagement and thereby maintain T-cell responses by preventing the delivery of a negative signal toward T-cells.

The invention also provides methods of using such compositions in the diagnosis, prognosis and therapy of diseases such as cancer.

Without being limited to any particular theory, the methods and compositions of the present invention, which combine a potent targeted anti-HER2/neu antibody with an anti-PD-1 antibody are capable of directly targeting the tumor by binding to HER2/neu on cancer cells thereby reducing/blocking NDF/heregulin activation of HER2/neu-HER-3 complexes and/or enhancing ADCC activity against HER2/neu positive tumors, and directly enhancing endogenous anti-tumor immune: responses, for example by binding to cell-surface PD-1 molecules that are present on the surfaces of exhausted and tolerant tumor-infiltrating lymphocytes, and thereby impairing the ability of such cell-surface molecules to bind to their receptor ligands and thereby promoting the activation of the immune system. These attributes permit such treatments and compositions to have utility in the treatment of cancer.

Reference will now be made in detail to the presently preferred embodiments of the invention, which, together with the drawings and the following examples, serve to explain the principles of the invention. These embodiments are described in sufficient detail to enable those skilled in the art to practice the invention, and it is to be understood that other embodiments may be utilized, and that structural, biological, and chemical changes may be made without departing from the spirit and scope of the present invention. Unless otherwise defined, all technical and scientific terms used herein have the same meaning as commonly understood by one of ordinary skill in the art to which this invention belongs.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as: MOLECULAR CLONING: A LABORATORY MANUAL, Fourth Edition (Sambrook et al Eds., 2012) Cold Spring Harbor Press, Cold Spring Harbor, N.Y.; CURRENT PROTOCOLS IN MOLECULAR BIOLOGY (Ausubel, F. M. et al., Eds., 1987) Greene Pub. Associates, New York, N.Y.; OLIGONUCLEOTIDE SYNTHESIS: METHODS AND APPLICATIONS (Methods in Molecular Biology), IMMUNOBIOLOGY 7 (Janeway, C. A. et al. 2007) Garland Science, London, UK; MONOCLONAL ANTIBODIES: A PRACTICAL APPROACH (Shepherd, P. et al Eds., 2000) Oxford University Press, USA, New York N.Y.; USING ANTIBODIES: A LABORATORY MANUAL (Harlow, E. et al. Eds., 1998) Cold Spring Harbor Laboratory Press, Cold Spring Harbor, N.Y.; and DEVITA, HELLMAN, AND ROSENBERG'S CANCER: PRINCIPLES & PRACTICE OF ONCOLOGY, EIGHTH EDTION, DeVita, V. et al. Eds. 2008, Lippincott Williams & Wilkins, Philadelphia, Pa. Antibody engineering is discussed in U.S. Provisional Patent Application Nos. 60/781,564; 60/945, 523; 61/015,106; and 61/019,051; and in US 20040185045; US 20040197347; US 20040197866; US 20050037000; US 20050064514; US 20050215767; US 20060134709; US 20060177439; US 20070004909; US 20070036799; US 20070037216; US 20070077246; US 20070244303; US 20080044429; US 20080050371; 11/869,410; 11/952,568; U.S. Pat. No. 7,112,439; WO 04/063351; WO 06/088494; WO 07/024249; WO 06/113665; WO 07/021841; WO 07/106707; and WO/2008/140603.

V. Definitions

This invention relates to the use of a pharmaceutical composition that comprises a first molecule that specifically binds to HER2/neu and a second molecule that specifically binds to a cell-surface receptor that is involved in regulating an immune checkpoint (or the ligand thereof) for the treatment of diseases such as cancer. The invention particularly relates to the embodiment wherein the second molecule binds to PD-1.

As used herein, the term "ADCC" refers to Antibody-Dependent Cellular Cytotoxicity, an in vitro cell-mediated reaction in which nonspecific cytotoxic cells that express FcγRs (e.g., monocytic cells such as natural killer (NK) cells and macrophages) recognize bound antibody on a target cell and subsequently cause lysis of the target cell.

As used herein, the term "antibody" refers to an immunoglobulin molecule capable of specific binding to a polypeptide or protein or a non-protein molecule due to the presence on such molecule of a particular domain or moiety or conformation (an "epitope"). An epitope-containing molecule may have immunogenic activity, such that it elicits an antibody production response in an animal; such molecules are termed "antigens". Epitope-containing molecules need not necessarily be immunogenic.

As used herein, the term "antibody" encompasses monoclonal antibodies, multispecific antibodies, human antibodies, humanized antibodies, synthetic antibodies, chimeric antibodies, polyclonal antibodies, camelized antibodies, single-chain Fvs (scFv), single-chain antibodies, immunologically active antibody fragments (e.g., antibody fragments capable of binding to an epitope, e.g., Fab fragments, Fab' fragments, F(ab')2 fragments, Fv fragments, fragments containing a VL and/or VH Domain, or that contain 1, 2, or 3 of the complementary determining regions (CDRs) of such VL Domain (i.e., $CDR_L1$, $CDR_L2$, and/or $CDR_L3$) or VH Domain (i.e., $CDR_H1$, $CDR_H2$, and/or $CDR_H3$)) that specifically bind an antigen, etc., bi-functional or multi-functional antibodies, disulfide-linked bispecific Fvs (sdFv), intrabodies, and diabodies, and epitope binding fragments of any of the above. In particular, the term "antibody" is intended to encompass immunoglobulin molecules and immunologically active fragments of immunoglobulin molecules, i.e., molecules that contain an antigen-binding site. Immunoglobulin molecules can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass (see, e.g., United States Patent Publication Nos.: 20040185045; 20050037000; 20050064514; 20050215767; 20070004909; 20070036799; 20070077246; and 20070244303). The last few decades have seen a revival of interest in the therapeutic potential of antibodies, and antibodies have become one of the leading classes of biotechnology-derived drugs (Chan, C. E. et al. (2009) "*The Use Of Antibodies In The Treatment Of Infectious Diseases*," Singapore Med. J. 50(7):663-666). Over 200 antibody-based drugs have been approved for use or are under development.

The term "chimeric antibody" refers to an antibody in which a portion of a heavy and/or light chain is identical to or homologous with an antibody from one species (e.g., mouse) or antibody class or subclass, while the remaining portion is identical to or homologous with an antibody of another species (e.g., human) or antibody class or subclass, so long as they exhibit the desired biological activity. Chimeric antibodies of interest herein include "primatized" antibodies comprising variable domain antigen binding sequences derived from a non-human primate (e.g., Old World Monkey, Ape, etc.) and human constant region sequences.

The term "monoclonal antibody" as used herein refers to an antibody of a population of substantially homogeneous antibodies, i.e., the individual antibodies comprising the population are identical except for possible antibodies possessing naturally occurring mutations that may be present in minor amounts, and the term "polyclonal antibody" as used herein refers to an antibody obtained from a population of heterogeneous antibodies. The term "monoclonal" indicates the character of the antibody as being a substantially homogeneous population of antibodies, and is not to be construed as requiring production of the antibody by any particular method (e.g., by hybridoma, phage selection, recombinant expression, transgenic animals, etc.). The term includes whole immunoglobulins as well as the fragments etc. described above under the definition of "antibody." Methods of making monoclonal antibodies are known in the art. One method which may be employed is the method of Kohler, G. et al. (1975) "*Continuous Cultures Of Fused Cells Secreting Antibody Of Predefined Specificity*," Nature 256:495-497 or a modification thereof. Typically, monoclonal antibodies are developed in mice, rats or rabbits. The antibodies are produced by immunizing an animal with an immunogenic amount of cells, cell extracts, or protein preparations that contain the desired epitope. The immunogen can be, but is not limited to, primary cells, cultured cell lines, cancerous cells, proteins, peptides, nucleic acids, or tissue. Cells used for immunization may be cultured for a period of time (e.g., at least 24 hours) prior to their use as an immunogen. Cells may be used as immunogens by themselves or in combination with a non-denaturing adjuvant, such as Ribi (see, e.g., Jennings, V. M. (1995) "*Review of Selected Adjuvants Used in Antibody Production*," ILAR J. 37(3):119-125). In general, cells should be kept intact and preferably viable when used as immunogens. Intact cells may allow antigens to be better detected than ruptured cells by the immunized animal. Use of denaturing or harsh adjuvants, e.g., Freud's adjuvant, may rupture cells and therefore is discouraged. The immunogen may be administered multiple times at periodic intervals such as, bi-weekly, or weekly, or may be administered in such a way as to maintain viability in the animal (e.g., in a tissue recombinant). Alternatively, existing monoclonal antibodies and any other equivalent antibodies that are specific for a desired pathogenic epitope can be sequenced and produced recombinantly by any means known in the art. In one embodiment, such an antibody is sequenced and the polynucleotide sequence is then cloned into a vector for expression or propagation. The sequence encoding the antibody of interest may be maintained in a vector in a host cell and the host cell can then be expanded and frozen for future use. The polynucleotide sequence of such antibodies may be used for genetic manipulation to generate the monospecific or multispecific (e.g., bispecific, trispecific and tetraspecific) molecules of the invention as well as an affinity optimized, a chimeric antibody, a humanized antibody, and/or a caninized antibody, to improve the affinity, or other characteristics of the antibody.

The term "humanized antibody" refers to a chimeric molecule, generally prepared using recombinant techniques, having an antigen-binding site of an immunoglobulin from a non-human species and a remaining immunoglobulin structure of the molecule that is based upon the structure and/or sequence of a human immunoglobulin. The antigen binding site may comprise either complete variable domains fused onto constant domains or only the CDRs grafted onto appropriate framework regions in the variable domains. Antigen-binding sites may be wild-type or modified by one or more amino acid substitutions. This eliminates the constant region as an immunogen in human individuals, but the possibility of an immune response to the foreign variable region remains (LoBuglio, A. F. et al (1989) "*Mouse/Human Chimeric Monoclonal Antibody In Man: Kinetics And Immune Response,*" Proc. Natl. Acad. Sci. (U.S.A.) 86:4220-4224). Another approach focuses not only on providing human-derived constant regions, but modifying the variable regions as well so as to reshape them as closely as possible to human form. It is known that the variable regions of both heavy and light chains contain three CDRs which vary in response to the antigens in question and determine binding capability, flanked by four framework regions (FRs) which are relatively conserved in a given species and which putatively provide a scaffolding for the CDRs. When non-human antibodies are prepared with respect to a particular antigen, the variable regions can be "reshaped" or "humanized" by grafting CDRs derived from a non-human antibody on the FRs present in the human antibody to be modified. Application of this approach to various antibodies has been reported by Sato, K. et al. (1993) "*Reshaping A Human Antibody To Inhibit The Interleukin 6-Dependent Tumor Cell Growth,*" Cancer Res 53:851-856. Riechmann, L. et al. (1988) "*Reshaping Human Antibodies for Therapy,*" Nature 332:323-327; Verhoeyen, M. et al. (1988) "*Reshaping Human Antibodies: Grafting An Antilysozyme Activity,*" Science 239:1534-1536; Kettleborough, C. A. et al. (1991) "*Humanization Of A Mouse Monoclonal Antibody By CDR-Grafting: The Importance Of Framework Residues On Loop Conformation,*" Protein Engineering 4:773-3783; Maeda, H. et al. (1991) "*Construction Of Reshaped Human Antibodies With HIV-Neutralizing Activity,*" Human Antibodies Hybridoma 2:124-134; Gorman, S. D. et al. (1991) "*Reshaping A Therapeutic CD4 Antibody,*" Proc. Natl. Acad. Sci. (U.S.A.) 88:4181-4185; Tempest, P. R. et al. (1991) "*Reshaping A Human Monoclonal Antibody To Inhibit Human Respiratory Syncytial Virus Infection in vivo,*" Bio/Technology 9:266-271; Co, M. S. et al. (1991) "*Humanized Antibodies For Antiviral Therapy,*" Proc. Natl. Acad. Sci. (U.S.A.) 88:2869-2873; Carter, P. et al. (1992) "*Humanization Of An Anti-p18her2 Antibody For Human Cancer Therapy,*" Proc. Natl. Acad. Sci. (U.S.A.) 89:4285-4289; and Co, M. S. et al. (1992) "*Chimeric And Humanized Antibodies With Specificity For The CD33 Antigen,*" J. Immunol. 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five or six) that are altered in their amino acid sequence(s) relative to the original antibody, which are also termed one or more CDRs "derived from" one or more CDRs from the original antibody (i.e., derived from such CDRs, derived from knowledge of the amino acid sequences of such CDRs, etc.). A polynucleotide sequence that encodes the variable domain of an antibody may be used to generate such derivatives and to improve the affinity, or other characteristics of such antibodies. The general principle in humanizing an antibody involves retaining the basic sequence of the antigen-binding site of the antibody, while swapping the non-human remainder of the antibody with human antibody sequences. There are four general steps to humanize a monoclonal antibody. These are: (1) determining the nucleotide and predicted amino acid sequence of the starting antibody light and heavy variable domains (2) designing the humanized antibody or caninized antibody, i.e., deciding which antibody framework region to use during the humanizing or canonizing process (3) the actual humanizing or caninizing methodologies/techniques and (4) the transfection and expression of the humanized antibody. See, for example, U.S. Pat. Nos. 4,816,567; 5,807,715; 5,866,692; and 6,331,415.

Natural antibodies (such as IgG antibodies) are composed of two Light Chains complexed with two Heavy Chains. Each light chain contains a Variable Domain (VL) and a Constant Domain (CL). Each heavy chain contains a Variable Domain (VH), three Constant Domains (CH1, CH2 and CH3), and a "Hinge" Domain ("H") located between the CH1 and CH2 Domains. The basic structural unit of naturally occurring immunoglobulins (e.g., IgG) is thus a tetramer having two light chains and two heavy chains, usually expressed as a glycoprotein of about 150,000 Da. The amino-terminal ("N-terminal") portion of each chain includes a Variable Domain of about 100 to 110 or more amino acids primarily responsible for antigen recognition. The carboxy-terminal ("C-terminal") portion of each chain defines a constant region, with light chains having a single Constant Domain and heavy chains usually having three Constant Domains and a Hinge Domain. Thus, the structure of the light chains of an IgG molecule is n-VL-CL-c and the structure of the IgG heavy chains is n-VH-CH1-H-CH2-CH3-c (where n and c represent, respectively, the N-terminus and the C-terminus of the polypeptide). The ability of an antibody to bind an epitope of an antigen depends upon the presence and amino acid sequence of the antibody's VL and VH Domains. Interaction of an antibody light chain and an antibody heavy chain and, in particular, interaction of its VL and VH Domains forms one of the two antigen-binding sites of a natural antibody. Natural antibodies are capable of binding to only one epitope species (i.e., they are monospecific), although they can bind multiple copies of that species (i.e., exhibiting bivalency or multivalency). The Variable Domains of an IgG molecule consist of the complementarity determining regions (CDR), which contain the residues in contact with epitope, and non-CDR segments, referred to as framework segments (FR), which in general maintain the structure and determine the positioning of the CDR loops so as to permit such contacting (although certain framework residues may also contact antigen). Thus, the VL and VH Domains have the structure n-FR1-CDR1-FR2-CDR2-FR3-CDR3-FR4-c. Polypeptides that are (or may serve as) the first, second and third CDR of an antibody Light Chain are herein respectively designated $CDR_L1$ Domain, $CDR_L2$ Domain, and $CDR_L3$ Domain. Similarly, polypeptides that are (or may serve as) the first, second and third CDR of an antibody heavy chain are herein respectively designated $CDR_H1$ Domain, $CDR_H2$ Domain, and $CDR_H3$ Domain. Thus, the terms $CDR_L1$ Domain, $CDR_L2$ Domain, $CDR_L3$ Domain, $CDR_H1$ Domain, $CDR_H2$ Domain, and $CDR_H3$ Domain are directed to polypeptides that when incorporated into a protein cause that protein to be able to bind to a specific epitope regardless of whether such protein is an antibody having light and heavy chains or a diabody or a single-chain binding molecule (e.g., an scFv, a BiTe, etc.), or is another type of protein. Accordingly, as used herein, the term "Antigen-Binding Domain" refers to that portion of an antigen-binding molecule that is responsible for the ability of such molecule to specifically bind an epitope of an antigen. An antigen-binding fragment may contain 1, 2, 3, 4, 5 or all 6 of the CDR Domains of such antibody and, although capable of specifically binding to such epitope, may exhibit a specificity, affinity or selectivity toward such epitope that differs from that of such antibody. Preferably, however, an antigen-binding fragment will contain all 6 of the CDR Domains of such antibody. An antigen-binding fragment of an antibody may be a single polypeptide chain (e.g., an scFv), or may comprise two or more polypeptide chains, each having an amino terminus and a carboxy terminus (e.g., a diabody, a Fab fragment, an $F(ab')_2$ fragment, etc.).

As used herein, the term "diabody" refers to a complex of two or more polypeptide chains or proteins, each comprising at least one $V_L$ and one $V_H$ domain or fragment thereof, wherein both domains are comprised within a single polypeptide chain, but are separated by an intervening linker that is too short to permit their association to form an epitope binding site; thus at least two polypeptide chains or proteins are required in order to form a diabody. In certain embodiments a "diabody molecule" includes molecules comprising an "F" or a "hinge-Fc Region" of an antibody. The polypeptide chains in the complex may be the same or different, e.g., the diabody molecule may be a homo-multimer or a hetero-multimer. In specific aspects, a "diabody molecule" includes dimers or tetramers or said polypeptide chains containing both a $V_L$ and $V_H$ domain (e.g., a homodimer diabody molecule, a heterodimer diabody molecule, etc.). The individual polypeptide chains comprising the multimeric proteins may be covalently joined to at least one other peptide of the multimer by interchain disulfide bonds.

As used herein, the term "cancer" refers to a disease characterized by the presence of a neoplasm or tumor resulting from abnormal uncontrolled growth of cells (such cells being "cancer cells"). As used herein, the term cancer explicitly includes, leukemias and lymphomas. In some embodiments, the term cancer refers to a disease characterized by the presence of a benign tumor, which has remained localized. In preferred embodiments, however, the term cancer refers to a disease characterized by the presence of a malignant tumor that has invaded neighboring body structures. Such tumors may additionally possess the ability to spread to distant sites. In some embodiments, the cancer is associated with cancer cells that express a specific cancer antigen. In some aspects, the term cancer as used herein specifically refers to a cancer expressing HER2/neu. Thus, the term "HER2/neu-expressing cancer" as used herein, refers to cancers that are characterized by the presence of cancer cells that express detectable levels of HER2/neu. The cancer cells of such HER2/neu-expressing cancers may express a high level of HER2/neu or a low level of HER2/neu. A "high level of HER2/neu" as used herein refers to a cancer characterized by the presence of cancer cells that exhibit a score of 2+ or more when using a HERCEPTEST® (Dako Cytomation California Inc., Carpenteria, Calif.) classification, or a subject or patient possessing cancer cells that have been identified as overexpressing Her2/neu, for example, by fluorescence in situ hybridization (FISH). A "low level of HER2" as used herein, refers to a cancer characterized by cancer cells that exhibit a score of less than 2+(e.g., 1+) in the HERCEPTEST® (Dako Cytomation California Inc., Carpenteria, Calif.) classification. Various diagnostic/prognostic assays are available to determine the level of HER2 expression by the cancer cells of a tumor. In one aspect, HER2 overexpression can be analyzed by immunohistochemistry (IHC), e.g., by using HERCEPTEST® (Dako). Accordingly, paraffin-embedded tissue sections from a tumor biopsy can be subjected to the IHC assay and accorded a HER2 protein staining intensity criteria. Alternatively, or additionally, FISH assays such as the INFORM™ (sold by Ventana, Ariz.) or PATHVISION™ (Vysis, Ill.) can be carried out on formalin-fixed, paraffin-embedded tumor tissue to determine the extent (if any) of HER2 overexpression in the tumor.

As used herein, the terms "disorder" and "disease" are used interchangeably to refer to a condition in a subject. In particular, the term "autoimmune disease" is used interchangeably with the term "autoimmune disorder" to refer to a condition in a subject characterized by cellular, tissue and/or organ injury caused by an immunologic reaction of the subject to its own cells, tissues and/or organs. The term "inflammatory disease" is used interchangeably with the term "inflammatory disorder" to refer to a condition in a subject characterized by inflammation, preferably chronic inflammation. Autoimmune disorders may or may not be associated with inflammation. Moreover, inflammation may or may not be caused by an autoimmune disorder. Thus, certain disorders may be characterized as both an autoimmune disorder and an inflammatory disorder, whereas other disorders may be characterized as being either only an autoimmune disorder or only an inflammatory disorder. Cancer is an example of a "proliferative disorder" (i.e., a disorder that is associated with some degree of abnormal cell proliferation).

As used herein, an "effective amount" of a pharmaceutical composition is an amount sufficient to effect beneficial or desired results including, without limitation, clinical results such as shrinking the size of a tumor (in the cancer context, for example, a tumor of breast, gastric or prostate cancer), retardation of cancer cell growth, delaying the development of metastasis, decreasing a symptom resulting from the disease, increasing the quality of life of those suffering from the disease, decreasing the dose of other medications required to treat the disease, enhancing the effect of another medication such as via targeting and/or internalization, delaying the progression of the disease, and/or prolonging survival of an individual. An effective amount can be administered in one or more administrations. For purposes of this invention, an effective amount of drug, compound, or pharmaceutical composition is an amount sufficient to reduce the proliferation of (or destroy) cancer cells or to reduce and/or delay the development, or growth, of metastases of cancer cells, either directly or indirectly. In some embodiments, an effective amount of a drug, compound, or pharmaceutical composition may or may not be achieved in conjunction with another drug, compound, or pharmaceutical composition. Thus, an "effective amount" may be considered in the context of administering one or more chemotherapeutic agents, and a single agent may be considered to be given in an effective amount if, in conjunction with one or more other agents, a desirable result may be or is achieved. While individual needs vary, determination of optimal ranges of effective amounts of each component is within the skill of the art. Typical dosages are discussed below.

The term "effector activity" refers to biological activities attributable to the interaction of an antibody Fc Region with an Fc receptor or ligand. An antibody may have one or more effector functions. Non-limiting examples of antibody effector functions include ADCC, C1q binding, complement dependent cytotoxicity (CDC), down regulation of cell-surface receptors (e.g., B-cell receptor; BCR), opsonization, opsonophagocytosis, cell binding, and rosetting. Effector functions include both those that operate after the binding of an antigen and those that operate independent of antigen binding.

The term "effector cell" as used herein refers to a cell of the immune system that expresses one or more Fc receptors and mediates one or more effector functions. Effector cells include but are not limited to monocytes, macrophages, neutrophils, dendritic cells, eosinophils, mast cells, platelets, B-cells, large granular lymphocytes, Langerhans' cells, natural killer (NK) cells, and may be from any organism including but not limited to humans, mice, rats, rabbits, and monkeys.

The terms "Fc receptor" or "FcR" are used herein to describe a receptor that binds to the Fc Region of an antibody. An exemplary FcR is a native sequence human FcR. An FcR may be one which binds an IgG antibody (a gamma receptor, "FcγR") and includes receptors of the FcγRI (CD64), FcγRII (CD32), FcγRIII (CD16), and FcγRIV subclasses, including allelic variants and alternatively spliced forms of these receptors, e.g., there are at least two known FcγRII receptors, FcγRIIA and FcγRIIB. The term FcR also includes the neonatal receptor, FcRn, which is responsible for the transfer of maternal IgGs to the fetus.

The term "glycosylation site" refers to an amino acid residue or residues recognized by a mammalian cell as a location for the attachment of an oligosaccharide (i.e., carbohydrates containing two or more simple sugars linked together). Amino acid residues to which carbohydrates, such as oligosaccharides, are attached are usually asparagine (N-linkage), serine (O-linkage), and threonine (O-linkage) residues. N-linked glycosylation refers to the attachment of an oligosaccharide moiety to the side chain of an asparagine residue. O-linked glycosylation refers to the attachment of an oligosaccharide moiety to a hydroxyamino acid, e.g., serine or threonine. The molecules of the invention may comprise one or more glycosylation sites, including N-linked and O-linked glycosylation sites. Any glycosylation site for N-linked or O-linked glycosylation known in the art may be used in accordance with the instant invention. The specific sites of attachment usually have a characteristic sequence of amino acids, referred to as a "glycosylation site sequence." The glycosylation site sequence for N-linked glycosylation is: N-X-S or N-X-T, where N indicates asparagine, X can be any of the conventional amino acids other than proline, S indicates serine and T indicates threonine. The Fc Region of native human IgG has two N-linked glycosylation sites, one in each of the CH2 domains, at the asparagine at position 297 (Asn 297). Glycosylation sites may be introduced into a molecule of the invention using methods well known in the art to which this invention pertains (see for example, IN VITRO MUTAGENESIS, RECOMBINANT DNA: A SHORT COURSE, J. D. Watson, et al. W. H. Freeman and Company, New York, 1983, chapter 8, pp. 106-116, which is incorporated herein by reference in its entirety. An exemplary method for introducing a glycosylation site into a molecule of the invention may comprise: modifying or mutating an amino acid sequence of the molecule so that the desired N-X-S or N-X-T sequence is obtained. likewise, glycosylation sites may be removed by modifying or mutating an amino acid sequence of an existing glycosylation site, for example, to alter an existing N-X-S or N-X-T sequence.

As used herein, the term "Human Anti-Mouse Antibody ("HAMA") response" refers to a deleterious immunogenic response that occurs when a human immune system recognizes a murine antibody as a foreign molecule and mounts an inflammatory response against it. A HAMA response can cause toxic shock or death. Chimeric and humanized antibodies reduce the likelihood of a HAMA response by decreasing the non-human portions of administered antibodies, but there is still potential for a Human Anti-Human Antibody response ("HAHA response") immune response to such antibodies.

As used herein, the term "heterologous" nucleic acid denotes DNA, RNA, etc. that is introduced into a host cell. The nucleic acid may be derived from any of a variety of sources including genomic DNA, mRNA, cDNA, synthetic DNA and fusions- or combinations of these. The nucleic acid may include a polynucleotide from the same cell or cell type as the host or recipient cell or a polynucleotide from a different cell type, for example, from a mammal or plant, and may, optionally, include marker or selection genes, for example, antibiotic resistance genes, temperature resistance genes, etc.

As used herein, the term "immunomodulatory agent" and variations thereof refer to an agent that modulates a host's immune system. In certain embodiments, an immunomodulatory agent is an immunosuppressant agent. In certain other embodiments, an immunomodulatory agent is an immunostimulatory agent. Immunomodulatory agents include, but are not limited to, small molecules, peptides, polypeptides, fusion proteins, antibodies, inorganic molecules, mimetic agents, and organic molecules.

As used herein, a molecule (e.g., an antibody) is said to "specifically" bind a region of another molecule (i.e., an "epitope") if it reacts or associates more frequently, more rapidly, with greater duration and/or with greater affinity with that region relative to alternative regions of the molecule or alternative molecules. For example, an antibody that specifically binds to a HER2/neu epitope is an antibody that binds such HER2/neu epitope with greater affinity, avidity, more readily, and/or with greater duration than it binds to other HER2/neu epitopes or to a non-HER2/neu epitope. Likewise, an antibody that specifically binds to an epitope of PD-1 binds such epitope with greater affinity, avidity, more readily, and/or with greater duration than it binds to other PD-1 epitopes or to a non-PD-1 epitope. It is also understood by reading this definition that, for example, an antibody (or moiety or epitope) that specifically binds to a first target may or may not specifically or preferentially bind to a second target. As such, "specific" binding does not necessarily require (although it can include) exclusive binding. Generally, unless the context clearly evidences to the contrary, reference to "binding" means "specific binding." The ability of an antibody to specifically bind to an epitope of an antigen may be determined by, for example, an immunoassay.

As used herein, the term "nucleic acid molecule" include DNA molecules (e.g., cDNA or genomic DNA), RNA molecules (e.g., mRNA), combinations of DNA and RNA molecules or hybrid DNA/RNA molecules, and analogs of DNA or RNA molecules. Such analogs can be generated using, for example, nucleotide analogs, which include, but are not limited to, inosine or tritylated bases. Such analogs can also comprise DNA or RNA molecules comprising modified backbones that lend beneficial attributes to the molecules such as, for example, nuclease resistance or an increased ability to cross cellular membranes. The nucleic acids or nucleotide sequences can be single-stranded, double-stranded, may contain both single-stranded and double-stranded portions, and may contain triple-stranded portions, but preferably is double-stranded DNA.

As used herein, the term "substantial sequence identity," refers to two or more sequences or subsequences (e.g., domains) that have at least about 80% amino acid residue identity, preferably at least about 90%, or at least about 95% identity when compared and aligned for maximum correspondence. Sequence identity between two similar sequences. (e.g., antibody variable domains) can be measured by algorithms such as that of Smith, T. F. & Waterman, M. S. (1981) "*Comparison Of Biosequences,*" Adv. Appl. Math. 2:482 [local homology algorithm]; Needleman, S. B. & Wunsch, C. D. (1970) "*A General Method Applicable To The Search For Similarities In The Amino Acid Sequence Of Two Proteins,*" J. Mol. Biol. 48:443 [homology alignment algorithm], Pearson, W. R. & Lipman, D. J. (1988) "*Improved Tools For Biological Sequence Comparison,*" Proc. Natl. Acad. Sci. (U.S.A.) 85:2444 [search for similarity method]; or Altschul, S. F. et al., (1990) "*Basic Local Alignment Search Tool,*" J. Mol. Biol. 215:403-10 [BLAST algorithm]. When using any of the aforementioned algorithms, the default parameters (for Window length, gap penalty, etc.) are used. A first amino acid sequence is said to be "substantially similar" to a second amino acid sequence when the degree of sequence identity is at least about 70% identical, preferably at least about 80%, or at least about 90%, or even at least about 95%, identical. A nucleic acid sequence is said to be "substantially similar" to a second sequence when either: (1) the degree of sequence identity is at least about 70% identical, preferably at least about 80%, or at least about 90%, or even at least about 95%, identical, or (2) a nucleic acid molecule comprising that nucleic acid sequence encodes a polypeptide that is at least about 70% identical, preferably at least about 80%, or at least about 90%, or even at least about 95%, identical to the polypeptide encoded by a nucleic acid molecule comprising the second sequence. Sequences that are substantially identical are also substantially similar.

When referring to antibodies, the assignment of amino acids to each domain is in accordance with Kabat et al., SEQUENCES OF PROTEINS OF IMMUNOLOGICAL INTEREST, 5$^{th}$ Ed. (National Institutes of Health, Bethesda, Md., (1991) ("Kabat et al."), which is expressly incorporated herein by reference. Throughout the present specification, the numbering of the constant residues in an IgG heavy chain "according to Kabat" refers to the numbering of the human IgG1 EU antibody as described in Kabat et al.

The term "Murine 4D5 Antibody" refers to the murine IgG$_1$ antibody disclosed in U.S. Pat. No. 5,677,171 as ATCC CRL 10463. Murine 4D5 Antibody binds Her2/neu and has a light chain variable domain having the amino acid sequence of SEQ ID NO:3 and a heavy chain variable domain having the amino acid sequence of SEQ ID NO:47. The term "Humanized 4D5 Antibody" refers to the IgG antibody disclosed in Carter, P. et al. (1992) ("*Humanization Of An Anti-P185her2 Antibody For Human Cancer Therapy,*" Proc. Natl. Acad. Sci. (U.S.A.) 89:4285-4289). Humanized 4D5 Antibody is reported to be capable of binding Her2/neu; it has a light chain variable region having the amino acid sequence of SEQ ID NO:5 and a heavy chain variable region having the amino acid sequence of SEQ ID NO:48.

The amino acid sequence of the Light Chain Variable Domain of Murine 4D5 Antibody is (SEQ ID NO:3) (CDR$_L$1 residues are underlined):

```
DIVMTQSHKF MSTSVGDRVS ITCKASQDVN TAVAWYQQKP

GHSPKLLIYS ASFRYTGVPD RFTGNRSGTD FTFTISSVQA

EDLAVYYCQQ HYTTPPTFGG GTKLEIK
```

The amino acid sequence of the Heavy Chain Variable Domain of Murine 4D5 Antibody is SEQ ID NO:47 (CDR$_H$ residues are underlined):

```
QVQLQQSGPE LVKPGASLKL SCTASGFNIK DTYIHWVKQR

PEQGLEWIGR IYPTNGYTRY DPKFQDKATI TADTSSNTAY

LQVSRLTSED TAVYYCSRWG GDGFYAMDYW GQGASVTVSS
```

The amino acid sequence of the Light Chain Variable Domain of Humanized 4D5 Antibody is (SEQ ID NO:5) (CDR$_L$ residues are underlined):

```
DIQMTQSPSS LSASVGDRVT ITCRASQDVN TAVAWYQQKP

GKAPKLLIYS ASFLESGVPS RFSGSRSGTD FTLTISSLQP

EDFATYYCQQ HYTTPPTFGQ GTKVEIK
```

The amino acid sequence of the Heavy Chain Variable Domain of Humanized 4D5 Antibody is (SEQ ID NO:48) (CDR$_H$ residues are underlined):

```
EVQLVESGGG LVQPGGSLRL SCAASGFNIK DTYIHWVRQA

PGKGLEWVAR IYPTNGYTRY ADSVKGRFTI SADTSKNTAY

LQMNSLRAED TAVYYCSRWG GDGFYAMDVW GQGTLVTVSS
```

The term "Chimeric 4D5 Antibody" refers to an IgG antibody that binds human Her2/neu and has a light chain having the amino acid sequence of SEQ ID NO:2 and a heavy chain having a wild-type Fe Region; the amino acid sequence of the heavy chain of Chimeric 4D5 Antibody is shown in SEQ ID NO:7. A "Variant Chimeric 4D5 Antibody" is an IgG antibody that binds Her2/neu and has a light chain and/or a heavy chain whose amino acid sequence(s) differ(s) from those of Chimeric 4D5 Antibody (e.g., an IgG antibody comprising a light chain having the amino acid

VI. Binding Molecules

A. Molecules That Specifically Bind HER2/neu

Molecules that specifically bind HER2/neu that are encompassed by the present invention include anti-HER2/neu antibodies capable of specifically binding to a continuous or discontinuous (e.g., conformational) epitope of human HER2/neu. The HER2/neu antibodies used in the methods of the present invention will preferably also exhibit the ability to bind to the HER2/neu molecules of one or more non-human species, especially, murine, rodent, canine, and primate species (especially cynomolgus monkey).

Antibodies to HER2/neu are provided below. Additional desired antibodies may be made by mutating a nucleic acid molecule that encodes a polypeptide chain of such antibodies and then screening for expressed antibodies that exhibit the ability to specifically bind to Her2/neu, by isolating new antibody-secreting hybridomas elicited using HER2/neu or a peptide fragment thereof, or by other means. The human HER/2 sequence has been described Yamamoto, T. et al. (1986) "*Similarity Of Protein Encoded By The Human c-erb-B-2 Gene To Epidermal Growth Factor Receptor*," Nature 319:230-234, and the sequence is available in GenBank as accession number X03363.

The present invention particularly encompasses variants of Chimeric 4D5 Antibody, and more particularly variants of such Chimeric 4D5 Antibody that specifically bind to HER2/neu, preferably human HER2/neu and that exhibit reduced glycosylation relative to. Murine 4D5 Antibody, due to the removal of a glycosylation site in the variable domain of the light chain. In particular, the preferred chimeric antibodies of the present invention lack a glycosylation site in the variable domain of the light chain of Murine 4D5 Antibody, which in the light chain of Murine 4D5 Antibody comprises an N-R-S sequence at positions 65, 66 and 67. Preferably the antibodies have enhanced binding affinity for HER2/neu, and more preferably the Variant Chimeric 4D5 Antibodies of the present invention have enhanced effector function, or both enhanced binding affinity for HER2/neu and enhanced effector function as compared to a murine 4D5 antibody.

In a preferred embodiment, the preferred variants of Chimeric 4D5 Antibody comprise a light chain (Chimeric 4D5 light chain) having or comprising the amino acid sequence of SEQ ID NO:2.

Amino acid sequence of Chimeric 4D5 Antibody light chain (SEQ ID NO:2) (CDR$_L$1 residues are underlined):

```
DIVMTQSHKF MSTSVGDRVS ITCKASQDVN TAVAWYQQKP

GHSPKLLIYS ASFRYTGVPD RFTGSRSGTD FTFTISSVQA

EDLAVYYCQQ HYTTPPTFGG GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC
```

An exemplary nucleic acid molecule that encodes the light chain of preferred Variant Chimeric 4D5 Antibodies is SEQ ID NO:1:

```
gacatcgtga tgacccagtc ccacaagttc atgtccacct ctgtgggcga tagggtcagc atcacctgca aggccagcca ggatgtgaat actgctgtag cctggtatca gcagaaacca ggacattctc ccaaactgct gatttactcc gcatccttcc ggtacactgg agtccctgat cgcttcactg gcagcagatc tgggacagat ttcactttca ccatcagcag tgtgcaggct gaagacctgg cagtttatta ctgtcagcaa cattatacta cacctcccac cttcggaggg ggtaccaagg tggagatcaa acgtacggtg gctgcaccat ctgtcttcat cttcccgcca tctgatgagc agttgaaatc tggaactgcc tctgttgtgt gcctgctgaa taacttctat cccagagagg ccaaagtaca gtggaaggtg gataacgccc tccaatcggg taactcccag gagagtgtca cagagcagga cagcaaggac agcacctaca gcctcagcag caccctgacg ctgagcaaag cagactacga gaaacacaaa gtctacgcct gcgaagtcac ccatcagggc ctgagctcgc ccgtcacaaa gagcttcaac aggggagagt gttag
```

Antibodies having such light chain amino acid sequence have a modification at positions 65 of the V$_L$ region and as such lack an N-linked glycosylation site found in Murine 4D5 Antibody (see FIG. 1, which depicts an exemplary comparison between the V$_L$ region amino acid sequences of a Chimeric 4D5 Antibody having an N65S modification (SEQ ID NO:4), and the murine (SEQ ID NO:3) and humanized (SEQ ID NO:5) 4D5 antibodies). In another preferred embodiment, the Variant Chimeric 4D5 Antibodies of the present invention have a V$_L$ region amino acid sequence of SEQ ID NO:4.

Amino acid sequence of Chimeric 4D5 V$_L$ region (SEQ ID NO:4) (CDR$_L$ residues are underlined):

```
DIVMTQSHKF MSTSVGDRVS ITCKASQDVN TAVAWYQQKP

GHSPKLLIYS ASFRYTGVPD RFTGSRSGTD FTFTISSVQA

EDLAVYYCQQ HYTTPPTFGG GTKVEIK
```

The Chimeric 4D5 Antibody comprises a heavy chain ("Chimeric 4D5 heavy chain") that has a wild-type Fc Region (SEQ ID NO:7), which may be encoded by the nucleic acid sequence of SEQ ID NO:6. These sequences are presented below:

Amino acid Sequence of Chimeric 4D5 heavy chain having wild-type Fc Region (SEQ ID NO: 7) (CDR$_H$ residues are underlined):

```
QVQLQQSGPE LVKPGASLKL SCTASGFNIK DTYIHWVKQR

PEQGLEWIGR IYPTNGYTRY DPKFQDKATI TADTSSNTAY

LQVSRLTSED TAVYYCSRWG GDGFYAMDYW GQGASVTVSS

ASTKGPSVFP LAPSSKSTSG GTAALGCLVK DYFPEPVTVS

WNSGALTSGV HTFPAVLQSS GLYSLSSVVT VPSSSLGTQT
```

```
YICNVNHKPS NTKVDKRVEP KSCDKTHTCP PCPAPELLGG

PSVFLFPPKP KDTLMISRTP EVTCVVVDVS HEDPEVKFNW

YVDGVEVHNA KTKPREEQYN STYRVVSVLT VLHQDWLNGK

EYKCKVSNKA LPAPIEKTIS KAKGQPREPQ VYTLPPSRDE

LTKNQVSLTC LVKGFYPSDI AVEWESNGQP ENNYKTTPPV

LDSDGSFFLY SKLTVDKSRW QQGNVFSCSV MHEALHNHYT

QKSLSLSPGK
```

An exemplary nucleic acid molecule that encodes Chimeric 4D5 heavy chain having a wild-type Fc Region (SEQ ID NO: 6):

```
caggttcagc tgcagcagtc tggccctgag ctggtgaagc caggggcctc actcaagttg tcctgtacag cttctggctt caacatcaaa gacacctata tccactgggt gaaacagagg cctgaacagg gcctggaatg gattggaagg atttatccta ccaatggcta tactagatat gacccaaagt tccaggacaa ggccactatc acagcagaca catcctccaa cacagcctac ctgcaagtca gccgcctgac atctgaggac actgccgtct attactgctc ccggtgggga ggggacggct tctatgctat ggactactgg ggtcaggagg cctccgtgac cgtgagctcc gcctccacca agggcccatc ggtcttcccc ctggcaccct cctccaagag cacctctggg ggcacagcgg ccctgggctg cctggtcaag gactacttcc ccgaaccggt gacggtgtcg tggaactcag gcgccctgac cagcggcgtg cacaccttcc cggctgtcct acagtcctca ggactctact ccctcagcag cgtggtgacc gtgccctcca gcagcttggg cacccagacc tacatctgca acgtgaatca caagcccagc aacaccaagg tggacaagag agttgagccc aaatcttgtg acaaaactca cacatgccca ccgtgcccag cacctgaact cctgggggga ccgtcagtct tcctcttccc cccaaaaccc aaggacaccc tcatgatctc ccggacccct gaggtcacat gcgtggtggt ggacgtgagc cacgaagacc ctgaggtcaa gttcaactgg tacgtggacg gcgtggaggt gcataatgcc aagacaaagc cgcgggagga gcagtacaac agcacgtacc gtgtggtcag cgtcctcacc gtcctgcacc aggactggct gaatggcaag gagtacaagt gcaaggtctc caacaaagcc ctcccagccc ccatcgagaa aaccatctcc aaagccaaag ggcagccccg agaaccacag gtgtacaccc tgcccccatc ccgggatgag ctgaccaaga accaggtcag cctgacctgc ctggtcaaag gcttctatcc cagcgacatc gccgtggagt gggagagcaa tgggcagccg gagaacaact acaagaccac gcctcccgtg ctggactccg acggctcctt cttcctctac agcaagctca
```

```
ccgtggacaa gagcaggtgg cagcagggga acgtcttctc atgctccgtg atgcatgagg ctctgcacaa ccactacacg cagaagagcc tctccctgtc tccgggtaaa tga
```

In other embodiments, the invention contemplates employing a Variant Chimeric 4D5 Antibody whose heavy chain comprises a variant Fc Region, and more preferably, an "FcMT1," "FcMT2," or "FcMT3" variant Fc Region. These sequences are presented below:

Amino acid Sequence of the heavy chain of a Variant Chimeric 4D5 Antibody having the FcMT1 variant Fc Region (SEQ ED NO:9) (CDR$_H$ residues are underlined)):

```
QVQLQQSGPE LVKPGASLKL SCTASGFNIK DTYIHWVKQR

PEQGLEWIGR IYPTNGYTRY DPKFQDKATI TADTSSNTAY

LQVSRLTSED TAVYYCSRWG GDGFYAMDYW GQGASVTVSS

ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKRVEP KSCDKTHTCP PCPAPELLGG

PSVFLLPPKP KDTLMISRTP EVTCVVVDVS HEDPEVKFNW

YVDGVEVHNA KTKPPEEQYN STLRVVSILT VLHQDWLNGK

EYKCKVSNKA LPAPIEKTIS KAKGQPREPQ VYTLPPSRDE

LTKNQVSLTC LVKGFYPSDI AVEWESNGQP ENNYKTTPLV

LDSDGSFFLY SKLTVDKSRW QQGNVFSCSV MHEALHNHYT

QKSLSLSPGK
```

An exemplary nucleic acid molecule that encodes a heavy chain of a Variant Chimeric 4D5 Antibody having the FcMT1 variant Fc Region (SEQ ID NO:8):

```
caggttcagc tgcagcagtc tggccctgag ctggtgaagc caggggcctc actcaagttg tcctgtacag cttctggctt caacatcaaa gacacctata tccactgggt gaaacagagg cctgaacagg gcctggaatg gattggaagg atttatccta ccaatggcta tactagatat gacccaaagt tccaggacaa ggccactatc acagcagaca catcctccaa cacagcctac ctgcaagtca gccgcctgac atctgaggac actgccgtct attactgctc ccggtgggga ggggacggct tctatgctat ggactactgg ggtcaggagg cctccgtgac cgtgagctcc gcctccacca agggcccatc ggtcttcccc ctggcaccct cctccaagag cacctctggg ggcacagcgg ccctgggctg cctggtcaag gactacttcc ccgaaccggt gacggtgtcg tggaactcag gcgccctgac cagcggcgtg cacaccttcc cggctgtcct acagtcctca ggactctact ccctcagcag cgtggtgacc gtgccctcca gcagcttggg cacccagacc tacatctgca acgtgaatca caagcccagc aacaccaagg
```

```
tggacaagag agttgagccc aaatcttgtg acaaaactca cacatgccca ccgtgccag cacctgaact cctgggggga ccgtcagtct tcctcttacc cccaaaaccc aaggacaccc tcatgatctc ccggacccct gaggtcacat gcgtggtggt ggacgtgagc cacgaagacc ctgaggtcaa gttcaactgg tacgtggacg gcgtggaggt gcataatgcc aagacaaagc cgccggagga gcagtacaac agcacgctcc gtgtggtcag catcctcacc gtcctgcacc aggactggct gaatggcaag gagtacaagt gcaaggtctc caacaaagcc ctcccagccc ccatcgagaa aaccatctcc aaagccaaag gcagccccg agaaccacag gtgtacaccc tgcccccatc ccgggatgag ctgaccaaga accaggtcag cctgacctgc ctggtcaaag gcttctatcc cagcgacatc gccgtggagt gggagagcaa tgggcagccg gagaacaact acaagaccac gcctctcgtg ctggactccg acggctcctt cttcctctac agcaagctca ccgtggacaa gagcaggtgg cagcagggga acgtcttctc atgctccgtg atgcatgagg ctctgcacaa ccactacacg cagaagagcc tctccctgtc tccgggtaaa tga
```

Amino acid Sequence of the heavy chain of a Variant Chimeric 4D5 Antibody having the FcMT2 variant Fc Region (SEQ ID NO:11) (CDR$_H$ residues are underlined):

```
QVQLQQSGPE LVKPGASLKL SCTASGFNIK DTYIHWVKQR

PEQGLEWIGR IYPTNGYTRY DPKFQDKATI TADTSSNTAY

LQVSRLTSED TAVYYCSRWG GDGFYAMDYW GQGASVTVSS

ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKRVEP KSCDKTHTCP PCPAPELVGG

PSVFLLPPKP KDTLMISRTP EVTCVVVDVS HEDPEVKFNW

YVDGVEVHNA KTKPPEEQYN STLRVVSVLT VLHQDWLNGK

EYKCKVSNKA LPAPIEKTIS KAKGQPREPQ VYTLPPSRDE

LTKNQVSLTC LVKGFYPSDI AVEWESNGQP ENNYKTTPLV

LDSDGSFFLY SKLTVDKSRW QQGNVFSCSV MHEALHNHYT

QKSLSLSPGK
```

An exemplary nucleic acid molecule that encodes a heavy chain of a Variant Chimeric 4D5 Antibody having the FcMT2 variant Fc Region (SEQ ID NO:10):

```
caggttcagc tgcagcagtc tggccctgag ctggtgaagc caggggcctc actcaagttg tcctgtacag cttctggctt caacatcaaa gacacctata tccactgggt gaaacagagg cctgaacagg gcctggaatg gattggaagg atttatccta ccaatggcta tactagatat gacccaaagt tccaggacaa
```

```
ggccactatc acagcagaca catcctccaa cacagcctac ctgcaagtca gccgcctgac atctgaggac actgccgtct attactgctc ccggtgggga ggggacggct tctatgctat ggactactgg ggtcaggag cctccgtgac cgtgagctcc gcctccacca agggcccatc ggtcttcccc ctggcaccct cctccaagag cacctctggg ggcacagcgg ccctgggctg cctggtcaag gactacttcc ccgaaccggt gacggtgtcg tggaactcag gcgccctgac cagcggcgtg cacaccttcc cggctgtcct acagtcctca ggactctact ccctcagcag cgtggtgacc gtgccctcca gcagcttggg cacccagacc tacatctgca acgtgaatca caagcccagc aacaccaagg tggacaagag agttgagccc aaatcttgtg acaaaactca cacatgccca ccgtgccag cacctgaact cgtgggggga ccgtcagtct tcctcttacc cccaaaaccc aaggacaccc tcatgatctc ccggacccct gaggtcacat gcgtggtggt ggacgtgagc cacgaagacc ctgaggtcaa gttcaactgg tacgtggacg gcgtggaggt gcataatgcc aagacaaagc cgccggagga gcagtacaac agcacgctcc gtgtggtcag cgtcctcacc gtcctgcacc aggactggct gaatggcaag gagtacaagt gcaaggtctc caacaaagcc ctcccagccc ccatcgagaa aaccatctcc aaagccaaag gcagccccg agaaccacag gtgtacaccc tgcccccatc ccgggatgag ctgaccaaga accaggtcag cctgacctgc ctggtcaaag gcttctatcc cagcgacatc gccgtggagt gggagagcaa tgggcagccg gagaacaact acaagaccac gcctctcgtg ctggactccg acggctcctt cttcctctac agcaagctca ccgtggacaa gagcaggtgg cagcagggga acgtcttctc atgctccgtg atgcatgagg ctctgcacaa ccactacacg cagaagagcc tctccctgtc tccgggtaaa tga
```

Amino acid Sequence of the heavy chain of a Variant Chimeric 4D5 Antibody having the FcMT3 variant Fc Region (SEQ ID NO: 13) (CDR$_H$ residues are underlined):

```
QVQLQQSGPE LVKPGASLKL SCTASGFNIK DTYIHWVKQR

PEQGLEWIGR IYPTNGYTRY DPKFQDKATI TADTSSNTAY

LQVSRLTSED TAVYYCSRWG GDGFYAMDYW GQGASVTVSS

ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKRVEP KSCDKTHTCP PCPAPELLGG

PSVFLLPPKP KDTLMISRTP EVTCVVVDVS HEDPEVKFNW

YVDGVEVHNA KTKPPEEQYN STLRVVSVLT VLHQDWLNGK
```

EYKCKVSNKA LPAPIEKTIS KAKGQPREPQ VYTLPPSRDE

LTKNQVSLTC LVKGFYPSDI AVEWESNGQP ENNYKTTPPV

LDSDGSFFLY SKLTVDKSRW QQGNVFSCSV MHEALHNHYT

QKSLSLSPGK

An exemplary nucleic acid molecule that encodes a heavy chain of a Variant Chimeric 4D5 Antibody having the FcMT3 variant Fc Region (SEQ ID NO: 12):

```
caggttcagc tgcagcagtc tggccctgag ctggtgaagc caggggcctc actcaagttg tcctgtacag cttctggctt caacatcaaa gacacctata tccactgggt gaaacagagg cctgaacagg gcctggaatg gattggaagg atttatccta ccaatggcta tactagatat gacccaaagt tccaggacaa ggccactatc acagcagaca catcctccaa cacagcctac ctgcaagtca gccgcctgac atctgaggac actgccgtct attactgctc ccggtgggga ggggacggct tctatgctat ggactactgg ggtcagggag cctccgtgac cgtgagctcc gcctccacca agggcccatc ggtcttcccc ctggcaccct cctccaagag cacctctggg ggcacagcgg ccctgggctg cctggtcaag gactacttcc ccgaaccggt gacggtgtcg tggaactcag gcgccctgac cagcggcgtg cacaccttcc cggctgtcct acagtcctca ggactctact ccctcagcag cgtggtgacc gtgccctcca gcagcttggg cacccagacc tacatctgca acgtgaatca caagcccagc aacaccaagg tggacaagag agttgagccc aaatcttgtg acaaaactca cacatgccca ccgtgccag cacctgaact cctggggga ccgtcagtct tcctcttacc cccaaaaccc aaggacaccc tcatgatctc ccggacccct gaggtcacat gcgtggtggt ggacgtgagc cacgaagacc ctgaggtcaa gttcaactgg tacgtggacg gcgtggaggt gcataatgcc aagacaaagc cgccggagga gcagtacaac agcacgctcc gtgtggtcag cgtcctcacc gtcctgcacc aggactggct gaatggcaag gagtacaagt gcaaggtctc caacaaagcc ctcccagccc ccatcgagaa aaccatctcc aaagccaaag gcagccccg agaaccacag gtgtacaccc tgcccccatc ccgggatgag ctgaccaaga accaggtcag cctgacctgc ctggtcaaag gcttctatcc cagcgacatc gccgtggagt gggagagcaa tgggcagccg gagaacaact acaagaccac gcctcccgtg ctggactccg acggctcctt cttcctctac agcaagctca ccgtggacaa gagcaggtgg cagcagggga acgtcttctc atgctccgtg atgcatgagg ctctgcacaa ccactacacg cagaagagcc tctccctgtc tccgggtaaa tga
```

In one embodiment, the invention is directed to the use of a Variant Chimeric 4D5 Antibody having a heavy chain that has a modification in the Fc Region, and is encoded by the nucleic acid sequence of SEQ ID NO:8 or that comprises the amino acid sequence of SEQ ID NO:9, or is encoded by the nucleic acid sequence of SEQ ID NO:10 or comprises the amino acid sequence of SEQ ID NO:11, or is encoded by the nucleic acid sequence of SEQ ID NO:12 or comprises the amino acid sequence of SEQ ID NO:13.

In one embodiment, the invention is directed to the use of an anti-HER2/neu antibody that comprises an immunoglobulin light chain having an N65S modification in the VL Domain, and an immunoglobulin heavy chain having a modified Fc Region. Preferably, such an anti-HER2/neu antibody will be a Chimeric 4D5 Antibody or a Variant Chimeric 4D5 Antibody that comprises a light chain having the amino acid sequence of SEQ ID NO:2, and a heavy chain having an amino acid sequence selected from the group consisting of SEQ ID NO:7, SEQ ID NO:9, SEQ ID NO:11, and SEQ ID NO:13. In some embodiments, an anti-HER2/neu antibody of the invention further comprises a light chain constant domain fused to a light chain variable domain, which in some embodiments comprises at least SEQ ID NO:4. In other embodiments, the antibody is modified, a fragment, or a modified fragment.

Chimeric 4D5 antibodies were constructed in accordance with the various embodiments of the invention, to enhance binding to activating low-affinity Fc receptors, and to not alter, or only minimally increase, binding to the low-affinity inhibitor receptor CD32B (FcγRIIb). The antibodies include the following wild-type and Fc-optimized antibodies:

ch4D5-wild-type Fc, which has a light chain having an amino acid sequence of SEQ ID NO:2, and a heavy chain having an amino acid sequence of SEQ ID NO:7. ch4D5-wild-type Fc has an N65S substitution on the light chain, which results in a de-glycosylated light chain.

ch4D5-FcMT1, which has a light chain having an amino acid sequence of SEQ ID NO:2, and a heavy chain having an amino acid sequence of SEQ ID NO:9. ch4D5-FcMT1 has an N65S substitution on the light chain, which results in a de-glycosylated light chain, and F243L, R292P, Y300L, V305I, and P396L substitutions on the heavy chain (all numbered according to Kabat). ch4D5-FcMT1 exhibits a 10-fold increase in binding to human CD16A (FcγRIII-A), and binding to CD16-158$^{Phe}$ is enhanced in a proportionally greater fashion than binding to CD16-158$^{Val}$.

ch4D5-FcMT2 ("margetuximab," CAS Reg. No.: 1350624-75-7), which has a light chain having an amino acid sequence of SEQ ID NO:2, and a heavy chain having an amino acid sequence of SEQ ID NO:11. Margetuximab has an N65S substitution on the light chain, which results in a de-glycosylated light chain, and L235V, F243L, R292P, Y300L, and P396L substitutions on the heavy chain (all numbered according to Kabat). This antibody is a further refinement of the ch4D5-FcMT1 antibody, and has similar CD16A binding properties, but also has a more favorable reduction in binding to CD32B (FcγRIIB).

ch4D5-FcMT3, which has a light chain having an amino acid sequence of SEQ ID NO:2, and a heavy chain having an amino acid sequence of SEQ ID NO:13. ch4D5-FcMT3 has an N65S substitution on the light chain, which results in a de-glycosylated light chain, and F243L, R292P, and Y300L substitutions on the heavy chain (all numbered according to Kabat). This antibody is a further refinement of the ch4D5-FcMT1 antibody, and has similar CD16A binding properties, but also has a more favorable reduction in binding to CD32B (FcγRIB).

ch4D5-N297Q (also referred to herein as "ch4D5-Ag"), which has a light chain having an amino acid sequence of SEQ ID NO:2, and a heavy chain having an N297Q substitution (numbered according to Kabat).

A comparison of the heavy chain sequences of the ch4D5-wild-type Fc and the Fc-optimized variants ch4D5-FcMT1, ch4D5-FcMT2, and ch4D5-FcMT3 is shown in FIG. 2. The CDRs are indicated with black bars underneath the pertinent residues.

B. Molecules that Specifically Bind PD-1

Molecules that specifically bind PD-1 encompassed by the invention include anti-PD-1 antibodies capable of binding to a continuous or discontinuous (e.g., conformational) portion (epitope) of human PD-1. The PD-1 antibodies used in the methods of the present invention will preferably also exhibit the ability to bind to the PD-1 molecules of one or more non-human species, especially, murine, rodent, canine, and primate species.

Antibodies that are specific for PD-1 are known (see, e.g., U.S. Patent Application No. 62/198,867; U.S. Pat. Nos. 5,952,136; 7,488,802; 7,521,051; 8,008,449; 8,088,905; 8,354,509; 8,552,154; 8,779,105; 8,900,587; 9,084,776; PCT Patent Publications WO 2004/056875; WO 2006/121168; WO 2008/156712; WO 2012/135408; WO 2012/145493; WO 2013/014668; WO 2014/179664; WO 2014/194302; and WO 2015/112800). Additional desired antibodies may be made by isolating antibody-secreting hybridomas elicited using PD-1 or a peptide fragment thereof. Human PD-1 (including a 20 amino acid residue signal sequence (shown underlined) and the 268 amino acid residue mature protein) has the amino acid sequence (SEQ ID NO:14):

```
MQIPQAPWPV VWAVLQLGWR PGWFLDSPDR PWNPPTFSPA

LLVVTEGDNA TFTCSFSNTS ESFVLNWYRM SPSNQTDKLA

AFPEDRSQPG QDCRFRVTQL PNGRDFHMSV VRARRNDSGT

YLCGAISLAP KAQIKESLRA ELRVTERRAE VPTAHPSPSP

RPAGQFQTLV VGVVGGLLGS LVLLVWVLAV ICSRAARGTI

GARRTGQPLK EDPSAVPVFS VDYGELDFQW REKTPEPPVP

CVPEQTEYAT IVFPSGMGTS SPARRGSADG PRSAQPLRPE

DGHCSWPL
```

Preferred anti-PD-1 antibodies possess the $V_L$ and/or $V_H$ Domains of anti-human PD-1 monoclonal antibodies "PD-1 mAb 1" (nivolumab, CAS Reg. No.:946414-94-4, also known as 5C4, BMS-936558, ONO-4538, MDX-1106, and marketed as OPDIVO® by Bristol-Myers Squibb); "PD-1 mAb 2" (pembrolizumab, (formerly known as lambrolizumab), CAS Reg. No.:1374853-91-4, also known as MK-3475, SCH-900475, and marketed as KEYTRUDA® by Merck); "PD-1 mAb 3" (EH12.2H7; Dana Farber); "PD-1 mAb 4" (pidilizumab, CAS Reg. No.: 1036730-42-3 also known as CT-011, CureTech); or any of the anti-PD-1 antibodies provided in Table 1; and more preferably possess 1, 2 or all 3 of the CDRs of the $V_L$ Region and/or 1, 2 or all 3 of the CDRs of the $V_H$ Domain of such anti-PD-1 monoclonal antibodies. Additional anti-PD-1 antibodies possessing unique binding characteristics useful in the methods and compositions of the instant inventions have recently been identified (see, U.S. Patent Application No. 62/198, 867). Particularly, preferred are PD-1-binding molecules which possess a humanized VH and/or VL Domain of the anti-PD-1 antibody "PD-1 mAb 5" (hPD-1 mAb 2, Macro-Genics); "PD-1 mAb 6" (hPD-1 mAb 7, MacroGenics); "PD-1 mAb 7" (hPD-1 mAb 9, MacroGenics); "PD-1 mAb 8" (hPD-1 mAb 15, MacroGenics); and more preferably possess 1, 2 or all 3 of the CDRs of the $V_L$ Region and/or 1, 2 or all 3 of the CDRs of the $V_H$ Domain of such anti-PD-1 monoclonal antibodies. Such preferred anti-PD-1 antibodies include antibodies having variant Fc Regions, bispecific (or multispecific) antibodies, chimeric or humanized antibodies, BiTes, diabodies, etc.

Amino acid sequence of the heavy chain variable domain of PD-1 mAb 1 (SEQ ID NO:15) ($CDR_H$ residues are underlined):

```
QVQLVESGGG VVQPGRSLRL DCKASGITFS NSGMHWVRQA

PGKGLEWVAV IWYDGSKRYY ADSVKGRFTI SRDNSKNTLF

LQMNSLRAED TAVYYCATND DYWGQGTLVT VSS
```

$CDR_H1$ of PD-1 mAb 1 (SEQ ID NO:16)

NSGMH $CDR_H2$ of PD-1 mAb 1 (SEQ ID NO:17)

VIWYDGSKRYYADSVKG $CDR_H3$ of PD-1 mAb 1 (SEQ ID NO:18)

NDDY

Amino acid sequence of the light chain variable domain of PD-1 mAb 1 (SEQ ID NO:19 $CDR_L1$ residues are underlined):

```
EIVLTQSPAT LSLSPGERAT LSCRASQSVS SYLAWYQQKP

GQAPRLLIYD ASNRATGIPA RFSGSGSGTD FTLTISSLEP

EDFAVYYCQQ SSNWPRTFGQ GTKVEIK
```

$CDR_L1$ of PD-1 mAb 1 (SEQ ID NO:20)

RASQSVSSYLA $CDR_L2$ of PD-1 mAb 1 (SEQ ID NO:21)

DASNRAT $CDR_L3$ of PD-1 mAb 1 (SEQ ID NO:22)

QQSSNWPRT

Amino acid sequence of the heavy chain variable domain of PD-1 mAb 2 (SEQ ID NO:23) ($CDR_H$ residues are underlined):

```
QVQLVQSGVE VKKPGASVKV SCKASGYTFT NYYMYWVRQA

PGQGLEWMGG INPSNGGTNF NEKFKNRVTL TTDSSTTTAY

MELKSLQFDD TAVYYCARRD YRFDMGFDYW GQGTTVTVSS
```

CDR$_H$1 of PD-1 mAb 2 (SEQ ID NO:24)

NYYMY

CDR$_H$2 of PD-1 mAb 2 (SEQ ID NO:25)

GINPSNGGTNFNEKFKN

CDR$_H$3 of PD-1 mAb 2 (SEQ ID NO:26)

RDYRFDMGFDY

Amino acid sequence of the light chain variable domain of PD-1 mAb 2 (SEQ ID NO:27) (CDR$_L$1 residues are underlined):

```
EIVLTQSPAT LSLSPGERAT LSCRASKGVS TSGYSYLHWY

QQKPGQAPRL LIYLASYLES GVPARFSGSG SGTDFTLTIS

SLEPEDFAVY YCQHSRDLPL TFGGGTKVEIK
```

CDR$_L$1 of PD-1 mAb 2 (SEQ ID NO:28)

RASKGVSTSGYSYLH

CDR$_L$2 of PD-1 mAb 2 (SEQ ID NO:29)

LASYLES

CDR$_L$3 of PD-1 mAb 2 (SEQ ID NO:30)

QHSRDLPLT

Amino acid sequence of the heavy chain variable domain of PD-1 mAb 3 (SEQ ID NO:31) (CDR$_H$ residues are underlined):

```
QVQLQQSGAE LAKPGASVQM SCKASGYSFT SSWIHWVKQR

PGQGLEWIGY IYPSTGFTEY NQKFKDKATL TADKSSSTAY

MQLSSLTSED SAVYYCARWR DSSGYHAMDY WGQGTSVTVSS
```

CDR$_H$1 of PD-1 mAb 3 (SEQ ID NO:32)

SSWIH

CDR$_H$2 of PD-1 mAb 3 (SEQ ID NO:33)

YIYPSTGFTEYNQKFKD

CDR$_H$3 of PD-1 mAb 3 (SEQ ID NO:34)

RWRDSSGYHAMDY

Amino acid sequence of the light chain variable domain of PD-1 mAb 3 (SEQ ID NO:35) (CDR$_L$ residues are underlined):

```
DIVLTQSPAS LTVSLGQRAT ISCRASQSVS TSGYSYMHWY

QQKPGQPPKL LIKFGSNLES GIPARFSGSG SGTDFTLNIH

PVEEEDTATY YCQHSWEIPY TFGGGTKLEI K
```

CDR$_L$1 of PD-1 mAb 3 (SEQ ID NO:36)

RASQSVSTSGYSYMH

CDR$_L$2 of PD-1 mAb 3 (SEQ ID NO:37)

FGSNLES

CDR$_L$3 of PD-1 mAb 3 (SEQ ID NO:38)

QHSWEIPYT

Amino acid sequence of the heavy chain variable domain of PD-1 mAb 4 (SEQ ID NO:39) (CDR$_H$ residues are underlined):

```
QVQLVQSGSE LKKPGASVKI SCKASGYTFT NYGMNWVRQA

PGQGLQWMGW INTDSGESTY AEEFKGRFVF SLDTSVNTAY

LQITSLTAED TGMYFCVRVG YDALDYWGQG TLVTVSS
```

CDR$_H$1 of PD-1 mAb 4 (SEQ ID NO:40)

NYGMN

CDR$_H$2 of PD-1 mAb 4 (SEQ ID NO:41)

WINTDSGESTYAEEFKG

CDR$_H$3 of PD-1 mAb 4 (SEQ ID NO:42)

VGYDALDY

Amino acid sequence of the light chain variable domain of PD-1 mAb 4 (SEQ ID NO:43) (CDR$_L$ residues are underlined):

```
EIVLTQSPSS LSASVGDRVT ITCSARSSVS YMHWFQQKPG

KAPKLWIYRT SNLASGVPSR FSGSGSGTSY CLTINSLQPE

DFATYYCQQR SSFPLTFGGG TKLEIK
```

CDR$_L$1 of PD-1 mAb 4 (SEQ ID NO:44)

SARSSVSYMH

CDR$_L$2 of PD-1 mAb 4 (SEQ ID NO:45)

RTSNLAS

CDR$_L$3 of PD-1 mAb 4 (SEQ ID NO:46)

QQRSSFPLT

Amino acid sequence of the heavy chain variable domain of PD-1 mAb 5 (SEQ ID NO:53) (CDR$_H$ residues are underlined):

EVQLVESGGG LVQPGGSLRL SCAASGFVFS SFGMHWVRQA
PGKGLEWVAY ISSGSMSIS ADTVKGRFTI SRDNAKNTLY
LQMNSLRTED TALYYCASLS DYFDYWGQGT TVTVSS

CDR$_H$1 of PD-1 mAb 5 (SEQ ID NO:54)

SFGMH

CDR$_H$2 of PD-1 mAb 5 (SEQ ID NO:55)

YISSGSMSISYADTVKG

CDR$_H$3 of PD-1 mAb 5 (SEQ ID NO:56)

LSDYFDY

Amino acid sequence of the light chain variable domain of PD-1 mAb 5 (SEQ ID NO:57) (CDR$_L$1 residues are underlined):

DVVMTQSPLS LPVTLGQPAS ISCRSSQSLV HSTGNTYLHW
YLQKPGQSPQ LLIYRVSNRF SGVPDRFSGS GSGTDFTLKI
SRVEAEDVGV YYCSQTTHVP WTFGQGTKLE IK

CDR$_L$1 of PD-1 mAb 5 (SEQ ID NO:58)

RSSQSLVHSTGNTYLH

CDR$_L$2 of PD-1 mAb 5 (SEQ ID NO:59)

RVSNRFS

CDR$_L$3 of PD-1 mAb 5 (SEQ ID NO:60)

SQTTHVPWT

Amino acid sequence of the heavy chain variable domain of PD-1 mAb 6 (SEQ ID NO:61 (CDR$_H$ residues are underlined):

QVQLVQSGAE VKKPGASVKV SCKASGYSFT SYWMNWVRQA
PGQGLEWXGV IHPSDSETWL DQKFKDRVTI TVDKSTSTAY
MELSSLRSED TAVYYCAREH YGTSPFAYWG QGTLVTVSS wherein X is I or A CDR$_H$1 of PD-1 mAb 6 (SEQ ID NO:62)

SYWMN

CDR$_H$2 of PD-1 mAb 6 (SEQ ID NO:63)

VIHPSDSETWLDQKFKD

CDR$_H$3 of PD-1 mAb 6 (SEQ ID NO:64)

EHYGTSPFAY

Amino acid sequence of the light chain variable domain of PD-1 mAb 6 (SEQ ID NO:65) (CDR$_L$1 residues are underlined):

EIVLTQSPAT LSLSPGERAT LSCRAX$_1$ESVD NYGMSFMNWF
QQKPGQPPKL LIHAASNX$_2$GS GVPSRFSGSG SGTDFTLTIS
SLEPEDFAVY FCQQSKEVPY TFGGGTKVEI K wherein $X_1$ is N or S and $X_2$ is Q or R; or $X_1$ is N and $X_2$ is Q; or $X_1$ is S and $X_2$ is Q; or $X_1$ is S and $X_2$ is R CDR$_L$1 of PD-1 mAb 6 (SEQ ID NO:66)

RAX$_1$ESVDNYGMSFMN wherein $X_1$ is as indicated above.

CDR$_L$2 of PD-1 mAb 6 (SEQ ID NO:67)

AASNX$_2$GS wherein $X_2$ is as indicated above.

CDR$_L$3 of PD-1 mAb 6 (SEQ ID NO:68)

QQSKEVPYT

In particular embodiments PD-1 mAb 6 comprises:
(a) SEQ ID NO:61, wherein X is I; and SEQ ID NO:65, wherein $X_1$ is N and $X_2$ is Q; or
(b) SEQ ID NO:61, wherein X is I; and SEQ ID NO:65, wherein $X_1$ is S and $X_2$ is Q.

Amino acid sequence of the heavy chain variable domain of PD-1 mAb 7 (SEQ ID NO:69) (CDR$_H$ residues are underlined):

EVQLVESGGG LX$_1$RPGGSLKL SCAASGFTFS SYLVX$_2$WVRQA
PGKGLEWX$_3$AT ISGGGGNTYY SDSVKGRFTI SRDNAKNSLY
LQMNSX$_4$RAED TATYYCARYG FDGAWFAYWG QGTLVTVSS wherein $X_1$ is V or A; $X_2$ is S or G; $X_3$ is V or T; $X_4$ is L or A; $X_1$ is V, $X_2$ is S, $X_3$ is V, and $X_4$ is L; or $X_1$ is A, $X_2$ is G, $X_3$ is T, and $X_4$ is A CDR$_H$1 of PD-1 mAb 7 (SEQ ID NO:70)

SYLVX$_2$ wherein $X_2$ is as indicated above.

CDR$_H$2 of PD-1 mAb 7 (SEQ ID NO:71)

TISGGGGNTYYSDSVKG

CDR$_H$3 of PD-1 mAb 7 (SEQ ID NO:72)

YGFDGAWFAY

Amino acid sequence of the light chain variable domain of PD-1 mAb 7 (SEQ ID NO:73) (CDR$_L$1 residues are underlined):

```
DIQMTQSPSS LSASVGDRVT ITCRASENIY X₁YLAWYQQKP

GKAPKLLIYX₂ AKTLAAGVPS RFSGSGSGTD FTLTISSLQP

EDFATYYCQH HYAVPWTFGQ GTKLEIK
``` wherein $X_1$ is N or S and $X_2$ is N or D; $X_1$ is S and $X_2$ is N; or $X_1$ is N and $X_2$ is D $CDR_L 1$ of PD-1 mAb 7 (SEQ ID NO:74)

```
RASENIYX₁YLA
``` wherein $X_1$ is as indicated above.

$CDR_L 2$ of PD-1 mAb 7 (SEQ ID NO:75)

```
X₂AKTLAA
``` wherein $X_2$ is as indicated above.

$CDR_L 3$ of PD-1 mAb 7 (SEQ ID NO:76)

```
QHHYAVPWT
```

In particular embodiments PD-1 mAb 7 comprises:
(a) SEQ ID NO:69, wherein $X_1$ is V, $X_2$ is S, $X_3$ is V, and $X_4$ is L; and SEQ ID NO:73, wherein $X_1$ is S and $X_2$ is N; or
(b) SEQ ID NO:69, wherein $X_1$ is A, $X_2$ is G, $X_3$ is T, and $X_4$ is A; and SEQ ID NO:73, wherein $X_1$ is N and $X_2$ is D.

Amino acid sequence of the heavy chain variable domain of PD-1 mAb 8 (SEQ ID NO:77) ($CDR_H$ residues are underlined):

```
EVQLVESGGG LVRPGGSLRL SCAASGFTFS SYLISWVRQA

PGKGLEWVAA ISGGGADTYY ADSVKGRFTI SRDNAKNSLY

LQMNSLRAED TATYYCARRG TYAMDYWGQG TLVTVSS
```

$CDR_H 1$ of PD-1 mAb 8 (SEQ ID NO:78)

```
SYLIS
```

$CDR_H 2$ of PD-1 mAb 8 (SEQ ID NO:79)

```
AISGGGADTYYADSVKG
```

$CDR_H 3$ of PD-1 mAb 8 (SEQ ID NO:80)

```
RGTYAMDY
```

Amino acid sequence of the light chain variable domain of PD-1 mAb 8 (SEQ ID NO:81) ($CDR_L 1$ residues are underlined):

```
DIQMTQSPSS LSASVGDRVT ITCRASENIY NYLAWYQQKP

GKAPKLLIYD AKTLAAGVPS RFSGSGSGTD FTLTISSLQP

EDFATYYCQH HYAVPWTFGQ GTKLEIK
```

$CDR_L 1$ of PD-1 mAb 8 (SEQ ID NO:82)

```
RASENIYNYLA
```

$CDR_L 2$ of PD-1 mAb 8 (SEQ ID NO:83)

```
DAKTLAA
```

$CDR_L 3$ of PD-1 mAb 8 (SEQ ID NO:84)

```
QHHYAVPWT
```

TABLE 1

Additional Anti-PD-1 Antibodies

| PD-1 Antibodies | Reference |
| --- | --- |
| PD1-17; PD1-28; PD1-33; PD1-35; and PD1-F2 | U.S. Pat. No. 7,488,802; 7,521,051 8,088,905; and PCT Patent Publication WO 2004/056875 |
| 17D8; 2D3; 4H1; 5C4; 4A11; 7D3; and 5F4 | U.S. Pat. No. 8,008,449; 8,779,105; 9,084,776; and PCT Patent Publication WO 2006/121168 |
| h1PD-1.08A; hPD-1.09A; 109A; KO9A; 409A; h409A11; h409A16; h409A17; Codon optimized 109A; and Codon optimized 409A | U.S. Pat. No. 8,354,509; 8,900,587; 5,952,136; and PCT Patent Publication WO 2008/156712 |
| 1E3; 1E8; and 1H3 | U.S. Patent Publication 2014/0044738; and PCT Patent Publication WO 2012/145493 |
| 9A2; 10B11; 6E9; APE1922; APE1923; APE1924; APE1950; APE1963; and APE2058 | PCT Patent Publication WO 2014/179664 |
| GA1; GA2; GB1; GB6; GH1; A2; C7; H7; SH-A4; SH-A9; RG1H10; RG1H11; RG2H7; RG2H10; RG3E12; RG4A6; RG5D9; RG1H10-H2A-22-1S; RG1H10-H2A-27-25; RG1H10-3C; RG1H10-16C; RG1H10-17C; RG1H10-19C; RG1H10-21C; and RG1H10-23C2 | U.S. Patent Publication 2014/0356363; and PCT Patent Publication WO 2014/194302 |
| H1M7789N; H1M7799N; H1M7800N; H2M7780N; H2M7788N; H2M7790N; H2M7791N; H2M7794N; H2M7795N; H2M7796N; H2M7798N; H4H9019P; H4xH9034P2; H4xH9035P2; H4xH9037P2; H4xH9045P2; H4xH9048P2; H4H9057P2; H4H9068P2; H4xH9119P2; H4xH9120P2; H4Xh9128p2; H4Xh9135p2; H4Xh9145p2; H4Xh8992p; H4Xh8999p; and H4Xh9008p; | U.S. Patent Publication 2015/0203579; and PCT Patent Publication WO 2015/112800 |
| PD-1 mAb 1; PD-1 mAb 2; hPD-1 mAb 2; PD-1 mAb 3; PD-1 mAb 4; PD-1 mAb 5; PD-1 mAb 6; PD-1 mAb 7; hPD-1 mAb 7; PD-1 mAb 8; PD-1 mAb 9; hPD-1 mAb 9; PD-1 mAb 10; PD-1 mAb 11; PD-1 mAb 12; PD-1 mAb 13; PD-1 mAb 14; PD-1 mAb 15; and hPD-1 mAb 15 | U.S. Patent Application No. 62/198,867 |

In certain embodiments PD-1 antibodies useful in the methods and compositions of the instant inventions comprise the $V_L$ and $V_H$ Domains of any of the antibodies provided above (e.g., PD-1 mAb 1, PD-1 mAb 2, PD-1 mAb 3, PD-1 mAb 4, PD-1 mAb 5, PD-1 mAb 6, PD-1 mAb 7, PD-1 mAb 8, or any of the anti-PD-1 antibodies in Table 1), a kappa CL Domain, and an IgG4 Fc Domain, optionally lacking the C-terminal lysine residue. Such antibodies will preferably comprise an IgG4 CH1 Domain and Hinge, and more preferably comprise a stabilized IgG4 Hinge comprising an S228P substitution (wherein the numbering is according to the EU index as in Kabat).

The amino acid sequence of a kappa CL Domain (SEQ ID NO:85) is:

```
RTVAAPSVFI FPPSDEQLKS GTASVVCLLN NFYPREAKVQ
WKVDNALQSG NSQESVTEQD SKDSTYSLSS TLTLSKADYE
KHKVYACEVT HQGLSSPVTK SFNRGEC
```

The amino acid sequence of an IgG4 CH1 Domain and Stabilized Hinge (SEQ ID NO:86) is:

```
ASTKGPSVFP LAPCSRSTSE STAALGCLVK DYFPEPVTVS
WNSGALTSGV HTFPAVLQSS GLYSLSSVVT VPSSSLGTKT
YTCNVDHKPS NTKVDKRVES KYGPPCPPCP
```

The amino acid sequence of IgG4 CH2-CH3 Domains (SEQ ID NO:52) is presented below.

An exemplary anti-PD-1 antibody designated "PD-1 mAb 6-ISQ" comprises: a light chain having the VL Domain of PD-1 mAb 6 (SEQ ID NO:65) wherein $X_1$ is S and $X_2$ is Q and a kappa CL (SEQ ID NO:85); and a heavy chain having the VH Domain of PD-1 mAb 6 (SEQ ID NO:61) wherein $X_1$ is I, an IgG4 CH Domain, a stabilized IgG 4 Hinge (SEQ ID NO:86), and IgG4 CH2-CH3 Domains (SEQ ID NO:52).

The amino acid sequence of the complete light chain of PD-1 mAb 6-ISQ (SEQ ID NO:87) is shown below ($CDR_L$ residues are underlined):

```
EIVLTQSPAT LSLSPGERAT LSCRASESVD NYGMSFMNWF
QQKPGQPPKL LIHAASNQGS GVPSRFSGSG SGTDFTLTIS
SLEPEDFAVY FCQQSKEVPY TFGGGTKVEI KRTVAAPSVF
IFPPSDEQLK SGTASVVCLL NNFYPREAKV QWKVDNALQS
GNSQESVTEQ DSKDSTYSLS STLTLSKADY EKHKVYACEV
THQGLSSPVT KSFNRGEC
```

The amino acid sequence of the complete heavy chain of PD-1 mAb 6-ISQ (SEQ ID NO:88) is shown below ($CDR_H$ residues are underlined):

```
QVQLVQSGAE VKKPGASVKV SCKASGYSFT SYWMNWVRQA
PGQGLEWIGV IHPSDSETWL DQKFKDRVTI TVDKSTSTAY
MELSSLRSED TAVYYCAREH YGTSPFAYWG QGTLVTVSSA
STKGPSVFPL APCSRSTSES TAALGCLVKD YFPEPVTVSW
NSGALTSGVH TFPAVLQSSG LYSLSSVVTV PSSSLGTKTY
TCNVDHKPSN TKVDKRVESK YGPPCPPCPA PEFLGGPSVF
LFPPKPKDTL MISRTPEVTC VVVDVSQEDP EVQFNWYVDG
VEVHNAKTKP REEQFNSTYR VVSVLTVLHQ DWLNGKEYKC
KVSNKGLPSS IEKTISKAKG QPREPQVYTL PPSQEEMTKN
QVSLTCLVKG FYPSDIAVEW ESNGQPENNY KTTPPVLDSD
GSFFLYSRLT VDKSRWQEGN VFSCSVMHEA LHNHYTQKSL
SLSLG
```

Another exemplary anti-PD-1 antibody is PD-1 mAb 1 (nivolumab), which is a human antibody comprising a light chain having a VL Domain (SEQ ID NO:19) and a kappa CL Domain (see for example, SEQ ID NO:85); and a heavy chain having a VH Domain (SEQ ID NO:15), an IgG4 CH Domain and stabilized hinge (see for example, SEQ ID NO:86), and IgG4 CH2-CH3 Domains (see for example, SEQ ID NO:54).

Another exemplary anti-PD-1 antibody is PD-1 mAb 2 (pembrolizumab), which is a humanized antibody comprising a light chain having a VL Domain (SEQ ID NO:27) and a kappa CL Domain (see for example, SEQ ID NO:85); and a heavy chain having a VH Domain (SEQ ID NO:23); an IgG4 CH1 and stabilized IgG4 Hinge (see for example, SEQ ID NO:86); and IgG4 CH2-CH3 Domains (see for example, SEQ ID NO:52).

C. Antibody Variants

It is also contemplated that antibody variants can be prepared. The variants may possess sequence modifications (e.g., substitutions, deletions and/or additions) at desired positions within their amino acid sequences relative to the native amino acid sequence. Those skilled in the art will appreciate that amino acid changes may alter post-translational processes of an antibody such as changing the number or position of glycosylation sites or altering the membrane anchoring characteristics. In a preferred embodiment, the antibody and variants are Fc Region variants.

Variants may have the same or altered activity as compared to a native antibody. For example, it may be desirable that the variant have the same activity, but be modified in a manner so that it is more stable or has a longer half-life in vivo, for example by conjugating the antibody with albumin or a salvage receptor binding epitope, as described, e.g., in U.S. Pat. No. 5,739,277. Or, for example, it may be desirable that an antibody have an increased binding affinity to antigen, but the same effector function as a native antibody, or it may be desirable that an antibody have the same binding affinity to antigen, but a decreased effector function. Activity may be tested by, e.g., using in vitro assays such as ELISA assays, surface plasmon resonance assays, radiolabeled protein binding assays (RIA), or immunoprecipitation assays.

Substantial modifications in function or immunological identity may be accomplished by selecting modifications that differ significantly in their effect on maintaining: (a) the structure of the polypeptide backbone in the area of the modification, for example, as a sheet or helical conformation, (b) the charge or hydrophobicity of the molecule at the target site, or (c) the bulk of the side chain. Scanning amino acid analysis can also be employed to identify one or more amino acids along a contiguous sequence, for example as described by Cunningham and Wells (1989) Science 244: 1081-1085. Among the preferred scanning amino acids are relatively small, neutral amino acids, such as alanine, glycine, serine, and cysteine. Alanine is typically a preferred scanning amino acid among this group because it is the most common amino acid, is frequently found in both buried and exposed positions, and because it eliminates the side chain beyond the beta-carbon and is less likely to alter the main-chain conformation of the variant. If alanine substitution does not yield adequate amounts of variant, an isosteric amino acid can be used. Further, any cysteine residue not involved in maintaining the proper conformation of the antibody or polypeptide may be substituted, generally with serine, to improve the oxidative stability of the molecule and prevent aberrant crosslinking. However, in certain circumstances, particularly where the antibody is an antibody fragment such as an Fv fragment, cysteine bond(s) may be added to the antibody or polypeptide to improve its stability.

The fact that a single amino acid alteration of a CDR residue can result in loss of functional binding (Rudikoff, S. etc. (1982) "*Single Amino Acid Substitution Altering Antigen-Binding Specificity*," Proc. Natl. Acad. Sci. (USA) 79(6):1979-1983) provides a means for systematically identifying alternative functional CDR sequences. In one preferred method for obtaining such variant CDRs, a polynucleotide encoding the CDR is mutagenized (for example via random mutagenesis or by a site-directed method (e.g., polymerase chain-mediated amplification with primers that encode the mutated locus)) to produce a CDR having a substituted amino acid residue. By comparing the identity of the relevant residue in the original (functional) CDR sequence to the identity of the substituted (non-functional) variant CDR sequence, the BLOSUM62.iij substitution score for that substitution can be identified. The BLOSUM system provides a matrix of amino acid substitutions created by analyzing a database of sequences for trusted alignments (Eddy, S. R. (2004) "*Where Did The BLOSUM62 Alignment Score Matrix Come From?*," Nature Biotech. 22(8):1035-1036; Henikoff, J. G. (1992) "*Amino acid substitution matrices from protein blocks*," Proc. Natl. Acad. Sci. (USA) 89:10915-10919; Karlin, S. et al. (1990) "*Methods For Assessing The Statistical Significance Of Molecular Sequence Features By Using General Scoring Schemes*," Proc. Natl. Acad. Sci. (USA) 87:2264-2268; Altschul, S. F. (1991) "*Amino Acid Substitution Matrices From An Information Theoretic Perspective*," J. Mol. Biol. 219, 555-565. Currently, the most advanced BLOSUM database is the BLOSUM62 database (BLOSUM62.iij). Table 2 below presents the BLOSUM62.iij substitution scores (the higher the score the more conservative the substitution and thus the more likely the substitution will not affect function). If an antigen-binding fragment comprising the resultant CDR fails to bind to ROR1, for example, then the BLOSUM62.iij substitution score is deemed to be insufficiently conservative, and a new candidate substitution is selected and produced having a higher substitution score. Thus, for example, if the original residue was glutamate (E), and the non-functional substitute residue was histidine (H), then the BLOSUM62.iij substitution score will be 0, and more conservative changes (such as to aspartate, asparagine, glutamine, or lysine) are preferred.

TABLE 2

BLOSUM62.iij Substitution Scores

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | +4 | −1 | −2 | −2 | 0 | −1 | −1 | 0 | −2 | −1 | −1 | −1 | −1 | −2 | −1 | +1 | 0 | −3 | −2 | 0 |
| R | −1 | +5 | 0 | −2 | −3 | +1 | 0 | −2 | 0 | −3 | −2 | +2 | −1 | −3 | −2 | −1 | −1 | −3 | −2 | −3 |
| N | −2 | 0 | +6 | +1 | −3 | 0 | 0 | 0 | +1 | −3 | −3 | 0 | −2 | −3 | −2 | +1 | 0 | −4 | −2 | −3 |
| D | −2 | −2 | +1 | +6 | −3 | 0 | +2 | −1 | −1 | −3 | −4 | −1 | −3 | −3 | −1 | 0 | −1 | −4 | −3 | −3 |
| C | 0 | −3 | −3 | −3 | +9 | −3 | −4 | −3 | −3 | −1 | −1 | −3 | −1 | −2 | −3 | −1 | −1 | −2 | −2 | −1 |
| Q | −1 | +1 | 0 | 0 | −3 | +5 | +2 | −2 | 0 | −3 | −2 | +1 | 0 | −3 | −1 | 0 | −1 | −2 | −1 | −2 |
| E | −1 | 0 | 0 | +2 | −4 | +2 | +5 | −2 | 0 | −3 | −3 | +1 | −2 | −3 | −1 | 0 | −1 | −3 | −2 | −2 |
| G | 0 | −2 | 0 | −1 | −3 | −2 | −2 | +6 | −2 | −4 | −4 | −2 | −3 | −3 | −2 | 0 | −2 | −2 | −3 | −3 |
| H | −2 | 0 | +1 | −1 | −3 | 0 | 0 | −2 | +8 | −3 | −3 | −1 | −2 | −1 | −2 | −1 | −2 | −2 | +2 | −3 |
| I | −1 | −3 | −3 | −3 | −1 | −3 | −3 | −4 | −3 | +4 | +2 | −3 | +1 | 0 | −3 | −2 | −1 | −3 | −1 | +3 |
| L | −1 | −2 | −3 | −4 | −1 | −2 | −3 | −4 | −3 | +2 | +4 | −2 | +2 | 0 | −3 | −2 | −1 | −2 | −1 | +1 |
| K | −1 | +2 | 0 | −1 | −3 | +1 | +1 | −2 | −1 | −3 | −2 | +5 | −1 | −3 | −1 | 0 | −1 | −3 | −2 | −2 |
| M | −1 | −1 | −2 | −3 | −1 | 0 | −2 | −3 | −2 | +1 | +2 | −1 | +5 | 0 | −2 | −1 | −1 | −1 | −1 | +1 |
| F | −2 | −3 | −3 | −3 | −2 | −3 | −3 | −3 | −1 | 0 | 0 | −3 | 0 | +6 | −4 | −2 | −2 | +1 | +3 | −1 |
| P | −1 | −2 | −2 | −1 | −3 | −1 | −1 | −2 | −2 | −3 | −3 | −1 | −2 | −4 | +7 | −1 | −1 | −4 | −3 | −2 |
| S | +1 | −1 | +1 | 0 | −1 | 0 | 0 | 0 | −1 | −2 | −2 | 0 | −1 | −2 | −1 | +4 | +1 | −3 | −2 | −2 |
| T | 0 | −1 | 0 | −1 | −1 | −1 | −1 | −2 | −2 | −1 | −1 | −1 | −1 | −2 | −1 | +1 | +5 | −2 | −2 | 0 |
| W | −3 | −3 | −4 | −4 | −2 | −2 | −3 | −2 | −2 | −3 | −2 | −3 | −1 | +1 | −4 | −3 | −2 | +11 | +2 | −3 |
| Y | −2 | −2 | −2 | −3 | −2 | −1 | −2 | −3 | +2 | −1 | −1 | −2 | −1 | +3 | −3 | −2 | −2 | +2 | +7 | −1 |
| V | 0 | −3 | −3 | −3 | −1 | −2 | −2 | −3 | −3 | +3 | +1 | −2 | +1 | −1 | −2 | −2 | 0 | −3 | −1 | +4 |

The invention thus contemplates the use of guided or random mutagenesis to identify improved CDRs.

D. Fc Region Variants

In traditional immune function, the interaction of antibody-antigen complexes with cells of the immune system results in a wide array of responses, ranging from effector functions such as ADCC, mast cell degranulation, and phagocytosis to immunomodulatory signals such as regulating lymphocyte proliferation and antibody secretion. All of these interactions are initiated through the binding of the Fc Region of antibodies or immune complexes to specialized cell-surface receptors on hematopoietic cells. The diversity of cellular responses triggered by antibodies and immune complexes results from the structural heterogeneity of the three Fc receptors: FcγRI (CD64), FcγRII (CD32), and FcγRIII (CD16). FcγRI (CD64), FcγRIIA (CD32A) and FcγRIII (CD16) are activating (i.e., immune system enhancing) receptors; FcγRIIB (CD32B) is an inhibiting (i.e., immune system dampening) receptor.

The amino acid sequence of the IgG1 Fc Region is shown below (as SEQ ID NO:49, numbered according to Kabat):

```
231        240        250        260        270        280
APELLGGPSV FLFPPKPKDT LMISRTPEVT CVVVDVSHED PEVKFNWYVD 290        300        310        320        330
GVEVHNAKTK PREEQYNSTY RVVSVLTVLH QDWLNGKEYK CKVSNKALPA 340        350        360        370        380
PIEKTISKAK GQPREPQVYT LPPSREEMTK NQVSLTCLVK GFYPSDIAVE 390        400        410        420        430
WESNGQPENN YKTTPPVLDS DGSFFLYSKL TVDKSRWQQG NVFSCSVMHE 440        447
ALHNHYTQKS LSLSPGX
``` as numbered by the EU index according to Kabat, wherein, X is a lysine (K) or is absent.

The amino acid sequence of the CH2-CH3 domain of an exemplary human IgG2 is (SEQ ID NO:50):

```
231        240        250        260        270        280
APPVA-GPSV FLFPPKPKDT LMISRTPEVT CVVVDVSHED PEVQFNWYVD 290        300        310        320        330
GVEVHNAKTK PREEQFNSTF RVVSVLTVVH QDWLNGKEYK CKVSNKGLPA 340        350        360        370        380
PIEKTISKTK GQPREPQVYT LPPSREEMTK NQVSLTCLVK GFYPSDISVE 390        400        410        420        430
WESNGQPENN YKTTPPMLDS DGSFFLYSKL TVDKSRWQQG NVFSCSVMHE 440        447
ALHNHYTQKS LSLSPGX
``` as numbered by the EU index according to Kabat, wherein, X is a lysine (K) or is absent.

The amino acid sequence of the CH2-CH3 Domain of an exemplary human IgG3 is (SEQ ID NO:51):

```
231        240        250        260        270        280
APELLGGPSV FLFPPKPKDT LMISRTPEVT CVVVDVSHED PEVQFKWYVD 290        300        310        320        330
GVEVHNAKTK PREEQYNSTF RVVSVLTVLH QDWLNGKEYK CKVSNKALPA 340        350        360        370        380
PIEKTISKTK GQPREPQVYT LPPSREEMTK NQVSLTCLVK GFYPSDIAVE 390        400        410        420        430
WESSGQPENN YNTTPPMLDS DGSFFLYSKL TVDKSRWQQG NI FSCSVMHE 440        447
ALHNRFTQKS LSLSPGX
``` as numbered by the EU index according to Kabat, wherein, X is a lysine (K) or is absent.

The amino acid sequence of the CH2-CH3 domain of an exemplary human IgG4 is (SEQ ID NO:52):

```
231        240        250        260        270        280
APEFLGGPSV FLFPPKPKDT LMISRTPEVT CVVVDVSQED PEVQFNWYVD 290        300        310        320        330
GVEVHNAKTK PREEQFNSTY RVVSVLTVLH QDWLNGKEYK CKVSNKGLPS 340        350        360        370        380
SIEKTISKAK GQPREPQVYT LPPSQEEMTK NQVSLTCLVK GFYPSDIAVE
```

```
          390        400        410        420        430
WESNGQPENN YKTTPPVLDS DGSFFLYSRL TVDKSRWQEG NVFSCSVMHE 440        447
ALHNHYTQKS LSLSLGX
``` as numbered by the EU index according to Kabat, wherein, X is a lysine (K) or is absent.

Polymorphisms have been observed at a number of different positions within antibody constant regions (e.g., Fc positions, including but not limited to positions 270, 272, 312, 315, 356, and 358 as numbered by the EU index as in Kabat), and thus slight differences between the presented sequence and sequences in the prior art can exist. Polymorphic forms of human immunoglobulins have been well-characterized. At present, 18 Gm allotypes are known: G1m (1, 2, 3, 17) or G1m (a, x, f, z), G2m (23) or G2m (n), G3m (5, 6, 10, 11, 13, 14, 15, 16, 21, 24, 26, 27, 28) or G3m (b1, c3, b3, b0, b3, b4, s, t, g1, c5, u, v, g5) (Lefranc, G. et al., in THE HUMAN IGG SUBCLASSES: MOLECULAR ANALYSIS OF STRUCTURE, FUNCTION AND REGULATION, (Shakib, F. (ed.) 1990, pp. 43-78, Pergamon, Oxford; Lefranc, G. et al., (1979) "*Gm, Am And Km Immunoglobulin Allotypes Of Two Populadons In Tunisia*," Hum. Genet. 50:199-211). It is specifically contemplated that the antibodies of the present invention may be incorporate any allotype, isoallotype, or haplotype of any immunoglobulin gene, and are not limited to the allotype, isoallotype or haplotype of the sequences provided herein. Furthermore, in some expression systems the C-terminal amino acid residue (bolded and underlined in SEQ ID NOs:49-52 above) of the CH3 Domain may be post-translationally removed. Accordingly, the C-terminal residue of the CH3 Domain (bolded and underlined above) is an optional amino acid residue in the antibodies used in the methods of the invention.

The molecules of the present invention may have variant Fc Regions. Modification of the Fc Region normally leads to an altered phenotype, for example altered serum half-life, altered stability, altered susceptibility to cellular enzymes or altered effector function. It may be desirable to modify the antibody of the invention with respect to effector function, so as to enhance the effectiveness of the antibody in treating cancer, for example. Reduction or elimination of effector function is desirable in certain cases, for example in the case of antibodies whose mechanism of action involves blocking or antagonism, but not killing of the cells bearing a target antigen. Increased effector function is generally desirable when directed to undesirable cells, such as tumor and foreign cells, where the FcγRs are expressed at low levels, for example, tumor specific B-cells with low levels of FcγRIIB (e.g., non-Hodgkin's lymphoma, CLL, and Burkitt's lymphoma). In said embodiments, molecules of the invention with conferred or enhanced effector function activity are useful for the treatment and/or prevention of a disease, disorder or infection where an enhanced efficacy of effector function activity is desired.

In certain embodiments, the molecules of the invention comprise one or more modifications to the amino acids of the Fc Region, which reduce the affinity and avidity of the Fc Region and, thus, the molecule of the invention, for one or more FcγR receptors. In other embodiments, the molecules of the invention comprise one or more modifications to the amino acids of the Fc Region, which increase the affinity and avidity of the Fc Region and, thus, the molecule of the invention, for one or more FcγR receptors. In other embodiments, the molecules comprise a variant Fc Region wherein said variant confers or mediates increased ADCC activity and/or an increased binding to FcγRIIA, relative to a molecule comprising no Fc Region or comprising a wild-type Fc Region. In alternate embodiments, the molecules comprise a variant Fc Region wherein said variant confers or mediates decreased ADCC activity (or other effector function) and/or an increased binding to FcγRIIB, relative to a molecule comprising no Fc Region or comprising a wild-type Fc Region.

In some embodiments, the invention encompasses molecules comprising a variant Fc Region, which variant Fc Region does not show a detectable binding to any FcγR, relative to a comparable molecule comprising the wild-type Fc Region. In other embodiments, the invention encompasses molecules comprising a variant Fc Region, which variant Fc Region only binds a single FcγR, preferably one of FcγRIIA, FcγRIIB, or FcγRIIIA.

The molecules of the present invention may comprise altered affinities for an activating and/or inhibitory Fcγ receptor. In one embodiment, the antibody or molecule comprises a variant Fc Region that has increased affinity for FcγRIIB and decreased affinity for FcγRIIIA and/or FcγRIIA, relative to a comparable molecule with a wild-type Fc Region. In another embodiment, the molecules of the present invention comprise a variant Fc Region, which has decreased affinity for FcγRIIB and increased affinity for FcγRIIIA and/or FcγRIIA, relative to a comparable molecule with a wild-type Fc Region. In yet another embodiment, the molecules of the present invention comprise a variant Fc Region that has decreased affinity for FcγRIIB and decreased affinity for FcγRIIIA and/or FcγRIIA, relative to a comparable molecule with a wild-type Fc Region. In still another embodiment, the molecules of the present invention comprise a variant Fc Region, which has unchanged affinity for FcγRIIB and decreased (or increased) affinity for FcγRIIIA and/or FcγRIIA, relative to a comparable molecule with a wild-type Fc Region.

In certain embodiments, the invention encompasses immunoglobulins comprising a variant Fc Region with an altered affinity for FcγRIIIA and/or FcγRIIA such that the immunoglobulin has an enhanced effector function, e.g., ADCC. Non-limiting examples of effector cell functions include ADCC, antibody dependent cellular phagocytosis (ADCP), phagocytosis, opsonization, opsonophagocytosis, cell binding, rosetting, C1q binding, and CDC.

In particularly preferred embodiments, the invention encompasses chimeric anti-HER2/neu antibodies that comprise a variant Fc Region wherein said variant confers or has an increased ADCC activity and/or an increased binding to FcγRIIIA (CD16A), as measured using methods known to one skilled in the art and exemplified herein. The ADCC assays used in accordance with the methods of the invention may be NK dependent or macrophage dependent.

In particularly preferred embodiments, the invention encompasses molecules, that specifically bind PD-1 that comprise a variant Fc Region wherein said variant confers or has a reduced ADCC activity and/or a decreased binding to FcγRIIIA (CD16A), as measured using methods known to one skilled in the art and exemplified herein. The ADCC assays used in accordance with the methods of the invention may be NK dependent or macrophage dependent. In additional preferred embodiments, the invention encompasses molecules, that specifically bind PD-1 that comprise a variant Fc Region wherein said variant confers or has a reduced CDC activity and/or an decreased binding to C1q, as measured using methods known to one skilled in the art and exemplified herein.

In a preferred embodiment, the alteration in affinity or effector function is at least 2-fold, preferably at least 4-fold, at least 5-fold, at least 6-fold, at least 7-fold, at least 8-fold, at least 9-fold, at least 10-fold, at least 50-fold, or at least 100-fold, relative to a comparable molecule comprising a wild-type Fc Region. In other embodiments of the invention, the variant Fc Region specifically binds one or more FcRs with at least 65%, preferably at least 70%, at least 75%, at least 80%, at least 85%, at least 90%, at least 95%, at least 100%, at least 125%, at least 150%, at least 175%, at least 200%, at least 225%, or at least 250% greater affinity relative to a molecule comprising a wild-type Fc Region. Such measurements can be in vivo or in vitro assays, and in a preferred embodiment are in vitro assays such as ELISA or surface plasmon resonance assays.

In different embodiments, the molecules comprise a variant Fc Region wherein said variant agonizes at least one activity of an FcγR receptor, or antagonizes at least one activity of an FcγR receptor. In a preferred embodiment, the molecules comprise a variant that agonizes (or antagonizes) one or more activities of FcγRIIB, for example, B-cell receptor-mediated signaling, activation of B-cells, B-cell proliferation, antibody production, intracellular calcium influx of B-cells, cell cycle progression, FcγRIIB-mediated inhibition of FcεRI signaling, phosphorylation of FcγRIIB, SHIP recruitment, SHIP phosphorylation and association with Shc, or activity of one or more downstream molecules (e.g., MAP kinase, JNK, p38, or Akt) in the FcγRIIB signal transduction pathway. In another embodiment, the molecules comprise a variant that agonizes (or antagonizes) one or more activities of FcεRI, for example, mast cell activation, calcium mobilization, degranulation, cytokine production, or serotonin release.

In certain embodiments, the molecules comprise an Fc Region comprising domains or regions from two or more IgG isotypes (e.g., IgG1, IgG2, IgG3 and IgG4). The various IgG isotypes exhibit differing physical and functional properties including serum half-life, complement-fixation, FcγR binding affinities and effector function activities (e.g. ADCC, CDC, etc.) due to differences in the amino acid sequences of their hinge and/or Fc Regions, for example as described in Flesch, B. K. and Neppert, J. (1999) "*Functions Of The Fc Receptors For Immunoglobulin G*," J. Clin. Lab. Anal. 14:141-156; Chappel, M. S. et al. (1993) "*Identifcation Of A Secondary Fc Gamma RI Binding Site Within A Genetically Engineered Human IgG Antibody*," J. Biol. Chem. 33:25124-25131; Chappel, M. S. et al. (1991) "*Identification Of The Fc Gamma Receptor Class I Binding Site In Human IgG Through The Use Of Recombinant IgG1/IgG2 HybridAndPoint-MutatedAntibodes*," Proc. Natl. Acad. Sci. (U.S.A.) 88:9036-9040; Brüggemann, M. et al. (1987) "*Comparison Of The Effector Functions Of Human Immunoglobulins Using A Matched Set Of Chimeric Antibodies*," J. Exp. Med 166:1351-1361. This type of variant Fc Region may be used alone, or in combination with an amino acid modification, to affect Fc-mediated effector function and/or binding activity. In combination, the amino acid modification and IgG hinge/Fc Region may display similar functionality (e.g., increased affinity for FcγRIIA) and may act additively or, more preferably, synergistically to modify the effector functionality in the molecule of the invention, relative to a molecule of the invention comprising a wild-type Fc Region. In other embodiments, the amino acid modification and IgG Fc Region may display opposite functionality (e.g., increased and decreased affinity for FcγRIIA, respectively) and may act to selectively temper or reduce a specific functionality in the molecule of the invention, relative to a molecule of the invention not comprising an Fc Region or comprising a wild-type Fc Region of the same isotype.

In a preferred specific embodiment, the molecules comprise a variant Fc Region, wherein said variant Fc Region comprises at least one amino acid modification relative to a wild-type Fc Region, such that said molecule has an altered affinity for an FcR, provided that said variant Fc Region does not have a substitution at positions that make a direct contact with FcγR based on crystallographic and structural analysis of Fc-FcR interactions such as those disclosed by Sondermann, P. et al. (2000) "*The 3.2-Å Crystal Structure Of The Human IgG1 Fc Fragment-Fc GammaRIII Complex,*" Nature 406:267-273. Examples of positions within the Fc Region that make a direct contact with FcγR are amino acid residues 234-239 (hinge region), amino acid residues 265-269 (B/C loop), amino acid residues 297-299 (C'/E loop), and amino acid residues 327-332 (F/G loop). In some embodiments, the molecules of the invention comprise variant Fc Regions comprise modification of at least one residue that does not make a direct contact with an FcγR based on structural and crystallographic analysis, e.g., is not within the Fc-FcγR binding site.

Variant Fc Regions are well known in the art, and any known Fc variant may be used in the present invention to confer or modify the effector function exhibited by a molecule of the invention comprising an Fc Region (or portion thereof) as functionally assayed, e.g., in an NK dependent or macrophage dependent assay. For example, Fc Region variants identified as altering effector function are disclosed in the Antibody Engineering Technology Art, and any suitable variant disclosed therein may be used in the present molecules.

In certain embodiments, the molecules comprise a variant Fc Region, having one or more amino acid modifications in one or more regions, which modification(s) alter (relative to a wild-type Fc Region) the Ratio of Affinities of the variant Fc Region to an activating FcγR (such as FcγRIIA or FcγRIIIA) relative to an inhibiting FcγR (such as FcγRIIB):

Ratio of Affinities=

$$\frac{\text{Wild-Type to Variant Change in Affinity to } Fc\gamma R_{Activating}}{\text{Wild-Type to Variant Change in Affinity to } Fc\gamma R_{Inhibiting}}$$

Where an Fc variant has a Ratio of Affinities greater than 1, the methods of the invention have particular use in providing a therapeutic or prophylactic treatment of a disease, disorder, or infection, or the amelioration of a symptom thereof, where an enhanced efficacy of effector cell function (e.g., ADCC) mediated by FcγR is desired, e.g., cancer or infectious disease. Where an Fc variant has a Ratio of Affinities less than 1, the methods of the invention have particular use in providing a therapeutic or prophylactic treatment of a disease or disorder, or the amelioration of a symptom thereof, where a decreased efficacy of effector cell function mediated by FcγR is desired, e.g., autoimmune or inflammatory disorders. Table 3 lists exemplary single, double, triple, quadruple and quintuple mutations by whether their Ratio of Affinities is greater than or less than 1, and more information concerning these mutations may be found in the Antibody Engineering Technology Art.

TABLE 3

Exemplary Single and Multiple Mutations Listed by Ratio of Affinities

| Single | Double | Triple | Quadruple | Quintuple |
|---|---|---|---|---|
| | | Ratio of Affinities > 1 | | |
| F243L | F243L & R292P | F243L, P247L & N421K | L234F, F243L, R292P & Y300L | L235V, F243L, R292P, Y300L & P396L |
| D270E | F243L & Y300L | F243L, R292P & Y300L | L235I, F243L, R292P & Y300L | L235P, F243L, R292P, Y300L & P396L |
| R292G | F243L & P396L | F243L, R292P & V305I | L235Q, F243L, R292P & Y300L | F243L, R292P, V305I, Y300L & P396L |
| R292P | D270E & P396L | F243L, R292P & P396L | F243L, P247L, D270E & N421K | |
| | R292P & Y300L | F243L, Y300L & P396L | F243L, R255L, D270E & P396L | |
| | R292P & V305I | P247L, D270E & N421K | F243L, D270E, G316D & R416G | |
| | R292P & P396L | R255L, D270E & P396L | F243L, D270E, K392T & P396L | |
| | Y300L & P396L | D270E, G316D & R416G | F243L, D270E, P396L & Q419H | |
| | P396L & Q419H | D270E, K392T & P396L | F243L, R292P, Y300L, & P396L | |
| | | D270E, P396L & Q419H | F243L, R292P, V305I & P396L | |
| | | V284M, R292L & K370N | P247L, D270E, Y300L & N421K | |
| | | R292P, Y300L & P396L | R255L, D270E, R292G & P396L | |
| | | | R255L, D270E, Y300L & P396L | |
| | | | D270E, G316D, P396L & R416G | |
| | | Ratio of Affinities < 1 | | |
| Y300L | F243L & P396L | F243L, R292P & V305I | | |
| P396L | P247L & N421K | | | |
| | R255L & P396L | | | |
| | R292P & V305I | | | |
| | K392T & P396L | | | |
| | P396L & Q419H | | | |

In a specific embodiment, in variant Fc Regions, any amino acid modifications (e.g., substitutions) at any of positions 235, 240, 241, 243, 244, 247, 262, 263, 269, 298, 328, or 330 and preferably one or more of the following residues: A240, I240, L241, L243, H244, N298, I328 or V330. In a different specific embodiment, in variant Fc Regions, any amino acid modifications (e.g., substitutions) at any of positions 268, 269, 270, 272, 276, 278, 283, 285, 286, 289, 292, 293, 301, 303, 305, 307, 309, 331, 333, 334, 335, 337, 338, 340, 360, 373, 376, 416, 419, 430, 434, 435, 437, 438 or 439 and preferably one or more of the following residues: H280, Q280, Y280, G290, S290, T290, Y290, N294, K295, P296, D298, N298, P298, V298, I300 or L300.

In a preferred embodiment, in variant Fc Regions that bind an FcγR with an altered affinity, any amino acid modifications (e.g., substitutions) at any of positions 255, 256, 258, 267, 268, 269, 270, 272, 276, 278, 280, 283, 285, 286, 289, 290, 292, 293, 294, 295, 296, 298, 300, 301, 303, 305, 307, 309, 312, 320, 322, 326, 329, 330, 332, 331, 333, 334, 335, 337, 338, 339, 340, 359, 360, 373, 376, 416, 419, 430, 434, 435, 437, 438 or 439. Preferably, the variant Fc Region has any of the following residues: A256, N268, Q272, D286, Q286, S286, A290, S290, A298, M301, A312, E320, M320, Q320, R320, E322, A326, D326, E326, N326, S326, K330, T339, A333, A334, E334, H334, L334, M334, Q334, V334, K335, Q335, A359, A360 or A430.

In a different embodiment, in variant Fc Regions that bind an FcγR (via its Fc Region) with a reduced affinity, any amino acid modifications (e.g., substitutions) at any of positions 252, 254, 265, 268, 269, 270, 278, 289, 292, 293, 294, 295, 296, 298, 300, 301, 303, 322, 324, 327, 329, 333, 335, 338, 340, 373, 376, 382, 388, 389, 414, 416, 419, 434, 435, 437, 438, or 439.

In a different embodiment, in variant Fc Regions that bind an FcγR (via its Fc Region) with an enhanced affinity, any amino acid modifications (e.g., substitutions) at any of positions 280, 283, 285, 286, 290, 294, 295, 298, 300, 301, 305, 307, 309, 312, 315, 331, 333, 334, 337, 340, 360, 378, 398, or 430. In a different embodiment, invariant Fc Regions that binds FcγRIIA with an enhanced affinity, any of the following residues: A255, A256, A258, A267, A268, N268, A272, Q272, A276, A280, A283, A285, A286, D286, Q286, S286, A290, S290, M301, E320, M320, Q320, R320, E322, A326, D326, E326, S326, K330, A331, Q335, A337 or A430.

Preferred variants include one or more modifications at any of positions: 228, 230, 231, 232, 233, 234, 235, 239, 240, 241, 243, 244, 245, 247, 262, 263, 264, 265, 266, 271, 273, 275, 281, 284, 291, 296, 297, 298, 299, 302, 304, 305, 313, 323, 325, 326, 328, 330 or 332.

Particularly preferred variants include one or more modifications selected from groups A-AI:

| | |
|---|---|
| A | 228E, 228K, 228Y or 228G; |
| B | 230A, 230E, 230Y or 230G; |
| C | 231E, 231K, 231Y, 231P or 231G; |
| D | 232E, 232K, 232Y, 232G; |
| E | 233D; |
| F | 234I or 234F; |
| G | 235D, 235Q, 235P, 235I or 235V; |
| H | 239D, 239E, 239N or 239Q; |
| I | 240A, 240I, 240M or 240T; |
| J | 243R, 243, 243Y, 243L, 243Q, 243W, 243H or 243I; |
| K | 244H; |
| L | 245A; |
| M | 247G, 247V or 247L; |
| N | 262A, 262E, 262I, 262T, 262E or 262F; |
| O | 263A, 263I, 263M or 263T; |
| P | 264F, 264E, 264R, 264I, 264A, 264T or 264W; |
| Q | 265F, 265Y, 265H, 265I, 265L, 265T, 265V, 265N or 265Q; |
| R | 266A, 266I, 266M or 266T; |
| S | 271D, 271E, 271N, 271Q, 271K, 271R, 271S, 271T, 271H, 271A, 271V, 271L, 271I, 271F, 271M, 271Y, 271W or 271G; |
| T | 273I; |
| U | 275L or 275W; |
| V | 281D, 281K, 281Y or 281P; |
| W | 284E, 284N, 284T, 284L, 284Y or 284M; |
| X | 291D, 291E, 291Q, 291T, 291H, 291I or 291G; |
| Y | 299A, 299D, 299E, 299F, 299G, 299H, 299I, 299K, 299L, 299M, 299N, 299P, 299Q, 299R, 299S, 299V, 299W or 299Y; |
| Z | 302I; |
| AA | 304D, 304N, 304T, 304H or 304L |
| AB | 305I; |
| AC | 313F; |
| AD | 323I; |
| AE | 325A, 325D, 325E, 325G, 325H, 325I, 325L, 325K, 325R, 325S, 325F, 325M, 325T, 325V, 325Y, 325W or 325P; |
| AF | 328D, 328Q, 328K, 328R, 328S, 328T, 328V, 328I, 328Y, 328W, 328P, 328G, 328A, 328E, 328F, 328H, 328M or 328N; |
| AG | 330L, 330Y, 330I or 330V; |
| AH | 332A, 332D, 332E, 332H, 332N, 332Q, 332T, 332K, 332R, 332S, 332V, 332L, 332F, 332M, 332W, 332P, 332G or 332Y; and |
| AI | 336E, 336K or 336Y |

Still more particularly preferred variants include one or more modifications selected from groups 1-105:

| Group | Variant |
|---|---|
| 1 | A330L/I332E |
| 2 | D265F/N297E/I332E |
| 3 | D265Y/N297D/I332E |
| 4 | D265Y/N297D/T299L/I332E |
| 5 | F241E/F243Q/V262T/V264F |
| 6 | F241E/F243Q/V262T/V264E/I332E |
| 7 | F241E/F243R/V262E/V264R |
| 8 | F241E/F243R/V262E/V264R/I332E |
| 9 | F241E/F243Y/V262T/V264R |
| 10 | F241E/F243Y/V262T/V264R/I332E |
| 11 | F241L/F243L/V262I/V264I |
| 12 | F241L/V262I |
| 13 | F241R/F243Q/V262T/V264R |
| 14 | F241R/F243Q/V262T/V264R/I332E |
| 15 | F241W/F243W/V262A/V264A |
| 16 | F241Y/F243Y/V262T/V264T |
| 17 | F241Y/F243Y/V262T/V264T/N297D/I332E |
| 18 | F243L/V262I/V264W |
| 19 | P243L/V264I |
| 20 | L328D/I332E |
| 21 | L328E/I332E |
| 22 | L328H/I332E |
| 23 | L328I/I332E |
| 24 | L328M/I332E |
| 25 | L328N/I332E |
| 26 | L328Q/I332E |
| 27 | L328T/I332E |
| 28 | L328V/I332E |
| 29 | N297D/A330Y/I332E |
| 30 | N297D/I332E |
| 31 | N297D/I332E/S239D/A330L |
| 32 | N297D/S298A/A330Y/I332E |
| 33 | N297D/T299L/I332E |
| 34 | N297D/T299F/I332E/N297D/T299H/I332E |
| 35 | N297D/T299I/I332E |
| 36 | N297D/T299L/I332E |
| 37 | N297D/T299V/I332E |
| 38 | N297E/I332E |
| 39 | N297S/I332E |
| 40 | P230A/E233D/I332E |
| 41 | P244H/P245A/P247V |
| 42 | S239D/A330L/I332E |
| 43 | S239D/A330Y/I332E |
| 44 | S239D/A330Y/I332E/K326E |
| 45 | S239D/A330Y/I332E/K326T |
| 46 | S239D/A330Y/I332E/L234I |
| 47 | S239D/A330Y/I332E/L235D |
| 48 | S239D/A330Y/I332E/V240I |
| 49 | S239D/A330Y/I332E/V264T |
| 50 | S239D/A330Y/I332E/V266I |
| 51 | S239D/D265F/N297D/I332E |
| 52 | S239D/D265H/N297D/I332E |
| 53 | S239D/D265I/N297D/I332E |
| 54 | S239D/D265L/N297D/I332E |
| 55 | S239D/D265T/N297D/I332E |
| 56 | S239D/D265V/N297D/I332E |
| 57 | S239D/D265Y/N297D/I332E |
| 58 | S239D/I332D |
| 59 | S239D/I332E |
| 60 | S239D/I332E/A330I |
| 61 | S239D/I332N |
| 62 | S239D/I332Q |
| 63 | S239D/N297D/I332E |
| 64 | S239D/N297D/I332E/A330Y |
| 65 | S239D/N297D/I332E/A330Y/F241S/F243H/V262T/V264T |
| 66 | S239D/N297D/I332E/K326E |
| 67 | S239D/N297D/I332E/L235D |
| 68 | S239D/S298A/I332E |
| 69 | S239D/V264I/A330L/I332E |
| 70 | S239D/V264I/I332E |
| 71 | S239D/V264I/S298A/I332E |
| 72 | S239E/D265N |
| 73 | S239E/D265Q |
| 74 | S239E/I332D |
| 75 | S239E/I332E |
| 76 | S239E/I332N |
| 77 | S239E/I332Q |
| 78 | S239E/N297D/I332E |
| 79 | S239E/V264I/A330Y/I332E |
| 80 | S239E/V264I/I332E |
| 81 | S239E/V264I/S298A/A330Y/I332E |
| 82 | S239N/A330L/I332E |
| 83 | S239N/A330Y/I332E |

| Group | Variant |
|---|---|
| 84 | S239N/I332D |
| 85 | S239N/I332E |
| 86 | S239N/I332N |
| 87 | S239N/I332Q |
| 88 | S239N/S298A/I332E |
| 89 | S239Q/I332D |
| 90 | S239Q/I332E |
| 91 | S239Q/I332N |
| 92 | S239Q/I332Q |
| 93 | S239Q/V264I/I332E |
| 94 | S298A/I332E |
| 95 | V264E/N297D/I332E |
| 96 | V264I/A330L/I332E |
| 97 | V264I/A330Y/I332E |
| 98 | V264I/I332E |
| 99 | V264I/S298A/I332E |
| 100 | Y296D/N297D/I332E |
| 101 | Y296E/N297D/I332E |
| 102 | Y296H/N297D/I332E |
| 103 | Y296N/N297D/I332E |
| 104 | Y296Q/N297I/I332E |
| 105 | Y296T/N297D/I332E |

In one embodiment, a molecule that specifically binds HER2/neu (e.g., an anti-HER2/neu antibody), and/or a molecule that specifically binds PD-1 (e.g., an anti-PD-1 antibody) will comprise a variant Fc Region having at least one modification in the Fc Region. In one embodiment, a molecule that specifically binds HER2/neu (e.g., an anti-HER2/neu antibody), will comprise a variant Fc Region having at least one modification that enhances binding to FcγRIIA and/or enhances ADCC activity relative to the same antibody comprising a wild-type Fc Region. In certain embodiments, the variant Fc Region comprises at least one substitution selected from the group consisting of L235V, F243L, R292P, Y300L, V305I, and P396L, wherein said numbering is that of the EU index as in Kabat.

In a specific embodiment, the variant Fc Region comprises:
(A) at least one substitution selected from the group consisting of F243L, R292P, Y300L, V305I, and P396L;
(B) at least two substitutions selected from the group consisting of:
  (1) F243L and P396L;
  (2) F243L and R292P; and
  (3) R292P and V305I;
(C) at least three substitutions selected from the group consisting of:
  (1) F243L, R292P and Y300L;
  (2) F243L, R292P and V305I;
  (3) F243L, R292P and P396L; and
  (4) R292P, V305I and P396L;
(D) at least four substitutions selected from the group consisting of:
  (1) F243L, R292P, Y300L and P396L; and
  (2) F243L, R292P, V305I and P396L; or
(E) at least the five substitutions selected from the group consisting of:
  (1) F243L, R292P, Y300L, V305I and P396L; and
  (2) L235V, F243L, R292P, Y300L and P396L.

In another specific embodiment, the variant Fc Region comprises substitutions of:
(A) F243L, R292P, and Y300L;
(B) L235V, F243L, R292P, Y300L, and P396L; or
(C) F243L, R292P, Y300L, V305I, and P396L.

In one embodiment, a molecule that specifically binds PD-1 (e.g., an anti-PD-1 antibody), will comprise a variant Fc Region having at least one modification that reduces binding to FcγRIIIA (CD16A) and/or reduces ADCC activity relative to the same antibody comprising a wild-type Fc Region. In certain embodiments, the variant Fc Region comprises at least one substitution selected from the group consisting of L234A, L235A, D265A, N297Q, and N297G, wherein said numbering is that of the EU index as in Kabat. In a specific embodiment, the variant Fc Region comprises the substitution of L234A and L235A.

Alternatively, an Fc Region which inherently exhibits decreased (or substantially no) binding to FcγRIIIA (CD16A) and/or reduced effector function (relative to the binding exhibited by the wild-type IgG1 Fc Region (SEQ ID NO:1)) is utilized. In a specific embodiment, a molecule that specifically binds HER2/neu (e.g., an anti-HER2/neu antibody), and/or a molecule that specifically binds PD-1 (e.g., an anti-PD-1 antibody) will comprise an IgG2 Fc Region (SEQ ID NO:50) or an IgG4 Fc Region (SEQ ID NO:52), optionally lacking the C-terminal amino acid residues. Where an IgG4 Fc Region in utilized the instant invention also encompasses the introduction of a stabilizing mutation such as S228P, as numbered by the EU index as set forth in Kabat (Lu et al., (2008) "*The Effect Of A Point Mutation On The Stability Of Igg4 As Monitored By Analytical Ultracentrifugation*," J. Pharmaceutical Sciences 97:960-969) to reduce the incidence of strand exchange. Other stabilizing mutations known in the art may be introduced into an IgG4 Fc Region (Peters, P et al., (2012) "*Engineering an Improved IgG4 Molecule with Reduced Disulfide Bond Heterogeneity and Increased Fab Domain Thermal Stability*," J. Biol. Chem. 287:24525-24533; PCT Patent Publication. No. WO 2008/145142). In a specific embodiment, a molecule that specifically binds PD-1 (e.g., an anti-PD-1 antibody), will comprise an IgG4 Fc Region and an S228P mutation.

In other embodiments, the invention encompasses the use of any Fc variant known in the art, such as those disclosed in Jefferis, R. et al. (2002) "*Interaction Sites On Human IgG-Fc For FcgammaR Current Models*," Immunol. Lett. 82:57-65; Presta, L. G. et al. (2002) "*Engineering Therapeutic Antibodies For Improved Function*," Biochem. Soc. Trans. 30:487-90; Idusogie, E. E. et al. (2001) "*Engineered Antibodies With Increased Activity To Recruit Complement*," J. Immunol. 166:2571-75; Shields, R. L. et al. (2001) "*High Resolution Mapping Of The Binding Site On Human IgG1 For Fc Gamma RI, Fc Gamma RII, Fc Gamma RIII, And FcRn And Design Of IgG1 Variants With Improved Binding To The Fc gamma R*," J. Biol. Chem. 276:6591-6604; Idusogie, E. E. et al. (2000) "*Mapping Of The C1q Binding Site On Rituxan, A Chimeric Antibody With A Human IgG Fc*," J. Immunol. 164:4178-84; Reddy, M. P. et al. (2000) "*Elimination Of Fc Receptor-Dependent Effector Functions Of A Modified IgG4 Monoclonal Antibody To Hunan CD4*," J. Immunol. 164:1925-1933; Xu, D. et al. (2000) "*In Vitro Characterization of Five Humanized OKT3 Effector Function Variant Antibodies*," Cell. Immunol. 200:16-26; Armour, K. L. et al. (1999) "*Recombinant human IgG Molecules Lacking Fcgamma Receptor I Binding And Monocyte Triggering Activities*," Eur. J. Immunol. 29:2613-24; Jefferis, R. et al. (1996) "*Modulation Of Fc(Gamma)R And Human Complement Activation By IgG3-Core Oligosaccharide Interactions*," Immunol. Lett. 54:101-04; Lund, J. et al. (1996) "*Multiple Interactions Of IgG With Its Core Oligosaccharide Can Modulate Recognition By Complement And Human Fc Gamma Receptor I And Influence The Synthesis Of Its Oligosaccharide Chains," J. Immunol. 157:4963-4969; Hutchins et al. (1995) "*Improved Biodistribution, Tumor Targeting, And Reduced Immunogenicity In Mice With A Gamma 4 Variant Of Campath-1H*," Proc. Natl. Acad. Sci. (U.S.A.) 92:11980-84; Jefferis, R. et al. (1995) "*Recognition Sites On Human IgG For Fc Gamma Receptors: The Role Of Glycosylation*," Immunol. Lett. 44:111-17; Lund, J. et al. (1995) "*Oligosaccharide-Protein Interactions In IgG Can Modulate Recognition By Fc Gamma Receptors*," FASEB J. 9:115-19; Alegre, M. L. et al. (1994) "*A Non-Activating "Humanized" And CD3 Monoclonal Antibody Retains Immunosuppressive Properties In Vivo*," Transplantation 57:1537-1543; Lund et al. (1992) "*Multiple Binding Sites On The CH2 Domain Of IgG For Mouse Fc Gamma R11*," Mol. Immunol. 29-53-59; Lund et al. (1991) "*Human Fc Gamma RI And Fc Gamma RH Interact With Distinct But Overlapping Sites On Human IgG*," J. Immunol. 147:2657-2662; Duncan, A. R. et al. (1988) "*Localization Of The Binding Site For The Human High-Affinity Fc Receptor On IgG*," Nature 332:563-564; U.S. Pat. Nos. 5,624,821; 5,885,573; 6,194,551; 7,276,586; and 7,317,091; and PCT Patent Publications No. WO 00/42072 and WO 99/58572. In some embodiments, the molecules of the invention further comprise one or more glycosylation sites, so that one or more carbohydrate moieties are covalently attached to the molecule. Preferably, the molecules of the invention with one or more glycosylation sites and/or one or more modifications in the Fc Region confer or have an enhanced antibody mediated effector function, e.g., enhanced ADCC activity, compared to the unmodified molecule. In some embodiments, the invention further comprises molecules comprising one or more modifications of amino acids that are directly or indirectly known to interact with a carbohydrate moiety of the Fc Region, including but not limited to amino acids at positions 241, 243, 244, 245, 245, 249, 256, 258, 260, 262, 264, 265, 296, 299, and 301. Amino acids that directly or indirectly interact with a carbohydrate moiety of an Fc Region are known in the art, see, e.g., Jefferis, R. et al. (1995) "*Recognition Sites On Human IgG For Fc Gamma Receptors: The Role Of Glycosylation*," Immunol. Lett. 44:111-17.

In another embodiment, the invention encompasses molecules that have been modified by introducing one or more glycosylation sites into one or more sites of the molecules, preferably without altering the functionality of the molecules, e.g., binding activity to target antigen or FcγR. Glycosylation sites may be introduced into the variable and/or constant region of the molecules of the invention.

Thus, in some embodiments, the invention encompasses methods of modifying the carbohydrate content of a molecule of the invention by adding or deleting a glycosylation site. Methods for modifying the carbohydrate content of antibodies (and molecules comprising antibody domains, e.g., Fc Region) are well known in the art and encompassed within the invention, see, e.g., U.S. Pat. No. 6,218,149; EP 0 359 096 B1; U.S. Patent Publication No. US 2002/ 0028486; WO 03/035835; U.S. Patent Publication No. 2003/ 0115614; U.S. Pat. Nos. 6,218,149; 6,472,511; all of which are incorporated herein by reference in their entirety. In other embodiments, the invention encompasses methods of modifying the carbohydrate content of a molecule of the invention by deleting one or more endogenous carbohydrate moieties of the molecule. In a specific embodiment, the invention encompasses shifting the glycosylation site of the Fc Region of an antibody, by modifying positions adjacent to 297. In a specific embodiment, the invention encompasses modifying position 296 so that position 296 and not position 297 is glycosylated.

Effector function can be modified by techniques such as those described in the Antibody Engineering Technology Art, or by other means. For example, cysteine residue(s) may be introduced in the Fc Region, thereby allowing interchain disulfide bond formation in this region, resulting in the generation of a homodimeric antibody that may have improved internalization capability and/or increased complement-mediated cell killing and ADCC. See Caron, P. C. et al. (1992) "*Engineered Humanized Dimeric Forms Of IgG Are More Effective Antibodies*," J. Exp. Med. 176:1191-1195; Shopes, B. (1992) "*A Genetically Engineered Human IgG Mutant With Enhanced Cytolytic Activity*," J. Immunol. 148(9):2918-2922. Homodimeric antibodies with enhanced anti-tumor activity may also be prepared using heterobifunctional cross-linkers as described in Wolff, E. A. et al. (1993) "*Monoclonal Antibody Homodimers: Enhanced Antitumor Activity In Nude Mice*," Cancer Research 53:2560-2565. Alternatively, an antibody can be engineered which has dual Fc Regions and may thereby have enhanced complement lysis and ADCC capabilities (Stevenson, G. T. et al. (1989) "*A Chimeric Antibody With Dual Fc Regions (bisFabFc) Prepared By Manipulations At The IgG Hinge*," Anti-Cancer Drug Design 3:219-230.

E. Polypeptide Conjugates

The molecules of the present invention may be recombinantly fused or chemically conjugated (including both covalent and non-covalent conjugations) to heterologous polypeptides or portions thereof to generate fusion proteins. Preferably, the molecule of the present invention (especially an antibody) is fused to at least 10, at least 15, at least 20, at least 25, at least 30, at least 40, at least 50, at least 60, at least 70, at least 80, at least 90 or at least 100 amino acids of the heterologous polypeptide to generate a desired fusion protein. The fusion does not necessarily need to be direct, but may occur through linker sequences. The molecules (e.g., antibodies and polypeptides) may be conjugated to a therapeutic agent in order to modify a given biological response, affect (e.g., increase) the serum half-life of the therapeutic agent, or target the therapeutic agent to a particular subset of cells. They may also be fused to marker sequences (e.g., a hexa-histidine peptide or a "flag" tag) to facilitate purification. Techniques for conjugating such therapeutic moieties to antibodies are well known; see, e.g., Hellstrom et al., "*Antibodies For Drug Delivery*," in CONTROLLED DRUG DELIVERY (2nd ed., Robinson et al. (eds.), 1987, pp. 623-53, Marcel Dekker, Inc.).

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of molecules of the invention (e.g., antibodies with higher affinities and lower dissociation rates). Molecules of the invention, or their encoding nucleic acids, may be further altered by being subjected to random mutagenesis by error-prone PCR, random nucleotide insertion or other methods prior to recombination. One or more portions of a polynucleotide encoding a molecule of the invention, may be recombined with one or more components, motifs, sections, parts, domains, fragments, etc. of one or more heterologous molecules.

F. Diabodies and DART® Diabodies

Diabodies and dual affinity retargeting reagents (and particularly DART® diabodies (MacroGenics, Inc.)) are also provided by the present invention. Accordingly, the present invention additionally encompasses diabody (especially, DART® diabody) molecules that comprise at least two covalently bonded polypeptide chains which form at least two epitope binding sites, one of which specifically binds to HER2/neu and a second of which binds to a cell-surface receptor (or a ligand thereof) that regulates an immune checkpoint. Preferably, such diabodies will bind to HER2/neu and PD-1. In particular, diabodies and DARTs comprising antigen-binding domains from an anti-HER2/neu antibody and an anti-PD-1 antibody of the invention are encompassed.

The design and construction of homodimeric diabodies and stable, covalently bonded heterodimeric non-monospecific diabodies is described in, for example, United States Patent Publications No. 2013-0295121; 2010-0174053 and 2009-0060910; European Patent Publication No. EP 2714079; EP 2601216; EP 2376109; EP 2158221 and PCT Publications No. WO 2012/162068; WO 2012/018687; WO 2010/080538; WO 2008/157379; WO 2006/113665 and Sloan, D. D. et al. (2015) "*Targeting HIV Reservoir in Infected CD4 T Cells by Dual-Affinity Re-targeting Molecules (DARTs) that Bind HIV Envelope and Recruit Cytotoxic T Cells*," PLoS Pathog. 11(11):e1005233. doi: 10.1371/journal.ppat.1005233; Al Hussaini, M. et al. (2015) "*Targeting CD123 In AML Using A T-Cell Directed Dual-Affinity Re-Targeting (DART®) Platform*," Blood 127(1): 122-131; Chichili, G. R. et al. (2015) "*A CD3xCD123 Bispecific DART For Redirecting Host T Cells To Myelogenous Leukemia: Preclinical Activity And Safety In Nonhuman Primates*," Sci. Transl. Med. 7(289):289ra82; Moore, P. A. et al. (2011) "*Application Of Dual Affinity Retargeting-Molecules To Achieve Optimal Redirected T-Cell Killing Of B-Cell Lymphoma*," Blood 117(17):4542-4551; Veri, M. C. et al (2010) "*Therapeutic Control Of B Cell Activation Via Recruitment Of Fcgamma Receptor IIb (CD32B) Inhibitory Function With A Novel Bispecific Antibody Scaffold*," Arthritis Rheum. 62(7):1933-1943; Johnson, S. et al (2010) "*Effector Cell Recruitment With Novel Fv-Based Dual-Affinity Re-Targeting Protein Leads To Potent Tumor Cytolysis And in vivo B-Cell Depletion*," J. Mol. Biol. 399(3):436-449; Marvin, J. S. et al. (2005) "*Recombinant Approaches To IgG-Like Bispecific Antibodies*," Acta Pharmacol. Sin. 26:649-658; Olafsen, T. et al. (2004) "*Covalent Disulfide-Linked Anti-CEA Diabody Allows Site-Specific Conjugation And Radiolabeling For Tumor Targeting Applications*," Prot. Engr. Des. Sel. 17:21-27; Holliger, P. et al. (1993) "*'Diabodies': Small Bivalent And Bispecific Antibody Fragments*," Proc. Natl. Acad. Sci. (U.S.A.) 90:6444-6448. Each polypeptide chain of a diabody molecule comprises a $V_L$ Region and a $V_H$ Region, from the same or different antibodies, which are covalently linked such that the domains are constrained from self-assembly. Interaction of two of the polypeptide chains will produce two $V_L$-$V_H$ pairings, forming two epitope binding sites, i.e., a bivalent molecule. The domains may be separated by a peptide linker, and the polypeptide chains may be engineered to comprise at least one cysteine residue on each chain, so that interchain disulfide bonds may be formed to stabilize the diabody.

In preferred embodiments, the first polypeptide chain of the diabody comprises:
 (i) a domain (A) comprising a binding region of a light chain variable domain of a first immunoglobulin (VL1) specific for an epitope of HER2/neu;
 (ii) a domain (B) comprising a binding region of a heavy chain variable domain of a second immunoglobulin (VH2) specific for an epitope of PD-1; and
 (iii) optionally, a domain (C).

The second polypeptide chain of such a diabody comprises:
 (i) a domain (D) comprising a binding region of a light chain variable domain of the second immunoglobulin (VL2) specific for such epitope of PD-1;
 (ii) a domain (E) comprising a binding region of a heavy chain variable domain of the first immunoglobulin (VH1) specific for such epitope of HER2/neu; and
 (iii) optionally, a domain (F).

The diabody domains (A) and (B) do not associate with one another to form an epitope binding site. Similarly, the diabody domains (D) and (E) do not associate with one another to form an epitope binding site. Rather, diabody domains (A) and (E) associate to form a binding site that binds the HER2/neu epitope and the diabody domains (B) and (D) associate to form a binding site that binds the PD-1 epitope.

The variable domains of the first and second polypeptide chains may alternatively be reversed, such that the first polypeptide chain of the diabody comprises:
 (i) a domain (A) comprising a binding region of a light chain variable domain of the second immunoglobulin (VL2) specific for an epitope of PD-1;
 (ii) a domain (B) comprising a binding region of a heavy chain variable domain of the first immunoglobulin (VH1) specific for an epitope of HER2/neu; and
 (iii) optionally, a domain (C);
and the second polypeptide chain of such a diabody comprises:
 (i) a domain (D) comprising a binding region of a light chain variable domain of a first immunoglobulin (VL1) specific for such epitope of HER2/neu;
 (ii) a domain (E) comprising a binding region of a heavy chain variable domain of a second immunoglobulin (VH2) specific for such epitope of PD-1; and
 (iii) optionally, a domain (F).

In the reversed configuration, diabody domains (A) and (E) associate to form a binding site that binds the PD-1 epitope and the diabody domains (B) and (D) associate to form a binding site that binds the HER2/neu epitope.

When present, Domains (C) and (F) are covalently associated together. Domain (C) and (F) may be heterodimer-promoting domains which facilitate the interaction of the first and second polypeptide chains. Heterodimerization domains useful in the productions of diabodies are described in, for example, PCT Publication Nos.: WO 2012/162068; WO 2012/018687; WO 2010/080538; WO 2008/157379; and WO 2006/113665, each incorporated herein by reference. Domains (C) and/or (F) may comprise an Fc domain or portion thereof (e.g. a CH2 domain, or CH3 domain). The Fc domain or portion thereof may be derived from any immunoglobulin isotype or allotype including, but not limited to, IgA, IgD, IgG, IgE and IgM. In preferred embodiments, the Fc domain (or portion thereof) is derived from IgG. In specific embodiments, the IgG isotype is IgG1, IgG2, IgG3 or IgG4 or an allotype thereof. In one embodiment, the diabody molecule comprises an Fc domain, which Fc domain comprises a CH2 domain and CH3 domain independently selected from any immunoglobulin isotype (i.e., an Fc domain comprising the CH2 domain derived from IgG and the CH3 domain derived from IgE, or the CH2 domain derived from IgG1 and the CH3 domain derived from IgG2, etc.). The Fc domain may be engineered into a polypeptide chain comprising the diabody molecule of the invention in any position relative to other domains or portions of said polypeptide chain (e.g., the Fc domain, or portion thereof, may be C-terminal to both the VL and VH domains of the polypeptide of the chain; or it may be N-terminal to both the VL and VH domains; or it may be N-terminal to one domain and C-terminal to another (i.e., between two domains of the polypeptide chain), etc.).

The Fc domains in the polypeptide chains of the diabody molecules preferentially dimerize, resulting in the formation of a diabody molecule that exhibits immunoglobulin-like properties, e.g., Fc-FcγR, interactions. Fc comprising diabodies may be dimers, e.g., comprised of two polypeptide chains, each comprising a VH domain, a VL domain and an Fc domain. Dimerization of said polypeptide chains results in a bivalent diabody comprising an Fc domain, albeit with a structure distinct from that of an unmodified bivalent antibody. Such diabody molecules will exhibit altered phenotypes relative to a wild-type immunoglobulin, e.g., altered serum half-life, binding properties, etc. In other embodiments, diabody molecules comprising Fc domains may be tetramers. Such tetramers comprise two 'heavier' polypeptide chains, i.e., a polypeptide chain comprising a VL, a VH and an Fc domain, and two 'lighter' polypeptide chains, i.e., polypeptide chain comprising a VL and a VH. The lighter and heavier chains interact to form a monomer, and said monomers interact via their unpaired Fc domains to form an Ig-like molecule. Such an Ig-like diabody is tetravalent.

Formation of a tetraspecific diabody molecule as described supra requires the interaction of four differing polypeptide chains. Such interactions are difficult to achieve with efficiency within a single cell recombinant production system, due to the many variants of potential chain mispairings. One solution to decrease the probability of mispairings, is to engineer "knobs-into-holes" type mutations into the desired polypeptide chain pairs. Such mutations favor heterodimerization over homodimerization. For example, with respect to Fc-Fc-interactions, an amino acid substitution (preferably a substitution with an amino acid comprising a bulky side group forming a "knob," e.g., tryptophan) can be introduced into the CH2 or CH3 domain such that steric interference will prevent interaction with a similarly mutated domain and will obligate the mutated domain to pair with a domain into which a complementary, or accommodating mutation has been engineered, i.e., the "hole" (e.g., a substitution with glycine). Such sets of mutations can be engineered into any pair of polypeptides comprising the diabody molecule, and further, engineered into any portion of the polypeptides chains of said pair. Methods of protein engineering to favor heterodimerization over homodimerization are well known in the art, in particular with respect to the engineering of immunoglobulin-like molecules, and are encompassed herein (see e.g., Ridgway et al. (1996) "*'Knobs-Into-Holes' Engineering Of Antibody CH3 Domains For Heavy Chain Heterodimerization*," Protein Engr. 9:617-621, Atwell et al. (1997) "*Stable Heterodimers From Remodeling The Domain Interface Of A Homodimer Using A Phage Display Library*," J. Mol. Biol. 270: 26-35, and Xe et al. (2005) "*A New Format Of Bispecific Antibody: Highly Efficient Heterodimerization, Expression And Tumor Cell Lysis*," J. Immunol. Methods 296:95-101; each of which is hereby incorporated herein by reference in its entirety.

The invention also encompasses diabody molecules comprising variant Fc or variant hinge-Fc domains (or portion thereof), which variant Fc domain comprises at least one amino acid modification (e.g. substitution, insertion deletion) relative to a comparable wild-type Fc domain or hinge-Fc domain (or portion thereof). Molecules comprising variant Fc domains or hinge-Fc domains (or portion thereof) (e.g., antibodies) normally have altered phenotypes relative to molecules comprising wild-type Fc domains or hinge-Fc domains or portions thereof. The variant phenotype may be expressed as altered serum half-life, altered stability, altered susceptibility to cellular enzymes or altered effector function as assayed in an NK dependent or macrophage dependent assay. Fc domain modifications identified as altering effector function are disclosed above.

The present invention also encompasses molecules comprising a hinge domain. The hinge domain be derived from any immunoglobulin isotype or allotype including IgA, IgD, IgG, IgE and IgM. In preferred embodiments, the hinge domain is derived from IgG, wherein the IgG isotype is IgG1, IgG2, IgG3 or IgG4, or an allotpye thereof. Said hinge domain may be engineered into a polypeptide chain comprising the diabody molecule together with an Fc domain such that the diabody molecule comprises a hinge-Fc domain. In certain embodiments, the hinge and Fc domain are independently selected from any immunoglobulin isotype known in the art or exemplified herein. In other embodiments the hinge and Fc domain are separated by at least one other domain of the polypeptide chain, e.g., the $V_L$ domain. The hinge domain, or optionally the hinge-Fc domain, may be engineered in to a polypeptide of the invention in any position relative to other domains or portions of said polypeptide chain. In certain embodiments, a polypeptide chain of the invention comprises a hinge domain, which hinge domain is at the C-terminus of the polypeptide chain, wherein said polypeptide chain does not comprise an Fc domain. In yet other embodiments, a polypeptide chain of the invention comprises a hinge-Fc domain, which hinge-Fc domain is at the C-terminus of the polypeptide chain. In further embodiments, a polypeptide chain of the invention comprises a hinge-Fc domain, which hinge-Fc domain is at the N-terminus of the polypeptide chains.

Although not intending to be bound by a particular mechanism of action, the diabody molecules of the invention exhibit enhanced therapeutic efficacy relative to therapeutic antibodies known in the art, in part, due to the ability of diabody to specifically bind a target cell which expresses a particular antigen (e.g., Her2/neu or PD-1) at reduced levels, for example, by virtue of the ability of the diabody to remain on the target cell longer due to an improved avidity of the diabody-epitope interaction. Thus, the diabodies of the invention have particular utility in treatment, prevention or management of a disease or disorder, such as cancer, in a sub-population, wherein the target antigen is expressed at low levels in the target cell population.

The diabody molecules can be produced using a variety of methods, including de novo protein synthesis and recombinant expression of nucleic acids encoding the binding proteins. The desired nucleic acid sequences can be produced by recombinant methods (e.g., PCR mutagenesis of an earlier prepared variant of the desired polynucleotide) or by solid-phase DNA synthesis. Preferably recombinant expression methods are used. Because of the degeneracy of the genetic code, a variety of nucleic acid sequences encode each immunoglobulin amino acid sequence, and the present invention includes all nucleic acids encoding the binding proteins described herein.

G. Production of Antibodies

The antibodies of the preferred embodiments of the invention may be produced or obtained in any of a variety of ways. For example, such antibodies may be obtained from plasma, synthetically, recombinantly or transgenically, via cell (e.g., hybridoma culture), etc. The production of synthetic proteins has been described in, e.g., Dawson, P. E. et al. (2000) "*Synthesis Of Native Proteins By Chemical Ligation*," Annu. Rev Biochem. 69:923-960; Wilken, J. et al (1998) "*Chemical Protein Synthesis,*" Curr. Opin. Biotechnol. 9(4):412-426; and Kochendoerfer, G. G. et al. (1999) "*Chemical Protein Synthesis,*" Curr. Opin. Chem. Biol. 3(6):665-671.

Antibodies may be made recombinantly by first isolating the antibodies made from host animals, obtaining the gene sequence, and using the gene sequence to express the antibody recombinantly in host cells (e.g., CHO cells). Vectors containing polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., wherein the vector is an infectious agent such as vaccinia virus). The choice of introducing vectors or polynucleotides will often depend on features of the host cell.

Any host cells capable of overexpressing heterologous DNAs can be used for the purpose of isolating the genes encoding the antibody, polypeptide or protein of interest. Non-limiting examples of suitable mammalian host cells include but are not limited to COS, HeLa, and CHO cells. Preferably, the host cells express the cDNAs at a level of about 5-fold higher, more preferably 10-fold higher, even more preferably 20-fold higher than that of the corresponding endogenous antibody or protein of interest, if present, in the host cells. Screening the host cells for a specific binding to HER2/neu or PD-1 is effected by an immunoassay or FACS. Production of antibodies via cell (e.g., hybridoma) culture has been described in, e.g., Laffly, E. et al. (2005) "*Monoclonal And Recombinant Antibodies, 30 Years After . . . ,*" Hum. Antibodies. 14(1-2):33-55; Aldington, S. et al. (2007) "*Scale-Up Of Monoclonal Antibody Purification Processes,*" J. Chromatogr. B Analyt. Technol. Biomed. Life Sci. 848(1):64-78; S. S. Farid (2006) J. Chromatogr. B Analyt. Technol. Biomed. Life Sci. 848(1):8-18; Birch, J. R. et al (2006) "*Antibody Production,*" Adv. Drug Deliv. Rev. 58(5-6):671-685; Even, M. S. et al. (2006) "*Serum-Free Hybridoma Culture: Ethical, Scientific And Safety Considerations,*" Trends Biotechnol. 24(3):105-108; Graumann, K. et al. (2006) "*Manufacturing Of Recombinant Therapeutic Proteins In Microbial Systems,*" Biotechnol. J. 1(2):164-86; U.S. Pat. No. 7,112,439; and U.S. Patent Publications Nos. 2.0070037216 and 20040197866.

Another method that may be employed is to express the antibody sequence in plants (e.g., tobacco) or transgenic milk. Suitable methods for expressing antibodies recombinantly in plants or milk have been disclosed (see, for example, Peeters, K. et al. (2001) "*Production Of Antibodies And Antibody Fragments In Plants,*" Vaccine 19:2756; Lonberg, N. et al. (1995) "*Human Antibodies From Transgenic Mice,*" Int. Rev. Immunol 13:65-93; and Pollock et al. (1999) "*Transgenic Milk As A Method For The Production Of Recombinant Antibodies,*" J. Immunol Methods 231:147-157).

Suitable methods for making derivatives of antibodies, e.g., humanized, optimized, single-chain, etc. are known in the art. Derivatives of antibodies having for example increased affinity for its antigen may be produced via phage display methods. The technology, referred to as affinity maturation, employs mutagenesis or CDR walking and re-selection using the cognate antigen to identify antibodies that bind with higher affinity to the antigen-when compared with the initial or parental antibody (see, e.g., Glaser, S. M. et al. (1992) "*Antibody Engineering By Codon-Based Mutagenesis In A Filamentous Phage Vector System,*" J. Immunology 149:3903; Wu, H. et al. (1998) "*Stepwise in vitro Affinity Maturation Of Vitaxin, An AlphaV Beta3-mAb,*" Proc. Natl. Acad. Sci. (U.S.A.) 95:6037-6042; Yelton, D. E. et al. (1995) "*Affinity Maturation Of The BR96 Anti-Carcinoma Antibody By Codon-Based Mutagenesis,*" J. Immunology 155:1994-2004; Schier, R et al. (1996) "*Isolation Of Picomolar Affinity anti-c-erbB-2 Single-Chain Fv By Molecular Evolution Of The Complementarity Determining Regions In The Center Of The Antibody Binding Site,*" J. Mol. Bio. 263:551-567).

Fully human antibodies (also referred to as completely human antibodies) may be produced using transgenic mice that are incapable of expressing endogenous immunoglobulin heavy and light chains genes, but which can express human heavy and light chain genes. An overview of this technology for producing human antibodies is described in, for example, Lonberg, N. et al. (1995) "*Human Antibodies From Transgenic Mice,*" Int. Rev. Immunol. 13:65-93, and U.S. Pat. No. 5,633,425. Fully human antibodies can also be produced using other techniques known in the art, including phage display libraries (as described by Hoogenboom, H. R. et al., (1991) "*By-Passing Immunisation. Human Antibodies From Synthetic Repertoires Of Germline $V_H$ Gene Segments Rearranged In Vitro,*" J. Mol. Biol. 227:381 and Marks, J. D. et al. (1991) "*By-Passing Immunization. Human Antibodies From V-Gene Libraries Displayed On Phage,*" J. Mol. Biol. 222:581) or"guided selection" (as described by, e.g., Jespers, L. S. et al. (1994) "*Guiding The Selection Of Human Antibodies From Phage Display Repertoires To A Single Epitope Of An Antigen,*" Biotechnology 12:899-903). Transgenic animals that are designed to produce a more desirable (e.g., fully human antibodies) or more robust immune response may also be used for generation of humanized or human antibodies. Examples of such technology are XENOMOUSE™ (Abgenix, Inc., Fremont, Calif.) and HUMAB-MOUSE® and TC MOUSE™ (both from Medarex, Inc., Princeton, N.J.).

The invention includes modifications to the antibodies described herein (i.e., anti-HER2/neu antibodies and anti-PD-1 antibodies), including functionally equivalent antibodies and fusion polypeptides that do not significantly affect the properties of such molecules as well as variants that have enhanced or decreased activity. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or use of chemical analogs. Amino acid residues which can be conservatively substituted for one another include but are not limited to: glycine/alanine; serine/threonine; valine/isoleucine/leucine; asparagine/glutamine; aspartic acid/glutamic acid; lysine/arginine; and phenylalanine/tyrosine. These polypeptides also include glycosylated and non-glycosylated polypeptides, as well as polypeptides with other post-translational modifications, such as, for example, glycosylation with different sugars, acetylation, and phosphorylation. Preferably, the amino acid substitutions would be conservative, i.e., the substituted amino acid would possess similar chemical properties as that of the original amino acid. Such conservative substitutions are known in the art, and examples have been provided above. Amino acid modifications can range from changing or modifying one or more amino acids to complete redesign of a region, such as the variable region. Changes in the variable region can alter binding affinity and/or specificity. Other methods of modification include using coupling techniques known in the art, including, but not limited to, enzymatic means, oxidative substitution and chelation. Modifications can be used, for example, for attachment of labels for immunoassay, such as the attachment of radioactive moieties for radioimmunoassay. Modified polypeptides are made using established procedures in the art and can be screened using standard assays known in the art.

H. Characterization of Binding Molecules

The binding molecules such as antibodies may be characterized in a variety of ways. In particular, antibodies may be assayed for the ability to specifically bind to an antigen, e.g., HER2/neu, PD-1, or, where the molecule comprises an Fc Region (or portion thereof) for the ability to exhibit Fc-FcγR interactions, i.e., specific binding of an Fc Region (or portion thereof) to an FcγR.

Immunoassays which can be used to analyze specific binding, cross-reactivity, and Fc-FcγR interactions include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunochromatographic assays, immunodiffusion assays, agglutination assays, complement-fixation assays, immunoradiometric assays, fluorescent immunoassays, and protein A immunoassays, etc. (see, e.g., CURRENT PROTOCOLS IN MOLECULAR BIOLOGY (Ausubel, F. M. et al., Eds., 1987) Greene Pub. Associates, New York, N.Y.).

Binding affinity for a target antigen is typically measured or determined by standard antibody-antigen assays, such as BIAcore competitive assays, saturation assays, or immunoassays such as ELISA or RIA. Fluorescence activated cell sorting (FACS), using any of the techniques known to those skilled in the art, may be used for immunological or functional based assays to characterize molecules of the invention. Surface plasmon resonance-based assays may be used to characterize the kinetic parameters of an antigen binding domain or Fc-FcγR binding.

Characterization of binding to FcγR by molecules comprising an Fc Region (or portion thereof) and/or comprising epitope binding domain specific for an FcγR may be performed according to the methods described in the Antibody Engineering Technology Art. Assays for effector cell functions are well known, for example as described in Perussia, B. et al. (2000) "*Assays for antibody-dependent cell-mediated cytotoxicity (ADCC) And Reverse ADCC (Redirected-Cytotoxicity) In Human Natural Killer Cells*," Methods Mol. Biol. 121:179-192; Lehmann, A. K. et al. (2000) "*Phagocytosis: Measurement By Flow Cytometry*," J. Immunol. Methods 243(1-2):229-242; Baggiolini, M. et al. (1998) "*Cellular Models For The Detection And Evaluation Of Drugs That Modulate Human Phagocyte Activity*," Experientia 44(10):841-848; Brown, E. J. (1994) "*In Vitro Assays Of Phagocytic Function Of Human Peripheral Blood Leukocytes: Receptor Modulation And Signal Transduction*," Methods Cell Biol. 45:147-164; and Munn, D. H. et al. (1990) "*Phagocytosis Of Tumor Cells By Human Monocytes Cultured In Recombinant Macrophage Colony-Stimulating Factor*," J. Exp. Med. 172:231-237.

VII. Methods of Treatment

Molecules that specifically bind to HER2/neu and molecules that specifically bind a cell-surface receptor (or its ligand) that is involved in regulating an immune checkpoint (especially PD-1) may be used for therapeutic purposes in individuals with cancer or other diseases. In one embodiment, molecules(s) having such binding specificity are administered concurrently. As used herein, such "concurrent" administration is intended to denote:

(A) the administration of a single pharmaceutical composition that contains both a molecule that specifically binds HER2/neu and a molecule that specifically binds a cell-surface receptor (or its ligand) that is involved in regulating an immune checkpoint (in particular PD-1). Such molecules may be the same molecule (e.g., a diabody), or may be distinct (e.g., an anti-HER2/neu antibody, or antigen-binding fragment thereof, and an anti-PD-1-antibody, or antigen-binding fragment thereof).

or (B) the separate administration of two or more pharmaceutical compositions, one composition of which contains a molecule that specifically binds HER2/neu and another composition of which contains a molecule that specifically binds a cell-surface receptor (or its ligand) that is involved in regulating an immune checkpoint (in particular PD-1), wherein the compositions are administered within a 24-hour period.

In a second embodiment, two distinct molecules are employed, and the molecules are administered "sequentially" (e.g., an anti-HER2/neu antibody is administered and, at a later time, an anti-PD-1 antibody is provided, of vice versa). In such sequential administration, the second administered composition is most preferably administered at least 24 hours, or more, after the administration of the first administered composition.

Providing a therapy or "treating" refers to any indicia of success in the treatment or amelioration of an injury, pathology or condition, including any objective or subjective parameter such as abatement, remission, diminishing of symptoms or making the injury, pathology or condition more tolerable to the patient, slowing in the rate of degeneration or decline, making the final point of degeneration less debilitating, or improving a patient's physical or mental well-being. The treatment or amelioration of symptoms can be based on objective or subjective parameters, including the results of a physical examination, neuropsychiatric exams, and/or a psychiatric evaluation.

Preferred subjects for treatment include animals, most preferably mammalian species such as humans or other primates, and domestic animals such as dogs, cats and the like, subject to disease and other pathological conditions. A "patient" refers to a subject, preferably mammalian (including human).

In one embodiment, a monoclonal anti-HER2/neu antibody and a monoclonal anti-PD-1 antibody can be used for immunotherapy directed at cancer cells of different tissues expressing HER2/neu, and particularly cancer cells such as breast cancer, glioblastoma, uterine cervical carcinoma, metastatic colorectal cancer, gastric cancer, hepatocellular carcinoma, leukemia, lung cancer, metastatic melanoma, vascularizing pancreatic cancer, and metastatic prostate cancer. Such immunotherapy may, for example, be sufficient to reduce cell division in the cancer cell, delay the development (e.g., onset and extent) of metastasis, and/or to promote the activity of the immune system on the cancer cells.

It is understood that the molecules are administered at a concentration that promotes binding at physiological (e.g., in vivo) conditions. The molecules (e.g., antibodies or diabodies) may be administered with additional agents that enhance or direct an individual's own immune response, such as an agent that strengthens ADCC.

In yet another embodiment, one or more of such molecules (e.g., antibodies or diabodies) may be conjugated to or associated with a radioactive molecule, toxin (e.g., calicheamicin), chemotherapeutic molecule, liposomes or other vesicles containing chemotherapeutic compounds and administered to an individual in need of such treatment to target these compounds to the cancer cell containing the antigen recognized by the antibody and thus eliminate cancer or diseased cells. Without being limited to any particular theory, the antibody (e.g., the anti-HER2/neu antibody) is internalized by the cell bearing HER2/neu at its surface, thus delivering the conjugated moiety to the cell to induce the therapeutic effect and the molecule that specifically binds to a cell-surface receptor (or its ligand) that is involved in regulating an immune checkpoint (especially PD-1) promotes the activation of the immune system.

In yet another embodiment, such molecules (e.g., antibodies or diabodies) can be employed as an adjuvant therapy at the time of the surgical removal of a tumor in order to delay, suppress or prevent the development of metastasis. The molecules can also be administered before surgery (neoadjuvant therapy) in order to decrease the size of the tumor and thus enable or simplify surgery, spare tissue during surgery, and for decrease any resulting disfigurement.

The anti-HER2/neu antibodies of the invention are particularly useful for the treatment and/or prevention of a disease, or disorder where an effector cell function (e.g., ADCC) mediated by FcγR is desired (e.g., cancer). For example, the anti-HER2/neu antibodies of the invention may bind a cell-surface antigen and an FcγR (e.g., FcγRIIIA) on an immune effector cell (e.g., NK cell), stimulating an effector function (e.g., ADCC, CDC, phagocytosis, opsonization, etc.) against said cell. In some embodiments, the anti-HER2/neu antibodies of the invention are especially suited for the treatment of cancers. The efficacy of standard monoclonal antibody therapy depends on the FcγR polymorphism of the subject. Cartron, G. et al. (2002) "*Therapeutic Activity Of Humanized Anti-CD20 Monoclonal Antibody And Polymorphism In IgG Fc Receptor FcganmaRIIIa Gene*," Blood 99:754-759; Weng, W. K. et al. (2003) "*Two Immunoglobulin G Fragment C Receptor Polymorphisms Independently Predict Response To Rituximab In Patients With Follicular Lymphoma*," J Clin Oncol. 21(21):3940-3947. These receptors are expressed on the surface of the effector cells and mediate ADCC. High affinity alleles improve the effector cells' ability to mediate ADCC. In particular, the anti-HER2/neu antibodies of the invention comprise a variant Fc Region that exhibits enhanced affinity to FcγR (relative to a wild-type Fc Region) on effector cells, thus providing better immunotherapy reagents for patients regardless of their FcγR polymorphism.

VIII. Treatable Disorders

Exemplary disorders that may be treated by various embodiments of the present invention include, but are not limited to, proliferative disorders, and especially cancer (and more especially, a HER2/neu-expressing cancer). In various embodiments, the invention encompasses methods and compositions for treatment, prevention or management of a disease or disorder in a subject, comprising administering to the subject a therapeutically effective amount a molecule that specifically binds HER2/neu and a molecule that specifically binds a cell-surface receptor (or its ligand) that is involved in regulating an immune checkpoint (e.g., PD-1). For example, molecules of the invention are particularly useful for the prevention, inhibition, reduction of growth or regression of primary tumors, and metastasis of cancer cells. Although not intending to be bound by a particular mechanism of action, molecules of the invention may mediate effector function against cancer cells, promote the activation of the immune system against cancer cells, cross-link cell-surface antigens and/or receptors on cancer cells and enhance apoptosis or negative growth regulatory signaling, or a combination thereof, resulting in tumor clearance and/or tumor reduction.

Antibodies with a decreased affinity for FcγRIIB and an increased affinity for FcγRIIIA and/or FcγRIIA may lead to an enhanced activating response upon FcγR binding and thus have enhanced therapeutic efficacy for treating and/or preventing cancer. Non-limiting examples of cancers treatable by the methods herein include acute myeloid lymphoma, adrenal carcinoma, adenocarcinoma, basal cancer, bladder cancer, bone cancer, bone and connective tissue sarcoma, brain cancer, breast cancer, bronchial cancer, cervical cancer, choriocarcinoma, chronic lymphocytic leukemia, chronic myelogenous leukemia, colon cancer, colorectal cancer, endometrial cancer, esophageal cancer, eye cancer, fallopian tube cancer, gall bladder cancer, gastrointestinal cancer, glioma, hairy cell leukemia, hepatoma, Hodgkin's disease, intrahepatic bile duct cancer, joint cancer, Kaposi's sarcoma, kidney cancer, larynx cancer, liver cancer, leukemia, lung cancer, lymphoblastic leukemia, lymphoma, malignant mesothelioma, medulloblastoma, melanoma, mesothelioma, middle ear cancer, multiple myeloma, myeloma, myxosarcoma, nasal cavity cancer, nasopharynx cancer, neuroblastoma, Non-Hodgkin's lymphoma, non-small cell lung cancer, nose cancer, oral cavity cancer, ovarian cancer, pancreatic cancer, penal cancer, peritoneum cancer, pharynx cancer, pituitary gland cancer, prostate cancer, rectal cancer, renal cancer, salivary gland cancer, skin cancer, soft tissue sarcoma, squamous cell carcinoma, stomach cancer, testicular cancer, thyroid cancer, urinary cancer, uterine cancer, vaginal cancer, vesticular cancer, vulval cancer, and Wilm's tumor.

In some embodiments, the cancer is a hematopoietic cancer or blood-related cancer, such as lymphoma, leukemia, myeloma, lymphoid malignancy, cancer of the spleen, and cancer of the lymph nodes. In a preferred embodiment, the cancer is a B-cell associated cancer, such as, for example, high, intermediate or low grade lymphoma (including B-cell lymphoma such as, for example, Burkitt's lymphoma, diffuse large cell lymphoma, follicular lymphoma, Hodgkin's lymphoma, mantle cell lymphoma, marginal zone lymphoma, mucosa-associated-lymphoid tissue B-cell lymphoma, non-Hodgkin's lymphoma, small lymphocytic lymphoma, and T-cell lymphomas) and leukemias (including chronic lymphocytic leukemia, such as B-cell leukemia (CD5+B lymphocytes), chronic myeloid leukemia, lymphoid leukemia, such as acute lymphoblastic leukemia, myelodysplasia, myeloid leukemia, such as acute myeloid leukemia, and secondary leukemia), multiple myeloma, such as plasma cell malignancy, and other hematological and/or B-cell or T-cell-associated cancers. Other exemplary cancers are cancers of additional hematopoietic cells, including polymorphonuclear leukocytes, such as basophils, eosinophils, neutrophils and monocytes, dendritic cells, platelets, erythrocytes and natural killer cells.

In some embodiments, the cancer is a cancer in which HER2/neu is expressed. In some embodiments, the cancer is a breast cancer, gastric cancer, prostate cancer, uterine cancer, ovarian cancer, colon cancer, endometrial cancer, adrenal carcinoma, non-small cell lung cancer, head and neck cancer, laryngeal cancer, liver cancer, renal cancer, glioblastoma, or pancreatic cancer in which HER2/neu is expressed.

IX. Pharmaceutical Compositions

Various formulations of the molecules of the invention (e.g., antibodies or diabodies) may be used for administration as the "active ingredients" of a pharmaceutical composition. In some embodiments, such molecules may be administered neat. In addition to the pharmacologically active agent(s), the compositions of the present invention may contain suitable pharmaceutically acceptable carriers comprising excipients and auxiliaries that are well known in the art and are relatively inert substances that facilitate administration of a pharmacologically effective substance or which facilitate processing of the active compounds into preparations that can be used pharmaceutically for delivery to the site of action. For example, an excipient can give form or consistency, or act as a diluent. Suitable excipients include, but are not limited to, stabilizing agents, wetting and emulsifying agents, salts for varying osmolarity, encapsulating agents, buffers, and skin penetration enhancers. The compositions can be in any suitable form, for example tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders, to name just a few non-limiting alternatives. Such compositions may be prepared by any known method, for example by admixing the active ingredient with the carrier(s) or excipient(s) under sterile conditions.

Suitable formulations for parenteral administration include aqueous solutions of the active compounds in water-soluble form, for example, water-soluble salts. In addition, suspensions of the active compounds as appropriate for oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances that increase the viscosity of the suspension and include, for example, sodium carboxymethyl cellulose, sorbitol, and/or dextran. Optionally, the suspension may also contain stabilizers. Liposomes can also be used to encapsulate the agent for delivery into the cell.

The pharmaceutical formulation for systemic administration according to the invention may be formulated for enteral, parenteral or topical administration. Indeed, all three types of formulation may be used simultaneously to achieve systemic administration of the active ingredient. Excipients as well as formulations for parenteral and nonparenteral drug delivery are set forth in REMINGTON: THE SCIENCE AND PRACTICE OF PHARMACY, 21st Edition, Lippincott Williams & Wilkins Publishing (2005). Suitable formulations for oral administration include hard or soft gelatin capsules, pills, tablets, including coated tablets, elixirs, suspensions, syrups or inhalations and controlled release forms thereof. Generally, these agents are formulated for administration by injection (e.g., intraperitoneally, intravenously, subcutaneously, intramuscularly, etc.), although other forms of administration (e.g., oral, mucosal, etc.) can be also used. Accordingly, molecules of the invention (e.g., anti-HER2/neu antibodies, anti-PD-1 antibodies) are preferably combined with pharmaceutically acceptable vehicles such as saline, Ringer's solution, dextrose solution, and the like.

The pharmaceutical compositions can also be formulated so as to provide quick, sustained or delayed release of their active ingredients after administration to the patient by employing procedures known in the art. The physical and chemical characteristics of the compositions of the invention may be modified or optimized according to the skill in the art, depending on the mode of administration and the particular disease or disorder to be treated. The compositions may be provided in unit dosage form, a sealed container, or as part of a kit, which may include instructions for use and/or a plurality of unit dosage forms.

In particular embodiments, the therapeutic agents can be incorporated into a composition, by, e.g., encapsulation in liposomes, microparticles, microcapsules, recombinant cells capable of expressing the antibody or fusion protein, receptor-mediated endocytosis (See, e.g., Wu G. Y. and Wu C. H. (1987) "*Receptor-Mediated In Vitro Gene Transformation By A Soluble DNA Carrier System*," J. Biol. Chem. 262: 4429-4432), construction of a nucleic acid as part of a retroviral or other vector, etc. In another particular embodiment, the therapeutic agents are supplied as a dry sterilized lyophilized powder or water free concentrate in a hermetically sealed container and can be reconstituted, e.g., with water or saline to the appropriate concentration for administration to a subject.

Preferably, the therapeutic agent is supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, or at least 75 mg. The lyophilized powder should be stored at between 2° C. and 8° C. in its original container and the molecules should be parenterally administered within 12 hours, preferably within 6 hours, within 5 hours, within 3 hours, or within 1 hour after being reconstituted. In an alternative embodiment, the therapeutic agents are supplied in liquid form in a hermetically sealed container indicating the quantity and concentration of the therapeutic agent. Preferably, the liquid form is supplied in a hermetically sealed container at least 1 mg/ml, more preferably at least 2.5 mg/ml, at least 5 mg/ml, at least 8 mg/ml, at least 10 mg/ml, at least 15 mg/kg, at least 25 mg/ml, at least 50 mg/ml, at least 100 mg/ml, at least 150 mg/ml, at least 200 mg/m of the molecules.

Where more than one therapeutic agent is to be administered the agents may be formulated together in the same formulation or may be formulated into separate compositions. Accordingly, in some embodiments the molecule that specifically binds HER2/neu and the molecule that specifically binds a cell-surface receptor (or its ligand) that is involved in regulating an immune checkpoint (e.g., PD-1) are formulated together in the same pharmaceutical composition. In alternative embodiments, the molecules are formulated in separate pharmaceutical compositions.

X. Kits

The compositions may also be included in a kit. The kit can include, in non-limiting aspects, a pharmaceutical composition comprising a therapeutic agent, instructions for administration and/or other components. In preferred embodiments, the kit can include a composition ready for administration. Containers of the kits can include a bottle, dispenser, package, compartment, or other types of containers, into which a component may be placed. The container can include indicia on its surface. The indicia, for example, can be a word, a phrase, an abbreviation, a picture, or a symbol. The containers can dispense a pre-determined amount of the component (e.g. compositions of the present invention). The composition can be dispensed in a spray, an aerosol, or in a liquid form or semi-solid form. The containers can have spray, pump, or squeeze mechanisms. In certain aspects, the kit can include a syringe for administering the compositions of the present invention.

Where there is more than one component in the kit, they may be packaged together, or the kit also will generally contain a second, third or other additional containers into which the additional components may be separately placed. The kits of the present invention also can include a container housing the components in close confinement for commercial sale. Such containers may include injection or blow-molded plastic containers into which the desired bottles, dispensers, or packages are retained. A kit can also include instructions for employing the kit components as well the use of any other compositions, compounds, agents, active ingredients, or objects not included in the kit. Instructions may include variations that can be implemented. The instructions can include an explanation of how to apply, use, and maintain the products or compositions, for example.

XI. Administration and Dosage

A variety of administration routes for the compositions of the present invention are available. The particular mode selected will depend, of course, upon the particular therapeutic agent selected, whether the administration is for prevention, diagnosis, or treatment of disease, the severity of the medical disorder being treated and dosage required for therapeutic efficacy. The methods of this invention may be practiced using any mode of administration that is medically acceptable, and produces effective levels of the active compounds without causing clinically unacceptable adverse effects. Such modes of administration include, but are not limited to, oral, buccal, sublingual, inhalation, mucosal, rectal, intranasal, topical, ocular, periocular, intraocular, transdermal, subcutaneous, intra-arterial, intravenous, intramuscular, parenteral, or infusion methodologies. In a specific embodiment, it may be desirable to administer the pharmaceutical compositions of the invention locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers.

As used herein, the term "therapeutically effective amount" means the total amount of each active component of the pharmaceutical composition or method that is sufficient to show a meaningful patient benefit, i.e., healing or amelioration of chronic conditions, a reduction in symptoms, an increase in rate of healing of such conditions, or a detectable change in the levels of a substance in the treated or surrounding tissue. When applied to an individual active ingredient, administered alone, the term refers to that ingredient alone. When applied to a combination, the term refers to combined amounts of the active ingredients that result in the therapeutic effect, whether administered in combination, serially, or simultaneously.

The precise dose to be employed in the formulations of the present invention will depend on the route of administration, and the seriousness of the condition, and should be decided according to the judgment of the practitioner and each patient's circumstances and can be determined by standard clinical techniques. Effective doses (i.e., doses sufficient to be effective in the treatment, prevention or amelioration of one or more symptoms associated with a disorder) may be extrapolated from dose-response curves derived from in vitro or animal model test systems. The particular dosage regimen, i.e., dose, timing and repetition, will thus depend on the particular individual and that individual's medical history, as well as the route of administration. The dosage and frequency of administration of the molecules of the invention may be reduced or altered by enhancing their uptake and/or tissue penetration, such as, for example, by lipidation.

In a preferred embodiment, the therapeutic agents of the invention are administered in metronomic dosing regimens, either by continuous infusion or frequent administration without extended rest periods. Such metronomic administration can involve dosing at constant intervals without rest periods. Typically, the therapeutic agents, in particular cytotoxic agents, are used at lower doses. Such dosing regimens encompass the chronic daily administration of relatively low doses for extended periods of time, which can minimize toxic side effects and eliminate rest periods. In certain embodiments, the therapeutic agents are delivered by chronic low-dose or continuous infusion ranging from about 24 hours to about 2 days, to about 1 week, to about 2 weeks, to about 3 weeks to about 1 month to about 2 months, to about 3 months, to about 4 months, to about 5 months, to about 6 months. The scheduling of such dose regimens can be optimized by the skilled oncologist.

Preferably the molecules of the present invention are administered using a treatment regimen comprising one or more doses, wherein the treatment regimen is administered over 2 days, 3 days, 4 days, 5 days, 6 days or 7 days. In certain embodiments, the treatment regimen comprises intermittently administering doses of the effective amount of such molecules (for example, administering a dose on day 1, day 2, day 3 and day 4 of a given week and not administering doses of the molecule on other days of the week. Especially encompassed is the administration of such molecules on day 5, day 6 and day 7 of the same week. Typically, there are 1, 2, 3, 4, 5 or more courses of treatment. Each course may be the same regimen or a different regimen.

In another embodiment, the administered dose escalates over the first quarter, first half or first two-thirds or three-quarters of the regimen(s) (e.g., over the first, second, or third regimens of a 4 course treatment) until the daily prophylactically or therapeutically effective amount of the molecule is achieved.

The dosage of such molecules administered to a patient may be calculated for use as a single agent therapy. Alternatively, the molecule may be used in combination with other therapeutic compositions and the dosage administered to a patient are lower than when said molecules are used as a single agent therapy. The dosage of such molecules (or a combination of such molecules) administered to a patient is typically at least about at least about 1.0 mg/kg body weight, at least about 3 mg/kg body weight, at least about 5 mg/kg body weight, at least about 10 mg/kg body weight, or at least about 20 mg/kg body weight. For antibodies encompassed by the invention, the dosage administered to a patient is typically 1.0 mg/kg to 100 mg/kg of the patient's body weight. Preferably, the dosage administered to a patient is between 1.0 mg/kg body weight and 20 mg/kg body weight, 1.0 mg/kg body weight and 10 mg/kg body weight, 1.0 mg/kg body weight and 5 mg/kg body weight, 2.0 mg/kg body weight and 20 mg/kg body weight, or 5 mg/kg body weight and 20 mg/kg of the patient's body weight In one embodiment, the dosage administered to a patient is between 6 mg/kg body weight and 18 mg/kg body weight. In another embodiment, the dosage administered to a patient is 6 mg/kg body weight, 10 mg/kg body weight, 15 mg/kg body weight, or 18 mg/kg body weight. The calculated dose will be administered based on the patient's body weight at baseline.

Significant (≥10%) change in body weight from baseline or established plateau weight should prompt recalculation of dose.

Alternatively, a fixed dosage of such molecules (or combination of such molecules) is administered to a patient regardless of body weight. For antibodies encompassed by the invention, the fixed dosage administered to a patient is typically between 50 mg to 500 mg. Preferably, the fixed dosage administered to a patient is between 50 mg and 300 mg, 100 mg and 300 mg, or 100 mg and 200 mg. In one embodiment, the fixed dosage administered to a patient is 200 mg.

Empirical considerations, such as the half-life, generally will contribute to the determination of the dosage. Antibodies, which are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is based on reducing the number of cancer cells, maintaining the reduction of cancer cells, reducing the proliferation of cancer cells, or delaying the development of metastasis. Alternatively, sustained continuous release formulations of anti-HER2/neu antibodies may be appropriate. Various formulations and devices for achieving sustained release are known in the art.

XII. Combination Therapies

The invention further encompasses administering a molecule that specifically binds HER2/neu and a molecule that specifically binds a cell-surface receptor (or its ligand) that is involved in regulating an immune checkpoint (e.g., PD-1) in further combination with other therapies known to those skilled in the art for the treatment or prevention of cancer, autoimmune disease, inflammation, or infectious disease, including but not limited to, current standard and experimental chemotherapies, hormonal therapies, biological therapies, immunotherapies, radiation therapies, or surgery. In some embodiments, the molecules of the invention (e.g. anti-HER2/neu and anti-PD-1 antibodies of the invention) are administered in combination with a therapeutically or prophylactically effective amount of one or more therapeutic agents known to those skilled in the art for the treatment and/or prevention of cancer, in particular a HER2/neu-expressing cancer.

As used herein, the term "combination" refers to the use of more than one therapeutic agent. The use of the term "combination" does not restrict the order in which therapeutic agents are administered to a subject with a disorder, nor does it mean that the agents are administered at exactly the same time, but rather it is meant that an antibody or polypeptide of the invention and the other agent are administered to a mammal in a sequence and within a time interval such that the antibody or polypeptide of the invention can act together with the other agent to provide an increased benefit than if they were administered otherwise. For example, each therapeutic agent (e.g., chemotherapy, radiation therapy, hormonal therapy or biological therapy) may be administered at the same time or sequentially in any order at different points in time; however, if not administered at the same time, they should be administered sufficiently close in time so as to provide the desired therapeutic or prophylactic effect. Each therapeutic agent can be administered separately, in any appropriate form and by any suitable route, e.g., one by the oral route and one parenterally.

In various embodiments, a first therapeutic agent can be administered prior to (e.g., 5 minutes before, 15 minutes before, 30 minutes before, 45 minutes before, 1 hour before, 2 hours-before, 4 hours before, 6 hours before, 12 hours before, 24 hours before, 48 hours before, 72 hours before, 96 hours before, 1 week before, 2 weeks before, 3 weeks before, 4 weeks before, 5 weeks before, 6 weeks before, 8 weeks before, or 12 weeks before), concomitantly with, or subsequent to (e.g., 5 minutes after, 15 minutes after, 30 minutes after, 45 minutes after, 1 hour after, 2 hours after, 4 hours after, 6 hours after, 12 hours after, 24 hours after, 48 hours after, 72 hours after, 96 hours after, 1 week after, 2 weeks after, 3 weeks after, 4 weeks after, 5 weeks after, 6 weeks after, 8 weeks after, or 12 weeks after) the administration of a second (or subsequent) therapeutic agent to a subject with a disorder. In preferred embodiments, two or more agents are administered within the same patient visit, or no more than 12 hours apart, no more than 24 hours apart, or no more than 48 hours apart.

Although, as discussed above, various dosing and administration routes may be employed in order to provide a combination of a molecule that specifically binds HER2/neu and a molecule that specifically binds a cell-surface receptor, or a ligand thereof, that regulates an immune checkpoint to recipient subjects in need thereof in accordance with the present invention, certain combinations, dosing and administrative routes are particularly preferred for use in such treatment. The use of a Variant Chimeric 4D5 Antibody of the invention (e.g., margetuximab) in combination with an anti-PD-1 antibody of the invention (e.g., pembrolizumab) in such dosing and administrative is particularly preferred.

A combination of a dose of a Variant Chimeric 4D5 Antibody and a dose of an anti-PD-1 antibody may be administered once or multiple times (wherein each administration of such a combination treatment regimen is herein referred to as a "cycle") each of which will comprise administration of 6 to 18 mg, preferably 0.6 mg, 10 mg, 15 mg or 18 mg of a Variant Chimeric 4D5 Antibody per kg of patient body weight, and either 1 to 10 mg, preferably 1 mg, 2 mg, 3 mg or 10 mg of an anti-PD-1 antibody per kg patient body weight, or a fixed 200 mg dose of an anti-PD-1 antibody. Most preferably a cycle will occur once every three weeks (±3 days) until remission of disease or unmanageable toxicity is observed.

In particularly preferred embodiments, a Variant Chimeric 4D5 Antibody (e.g., margetuximab) and an anti-PD-1 antibody (e.g., pembrolizumab) are administered to the subject by IV infusion about every three weeks (+3 days) for a duration of at least 1 month or more, at least 3 months or more, or at least 6 months or more, or at least 12 months or more. A treatment duration of at least 6 months or more, or for at least 12 months or more, or until remission of disease or unmanageable toxicity is observed, is particularly preferred. In such IV administration the Variant Chimeric 4D5 Antibody and the anti PD-1 antibody may be administered together or sequentially. In particularly preferred embodiments, the Variant Chimeric 4D5 Antibody and the anti-PD-1 antibody are administered to the subject sequentially by IV infusion no more than 24 hours apart. In such sequential administration the Variant Chimeric 4D5 Antibody may be administered prior to, or subsequent to, the administration of the anti-PD-1 antibody.

It is particularly preferred to provide a subject with multiple doses of a combination of the Variant Chimeric 4D5 Antibody and the anti-PD-1 antibody. A treatment regimen may thus comprise 1 cycle, at least 2 cycles or more than 2 cycles, at least 3 cycles or more than 3 cycles, at least 4 cycles or more than 4 cycles, at least 5 cycles or more than 5 cycles, or at least 6 cycles or more than 6 cycles. The dosage of each antibody in each such cycle may be the same or may vary from the prior administered dosage. Thus, for example, the therapy may comprise the administration of a "first" (or "loading") dose of the Variant Chimeric 4D5 Antibody followed by a lowered "second" dose of the Variant Chimeric 4D5 Antibody.

In some embodiments, the Variant Chimeric 4D5 Antibody is administered at a first dose of approximately 6, 10, 15 or 18 mg/kg, followed by administration of a second lower dose, wherein the second dose is administered about three weeks (±3 days) following the administration of the first dose. For example, where the first dose of the Variant Chimeric 4D5 Antibody is approximately 18 mg/kg body weight, the second dose will be less than 18 mg/kg body weight, (e.g., approximately 3 mg/kg body weight, approximately 6 mg/kg body weight, approximately 8 mg/kg body weight, approximately 10 mg/kg body weight, or approximately 15 mg/kg body weight). In some embodiments, additional subsequent doses of the Variant Chimeric 4D5 Antibody are administered, wherein the subsequent doses are administered at three weeks (±3 days) following the administration of the second dose, or previous subsequent dose. In some embodiments, the subsequent doses are administered at the same concentration as the second lower dose. In preferred embodiments, the same dose of Variant Chimeric 4D5 Antibody is administered over the entire course of treatment.

It is preferred that the antibodies not be administered as an IV push or bolus, but rather that such administration be accomplished by IV infusion. The antibodies are thus preferably diluted into an infusion bag comprising a suitable diluent, e.g., 0.9% sodium chloride. Since infusion or allergic reactions may occur, premedication for the prevention of such infusion reactions is recommended and precautions for anaphylaxis should be observed during the antibody administration. It is particularly preferable for the IV infusion to be administered to the subject over a period of between 30 minutes and 24 hours. In certain embodiments, the IV infusion is preferably delivered over a period of 30-180 minutes, or 30-120 minutes, or 30-90 minutes, or over a period of 60 minutes, or over a lesser period, if the subject does not exhibit signs or symptoms of an adverse infusion reaction.

Accordingly, a preferred method of treating cancer is provided, the method comprising administering to a subject in need thereof a Variant Chimeric 4D5 Antibody at a dosage of approximately 6 to 18 mg/kg body weight and an anti-PD-1 antibody at a fixed dosage of approximately 200 mg, wherein each of the antibodies is administered every three weeks (±3 days). In one embodiment, the Variant Chimeric 4D5 Antibody is administered at a dosage of approximately 6, 10, 15, or 18 mg/kg body weight. In a further embodiment, the Variant Chimeric 4D5 Antibody is administered at a dosage of approximately 6 mg/kg body weight and the anti-PD-1 antibody is administered at a fixed dosage of 200 mg. In a further embodiment, the Variant Chimeric 4D5 Antibody is administered at a dosage of approximately 10 mg/kg body weight and the anti-PD-1 antibody is administered at a fixed dosage of approximately 200 mg. In a further embodiment, the Variant Chimeric 4D5 Antibody is administered at a dosage of approximately 15 mg/kg body weight and the anti-PD-1 antibody is administered at a fixed dosage of approximately 200 mg. In a further embodiment, the Variant Chimeric 4D5 Antibody is administered at a dosage of approximately 18 mg/kg body weight and the anti-PD-1 antibody is administered at a fixed dosage of approximately 200 mg. In any of the above embodiments, the Variant Chimeric 4D5 Antibody and the anti-PD-1 antibody are administered by IV infusion within a 24-hour period. In any of the above embodiments, the cancer is a HER2/neu expressing cancer. In any of the above embodiments, the Variant Chimeric 4D5 Antibody is margetuximab and the anti-PD-1 antibody is pembrolizumab. In any of the above embodiments, the Variant Chimeric 4D5 Antibody is margetuximab and the anti-PD-1 antibody is nivolumab. In any of the above embodiments, the Variant Chimeric 4D5 Antibody is margetuximab and the anti-PD-1 antibody is pidilizumab. In any of the above embodiments, the Variant Chimeric 4D5 Antibody is margetuximab and the anti-PD-1 antibody is EH12.2H7. In any of the above embodiments, the Variant Chimeric 4D5 Antibody is margetuximab and the anti-PD-1 antibody is hPD-1 mAb 2. In any of the above embodiments, the Variant Chimeric 4D5 Antibody is margetuximab and the anti-PD-1 antibody is hPD-1 mAb 7. In any of the above embodiments, the Variant Chimeric 4D5 Antibody is margetuximab and the anti-PD-1 antibody is hPD-1 mAb 9. In any of the above embodiments, the Variant Chimeric 4D5 Antibody is margetuximab and the anti-PD-1 antibody is hPD-1 mAb 15. In any of the above embodiments, the Variant Chimeric 4D5 Antibody is margetuximab and the anti-PD-1 antibody is selected from the antibodies provide in Table 1.

Another preferred method of treating cancer is provided, the method comprising administering to a subject in need thereof a Variant Chimeric 4D5 Antibody at a dosage of approximately 6 to 18 mg/kg-body weight- and an anti-PD-1 antibody at a dosage of approximately 1 to 10 mg/kg, wherein each of the antibodies is administered every three weeks (±3 days). In one embodiment, the Variant Chimeric 4D5 Antibody is administered at a dosage of approximately 6, 10, 15, or 18 mg/kg body weight. In a further embodiment, the anti-PD-1 antibody is administered at a dosage of approximately 1, 2, 3 or 10 mg/kg body weight. In a further embodiment, the Variant Chimeric 4D5 Antibody is administered at a dosage of approximately 6 mg/kg body weight and the anti-PD-1 antibody is administered at a dosage of approximately 1 mg/kg body weight. In a further embodiment, the Variant Chimeric 4D5 Antibody is administered at a dosage of approximately 6 mg/kg body weight and the anti-PD-1 antibody is administered at a dosage of approximately 2 mg/kg body weight. In a further embodiment, the Variant Chimeric 4D5 Antibody is administered at a dosage of approximately 6 mg/kg body weight and the anti-PD-1 antibody is administered at a dosage of approximately 10 mg/kg body weight. In a further embodiment, the Variant Chimeric 4D5 Antibody is administered at a dosage of approximately 10 mg/kg bodyweight and the anti-PD-1 antibody is administered at a dosage of approximately 1 mg/kg body weight. In a further embodiment, the Variant Chimeric 4D5 Antibody is administered at a dosage of approximately 10 mg/kg body weight and the anti-PD-1 antibody is administered at a dosage of approximately 2 mg/kg body weight. In a further embodiment, the Variant Chimeric 4D5 Antibody is administered at a dosage of approximately 10 mg/kg body weight and the anti-PD-1 antibody is administered at a dosage of approximately 10 mg/kg body weight. In a further embodiment, the Variant Chimeric 4D5 Antibody is administered at a dosage of approximately 15 mg/kg body weight and the anti-PD-1 antibody is administered at a dosage of approximately 1 mg/kg body weight. In a further embodiment, the Variant Chimeric 4D5 Antibody is administered at a dosage of approximately 16 mg/kg body weight and the anti-PD-1 antibody is administered at a dosage of approximately 2 mg/kg body weight. In a further embodiment, the Variant Chimeric 4D5 Antibody is administered at a dosage of approximately 15 mg/kg body weight and the anti-PD-1 antibody is administered at a dosage of approximately 10 mg/kg body weight. In any of the above embodiments, the Variant Chimeric 4D5 Antibody and the anti-PD-1 antibody are administered by IV infusion within a 24-hour period. In any of the above embodiments, the cancer is a HER2/neu expressing cancer. In any of the above embodiments, the Variant Chimeric 4D5 Antibody is margetuximab and the anti-PD-1 antibody is pembrolizumab. In any of the above embodiments, the Variant Chimeric 4D5 Antibody is margetuximab and the anti-PD-1 antibody is nivolumab. In any of the above embodiments, the Variant Chimeric 4D5 Antibody is margetuximab and the anti-PD-1 antibody is pidilizumab. In any of the above embodiments, the Variant Chimeric 4D5 Antibody is margetuximab and the anti-PD-1 antibody is EH12.2H7. In any of the above embodiments, the Variant Chimeric 4D5 Antibody is margetuximab and the anti-PD-1 antibody is hPD-1 mAb 2. In any of the above embodiments, the Variant Chimeric 4D5 Antibody is margetuximab and the anti-PD-1 antibody is hPD-1 mAb 7. In any of the above embodiments, the Variant Chimeric 4D5 Antibody is margetuximab and the anti-PD-1 antibody is hPD-1 mAb 9. In any of the above embodiments, the Variant Chimeric 4D5 Antibody is margetuximab and the anti-PD-1 antibody is hPD-1 mAb 15. In any of the above embodiments, the Variant Chimeric 4D5 Antibody is margetuximab and the anti-PD-1 antibody is selected from the antibodies provide in Table 1.

In certain embodiments, the therapeutic agents are cyclically administered to a subject. Such cycling therapy involves the administration of a first agent for a period of time, followed by the administration of a second agent and/or third agent for a period of time and repeating this sequential administration. Cycling therapy can reduce the development of resistance to one or more of the therapies, avoid or reduce the side effects of one of the therapies, and/or improves the efficacy of the treatment. Exemplary cycles are about once every week, about once every 10 days, about once every two weeks, and about once every three weeks. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

In an embodiment for the treatment of a cell proliferative disorder, an molecule of the present invention (e.g., anti-HER2/neu antibody, anti-PD-1 antibody) is conjugated to, or administered in further combination with, another therapeutic agent, such as, but not limited to, an alkylating agent (e.g., mechlorethamine or cisplatin), angiogenesis inhibitor, anthracycline (e.g., daunorubicin/daunomycin or doxorubicin), antibiotic (e.g., dactinomycin, bleomycin, or anthramycin), antibody (e.g., an anti-VEGF antibody such as bevacizumab (sold as AVASTIN® by Genentech, Inc.), an anti-EGFR antibody such as panitumumab (sold as VECTIBIX® by Amgen, Inc.), or an anti-integrin antibody such as natalizumab (sold as TYSABRI® by Biogen Idec and Elan Pharmaceuticals, Inc.)), an antimetabolite (e.g., methotrexate or 5-fluorouracil), an anti-mitotic agent (e.g., vincristine or paclitaxel), a cytotoxin (e.g., a cytostatic or cytocidal agent), a hormone therapy agent (e.g., a selective estrogen receptor modulator (e.g., tamoxifen or raloxifene), aromatase inhibitor, luteinizing hormone-releasing hormone analog, progestational agent, adrenocorticosteroid, estrogen, androgen, anti-estrogen agent, androgen receptor blocking agent, 5-alpha reductase inhibitor, adrenal production inhibitor, etc.), a matrix metalloprotease inhibitor, a radioactive element (e.g., alpha-emitters, gamma-emitters, etc.), or any other chemotherapeutic agent.

Non-limiting examples of suitable angiogenesis inhibitors include ABT-627; angiostatin (plasminogen fragment); angiozyme; antiangiogenic antithrombin III; Bay 12-9566; benefin; bevacizumab; BMS-275291; bisphosphonates; cartilage-derived inhibitor (CDI); CAI; CD59 complement fragment; CEP-7055; Col 3; combretastatin A-4; endostatin (collagen XVIII fragment); farnesyl transferase inhibitors (FTI); fibronectin fragment; gro-beta; halofuginone; heparinases; heparin hexasaccharide fragment; HMV833; human chorionic gonadotropin (hCG); IM-862; interferon alpha/beta/gamma; interferon inducible protein (IP-10); interleukin-12; kringle 5 (plasminogen fragment); marimastat; metalloproteinase inhibitors (TIMPs); 2-methoxyestradiol; MMI 270 (CGS 27023A); MoAb IMC-1C11; neovastat; NM-3; panzem; PI-88; placental ribonuclease inhibitor; plasminogen activator inhibitor, platelet factor-4 (PF4); prinomastat; prolactin 16 kDa fragment; proliferin-related protein (PRP); PTK 787/ZK 222594; retinoids; solimastat; squalamine; SS 3304; SU 5416; SU6668; SU11248; tetrahydrocortisol-S; tetrathiomolybdate; thalidomide; thrombospondin-1 (TSP-1); TNP-470; transforming growth factor-beta (TGF-b); vasculostatin; vasostatin (calreticulin fragment); ZD6126; and ZD 6474.

Non-limiting examples of additional antibodies for the treatment of a cell proliferative disorder include antibodies to 17-1A, $\alpha v\beta_3$, AFP, CD3, CD18, CD20, CD22, CD33, CD44, CD52, CEA, CTLA-4, DNA-associated proteins, EGF receptor, Ep-CAM, GD2-ganglioside, gp IIIb/IIIa, gp72, HLA-DR 10 beta, HLA-DR antigen, IgE, ganglioside GD3, MUC-1, nuC242, PEM antigen, SK-1 antigen, tumor antigen CA125, tumor antigen MUC1, VEGF, and VEQF-receptor.

XII. Examples

Having now generally described the invention, the same will be more readily understood through reference to the following examples, which are provided by way of illustration and are not intended to be limiting of the present invention unless specified.

Example 1

BIACore Affinity Determinations

The kinetic parameters of the binding of eluted and purified antibodies were analyzed using a BIAcore assay (BIAcore® instrument 1000, BIAcore Inc., Piscataway, N.J.) and associated software. HER-2 was immobilized on one of the four flow cells (flow cell 2) of a sensor chip surface through amine coupling chemistry (by modification of carboxymethyl groups with mixture of NHS/EDC) such that about 1-000 response units (RU) of receptor was immobilized on the surface. Following this, the unreacted active esters were "capped off" with an injection of 1M Et-NH2. Once a suitable surface was prepared, ch4D5-FcWT (wild-type Fc), ch4D5, and trastuzumab (control) were injected at concentrations of 6.25-200 nM over the surface at a flow rate of 70 mL/min for 180 sec.

Once an entire data set was collected, the resulting binding curves were globally fitted and the rate constants and apparent equilibrium binding constant were calculated using computer algorithms supplied by the manufacturer, as described in the BIAevaluation Software Handbook available from BIAcore, Inc. FIG. 3 shows the graphical results of the SPR analysis, and the calculated constants are provided in Table 4.

TABLE 4

Kinetic and Equilibrium Constants Calculated from BIAcore Data

| Analyte | Ka1 (1/mole*s) | Kd1 (1/s) | $K_D$ (nm) |
| --- | --- | --- | --- |
| ch4D5-wild-type Fc | $1.7 \times 10^5$ | $\sim 3.2 \times 10^{-7}$ (est.) | — |
| ch4D5 | $1.1 \times 10^5$ | $\sim 6.3 \times 10^{-6}$ (est.) | — |
| trastuzumab | $1.6 \times 10^5$ | $1.3 \times 10^{-4}$ | 0.8 |

Example 2

Apoptosis

Various cell lines were incubated overnight with ch4D5 and ch4D5-FcMT1. Apoptosis was assayed by FACS analysis, and results are shown in Table 5.

TABLE 5

| | Experiment 1 | | Experiment 2 | |
| --- | --- | --- | --- | --- |
| Cell Lines | ch4D5 | ch4D5 FcMT1 | ch4D5 | ch4D5 FcMT1 |
| SKBR3 | 35% | 30% | 15% | 10% |
| JIMT | 10% | 10% | 12-30% | 10-30% |
| BT474 | 0 | 0 | 0 | 0 |
| MCF-7 | 0 | 0 | 0 | 0 |
| MDA MB 435 | 0 | 0 | 0 | 0 |
| MDA MB 468 | 10% | 10% | 5% | 0 |
| MDA MB 361 | 0 | 0 | 12% | 10% |
| MDA MB 453 | 20% | 20% | 20% | 20% |
| MDA MB 231 | 0 | 0 | 0 | 0 |
| ZR-75-1 | 0 | 0 | 0 | 0 |
| A549 | 0 | 0 | 0 | 0 |
| SKOV3 | 0 | 0 | 0 | 0 |
| HT-29 | 0 | 0 | 0 | 0 |
| OVCAR-3 | 10% | 14% | 5% | 19% |
| OVCAR-8 | 0 | 0 | 0 | 0 |
| BT-20 | 12% | 10% | 20% | 15% |

Example 3

Proliferation

Figure 4:
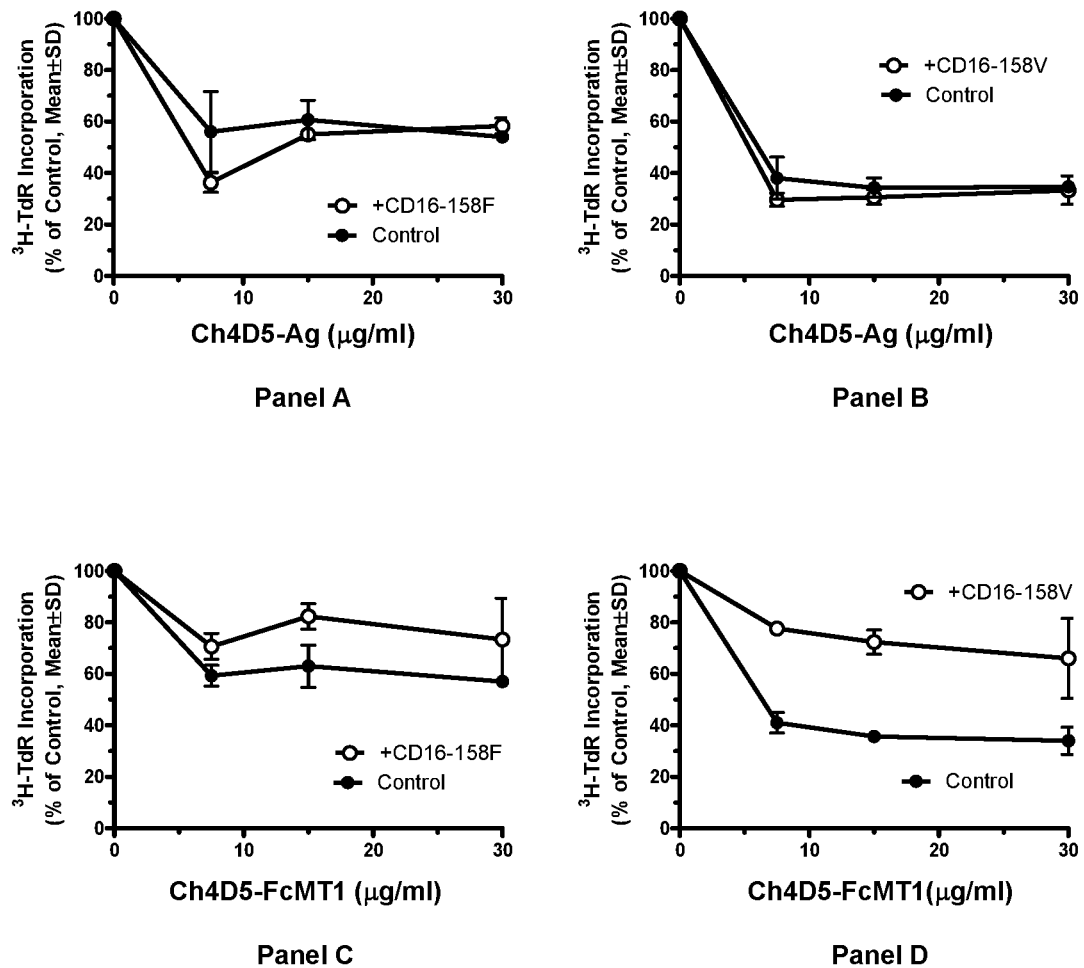
FIG. 4 (Panels A-D) depicts the effect of ch4D5-Ag (Panels A and B) and Ch4D-FcMT1 (Panels B and D) on the proliferation of CD16-158F+(Panels A and C) or CD16-158V+(Panels B and D) SKBR3 cells In vitro.

[$^3$H]Thymidine ([$^3$H]TdR) incorporation into DNA was used as a biochemical index of SKBR3 cell proliferation, to compare the effects of various Chimeric 4D5 antibodies of the present invention. The effect of ch4D5-Ag, ch4D5, and Ch4D-FcMT1 on CD16-158F+ and CD16-158V+ cells were studied and compared to controls. Results are depicted in FIG. 4.

Example 4

Anti-Tumor Activity in Mice (Breast Cancer Model)

Figure 5:
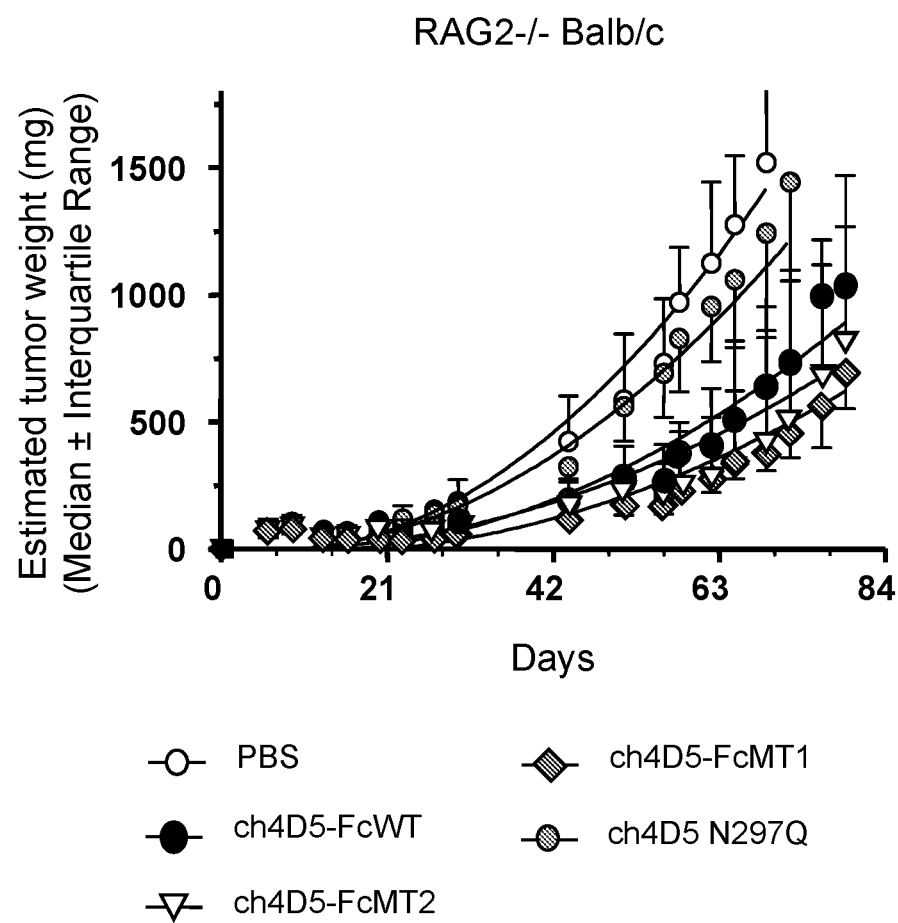
FIG. 5 depicts the enhanced anti-tumor activity of various antibodies of the present invention in non-transgenic mice.
Figure 6:
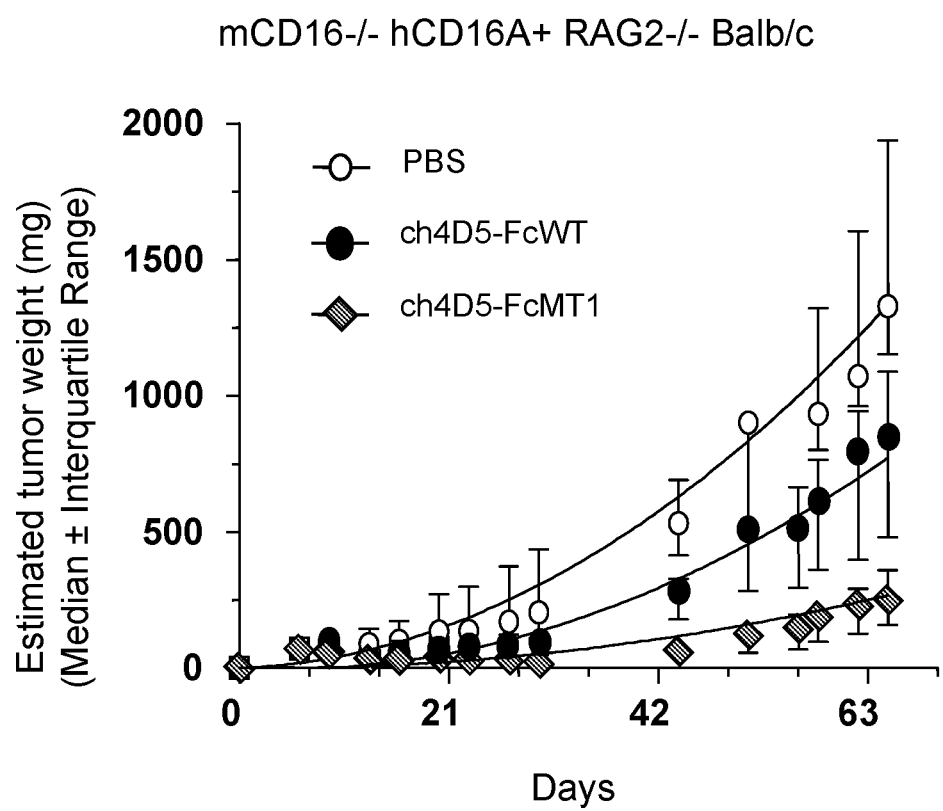
FIG. 6 depicts the enhanced anti-tumor activity of various antibodies of the present invention in hCD16A transgenic mice.

Anti-tumor activity of various antibodies was studied in a breast cancer model using non-transgenic and transgenic (hCD16A) mice. Fifty Balb/c RAG2−/− non-transgenic mice were injected subcutaneously (s.c.) at day 0 with JMT-1 breast cancer ells. Mice were divided into five groups of 10 mice each, and treated intraperitoneously (IP) weekly for 8 weeks with ch4D5 N297Q, ch4D5-wild-type Fc, ch4D5-FcMT1, ch4D5-FcMT2, or PBS (negative control). Tumor development is monitored twice per week, using calipers, and tumor weight is estimated by the following formula: tumor weight (length×width$^2$)/2. Results are shown in FIG. 5. Twenty-three Balb/c RAG2−/− mCD16−/− hCD16A+ transgenic mice were injected s.c. at day 0 with JIMT-1 breast cancer cells. Mice were divided into three groups, and treated intraperitoneously (IP) weekly for 8 weeks with ch4D5-wild-type Fc (n=8), ch4D5-FcMT1 (n=8), or PBS (negative control; n=7). Tumor development is monitored twice per week, using calipers, and tumor weight is estimated by the following formula: tumor weight=(length×width$^2$)/2. Results are shown in FIG. 6.

Example 5

Anti-Tumor Activity in Mice (Ovarian Cancer Model)

Figure 7:
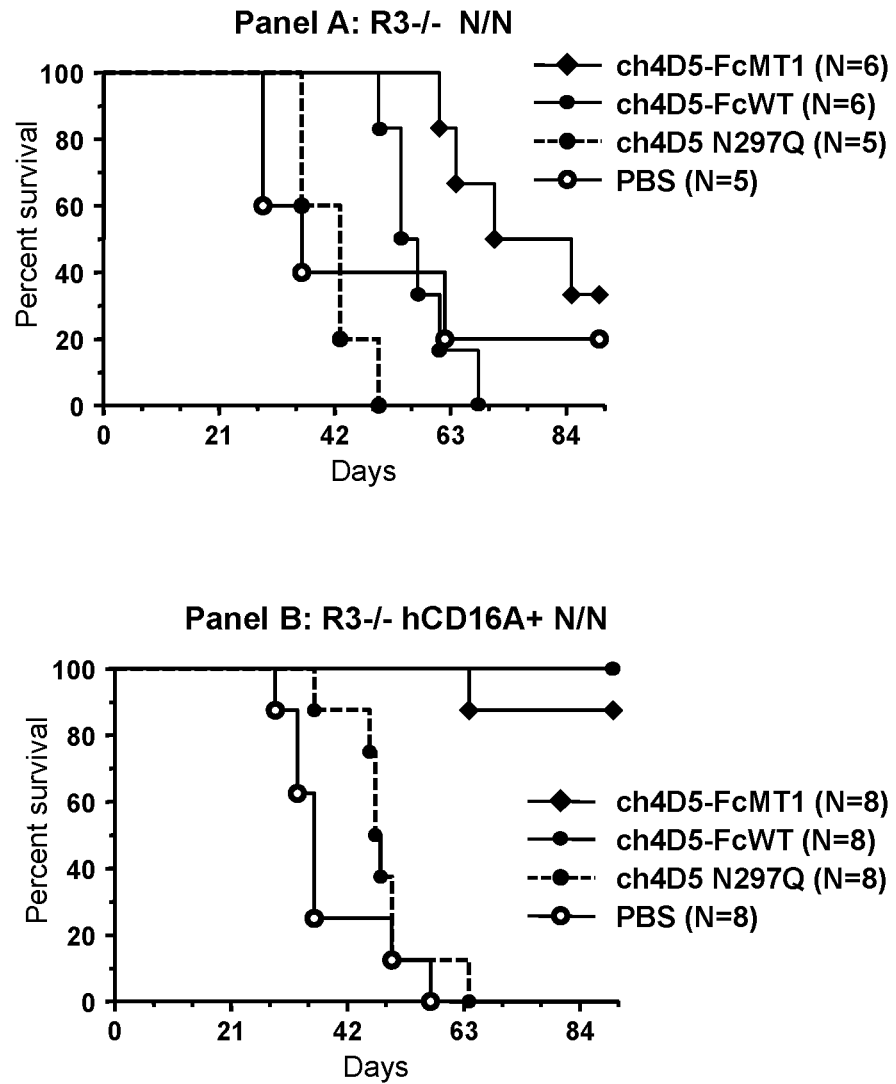
FIG. 7 (Panels A-B) depicts the role of mFcRIV and hCD16A in tumor growth inhibition by various antibodies of the present invention in non-transgenic and transgenic mice.
Figure 8:
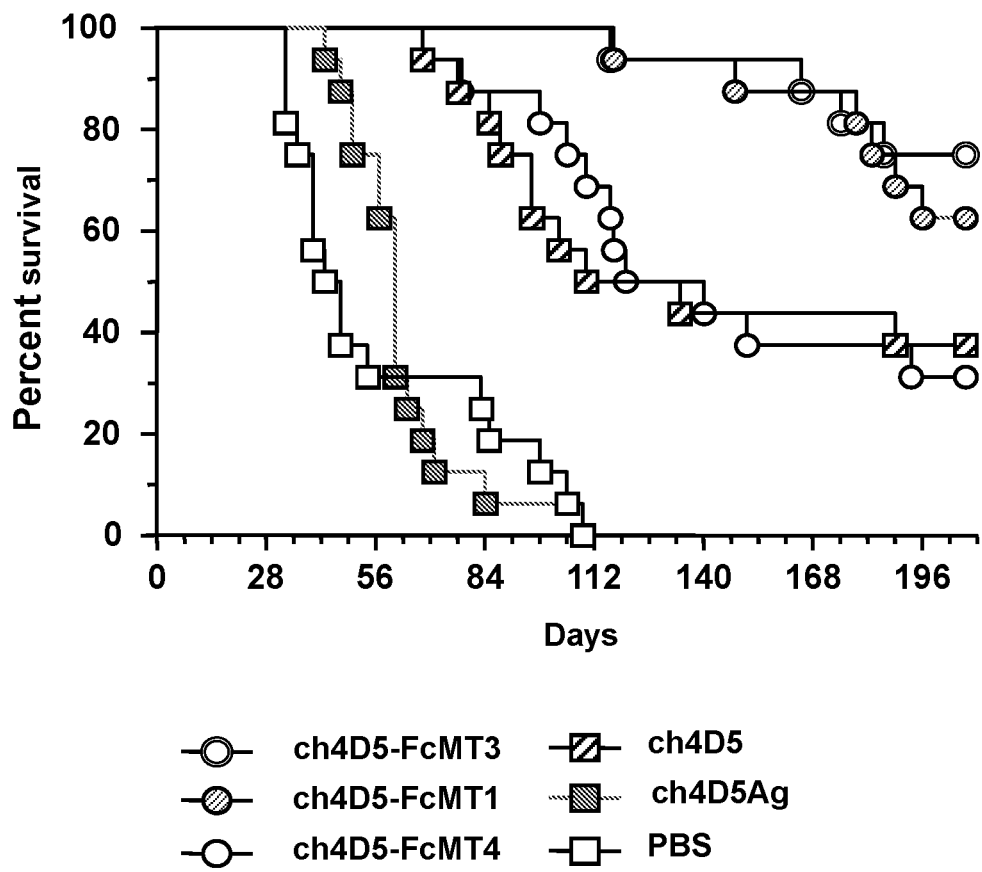
FIG. 8 depicts the enhanced anti-tumor activity of various antibodies of the present invention in hCD16A transgenic mice.

Anti-tumor activity of various antibodies was studied in an ovarian cancer model using non-transgenic and transgenic (hCD16A) mice. 22 R3−/− N/N non-transgenic mice from MacroGenics breeding colony were injected s.c. at day 0 with SKOV-3 ovarian cancer cells. Mice were divided into four groups, and treated intraperitoneously (IP) weekly for 8 weeks with ch4D5 N297Q (n=5), ch4D5-wild-type Fc (n=6), ch4D5-FcMT1 (n=6), or PBS (negative control; n=5). Tumor development is monitored twice per week, using calipers, and tumor weight is estimated by the following formula: tumor weight=(length×width$^2$)/2. The effect of such treatment on survival is shown in FIG. 7, Panel A. 32 R3−/− N/N hCD16A+ transgenic mice from MacroGenics breeding colony were injected s.c. at day 0 with SKOV-3 ovarian cancer cells. Mice were divided into four groups, and treated intraperitoneously (IP) weekly for 8 weeks with ch4D5 N297Q (n=8), ch4D5-wild-type Fc (n=8), ch4D5-FcMT1 (n=8), or PBS (negative control; n=8). Tumor development is monitored twice per week, using calipers, and tumor weight is estimated by the following formula: tumor weight=(length×width$^2$)/2. The effect of such treatment on survival is shown in FIG. 7, Panel B. 96 mCD16−/− huCD16A FoxN1−/− (nu/nu) transgenic mice from MacroGenics breeding colony were injected s.c. at day 0 with SKOV-3 ovarian cancer cells. Mice were divided into six groups of 16 mice each, and treated intraperitoneally (IP) weekly for 8 weeks with ch4D5-FcMT3, ch4D5-FcMT1, ch4D5-FcMT4, ch4D5, ch4D5Ag, or PBS (negative control). Tumor development is monitored twice per week, using calipers, and tumor weight is estimated by the following formula: tumor weight=(length×width$^2$)/2. The effect of such treatment on survival is shown in FIG. 8.

Example 6

ADCC Assay in Various Cancer Cell Lines

Figure 9:
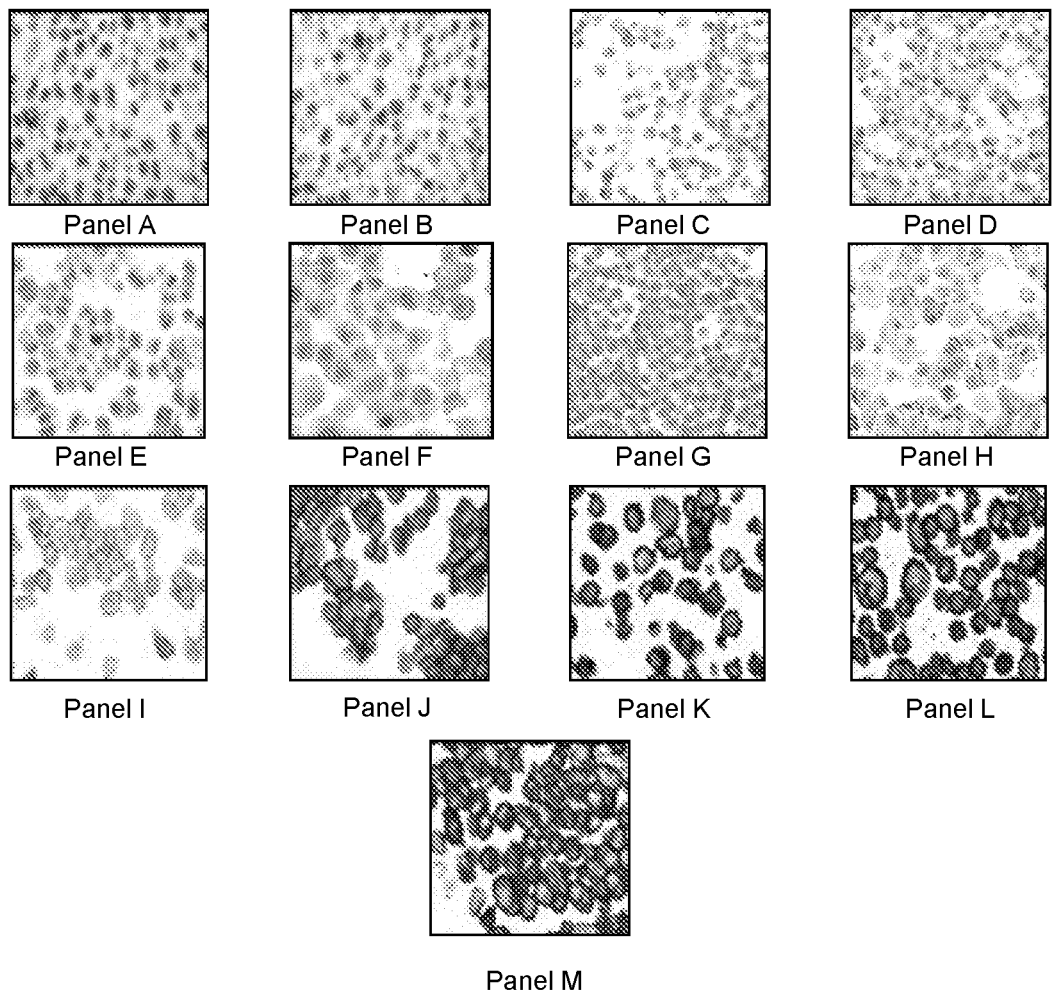
FIG. 9 (Panels A-M) illustrates representative immunohistochemical staining of cells from various cancer cell lines for HER2/neu. Panels A-L represent the different cell lines, i.e., Panel A: MDA-MB-435; Panel B: MDA-MB-231; Panel C: A549; Panel D: OVCAR-8; Panel E: MCF-7; Panel F: BT-20; Panel G: HT-29; Panel H: ZR75-1; Panel I: JIMT-1; Panel J: MDA-MB-453; Panel K: BT-474; Panel L: SKBR-3; and Panel M: mSKOV-3.
Figure 11:
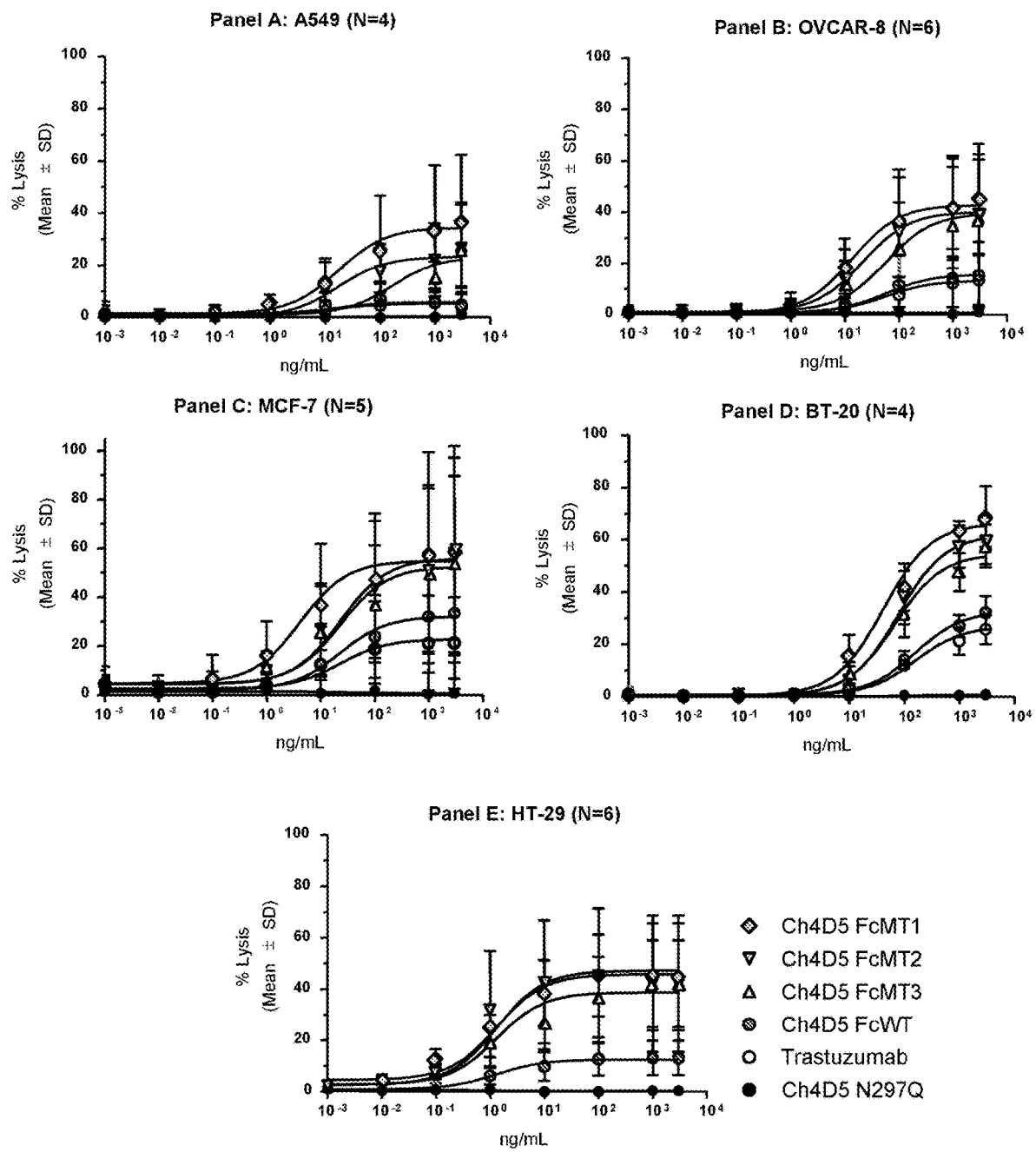
FIG. 11 (Panels A-E) depicts the results of ADCC assays performed to test the ability of Variant Chimeric 4D5 Antibodies of the present invention to mediate ADCC in cancer cell lines (A549 in Panel A; OVCAR-8 in Panel B; MCF-7 in Panel C; BT-20 in Panel D; HT-29 in Panel E) having low HER2/neu expression levels (DAKO score of 1+).
Figure 13:
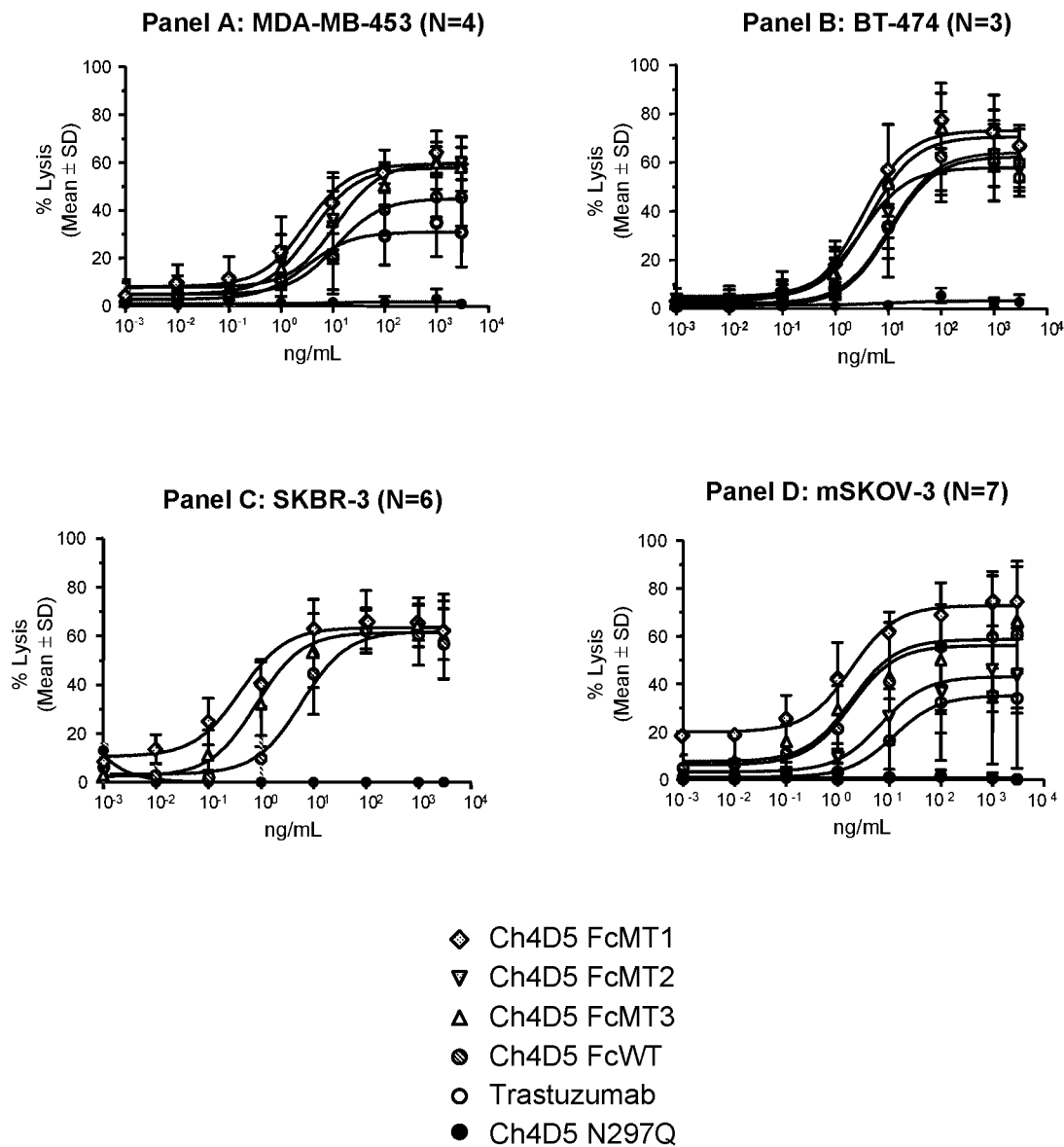
FIG. 13 (Panels A-C) depicts the results of ADCC assays performed to test the ability of Variant Chimeric 4D5 Antibodies of the present invention to mediate ADCC in cancer cell lines (MDA-MB-453 in Panel A; BT-474 in Panel B; SKBR-3 in Panel C; mSKOV-3 in Panel D) having high HER2/neu expression levels (DAKO score of 3+).

FIG. 9 illustrates representative immunohistochemical staining of various cancer cell lines for HER2/neu. Cell lines were ranked according to their HER2/neu staining intensity as specified in the HER2/neu test kit sold as DAKO HerceptTest™ (DakoCytomation, Glostrup, Denmark): missing HER2/neu staining (DAKO score 0); weak HER2/neu staining (DAKOscore 1+); moderate HER2/neu staining (DAKO score 2+); and strong HER2/neu staining (DAKO score 3+). Panels A-M represent the various cell lines, as shown in Table 6.

TABLE 6

DAKO Staining of Various Cancer Cell Lines in FIG. 9

| Panel | Cell Line | Description | Sites/Cell | Score |
|---|---|---|---|---|
| A | MDA-MB-435 | Breast carcinoma | $4.7 \times 10^3$ | 0 |
| B | MDA-MB-231 | Breast adenocarcinoma | $1.6 \times 10^4$ | 0 |
| C | A549 | Lung adenocarcinoma | $3.4 \times 10^4$ | 1+ |
| D | OVCAR-8 | Ovarian carcinoma | $4.4 \times 10^4$ | 1+ |
| E | MCF-7 | Breast adenocarcinoma | $4.5 \times 10^4$ | 1+ |
| F | BT-20 | Ductal carcinoma | $6.9 \times 10^4$ | 1+ |
| G | HT-29 | Colon/Colorectal cancer | $9.4 \times 10^4$ | 1+ |
| H | ZR75-1 | Ductal carcinoma | $1.4 \times 10^5$ | 2+ |
| I | JIMT-1 | Breast carcinoma | $2.0 \times 10^5$ | 2+ |
| J | MDA-MB-453 | Breast carcinoma | $2.8 \times 10^5$ | 3+ |
| K | BT-474 | Ductal carcinoma | $2.0 \times 10^6$ | 3+ |
| L | SKBR-3 | Breast carcinoma | $3.0 \times 10^6$ | 3+ |
| M | mSKOV-3 | Ovarian cancer | $4.0 \times 10^6$ | 3+ |

Several ch4D5 antibodies including ch4D5 antibodies having Fc variant domains were tested for the ability to mediate ADCC in the cancer cell lines, including ch4D5-FcMT1, ch4D5-FcMT2, ch4D5-FcMT3, ch4D5-FcWT (wild-type Fc), ch4D5 N297Q and trastuzumab (as a control). Data from valid assays (SR≤20% MR, AICC≤50% MR) is reported in Table 7, where $EC_{50}$ estimates were considered valid only if the model fit a max lysis of >20%. Comparison of $EC_{50}$ and max lysis parameters was performed by asking whether the best fit values obtained for the F-optimized antibodies were statistically different from those obtained for the Fc wild-type ch4D5 antibody by the sum-of-squares F test. Data were also fitted to sigmoidal dose-response models as shown in FIGS. 10-13.

TABLE 7

ADCC Assays in Various Cell Lines

| Cell Line | Antibody | EC50 (ng/mL) | p | Max Lysis (%) | p | Figure (Panel) |
|---|---|---|---|---|---|---|
| MDA-MB-435 | ch4D5-FcMT1 | ND | — | 5 | NS | 10 (A) |
| | ch4D5-FcMT2 | ND | — | 13 | NS | |
| | ch4D5-FcMT3 | ND | — | 7 | NS | |
| | ch4D5-FcWT | ND | — | 7 | — | |
| | trastuzumab | ND | — | 7 | NS | |
| MDA-MB-231 | ch4D5-FcMT1 | 4 | NS | 27 | NS | 10 (B) |
| | ch4D5-FcMT2 | 12 | NS | 29 | NS | |
| | ch4D5-FcMT3 | ? | ? | 24 | NS | |
| | ch4D5-FcWT | 9 | — | 27 | — | |
| | trastuzumab | 7 | NS | 22 | NS | |
| A549 | ch4D5-FcMT1 | 14 | — | 34 | <0.01 | 11 (A) |
| | ch4D5-FcMT2 | 21 | — | 24 | <0.01 | |
| | ch4D5-FcMT3 | >100 | — | 23 | <0.01 | |
| | ch4D5-FcWT | ND | — | 6 | — | |
| | trastuzumab | ND | — | 5 | NS | |
| OVCAR-8 | ch4D5-FcMT1 | 14 | <0.01 | 43 | <0.01 | 11 (B) |
| | ch4D5-FcMT2 | 21 | <0.05 | 40 | <0.01 | |
| | ch4D5-FcMT3 | 26 | NS | 36 | <0.01 | |
| | ch4D5-FcWT | 57 | — | 16 | — | |
| | trastuzumab | 37 | NS | 13 | NS | |
| MCF-7 | ch4D5-FcMT1 | 4 | <0.05 | 55 | <0.01 | 11 (C) |
| | ch4D5-FcMT2 | 9 | NS | 51 | <0.01 | |
| | ch4D5-FcMT3 | 8 | NS | 48 | <0.01 | |
| | ch4D5-FcWT | 23 | NS | 32 | — | |
| | trastuzumab | 9 | — | 21 | NS | |
| BT-20 | ch4D5-FcMT1 | 42 | <0.01 | 66 | <0.01 | 11 (D) |
| | ch4D5-FcMT2 | 78 | <0.01 | 62 | <0.01 | |
| | ch4D5-FcMT3 | 67 | <0.01 | 55 | <0.01 | |

TABLE 7-continued

ADCC Assays in Various Cell Lines

| Cell Line | Antibody | EC50 (ng/mL) | p | Max Lysis (%) | p | Figure (Panel) |
|---|---|---|---|---|---|---|
| | ch4D5-FcWT | >100 | — | 33 | — | |
| | trastuzumab | >100 | NS | 25 | NS | |
| HT-29 | ch4D5-FcMT1 | 0.4 | — | 43 | <0.01 | 11 (E) |
| | ch4D5-FcMT2 | 0.5 | — | 44 | <0.01 | |
| | ch4D5-FcMT3 | 1 | — | 38 | <0.01 | |
| | ch4D5-FcWT | ND | — | 13 | — | |
| ZR75-1 | ch4D5-FcMT1 | 14 | <0.01 | 78 | <0.01 | 12 (A) |
| | ch4D5-FcMT2 | 20 | NS | 67 | <0.01 | |
| | ch4D5-FcMT3 | 26 | <0.01 | 63 | <0.01 | |
| | ch4D5-FcWT | 38 | — | 38 | — | |
| | trastuzumab | ND | — | 23 | <0.01 | |
| JIMT-1 | ch4D5-FcMT1 | 8 | NS | 73 | <0.01 | 12 (B) |
| | ch4D5-FcMT2 | 7 | <0.05 | 70 | <0.01 | |
| | ch4D5-FcMT3 | 10 | NS | 65 | <0.01 | |
| | ch4D5-FcWT | 22 | — | 43 | — | |
| | trastuzumab | 10 | NS | 34 | NS | |
| MDA-MB-453 | ch4D5-FcMT1 | 3 | <0.05 | 59 | <0.01 | 13 (A) |
| | ch4D5-FcMT2 | 4 | <0.05 | 58 | <0.01 | |
| | ch4D5-FcMT3 | 6 | NS | 57 | <0.01 | |
| | ch4D5-FcWT | 11 | — | 45 | — | |
| | trastuzumab | 3 | <0.05 | 31 | <0.01 | |
| BT-474 | ch4D5-FcMT1 | 3 | <0.01 | 73 | <0.01 | 13 (B) |
| | ch4D5-FcMT2 | 3 | <0.05 | 58 | NS | |
| | ch4D5-FcMT3 | 4 | <0.05 | 71 | NS | |
| | ch4D5-FcWT | 11 | — | 64 | — | |
| | trastuzumab | 7 | NS | 60 | NS | |
| SKBR-3 | ch4D5-FcMT1 | 0.4 | <0.01 | 64 | NS | 13 (C) |
| | ch4D5-FcMT3 | 0.8 | <0.01 | 61 | NS | |
| | ch4D5-FcWT | 6 | — | 62 | — | |
| mSKOV-3 | ch4D5-FcMT1 | 1.2 | NS | 71 | <0.01 | 13 (D) |
| | ch4D5-FcMT2 | 7 | <0.05 | 43 | <0.05 | |
| | ch4D5-FcMT3 | 0.9 | <0.05 | 56 | NS | |
| | ch4D5-FcWT | 3 | — | 58 | — | |

Example 7

Figure 14:
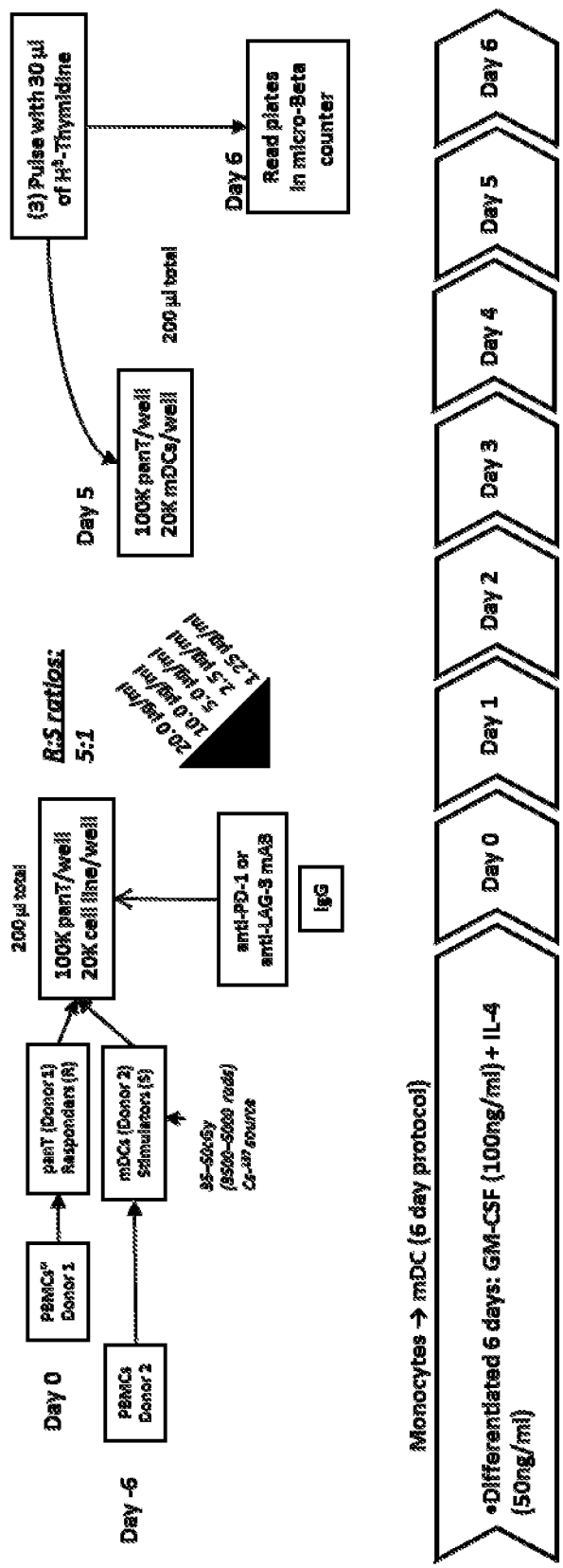
FIG. 14 shows a diagram of the protocol for assessing the ability of anti-PD-1 antibodies to enhance the proliferation of T-cells.
Figure 15:
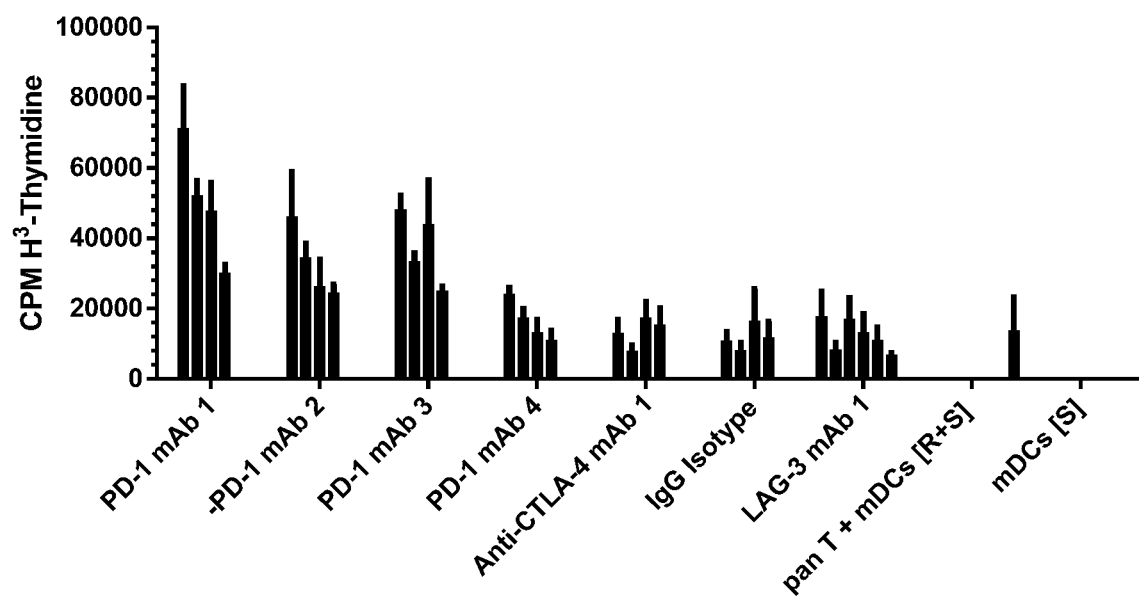
FIG. 15 shows that the addition of PD-1 mAb 1 (5C4; BMS-936558; Bristol-Myers Squibb, nivolumab), PD-1 mAb 2 (MK-3475; Merck, pembrolizumab (formerly lambrolizumab)) and PD-1 mAb 3 (EH12.2H7; Dana Farber) at the start of the allo-MLR assay, induced a strong T-cell proliferation response compared to IgG1 isotype control antibody. Also shown are the proliferative responses obtained with PD-1 mAb 4 (CT-011; CureTech, pidilizumab), an anti-CTLA mAb and LAG-3 mAb. Responder (R) cells are pan T-cells; stimulator (S) cells are mature dendritic cells (mDCs).

Activity of Monoclonal Antibodies Against Costimulatory or Checkpoint Targets on T-Cell Proliferation Within the context of the allo-MLR assay, T-cells are induced to proliferate in response to HLA-mismatching (Latchman, Y. E. et al. (2004) "*PD-L-Deficient Mice Show That PD-L1 On T-Cells, Antigen-Presenting Cells, And Host Tissues Negatively Regulates T-Cells.*" Proc. Natl. Acad. Sci. (U.S.A.) 101(29):10691-10696; Wang, W. et al. (2008) "*PD-L1/PD-1 Signal Deficiency Promotes Allogeneic Immune Responses And Accelerates Heart Allograft Rejection,*" Transplantation 86(6):836-44) or mitogenic/pharmacological stimulation. Agonist antibodies that target costimulatory molecules are known to induce proliferative responses by re-enforcing T-cell signaling and stabilizing transcription factors that promote or drive T-cell effector function (Melero, I. et al. (2013) "*Agonist Antibodies to TNFR Molecules That Costimulate T and NK Cells,*" Clin. Cancer Res. 19(5):1044-1053). Similarly, antagonist antibodies that target key checkpoint molecules that negatively regulate T-cell responses (checkpoint inhibitors) can induce proliferative responses by maintaining T-cell signaling and effector function and thereby improving anti-tumor immunity (Capece, D. et al. (2012) "*Targeting Costimulatory Molecules to Improve Antitumor Immunity,*" J. Biomed. Biotech. 2012:926321). The effect of monoclonal antibodies against costimulatory or checkpoint targets on proliferation in response to alloantigen can be easily measure in short-term mixed lymphocyte (allo-MLR) reactions by following the incorporation of $^3$H-thymidine. To address ability of antibodies against checkpoint inhibitors to enhance proliferation, anti-PD-1 or anti-LAG-3 mAbs were generated, purified, and exogenously added at the initiation of allo-MLR assay at 20, 10, 5, 2.5, and 1.25 µg/ml (FIG. 14). At the end of 5-6 days, the 96-well plated was pulse with $^3$H-thymidine and cultured for 18 hrs to measure proliferation. Several benchmark antibodies against human PD-1, LAG-3, and CTLA-4 were evaluated in their capacity to enhance T-cell proliferation in response to allo-antigen stimulation. As shown in FIG. 15, the addition of PD-1 mAb 1 (5C4 (BMS-936558), PD-1 mAb 2 (MK-3475; Merck, lambrolizumab), or PD-1 mAb 3 (EH12.2H7; Dana Farber) at the start of the allo-MLR assay, induced strong T-cell proliferation compared to IgG1 isotype control antibody or the control wells containing responders and stimulators. Wells containing irradiated stimulator cells alone demonstrated no proliferation. Although a dose dependent proliferative response was observed, PD-1 mAb 4 (CT-011; CureTech, BAT-1) showed minimal proliferation compared to PD-1 mAb 1 (5C4 (BMS-936558), PD-1 mAb 2 (MK-3475; Merck, lambrolizumab), or PD-1 mAb 3 (EH12.2H7; Dana Farber). A slight dose dependent proliferative response was also observed with LAG-3 mAb 1 (25F7; BMS-986016, Medarex/BMS), which compared similarly to Yervoy® ipilimumab, an anti-CTLA-4 mAb (Bristol-Myers Squib).

Example 8

Dose-Escalation Study Of Margetuximab And Pembrolizumab

A dose escalation study is performed to determine the Maximum Tolerated Dose (MTD) or Maximum Administered Dose (MAD) (if no MTD is defined) of escalating doses of margetuximab administered in combination with a fixed dose of approximately 200 mg pembrolizumab. This may be followed by a cohort expansion phase to further define the safety and initial efficacy of the combination with the margetuximab dose established in the dose escalation study. Both margetuximab and pembrolizumab are administered once every 3 weeks. Both agents are administered on the same day, with pembrolizumab administered first, followed by margetuximab. Each cycle of therapy is defined as 3 weeks, in which margetuximab and pembrolizumab are given on Day 1. Tumor assessments may be performed during the study, preferably at the end of every two cycles of treatment (i.e., every 6 weeks [end of Cycles 2, 4, 6, etc.]).

Margetuximab may be evaluated in two sequential escalating doses, approximately 10 mg/kg body weight and approximately 15 mg/kg body weight, in combination with 200 mg pembrolizumab in cohort patients. If it is determined that the MTD is exceeded in the first dose cohort, a dose de-escalation cohort to evaluate a lower dose of margetuximab (6 mg/kg) in combination with 200 mg pembrolizumab may be utilized. A higher dose of margetuximab (e.g., 18 mg/kg) may be explored during the dose escalation portion of the study.

For a cohort expansion phase additional patients are enrolled and will receive margetuximab at the MTD (or MAD) established from the dose escalation phase of the study in combination with 200 mg pembrolizumab.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method of treating cancer, comprising administering to a subject in need thereof:
   (A) a Variant Chimeric 4D5 Antibody comprising a light chain variable domain comprising the amino acid sequence of SEQ ID NO:4, and a heavy chain that comprises a variant Fc Region that exhibits enhanced ADCC activity relative to a comparable antibody that comprises a wild-type IgG1 Fc Region, wherein said heavy chain comprises an amino acid sequence selected from the group consisting of SEQ ID NO:9, SEQ ID NO:11, and SEQ ID NO:13, and
   (B) an anti-PD-1 antibody or a molecule that specifically binds PD-1 that comprises an antigen-binding fragment of said anti-PD-1 antibody, wherein said anti-PD-1 antibody and said antigen-binding fragment comprise:
   (a) a variant Fc Region that comprises at least one modification relative to a wild-type IgG1 Fc Region or an IgG4 Fc Region, wherein said variant Fc Region of said molecule exhibits reduced ADCC activity relative to a comparable molecule that comprises said wild-type IgG1 Fc Region; and
   (b)
   (1) the three heavy chain CDRs and the three light chain CDRs of antibody hPD-1 mAb 2;
   (2) the three heavy chain CDRs and the three light chain CDRs of antibody PD-1 mAb 6-ISQ;
   (3) the three heavy chain CDRs and the three light chain CDRs of antibody hPD-1 mAb 7;
   (4) the three heavy chain CDRs and the three light chain CDRs of antibody hPD-1 mAb 9; or
   (5) the three heavy chain CDRs and the three light chain CDRs of antibody hPD-1 mAb 15.

2. The method of claim 1 wherein said anti-PD-1 antibody and said molecule that comprises an antigen-binding fragment of said anti-PD-1 antibody comprise:
   (1) the heavy chain variable domain and the light chain variable domain of antibody hPD-1 mAb 2;
   (2) the heavy chain variable domain and the light chain variable domain of antibody PD-1 mAb 6-ISQ;
   (3) the heavy chain variable domain and the light chain variable domain of antibody hPD-1 mAb 7;
   (4) the heavy chain variable domain and the light chain variable domain of antibody hPD-1 mAb 9;
   (5) the heavy chain variable domain and the light chain variable domain of antibody hPD-1 mAb 15.

3. The method of claim 1, wherein said method comprises administering anti-PD-1 antibody hPD-1 mAb 2, antibody PD-1 mAb 6-ISQ, antibody hPD-1 mAb 7, antibody hPD-1 mAb 9, or antibody hPD-1 mAb 15 to said subject.

4. The method of claim 1, wherein said Variant Chimeric 4D5 Antibody is administered at a dosage of approximately 6-18 mg/kg every three weeks and said anti-PD-1 antibody is administered at a fixed dosage of approximately 50 mg to 500 mg, every three weeks.

5. The method of claim 1, wherein said Variant Chimeric 4D5 Antibody is administered at a dosage of approximately 6-18 mg/kg every three weeks and said anti-PD-1 antibody is administered at a dosage of approximately 1-10 mg/kg, every three weeks.

6. The method of claim 4, wherein said Variant Chimeric 4D5 Antibody is administered at a dosage selected from the group consisting of 6 mg/kg, 10 mg/kg, 15 mg/kg and 18 mg/kg, every three weeks.

7. The method of claim 5 wherein said anti-PD-1 antibody is administered at a dosage selected from the group consisting of 1 mg/kg, 2 mg/kg, 3 mg/kg and 10 mg/kg, every three weeks.

8. The method of claim 1, wherein said Variant Chimeric 4D5 Antibody and said anti-PD-1 antibody or said molecule that comprises an antigen-binding fragment of said anti-PD-1 antibody are administered concurrently to said subject in a single pharmaceutical composition.

9. The method of claim 1, wherein said Variant Chimeric 4D5 Antibody and said anti-PD-1 antibody or said molecule that comprises an antigen-binding fragment of said anti-PD-1 antibody are administered concurrently to said subject in separate pharmaceutical compositions, wherein said separate compositions are administered within a 24-hour period.

10. The method of claim 1, wherein said Variant Chimeric 4D5 Antibody and said anti-PD-1 antibody or said molecule that comprises an antigen-binding fragment of said anti-PD-1 antibody are administered sequentially to said subject in separate pharmaceutical compositions, wherein the second administered composition is administered at least 24 hours after the administration of the first administered composition.

11. The method of claim 1, wherein said cancer is a cancer in which HER2/neu is expressed.

12. The method of claim 11, wherein said cancer is a breast cancer, gastric cancer, prostate cancer, uterine cancer, ovarian cancer, colon cancer, endometrial cancer, adrenal carcinoma, non-small cell lung cancer, head and neck cancer, laryngeal cancer, liver cancer, renal cancer, glioblastoma, or pancreatic cancer.

13. The method of claim 1, wherein said treatment further comprises the step of administering a third therapeutic agent, wherein said third therapeutic agent is selected from the group consisting of an anti-angiogenic agent, an antineoplastic agent, a chemotherapeutic agent, and a cytotoxic agent.

14. The method of claim 13, wherein the third therapeutic agent is administered concurrently with said Variant Chimeric 4D5 Antibody and/or said anti-PD-1 antibody or said molecule that comprises an antigen-binding fragment of said anti-PD-1 antibody.

15. The method of claim 13, wherein the third therapeutic agent is administered separately from said Variant Chimeric 4D5 Antibody and/or said anti-PD-1 antibody or said molecule that comprises an antigen-binding fragment of said anti-PD-1 antibody.

16. The method of claim 1, wherein said Variant Chimeric 4D5 Antibody is margetuximab.

17. The method of claim 3 wherein said anti-PD-1 antibody is antibody hPD-1 mAb 7.

18. The method of claim 1, wherein:
(a) said Variant Chimeric 4D5 Antibody is for administration at a dosage of approximately 6-18 mg/kg and said anti-PD-1 antibody is for administration at a fixed dosage of approximately 100-500 mg; or
(b) said Variant Chimeric 4D5 Antibody is for administration at a dosage of approximately 6-18 mg/kg and said anti-PD-1 antibody is for administration at a dosage of approximately 1-10 mg/kg.

19. The method of claim 3, wherein said anti-PD-1 antibody is PD-1 mAb 6-ISQ.

20. The method of claim 3, wherein:
(a) said Variant Chimeric 4D5 Antibody is for administration at a dosage of approximately 6-18 mg/kg and said anti-PD-1 antibody is for administration at a fixed dosage of approximately 100-500 mg; or
(b) said Variant Chimeric 4D5 Antibody is for administration at a dosage of approximately 6-18 mg/kg and said anti-PD-1 antibody is for administration at a dosage of approximately 1-10 mg/kg.

* * * * *